US010675021B2

(12) United States Patent
Harris et al.

(10) Patent No.: US 10,675,021 B2
(45) Date of Patent: Jun. 9, 2020

(54) CIRCULAR STAPLING SYSTEM COMPRISING ROTARY FIRING SYSTEM

(71) Applicant: Ethicon Endo-Surgery, LLC, Guaynabo, PR (US)

(72) Inventors: Jason L. Harris, Lebanon, OH (US); Frederick E. Shelton, IV, Hillsboro, OH (US); Dean L. Garner, Cincinnati, OH (US)

(73) Assignee: Ethicon LLC, Guaynabo, PR (US)

(*) Notice: Subject to any disclaimer, the term of this patent is extended or adjusted under 35 U.S.C. 154(b) by 841 days.

(21) Appl. No.: 15/089,309

(22) Filed: Apr. 1, 2016

(65) Prior Publication Data

US 2017/0281169 A1    Oct. 5, 2017

(51) Int. Cl.
*A61B 17/115* (2006.01)
*A61B 17/072* (2006.01)
(Continued)

(52) U.S. Cl.
CPC ...... *A61B 17/072* (2013.01); *A61B 17/00234* (2013.01); *A61B 17/068* (2013.01); *A61B 17/0686* (2013.01); *A61B 17/07207* (2013.01); *A61B 17/105* (2013.01); *A61B 17/115* (2013.01); *A61B 17/1155* (2013.01); *A61B 17/32* (2013.01); *A61B 17/3211* (2013.01); *A61B 17/0644* (2013.01); *A61B 17/07292* (2013.01); *A61B 17/29* (2013.01); *A61B 17/320092* (2013.01); *A61B 90/37* (2016.02); *A61B 2017/00017* (2013.01); *A61B 2017/00022* (2013.01); *A61B 2017/0046* (2013.01); *A61B 2017/00115* (2013.01);
(Continued)

(58) Field of Classification Search
CPC .......... A61B 17/07207; A61B 17/1155; A61B 2017/07278
USPC ....................................... 623/2.11; 227/178.1
See application file for complete search history.

(56) References Cited

U.S. PATENT DOCUMENTS 971,519 A    10/1910   Brannen
2,224,882 A   12/1940   Peck
(Continued)

FOREIGN PATENT DOCUMENTS

AU    2008207624 A1    3/2009
AU    2010214687 A1    9/2010
(Continued)

OTHER PUBLICATIONS

Disclosed Anonymously, "Motor-Driven Surgical Stapler Improvements," Research Disclosure Database No. 526041, Published: Feb. 2008.
(Continued)

*Primary Examiner* — Gloria R Weeks

(57) ABSTRACT

An end effector for use with a surgical stapler is disclosed, the end effector comprises a cartridge body comprising a longitudinal axis and a plurality of staple cavities defined in the cartridge body. The staple cavities comprise a first annular row of staple cavities extending around the longitudinal axis and a second annular row of staple cavities extending around the longitudinal axis. The end effector further comprises staples removably stored in the staple cavities and a ramp rotatable about the longitudinal axis to sequentially eject the staples from the staple cavities.

27 Claims, 64 Drawing Sheets

(51) Int. Cl.

| | | |
|---|---|---|
| *A61B 17/068* | (2006.01) | |
| *A61B 17/00* | (2006.01) | |
| *A61B 17/10* | (2006.01) | |
| *A61B 17/32* | (2006.01) | |
| *A61B 17/3211* | (2006.01) | |
| *A61B 90/00* | (2016.01) | |
| *A61B 17/064* | (2006.01) | |
| *A61B 17/29* | (2006.01) | |

(52) U.S. Cl.
CPC ........... A61B 2017/00128 (2013.01); A61B 2017/00199 (2013.01); A61B 2017/00305 (2013.01); A61B 2017/00367 (2013.01); A61B 2017/00398 (2013.01); A61B 2017/00407 (2013.01); A61B 2017/00424 (2013.01); A61B 2017/00464 (2013.01); A61B 2017/00473 (2013.01); A61B 2017/00477 (2013.01); A61B 2017/00734 (2013.01); A61B 2017/00818 (2013.01); A61B 2017/00946 (2013.01); A61B 2017/07214 (2013.01); A61B 2017/07221 (2013.01); A61B 2017/07228 (2013.01); A61B 2017/07235 (2013.01); A61B 2017/07242 (2013.01); A61B 2017/07257 (2013.01); A61B 2017/07264 (2013.01); A61B 2017/07271 (2013.01); A61B 2017/07278 (2013.01); A61B 2017/07285 (2013.01); A61B 2017/291 (2013.01); A61B 2017/292 (2013.01); A61B 2017/2903 (2013.01); A61B 2017/2905 (2013.01); A61B 2017/2912 (2013.01); A61B 2017/2922 (2013.01); A61B 2017/2923 (2013.01); A61B 2017/2927 (2013.01); A61B 2017/2932 (2013.01); A61B 2017/2946 (2013.01); A61B 2090/034 (2016.02); A61B 2090/0808 (2016.02); A61B 2090/0811 (2016.02); A61B 2090/0814 (2016.02); A61B 2090/08021 (2016.02)

(56) References Cited

U.S. PATENT DOCUMENTS

| | | |
|---|---|---|
| 2,445,071 A | 7/1948 | Kovacs |
| 2,457,274 A | 12/1948 | Rifken |
| 2,718,894 A | 9/1955 | Gresham |
| 2,742,955 A | 4/1956 | Dominguez |
| D180,713 S | 7/1957 | Hammond |
| 2,853,074 A | 9/1958 | Olson |
| 3,080,564 A | 3/1963 | Strekopitov et al. |
| 3,166,072 A | 1/1965 | Sullivan, Jr. |
| 3,266,494 A | 8/1966 | Brownrigg et al. |
| 3,348,595 A | 10/1967 | Stevens, Jr. |
| 3,357,070 A | 12/1967 | Soloan |
| 3,359,978 A | 12/1967 | Smith, Jr. |
| 3,490,675 A | 1/1970 | Green et al. |
| 3,494,533 A | 2/1970 | Green et al. |
| 3,551,987 A | 1/1971 | Wilkinson |
| 3,643,851 A | 2/1972 | Green et al. |
| 3,662,939 A * | 5/1972 | Bryan ............... A61B 17/0684 227/109 |
| 3,717,294 A | 2/1973 | Green |
| 3,744,495 A | 7/1973 | Johnson |
| 3,746,002 A | 7/1973 | Haller |
| 3,819,100 A * | 6/1974 | Noiles ............... A61B 17/0684 227/121 |
| 3,863,639 A | 2/1975 | Kleaveland |
| RE28,932 E | 8/1976 | Noiles et al. |
| 4,111,206 A | 9/1978 | Vishnevsky et al. |
| 4,138,055 A | 2/1979 | Harrison |
| 4,190,042 A | 2/1980 | Sinnreich |
| 4,198,982 A | 4/1980 | Fortner et al. |
| 4,207,898 A | 6/1980 | Becht |
| 4,272,002 A | 6/1981 | Moshofsky |
| 4,274,398 A | 6/1981 | Scott, Jr. |
| 4,289,133 A | 9/1981 | Rothfuss |
| 4,304,236 A | 12/1981 | Conta et al. |
| 4,305,539 A | 12/1981 | Korolkov et al. |
| 4,331,277 A | 5/1982 | Green |
| 4,379,457 A | 4/1983 | Gravener et al. |
| 4,383,634 A | 5/1983 | Green |
| 4,396,139 A | 8/1983 | Hall et al. |
| 4,397,311 A | 8/1983 | Kanshin et al. |
| 4,402,445 A | 9/1983 | Green |
| 4,408,692 A | 10/1983 | Sigel et al. |
| 4,415,112 A | 11/1983 | Green |
| 4,417,890 A | 11/1983 | Dennehey et al. |
| 4,429,695 A | 2/1984 | Green |
| 4,434,796 A | 3/1984 | Karapetian et al. |
| 4,438,659 A | 3/1984 | Desplats |
| 4,473,077 A | 9/1984 | Noiles et al. |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,527,724 A | 7/1985 | Chow et al. |
| 4,530,453 A | 7/1985 | Green |
| 4,566,620 A | 1/1986 | Green et al. |
| 4,573,468 A | 3/1986 | Conta et al. |
| 4,573,622 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,605,001 A | 8/1986 | Rothfuss et al. |
| 4,605,004 A | 8/1986 | Di Giovanni et al. |
| 4,608,981 A | 9/1986 | Rothfuss et al. |
| 4,610,383 A | 9/1986 | Rothfuss et al. |
| 4,612,933 A | 9/1986 | Brinkerhoff et al. |
| 4,619,262 A | 10/1986 | Taylor |
| 4,619,391 A | 10/1986 | Sharkany et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,664,305 A | 5/1987 | Blake, III et al. |
| 4,669,647 A | 6/1987 | Storace |
| 4,671,445 A | 6/1987 | Barker et al. |
| 4,684,051 A | 8/1987 | Akopov et al. |
| 4,697,312 A | 10/1987 | Freyer |
| 4,700,703 A | 10/1987 | Resnick et al. |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,818,121 A | 4/1989 | Volk |
| 4,819,853 A | 4/1989 | Green |
| 4,821,939 A | 4/1989 | Green |
| 4,827,911 A | 5/1989 | Broadwin et al. |
| 4,844,068 A | 7/1989 | Arata et al. |
| 4,848,637 A | 7/1989 | Pruitt |
| 4,865,030 A | 9/1989 | Polyak |
| 4,869,414 A | 9/1989 | Green et al. |
| 4,869,415 A | 9/1989 | Fox |

(56) References Cited

U.S. PATENT DOCUMENTS

| | | |
|---|---|---|
| 4,873,977 A | 10/1989 | Avant et al. |
| 4,892,244 A | 1/1990 | Fox et al. |
| 4,893,622 A | 1/1990 | Green et al. |
| 4,896,678 A | 1/1990 | Ogawa |
| 4,903,697 A | 2/1990 | Resnick et al. |
| 4,909,789 A | 3/1990 | Taguchi et al. |
| 4,914,789 A | 4/1990 | Pedersen |
| 4,921,479 A | 5/1990 | Grayzel |
| 4,930,674 A | 6/1990 | Barak |
| 4,931,047 A | 6/1990 | Broadwin et al. |
| 4,938,408 A | 7/1990 | Bedi et al. |
| 4,941,623 A | 7/1990 | Pruitt |
| 4,944,443 A | 7/1990 | Oddsen et al. |
| 4,973,302 A | 11/1990 | Armour et al. |
| 4,978,333 A | 12/1990 | Broadwin et al. |
| 4,984,564 A | 1/1991 | Yuen |
| 4,986,808 A | 1/1991 | Broadwin et al. |
| 5,002,553 A | 3/1991 | Shiber |
| 5,014,899 A | 5/1991 | Presty et al. |
| 5,015,227 A | 5/1991 | Broadwin et al. |
| 5,016,575 A | 5/1991 | Gordon |
| 5,027,834 A | 7/1991 | Pruitt |
| 5,038,109 A | 8/1991 | Goble et al. |
| D319,903 S | 9/1991 | Barner |
| 5,065,929 A | 11/1991 | Schulze et al. |
| 5,071,430 A | 12/1991 | de Salis et al. |
| 5,074,454 A | 12/1991 | Peters |
| 5,080,088 A | 1/1992 | LeVahn |
| 5,082,005 A | 1/1992 | Kaldany |
| 5,084,057 A | 1/1992 | Green et al. |
| 5,088,997 A | 2/1992 | Delahuerga et al. |
| 5,098,360 A | 3/1992 | Hirota |
| 5,104,025 A | 4/1992 | Main et al. |
| 5,104,397 A | 4/1992 | Vasconcelos et al. |
| 5,108,368 A | 4/1992 | Hammerslag et al. |
| 5,116,349 A | 5/1992 | Aranyi |
| 5,119,983 A | 6/1992 | Green et al. |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,156,315 A | 10/1992 | Green et al. |
| 5,156,609 A | 10/1992 | Nakao et al. |
| 5,158,567 A | 10/1992 | Green |
| 5,170,925 A | 12/1992 | Madden et al. |
| 5,171,247 A | 12/1992 | Hughett et al. |
| 5,171,249 A | 12/1992 | Stefanchik et al. |
| 5,190,517 A | 3/1993 | Zieve et al. |
| 5,195,505 A | 3/1993 | Josefsen |
| 5,197,649 A | 3/1993 | Bessler et al. |
| 5,205,459 A | 4/1993 | Brinkerhoff et al. |
| 5,211,649 A | 5/1993 | Kohler et al. |
| 5,211,655 A | 5/1993 | Hasson |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,258,009 A | 11/1993 | Conners |
| 5,258,012 A | 11/1993 | Luscombe et al. |
| 5,263,629 A | 11/1993 | Trumbull et al. |
| 5,263,937 A | 11/1993 | Shipp |
| 5,271,543 A | 12/1993 | Grant et al. |
| 5,275,322 A | 1/1994 | Brinkerhoff et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,945 A | 2/1994 | Brinkerhoff et al. |
| 5,304,204 A | 4/1994 | Bregen |
| 5,309,896 A | 5/1994 | Moll et al. |
| 5,309,927 A | 5/1994 | Welch |
| 5,312,023 A | 5/1994 | Green et al. |
| 5,312,329 A | 5/1994 | Beaty et al. |
| 5,314,445 A | 5/1994 | Heidmueller nee Degwitz et al. |
| 5,330,502 A | 7/1994 | Hassler et al. |
| 5,333,772 A | 8/1994 | Rothfuss et al. |
| 5,333,773 A | 8/1994 | Main et al. |
| 5,336,232 A | 8/1994 | Green et al. |
| 5,342,385 A | 8/1994 | Norelli et al. |
| 5,342,395 A | 8/1994 | Jarrett et al. |
| 5,342,396 A | 8/1994 | Cook |
| 5,346,115 A | 9/1994 | Perouse et al. |
| 5,346,504 A | 9/1994 | Ortiz et al. |
| 5,350,104 A | 9/1994 | Main et al. |
| 5,350,400 A | 9/1994 | Esposito et al. |
| 5,354,250 A | 10/1994 | Christensen |
| 5,354,303 A | 10/1994 | Spaeth et al. |
| 5,358,506 A | 10/1994 | Green et al. |
| 5,364,001 A | 11/1994 | Bryan |
| 5,366,134 A | 11/1994 | Green et al. |
| 5,366,479 A | 11/1994 | McGarry et al. |
| 5,370,645 A | 12/1994 | Klicek et al. |
| 5,372,596 A | 12/1994 | Klicek et al. |
| 5,374,277 A | 12/1994 | Hassler |
| 5,375,588 A | 12/1994 | Yoon |
| 5,381,588 A | 1/1995 | Nelson |
| 5,382,247 A | 1/1995 | Cimino et al. |
| 5,383,880 A | 1/1995 | Hooven |
| 5,383,888 A | 1/1995 | Zvenyatsky et al. |
| 5,383,895 A | 1/1995 | Holmes et al. |
| 5,389,102 A | 2/1995 | Green et al. |
| 5,389,104 A | 2/1995 | Hahnen et al. |
| 5,391,180 A | 2/1995 | Tovey et al. |
| 5,395,030 A | 3/1995 | Kuramoto et al. |
| 5,395,033 A | 3/1995 | Byrne et al. |
| 5,395,384 A | 3/1995 | Duthoit et al. |
| 5,397,324 A | 3/1995 | Carroll et al. |
| 5,403,312 A | 4/1995 | Yates et al. |
| 5,404,870 A | 4/1995 | Brinkerhoff et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,411,508 A | 5/1995 | Bessler et al. |
| 5,413,267 A | 5/1995 | Solyntjes et al. |
| 5,413,272 A | 5/1995 | Green et al. |
| 5,413,573 A | 5/1995 | Koivukangas |
| 5,415,334 A | 5/1995 | Williamson et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,431,668 A | 7/1995 | Burbank, III et al. |
| 5,433,721 A | 7/1995 | Hooven et al. |
| 5,438,302 A | 8/1995 | Goble |
| 5,441,483 A | 8/1995 | Avitall |
| 5,441,494 A | 8/1995 | Ortiz |
| 5,445,644 A | 8/1995 | Pietrafitta et al. |
| 5,447,265 A | 9/1995 | Vidal et al. |
| 5,447,417 A | 9/1995 | Kuhl et al. |
| 5,449,355 A | 9/1995 | Rhum et al. |
| 5,449,365 A | 9/1995 | Green et al. |
| 5,452,836 A | 9/1995 | Huitema et al. |
| 5,452,837 A | 9/1995 | Williamson, IV et al. |
| 5,458,279 A | 10/1995 | Plyley |
| 5,462,215 A | 10/1995 | Viola et al. |
| 5,465,819 A | 11/1995 | Weilant et al. |
| 5,465,894 A | 11/1995 | Clark et al. |
| 5,465,896 A | 11/1995 | Allen et al. |
| 5,466,020 A | 11/1995 | Page et al. |
| 5,470,006 A | 11/1995 | Rodak |
| 5,470,009 A | 11/1995 | Rodak |
| 5,472,442 A | 12/1995 | Klicek |
| 5,474,057 A | 12/1995 | Makower et al. |
| 5,474,566 A | 12/1995 | Alesi et al. |

(56) References Cited

U.S. PATENT DOCUMENTS

| | | |
|---|---|---|
| 5,476,479 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,490,819 A | 2/1996 | Nicholas et al. |
| 5,496,312 A | 3/1996 | Klicek |
| 5,496,317 A | 3/1996 | Goble et al. |
| 5,497,933 A | 3/1996 | DeFonzo et al. |
| 5,498,201 A | 3/1996 | Volk |
| 5,503,320 A | 4/1996 | Webster et al. |
| 5,503,635 A | 4/1996 | Sauer et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,678 A | 5/1996 | Heckele et al. |
| 5,520,700 A | 5/1996 | Beyar et al. |
| 5,527,264 A | 6/1996 | Moll et al. |
| 5,529,235 A | 6/1996 | Boiarski et al. |
| 5,531,856 A | 7/1996 | Moll et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,547,117 A | 8/1996 | Hamblin et al. |
| 5,549,621 A | 8/1996 | Bessler et al. |
| 5,549,637 A | 8/1996 | Crainich |
| 5,551,622 A | 9/1996 | Yoon |
| 5,553,765 A | 9/1996 | Knodel et al. |
| 5,554,169 A | 9/1996 | Green et al. |
| 5,556,416 A | 9/1996 | Clark et al. |
| 5,556,918 A | 9/1996 | Brodt et al. |
| 5,558,665 A | 9/1996 | Kieturakis |
| D374,758 S | 10/1996 | Armenta et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,564,615 A | 10/1996 | Bishop et al. |
| 5,571,116 A | 11/1996 | Bolanos et al. |
| 5,571,285 A | 11/1996 | Chow et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,599,344 A | 2/1997 | Paterson |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,937 A | 3/1997 | Garrison et al. |
| 5,613,966 A | 3/1997 | Makower et al. |
| 5,615,820 A | 4/1997 | Viola |
| 5,618,303 A | 4/1997 | Marlow et al. |
| 5,618,307 A | 4/1997 | Donlon et al. |
| 5,619,992 A | 4/1997 | Guthrie et al. |
| 5,620,452 A | 4/1997 | Yoon |
| 5,624,452 A | 4/1997 | Yates |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,644,799 A | 7/1997 | Armenta et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,651,491 A | 7/1997 | Heaton et al. |
| 5,651,762 A | 7/1997 | Bridges |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,685,826 A | 11/1997 | Bonutti |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,695,494 A | 12/1997 | Becker |
| 5,695,504 A | 12/1997 | Gifford, III et al. |
| 5,695,524 A | 12/1997 | Kelley et al. |
| 5,697,543 A | 12/1997 | Burdorff |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |

(56) References Cited

U.S. PATENT DOCUMENTS

| | | |
|---|---|---|
| 5,709,680 A | 1/1998 | Yates et al. |
| 5,709,706 A | 1/1998 | Kienzle et al. |
| 5,711,472 A | 1/1998 | Bryan |
| 5,713,505 A | 2/1998 | Huitema |
| 5,713,895 A | 2/1998 | Lontine et al. |
| 5,715,604 A | 2/1998 | Lanzoni |
| 5,715,987 A | 2/1998 | Kelley et al. |
| 5,716,366 A | 2/1998 | Yates |
| 5,718,359 A | 2/1998 | Palmer et al. |
| 5,718,360 A | 2/1998 | Green et al. |
| 5,718,624 A | 2/1998 | Volk |
| 5,720,744 A | 2/1998 | Eggleston et al. |
| 5,725,536 A | 3/1998 | Oberlin et al. |
| 5,725,554 A | 3/1998 | Simon et al. |
| 5,728,121 A | 3/1998 | Bimbo et al. |
| 5,730,758 A | 3/1998 | Allgeyer |
| 5,732,871 A | 3/1998 | Clark et al. |
| 5,732,872 A | 3/1998 | Bolduc et al. |
| 5,735,874 A | 4/1998 | Measamer et al. |
| 5,738,629 A | 4/1998 | Moll et al. |
| 5,741,271 A | 4/1998 | Nakao et al. |
| 5,743,456 A | 4/1998 | Jones et al. |
| 5,749,778 A | 5/1998 | Volk |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,752,970 A | 5/1998 | Yoon |
| 5,758,814 A * | 6/1998 | Gallagher ............ A61B 17/115 227/176.1 |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,859 A | 7/1998 | Nicholas et al. |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,797,959 A | 8/1998 | Castro et al. |
| 5,799,857 A | 9/1998 | Robertson et al. |
| 5,800,379 A | 9/1998 | Edwards |
| 5,807,376 A | 9/1998 | Viola et al. |
| 5,807,378 A | 9/1998 | Jensen et al. |
| 5,810,721 A | 9/1998 | Mueller et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,817,084 A | 10/1998 | Jensen |
| 5,817,093 A | 10/1998 | Williamson, IV et al. |
| 5,820,009 A | 10/1998 | Melling et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,830,598 A | 11/1998 | Patterson |
| 5,833,695 A | 11/1998 | Yoon |
| 5,836,503 A | 11/1998 | Ehrenfels et al. |
| 5,839,369 A | 11/1998 | Chatterjee et al. |
| 5,839,639 A | 11/1998 | Sauer et al. |
| 5,843,021 A | 12/1998 | Edwards et al. |
| 5,843,096 A | 12/1998 | Igaki et al. |
| D404,525 S | 1/1999 | Knudsen |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,876,401 A | 3/1999 | Schulze et al. |
| 5,878,937 A | 3/1999 | Green et al. |
| 5,891,558 A | 4/1999 | Bell et al. |
| 5,893,506 A | 4/1999 | Powell |
| 5,894,979 A | 4/1999 | Powell |
| 5,897,552 A | 4/1999 | Edwards et al. |
| 5,897,562 A | 4/1999 | Bolanos et al. |
| 5,901,895 A | 5/1999 | Heaton et al. |
| 5,902,312 A | 5/1999 | Frater et al. |
| 5,906,577 A | 5/1999 | Beane et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,931,853 A | 8/1999 | McEwen et al. |
| 5,937,867 A | 8/1999 | Williams |
| 5,937,951 A | 8/1999 | Izuchukwu et al. |
| 5,938,667 A | 8/1999 | Peyser et al. |
| 5,941,442 A | 8/1999 | Geiste et al. |
| 5,944,715 A | 8/1999 | Goble et al. |
| 5,947,984 A | 9/1999 | Whipple |
| 5,947,996 A | 9/1999 | Logeman |
| 5,951,552 A | 9/1999 | Long et al. |
| 5,951,576 A | 9/1999 | Wakabayashi |
| 5,954,259 A | 9/1999 | Viola et al. |
| 5,964,774 A | 10/1999 | McKean et al. |
| 5,997,528 A | 12/1999 | Bisch et al. |
| 5,997,552 A | 12/1999 | Person et al. |
| 6,003,517 A | 12/1999 | Sheffield et al. |
| 6,004,319 A | 12/1999 | Goble et al. |
| 6,010,054 A | 1/2000 | Johnson et al. |
| 6,012,494 A | 1/2000 | Balazs |
| 6,015,406 A | 1/2000 | Goble et al. |
| 6,017,356 A | 1/2000 | Frederick et al. |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,399 A | 3/2000 | Gines |
| 6,039,734 A | 3/2000 | Goble |
| 6,045,560 A | 4/2000 | McKean et al. |
| 6,050,172 A | 4/2000 | Corves et al. |
| 6,050,472 A | 4/2000 | Shibata |
| 6,050,996 A | 4/2000 | Schmaltz et al. |
| 6,053,390 A | 4/2000 | Green et al. |
| RE36,720 E | 5/2000 | Green et al. |
| 6,056,735 A | 5/2000 | Okada et al. |
| 6,063,025 A | 5/2000 | Bridges et al. |
| 6,063,097 A | 5/2000 | Oi et al. |
| 6,066,132 A | 5/2000 | Chen et al. |
| 6,068,627 A | 5/2000 | Orszulak et al. |
| 6,074,401 A | 6/2000 | Gardiner et al. |
| 6,079,606 A | 6/2000 | Milliman et al. |
| 6,083,191 A | 7/2000 | Rose |
| 6,083,234 A | 7/2000 | Nicholas et al. |
| 6,083,241 A | 7/2000 | Longo et al. |
| 6,083,242 A | 7/2000 | Cook |
| 6,086,600 A | 7/2000 | Kortenbach |
| 6,093,186 A | 7/2000 | Goble |
| 6,099,551 A | 8/2000 | Gabbay |
| 6,102,271 A | 8/2000 | Longo et al. |
| 6,109,500 A | 8/2000 | Alli et al. |
| 6,117,148 A | 9/2000 | Ravo et al. |
| 6,117,158 A | 9/2000 | Measamer et al. |
| 6,119,913 A | 9/2000 | Adams et al. |
| H001904 H | 10/2000 | Yates et al. |

(56) References Cited

U.S. PATENT DOCUMENTS

| | | |
|---|---|---|
| 6,126,058 A | 10/2000 | Adams et al. |
| 6,131,790 A | 10/2000 | Piraka |
| 6,142,933 A | 11/2000 | Longo et al. |
| 6,149,660 A | 11/2000 | Laufer et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,161,263 A | 12/2000 | Anderson |
| 6,162,208 A | 12/2000 | Hipps |
| 6,165,188 A | 12/2000 | Saadat et al. |
| 6,171,330 B1 | 1/2001 | Benchetrit |
| 6,174,318 B1 | 1/2001 | Bates et al. |
| 6,179,195 B1 | 1/2001 | Adams et al. |
| 6,187,003 B1 | 2/2001 | Buysse et al. |
| 6,193,129 B1 | 2/2001 | Bittner et al. |
| 6,202,914 B1 | 3/2001 | Geiste et al. |
| 6,210,403 B1 | 4/2001 | Klicek |
| 6,213,999 B1 | 4/2001 | Platt, Jr. et al. |
| 6,214,020 B1 | 4/2001 | Mulhauser et al. |
| 6,214,028 B1 | 4/2001 | Yoon et al. |
| 6,216,698 B1 | 4/2001 | Regula |
| 6,221,007 B1 | 4/2001 | Green |
| 6,228,081 B1 | 5/2001 | Goble |
| 6,228,083 B1 | 5/2001 | Lands et al. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,248,117 B1 | 6/2001 | Blatter |
| 6,250,532 B1 | 6/2001 | Green et al. |
| 6,254,534 B1 | 7/2001 | Butler et al. |
| 6,258,107 B1 | 7/2001 | Balazs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,267,772 B1 | 7/2001 | Mulhauser et al. |
| 6,273,897 B1 | 8/2001 | Dalessandro et al. |
| 6,277,114 B1 | 8/2001 | Bullivant et al. |
| 6,293,927 B1 | 9/2001 | McGuckin, Jr. |
| 6,302,311 B1 | 10/2001 | Adams et al. |
| 6,309,403 B1 | 10/2001 | Minor et al. |
| 6,315,184 B1 | 11/2001 | Whitman |
| 6,322,494 B1 | 11/2001 | Bullivant et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,352,503 B1 | 3/2002 | Matsui et al. |
| 6,354,325 B1 | 3/2002 | Warnes et al. |
| 6,358,224 B1 | 3/2002 | Tims et al. |
| 6,364,888 B1 | 4/2002 | Niemeyer et al. |
| 6,387,113 B1 | 5/2002 | Hawkins et al. |
| 6,391,038 B2 | 5/2002 | Vargas et al. |
| 6,398,797 B2 | 6/2002 | Bombard et al. |
| 6,402,766 B2 | 6/2002 | Bowman et al. |
| H002037 H | 7/2002 | Yates et al. |
| RE37,814 E | 8/2002 | Allgeyer |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,447,523 B1 | 9/2002 | Middleman et al. |
| 6,450,391 B1 | 9/2002 | Kayan et al. |
| 6,458,077 B1 | 10/2002 | Boebel et al. |
| 6,478,210 B2 | 11/2002 | Adams et al. |
| 6,488,196 B1 * | 12/2002 | Fenton, Jr. ............ A61B 17/068 227/175.1 |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,494,885 B1 | 12/2002 | Dhindsa |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,517,528 B1 | 2/2003 | Pantages et al. |
| 6,517,565 B1 | 2/2003 | Whitman et al. |
| 6,517,566 B1 | 2/2003 | Hovland et al. |
| 6,533,157 B1 | 3/2003 | Whitman |
| 6,540,737 B2 | 4/2003 | Bacher et al. |
| 6,543,456 B1 | 4/2003 | Freeman |
| 6,551,333 B2 | 4/2003 | Kuhns et al. |
| 6,558,379 B1 | 5/2003 | Batchelor et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,364 B2 | 6/2003 | Butler et al. |
| 6,585,144 B2 | 7/2003 | Adams et al. |
| 6,588,643 B2 | 7/2003 | Bolduc et al. |
| 6,589,118 B1 | 7/2003 | Soma et al. |
| 6,592,597 B2 | 7/2003 | Grant et al. |
| 6,601,749 B2 | 8/2003 | Sullivan et al. |
| 6,605,078 B2 | 8/2003 | Adams |
| 6,607,475 B2 | 8/2003 | Doyle et al. |
| 6,616,686 B2 | 9/2003 | Coleman et al. |
| 6,619,529 B2 | 9/2003 | Green et al. |
| 6,629,630 B2 | 10/2003 | Adams |
| 6,629,988 B2 | 10/2003 | Weadock |
| 6,638,285 B2 | 10/2003 | Gabbay |
| 6,638,297 B1 | 10/2003 | Huitema |
| 6,644,532 B2 | 11/2003 | Green et al. |
| 6,645,201 B1 | 11/2003 | Utley et al. |
| 6,648,901 B2 | 11/2003 | Fleischman et al. |
| 6,656,193 B2 | 12/2003 | Grant et al. |
| 6,666,854 B1 | 12/2003 | Lange |
| 6,669,073 B2 | 12/2003 | Milliman et al. |
| 6,670,806 B2 | 12/2003 | Wendt et al. |
| 6,676,660 B2 | 1/2004 | Wampler et al. |
| 6,681,978 B2 | 1/2004 | Geiste et al. |
| 6,681,979 B2 | 1/2004 | Whitman |
| 6,682,528 B2 | 1/2004 | Frazier et al. |
| 6,692,507 B2 | 2/2004 | Pugsley et al. |
| 6,695,198 B2 | 2/2004 | Adams et al. |
| 6,695,199 B2 | 2/2004 | Whitman |
| 6,698,643 B2 | 3/2004 | Whitman |
| 6,699,235 B2 | 3/2004 | Wallace et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,109 B2 | 4/2004 | Solingen |
| 6,726,697 B2 | 4/2004 | Nicholas et al. |
| 6,736,825 B2 | 5/2004 | Blatter et al. |
| 6,749,560 B1 | 6/2004 | Konstorum et al. |
| 6,749,600 B1 | 6/2004 | Levy |
| 6,752,816 B2 | 6/2004 | Culp et al. |
| 6,755,338 B2 | 6/2004 | Hahnen et al. |
| 6,761,685 B2 | 7/2004 | Adams et al. |
| 6,769,590 B2 | 8/2004 | Vresh et al. |
| 6,769,594 B2 | 8/2004 | Orban, III |
| 6,773,438 B1 | 8/2004 | Knodel et al. |
| 6,780,151 B2 | 8/2004 | Grabover et al. |
| 6,786,382 B1 | 9/2004 | Hoffman |
| 6,786,896 B1 | 9/2004 | Madhani et al. |
| 6,793,652 B1 | 9/2004 | Whitman et al. |
| 6,793,661 B2 | 9/2004 | Hamilton et al. |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,820,791 B2 | 11/2004 | Adams |
| 6,821,284 B2 | 11/2004 | Sturtz et al. |

(56) References Cited

U.S. PATENT DOCUMENTS

| | | |
|---|---|---|
| 6,827,246 B2 | 12/2004 | Sullivan et al. |
| 6,827,712 B2 | 12/2004 | Tovey et al. |
| 6,830,174 B2 | 12/2004 | Hillstead et al. |
| 6,835,199 B2 | 12/2004 | McGuckin, Jr. et al. |
| 6,835,336 B2 | 12/2004 | Watt |
| 6,840,423 B2 | 1/2005 | Adams et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,858,005 B2 | 2/2005 | Ohline et al. |
| RE38,708 E | 3/2005 | Bolanos et al. |
| 6,866,178 B2 | 3/2005 | Adams et al. |
| 6,866,671 B2 | 3/2005 | Tierney et al. |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,905,057 B2 | 6/2005 | Swayze et al. |
| 6,908,472 B2 | 6/2005 | Wiener et al. |
| 6,913,608 B2 | 7/2005 | Liddicoat et al. |
| 6,913,613 B2 | 7/2005 | Schwarz et al. |
| 6,932,810 B2 | 8/2005 | Ryan |
| 6,936,042 B2 | 8/2005 | Wallace et al. |
| 6,939,358 B2 | 9/2005 | Palacios et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,220 B2 | 11/2005 | Marino et al. |
| 6,964,363 B2 | 11/2005 | Wales et al. |
| 6,969,395 B2 | 11/2005 | Eskuri |
| 6,971,988 B2 | 12/2005 | Orban, III |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,978 B2 | 1/2006 | Gannoe |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,995,729 B2 | 2/2006 | Govari et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,408 B2 | 2/2006 | Knodel et al. |
| 7,008,435 B2 | 3/2006 | Cummins |
| 7,018,357 B2 | 3/2006 | Emmons |
| 7,032,798 B2 | 4/2006 | Whitman et al. |
| 7,032,799 B2 | 4/2006 | Viola et al. |
| 7,037,314 B2 | 5/2006 | Armstrong |
| 7,044,352 B2 | 5/2006 | Shelton, IV et al. |
| 7,044,353 B2 | 5/2006 | Mastri et al. |
| 7,052,454 B2 | 5/2006 | Taylor |
| 7,052,494 B2 | 5/2006 | Goble et al. |
| 7,055,731 B2 | 6/2006 | Shelton, IV et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,712 B2 | 6/2006 | Vargas et al. |
| 7,066,944 B2 | 6/2006 | Laufer et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,083,626 B2 | 8/2006 | Hart et al. |
| 7,087,071 B2 | 8/2006 | Nicholas et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,247 B2 | 8/2006 | Monassevitch et al. |
| 7,097,089 B2 | 8/2006 | Marczyk |
| 7,097,644 B2 | 8/2006 | Long |
| 7,108,701 B2 | 9/2006 | Evens et al. |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,119,534 B2 | 10/2006 | Butzmann |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,981 B2 | 11/2006 | Long |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,637 B2 | 12/2006 | Goble |
| 7,147,650 B2 | 12/2006 | Lee |
| 7,150,748 B2 | 12/2006 | Ebbutt et al. |
| 7,156,863 B2 | 1/2007 | Sonnenschein et al. |
| 7,159,750 B2 | 1/2007 | Racenet et al. |
| 7,160,299 B2 | 1/2007 | Baily |
| 7,168,604 B2 | 1/2007 | Milliman et al. |
| 7,172,104 B2 | 2/2007 | Scirica et al. |
| 7,179,267 B2 | 2/2007 | Nolan et al. |
| 7,182,239 B1 | 2/2007 | Myers |
| 7,188,758 B2 | 3/2007 | Viola et al. |
| 7,199,537 B2 | 4/2007 | Okamura et al. |
| 7,204,404 B2 | 4/2007 | Nguyen et al. |
| 7,204,835 B2 | 4/2007 | Latterell et al. |
| 7,207,471 B2 | 4/2007 | Heinrich et al. |
| 7,207,472 B2 | 4/2007 | Wukusick et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,213,736 B2 | 5/2007 | Wales et al. |
| 7,220,272 B2 | 5/2007 | Weadock |
| 7,225,963 B2 | 6/2007 | Scirica |
| 7,225,964 B2 | 6/2007 | Mastri et al. |
| 7,229,408 B2 | 6/2007 | Douglas et al. |
| 7,234,624 B2 | 6/2007 | Gresham et al. |
| 7,235,089 B1 | 6/2007 | McGuckin, Jr. |
| 7,237,708 B1 | 7/2007 | Guy et al. |
| 7,238,195 B2 | 7/2007 | Viola |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,258,262 B2 | 8/2007 | Mastri et al. |
| 7,258,546 B2 | 8/2007 | Beier et al. |
| 7,267,679 B2 | 9/2007 | McGuckin, Jr. et al. |
| 7,278,562 B2 | 10/2007 | Mastri et al. |
| 7,278,563 B1 | 10/2007 | Green |
| 7,282,048 B2 | 10/2007 | Goble et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,203 B2 | 2/2008 | Papineau et al. |
| 7,328,828 B2 | 2/2008 | Ortiz et al. |
| 7,328,829 B2 | 2/2008 | Arad et al. |
| 7,331,340 B2 | 2/2008 | Barney |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,336,048 B2 | 2/2008 | Lohr |

(56) References Cited

U.S. PATENT DOCUMENTS

| | | |
|---|---|---|
| 7,338,505 B2 | 3/2008 | Belson |
| 7,338,513 B2 | 3/2008 | Lee et al. |
| 7,343,920 B2 | 3/2008 | Toby et al. |
| RE40,237 E | 4/2008 | Bilotti et al. |
| 7,354,447 B2 | 4/2008 | Shelton, IV et al. |
| 7,357,287 B2 | 4/2008 | Shelton, IV et al. |
| 7,357,806 B2 | 4/2008 | Rivera et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,487,899 B2 | 2/2009 | Shelton, IV et al. |
| 7,490,749 B2 | 2/2009 | Schall et al. |
| 7,491,232 B2 | 2/2009 | Bolduc et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,615,067 B2 | 11/2009 | Lee et al. |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,095 B2 | 1/2010 | Viola |
| 7,644,848 B2 | 1/2010 | Swayze et al. |
| 7,645,230 B2 | 1/2010 | Mikkaichi et al. |
| 7,648,519 B2 | 1/2010 | Lee et al. |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,255 B2 | 3/2010 | Braun |
| 7,677,525 B2 | 3/2010 | Sanchez et al. |
| 7,682,686 B2 | 3/2010 | Curro et al. |
| 7,686,201 B2 | 3/2010 | Csiky |
| 7,686,826 B2 | 3/2010 | Lee et al. |
| 7,691,098 B2 | 4/2010 | Wallace et al. |
| 7,694,864 B2 | 4/2010 | Okada et al. |
| 7,694,865 B2 | 4/2010 | Scirica |
| 7,695,485 B2 | 4/2010 | Whitman et al. |
| 7,699,204 B2 | 4/2010 | Viola |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,703,653 B2 | 4/2010 | Shah et al. |
| 7,708,180 B2 | 5/2010 | Murray et al. |
| 7,708,181 B2 | 5/2010 | Cole et al. |

(56) References Cited

U.S. PATENT DOCUMENTS

| | | |
|---|---|---|
| 7,708,182 B2 | 5/2010 | Viola |
| 7,708,758 B2 | 5/2010 | Lee et al. |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,736,306 B2 | 6/2010 | Brustad et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,776,060 B2 | 8/2010 | Mooradian et al. |
| 7,780,054 B2 | 8/2010 | Wales |
| 7,780,055 B2 | 8/2010 | Scirica et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,803,151 B2 | 9/2010 | Whitman |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,823,592 B2 | 11/2010 | Bettuchi et al. |
| 7,823,760 B2 | 11/2010 | Zemlok et al. |
| 7,824,426 B2 | 11/2010 | Racenet et al. |
| 7,828,189 B2 | 11/2010 | Holsten et al. |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,862,502 B2 | 1/2011 | Pool et al. |
| 7,866,525 B2 | 1/2011 | Scirica |
| 7,866,527 B2 | 1/2011 | Hall et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,461 B2 | 2/2011 | Albrecht et al. |
| 7,886,951 B2 | 2/2011 | Hessler |
| 7,886,952 B2 | 2/2011 | Scirica et al. |
| 7,886,953 B2 | 2/2011 | Schwemberger et al. |
| 7,891,531 B1 | 2/2011 | Ward |
| 7,891,532 B2 | 2/2011 | Mastri et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,877 B2 | 3/2011 | Hall et al. |
| 7,896,897 B2 | 3/2011 | Gresham et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese, III et al. |
| 7,905,902 B2 | 3/2011 | Huitema et al. |
| 7,909,039 B2 | 3/2011 | Hur |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,931,660 B2 | 4/2011 | Aranyi et al. |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,942,303 B2 | 5/2011 | Shah |
| 7,942,890 B2 | 5/2011 | D'Agostino et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,955,253 B2 | 6/2011 | Ewers et al. |
| 7,955,257 B2 | 6/2011 | Frasier et al. |
| 7,959,050 B2 | 6/2011 | Smith et al. |
| 7,959,051 B2 | 6/2011 | Smith et al. |
| 7,963,432 B2 | 6/2011 | Knodel et al. |
| 7,963,433 B2 | 6/2011 | Whitman et al. |
| 7,966,799 B2 | 6/2011 | Morgan et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,976,563 B2 | 7/2011 | Summerer |
| 7,980,443 B2 | 7/2011 | Scheib et al. |
| 7,981,132 B2 | 7/2011 | Dubrul et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,997,469 B2 | 8/2011 | Olson et al. |

(56) References Cited

U.S. PATENT DOCUMENTS

| | | |
|---|---|---|
| 8,002,696 B2 | 8/2011 | Suzuki |
| 8,002,795 B2 | 8/2011 | Beetel |
| 8,006,885 B2 | 8/2011 | Marczyk |
| 8,006,889 B2 | 8/2011 | Adams et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,020,742 B2 | 9/2011 | Marczyk |
| 8,020,743 B2 | 9/2011 | Shelton, IV |
| 8,021,389 B2 | 9/2011 | Molz, IV |
| 8,025,199 B2 | 9/2011 | Whitman et al. |
| 8,028,883 B2 | 10/2011 | Stopek |
| 8,028,884 B2 | 10/2011 | Sniffin et al. |
| 8,028,885 B2 | 10/2011 | Smith et al. |
| 8,033,438 B2 | 10/2011 | Scirica |
| 8,033,440 B2 | 10/2011 | Wenchell et al. |
| 8,034,077 B2 | 10/2011 | Smith et al. |
| 8,035,487 B2 | 10/2011 | Malackowski |
| 8,038,045 B2 | 10/2011 | Bettuchi et al. |
| 8,038,046 B2 | 10/2011 | Smith et al. |
| 8,043,207 B2 | 10/2011 | Adams |
| 8,043,328 B2 | 10/2011 | Hahnen et al. |
| 8,047,236 B2 | 11/2011 | Perry |
| 8,056,787 B2 | 11/2011 | Boudreaux et al. |
| 8,056,788 B2 | 11/2011 | Mastri et al. |
| 8,061,558 B2 | 11/2011 | Jordan et al. |
| 8,062,330 B2 | 11/2011 | Prommersberger et al. |
| 8,066,167 B2 | 11/2011 | Measamer et al. |
| 8,066,168 B2 | 11/2011 | Vidal et al. |
| D650,074 S | 12/2011 | Hunt et al. |
| 8,074,858 B2 | 12/2011 | Marczyk |
| 8,075,476 B2 | 12/2011 | Vargas |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,091,756 B2 | 1/2012 | Viola |
| 8,092,932 B2 | 1/2012 | Phillips et al. |
| 8,096,457 B1 | 1/2012 | Manoux et al. |
| 8,097,017 B2 | 1/2012 | Viola |
| 8,100,310 B2 | 1/2012 | Zemlok |
| 8,105,350 B2 | 1/2012 | Lee et al. |
| 8,109,426 B2 | 2/2012 | Milliman et al. |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,123,767 B2 | 2/2012 | Bauman et al. |
| 8,127,975 B2 | 3/2012 | Olson et al. |
| 8,127,976 B2 | 3/2012 | Scirica et al. |
| 8,128,559 B2 | 3/2012 | Minnelli |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,136,712 B2 | 3/2012 | Zingman |
| 8,136,713 B2 | 3/2012 | Hathaway et al. |
| 8,140,417 B2 | 3/2012 | Shibata |
| 8,141,762 B2 | 3/2012 | Bedi et al. |
| 8,141,763 B2 | 3/2012 | Milliman |
| 8,146,790 B2 | 4/2012 | Milliman |
| 8,147,456 B2 | 4/2012 | Fisher et al. |
| 8,152,041 B2 | 4/2012 | Kostrzewski |
| 8,152,756 B2 | 4/2012 | Webster et al. |
| 8,152,773 B2 | 4/2012 | Albrecht et al. |
| 8,157,145 B2 | 4/2012 | Shelton, IV et al. |
| 8,157,148 B2 | 4/2012 | Scirica |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,162,197 B2 | 4/2012 | Mastri et al. |
| 8,162,933 B2 | 4/2012 | Francischelli et al. |
| 8,167,185 B2 | 5/2012 | Shelton, IV et al. |
| 8,167,895 B2 | 5/2012 | D'Agostino et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,186,555 B2 | 5/2012 | Shelton, IV et al. |
| 8,186,560 B2 | 5/2012 | Hess et al. |
| 8,191,752 B2 | 6/2012 | Scirica |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,533 B2 | 7/2012 | Viola et al. |
| 8,220,688 B2 | 7/2012 | Laurent et al. |
| 8,220,690 B2 | 7/2012 | Hess et al. |
| 8,225,799 B2 | 7/2012 | Bettuchi |
| 8,226,553 B2 | 7/2012 | Shelton, IV et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,257,251 B2 | 9/2012 | Shelton, IV et al. |
| 8,267,300 B2 | 9/2012 | Boudreaux |
| 8,272,553 B2 | 9/2012 | Mastri et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,286,845 B2 | 10/2012 | Perry et al. |
| 8,286,846 B2 | 10/2012 | Smith et al. |
| 8,287,561 B2 | 10/2012 | Nunez et al. |
| 8,292,151 B2 | 10/2012 | Viola |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,189 B2 | 10/2012 | Fisher et al. |
| 8,308,040 B2 | 11/2012 | Huang et al. |
| 8,308,042 B2 | 11/2012 | Aranyi |
| 8,308,043 B2 | 11/2012 | Bindra et al. |
| 8,308,046 B2 | 11/2012 | Prommersberger |
| 8,308,638 B2 | 11/2012 | Hart |
| 8,313,496 B2 | 11/2012 | Sauer et al. |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,744 B2 | 11/2012 | Kirschenman |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,328,062 B2 | 12/2012 | Viola |
| 8,328,063 B2 | 12/2012 | Milliman et al. |
| 8,328,064 B2 | 12/2012 | Racenet et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,336,753 B2 | 12/2012 | Olson et al. |
| 8,337,517 B2 | 12/2012 | Van Dalen |
| 8,348,123 B2 | 1/2013 | Scirica et al. |
| 8,348,127 B2 | 1/2013 | Marczyk |

(56) References Cited

U.S. PATENT DOCUMENTS

| | | |
|---|---|---|
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,973 B1 | 2/2013 | White et al. |
| 8,365,975 B1 | 2/2013 | Manoux et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,377,029 B2 | 2/2013 | Nagao et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,398,633 B2 | 3/2013 | Mueller |
| 8,398,669 B2 | 3/2013 | Kim |
| 8,403,198 B2 | 3/2013 | Sorrentino et al. |
| 8,403,945 B2 | 3/2013 | Whitfield et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,439,246 B1 | 5/2013 | Knodel |
| 8,444,036 B2 | 5/2013 | Shelton, IV |
| 8,453,904 B2 | 6/2013 | Eskaros et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,515 B2 | 6/2013 | Drew et al. |
| 8,469,973 B2 | 6/2013 | Meade et al. |
| 8,470,355 B2 | 6/2013 | Skalla et al. |
| 8,474,677 B2 | 7/2013 | Woodard, Jr. et al. |
| 8,475,454 B1 | 7/2013 | Alshemari |
| 8,475,457 B2 | 7/2013 | Shano |
| 8,479,967 B2 | 7/2013 | Marczyk |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,485,414 B2 | 7/2013 | Criscuolo et al. |
| 8,485,970 B2 | 7/2013 | Widenhouse et al. |
| 8,490,853 B2 | 7/2013 | Criscuolo et al. |
| 8,491,603 B2 | 7/2013 | Yeung et al. |
| 8,496,156 B2 | 7/2013 | Sniffin et al. |
| 8,499,993 B2 | 8/2013 | Shelton, IV et al. |
| 8,506,555 B2 | 8/2013 | Ruiz Morales |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,517,931 B2 | 8/2013 | Minnelli et al. |
| 8,523,043 B2 | 9/2013 | Ullrich et al. |
| 8,523,881 B2 | 9/2013 | Cabiri et al. |
| 8,529,600 B2 | 9/2013 | Woodard, Jr. et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,550,984 B2 | 10/2013 | Takemoto |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,655 B2 | 10/2013 | Nalagatla et al. |
| 8,567,656 B2 | 10/2013 | Shelton, IV et al. |
| 8,568,425 B2 | 10/2013 | Ross et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,464 B2 | 11/2013 | Nalagatla et al. |
| 8,573,465 B2 | 11/2013 | Shelton, IV |
| 8,579,176 B2 | 11/2013 | Smith et al. |
| 8,579,178 B2 | 11/2013 | Holsten et al. |
| 8,579,937 B2 | 11/2013 | Gresham |
| 8,584,919 B2 | 11/2013 | Hueil et al. |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,602,287 B2 | 12/2013 | Yates et al. |
| 8,602,288 B2 | 12/2013 | Shelton, IV et al. |
| 8,603,089 B2 | 12/2013 | Viola |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,995 B2 | 1/2014 | Smith et al. |
| 8,631,987 B2 | 1/2014 | Shelton, IV et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,191 B2 | 1/2014 | Meagher |
| 8,636,736 B2 | 1/2014 | Yates et al. |
| 8,640,788 B2 | 2/2014 | Dachs, II et al. |
| 8,640,940 B2 | 2/2014 | Ohdaira |
| 8,652,120 B2 | 2/2014 | Giordano et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,839 B2 | 3/2014 | Ewers et al. |
| 8,672,951 B2 | 3/2014 | Smith et al. |
| 8,678,263 B2 | 3/2014 | Viola |
| 8,679,154 B2 | 3/2014 | Smith et al. |
| 8,679,156 B2 | 3/2014 | Smith et al. |
| 8,684,253 B2 | 4/2014 | Giordano et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,213 B2 | 4/2014 | Shelton, IV et al. |
| 8,714,429 B2 | 5/2014 | Demmy |
| 8,714,430 B2 | 5/2014 | Natarajan et al. |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,199 B2 | 5/2014 | Wenchell |

(56) References Cited

U.S. PATENT DOCUMENTS

| | | |
|---|---|---|
| 8,727,961 B2 | 5/2014 | Ziv |
| 8,733,612 B2 | 5/2014 | Ma |
| 8,733,613 B2 | 5/2014 | Huitema et al. |
| 8,734,336 B2 | 5/2014 | Bonadio et al. |
| 8,734,478 B2 | 5/2014 | Widenhouse et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,970 B2 | 6/2014 | Hamman et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,235 B2 | 6/2014 | Jaworek |
| 8,758,391 B2 | 6/2014 | Swayze et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,764,773 B2 | 7/2014 | Harari et al. |
| 8,770,458 B2 | 7/2014 | Scirica |
| 8,770,459 B2 | 7/2014 | Racenet et al. |
| 8,770,460 B2 | 7/2014 | Belzer |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,794,497 B2 | 8/2014 | Zingman |
| 8,795,308 B2 | 8/2014 | Valin |
| 8,800,837 B2 | 8/2014 | Zemlok |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,806,973 B2 | 8/2014 | Ross et al. |
| 8,808,311 B2 | 8/2014 | Heinrich et al. |
| 8,808,325 B2 | 8/2014 | Hess et al. |
| 8,814,024 B2 | 8/2014 | Woodard, Jr. et al. |
| 8,814,788 B2 | 8/2014 | Gan |
| 8,820,603 B2 | 9/2014 | Shelton, IV et al. |
| 8,820,605 B2 | 9/2014 | Shelton, IV |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,632 B2 | 9/2014 | Swensgard |
| 8,834,464 B2 | 9/2014 | Stewart et al. |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,870,911 B2 | 10/2014 | Williams et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,888,695 B2 | 11/2014 | Piskun et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,899,462 B2 | 12/2014 | Kostrzewski et al. |
| 8,899,463 B2 | 12/2014 | Schall et al. |
| 8,899,465 B2 | 12/2014 | Shelton, IV et al. |
| 8,899,466 B2 | 12/2014 | Baxter, III et al. |
| 8,905,977 B2 | 12/2014 | Shelton et al. |
| 8,910,847 B2 | 12/2014 | Nalagatla et al. |
| 8,911,471 B2 | 12/2014 | Spivey et al. |
| 8,920,433 B2 | 12/2014 | Barrier et al. |
| 8,920,435 B2 | 12/2014 | Smith et al. |
| 8,920,443 B2 | 12/2014 | Hiles et al. |
| 8,925,782 B2 | 1/2015 | Shelton, IV |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,242 B1 | 1/2015 | Sardo |
| 8,931,682 B2 | 1/2015 | Timm et al. |
| 8,945,163 B2 | 2/2015 | Voegele et al. |
| 8,955,732 B2 | 2/2015 | Zemlok et al. |
| 8,956,390 B2 | 2/2015 | Shah et al. |
| 8,960,519 B2 | 2/2015 | Whitman et al. |
| 8,961,541 B2 | 2/2015 | Houser |
| 8,967,443 B2 | 3/2015 | McCuen |
| 8,967,446 B2 | 3/2015 | Beardsley et al. |
| 8,967,448 B2 | 3/2015 | Carter et al. |
| 8,973,803 B2 | 3/2015 | Hall et al. |
| 8,973,804 B2 | 3/2015 | Hess et al. |
| 8,974,440 B2 | 3/2015 | Farritor et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,998,058 B2 | 4/2015 | Moore et al. |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,016,541 B2 | 4/2015 | Viola et al. |
| 9,016,542 B2 | 4/2015 | Shelton, IV et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,050,120 B2 | 6/2015 | Swarup et al. |
| 9,055,941 B2 | 6/2015 | Schmid et al. |
| 9,055,942 B2 | 6/2015 | Balbierz et al. |
| 9,055,944 B2 | 6/2015 | Hodgkinson et al. |
| 9,055,945 B2 | 6/2015 | Miksza et al. |
| 9,060,770 B2 | 6/2015 | Shelton, IV et al. |
| 9,060,894 B2 | 6/2015 | Wubbeling |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,089,326 B2 | 7/2015 | Krumanaker et al. |
| 9,089,330 B2 | 7/2015 | Widenhouse et al. |
| 9,089,352 B2 | 7/2015 | Jeong |
| 9,095,339 B2 | 8/2015 | Moore et al. |
| 9,095,340 B2 | 8/2015 | Felder et al. |
| 9,095,362 B2 | 8/2015 | Dachs, II et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,874 B2 | 8/2015 | Shelton, IV et al. |
| 9,113,880 B2 | 8/2015 | Zemlok et al. |

(56) References Cited

U.S. PATENT DOCUMENTS

| | | |
|---|---|---|
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,119,957 B2 | 9/2015 | Gantz et al. |
| 9,125,654 B2 | 9/2015 | Aronhalt et al. |
| 9,125,662 B2 | 9/2015 | Shelton, IV |
| 9,131,835 B2 | 9/2015 | Widenhouse et al. |
| 9,131,940 B2 | 9/2015 | Huitema et al. |
| 9,138,225 B2 | 9/2015 | Huang et al. |
| 9,149,274 B2 | 10/2015 | Spivey et al. |
| 9,155,536 B1 | 10/2015 | Hausen et al. |
| 9,168,038 B2 | 10/2015 | Shelton, IV et al. |
| 9,173,978 B2 | 11/2015 | Kelly et al. |
| 9,179,911 B2 | 11/2015 | Morgan et al. |
| 9,179,912 B2 | 11/2015 | Yates et al. |
| 9,186,143 B2 | 11/2015 | Timm et al. |
| 9,186,148 B2 | 11/2015 | Felder et al. |
| 9,198,661 B2 | 12/2015 | Swensgard |
| 9,198,662 B2 | 12/2015 | Barton et al. |
| 9,204,830 B2 | 12/2015 | Zand et al. |
| 9,204,879 B2 | 12/2015 | Shelton, IV |
| 9,204,880 B2 | 12/2015 | Baxter, III et al. |
| 9,211,120 B2 | 12/2015 | Scheib et al. |
| 9,211,122 B2 | 12/2015 | Hagerty et al. |
| 9,216,019 B2 | 12/2015 | Schmid et al. |
| 9,220,500 B2 | 12/2015 | Swayze et al. |
| 9,220,501 B2 | 12/2015 | Baxter, III et al. |
| 9,220,559 B2 | 12/2015 | Worrell et al. |
| 9,226,751 B2 | 1/2016 | Shelton, IV et al. |
| 9,232,941 B2 | 1/2016 | Mandakolathur Vasudevan et al. |
| 9,232,945 B2 | 1/2016 | Zingman |
| 9,237,891 B2 | 1/2016 | Shelton, IV |
| 9,241,714 B2 | 1/2016 | Timm et al. |
| 9,265,581 B2 | 2/2016 | Navve et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,463 B2 | 3/2016 | Viola et al. |
| 9,295,464 B2 | 3/2016 | Shelton, IV et al. |
| 9,295,784 B2 | 3/2016 | Eggert et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,763 B2 | 4/2016 | Qiao et al. |
| 9,307,965 B2 | 4/2016 | Ming et al. |
| 9,307,986 B2 | 4/2016 | Hall et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,314,246 B2 | 4/2016 | Shelton, IV et al. |
| 9,314,247 B2 | 4/2016 | Shelton, IV et al. |
| 9,320,518 B2 | 4/2016 | Henderson et al. |
| 9,320,521 B2 | 4/2016 | Shelton, IV et al. |
| 9,320,522 B2 | 4/2016 | Carley et al. |
| 9,320,523 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,812 B2 | 5/2016 | Waaler et al. |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,082 B2 | 5/2016 | Wei et al. |
| 9,345,477 B2 | 5/2016 | Anim et al. |
| 9,345,481 B2 | 5/2016 | Hall et al. |
| 9,351,724 B2 | 5/2016 | Penna |
| 9,351,726 B2 | 5/2016 | Leimbach et al. |
| 9,351,727 B2 | 5/2016 | Leimbach et al. |
| 9,351,730 B2 | 5/2016 | Schmid et al. |
| 9,351,734 B2 | 5/2016 | Prior |
| 9,358,003 B2 | 6/2016 | Hall et al. |
| 9,358,005 B2 | 6/2016 | Shelton, IV et al. |
| 9,364,200 B2 | 6/2016 | Whitman et al. |
| 9,364,217 B2 | 6/2016 | Kostrzewski et al. |
| 9,364,219 B2 | 6/2016 | Olson et al. |
| 9,364,230 B2 | 6/2016 | Shelton, IV et al. |
| 9,364,233 B2 | 6/2016 | Alexander, III et al. |
| 9,370,358 B2 | 6/2016 | Shelton, IV et al. |
| 9,370,364 B2 | 6/2016 | Smith et al. |
| 9,371,226 B2 | 6/2016 | Fox et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,393,015 B2 | 7/2016 | Laurent et al. |
| 9,398,911 B2 | 7/2016 | Auld |
| 9,402,626 B2 | 8/2016 | Ortiz et al. |
| 9,408,604 B2 | 8/2016 | Shelton, IV et al. |
| 9,408,606 B2 | 8/2016 | Shelton, IV |
| 9,414,838 B2 | 8/2016 | Shelton, IV et al. |
| 9,421,060 B2 | 8/2016 | Monson et al. |
| 9,427,223 B2 | 8/2016 | Park et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,651 B2 | 9/2016 | Smith et al. |
| 9,451,958 B2 | 9/2016 | Shelton, IV et al. |
| 9,451,980 B2 | 9/2016 | Alfieri |
| 9,463,260 B2 | 10/2016 | Stopek |
| 9,468,438 B2 | 10/2016 | Baber et al. |
| 9,474,519 B2 | 10/2016 | Brustad et al. |
| 9,480,476 B2 | 11/2016 | Aldridge et al. |
| 9,486,132 B2 | 11/2016 | Green |
| 9,486,200 B2 | 11/2016 | Melsheimer et al. |
| 9,486,213 B2 | 11/2016 | Altman et al. |
| 9,486,214 B2 | 11/2016 | Shelton, IV |
| 9,486,302 B2 | 11/2016 | Boey et al. |
| 9,492,154 B2 | 11/2016 | Melsheimer et al. |
| 9,492,167 B2 | 11/2016 | Shelton, IV et al. |
| 9,492,170 B2 | 11/2016 | Bear et al. |
| 9,498,219 B2 | 11/2016 | Moore et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,517,070 B2 | 12/2016 | Mulreed |
| 9,521,996 B2 | 12/2016 | Armstrong |
| 9,522,029 B2 | 12/2016 | Yates et al. |
| 9,549,732 B2 | 1/2017 | Yates et al. |
| 9,549,738 B2 | 1/2017 | Mandakolathur Vasudevan et al. |
| 9,554,794 B2 | 1/2017 | Baber et al. |
| 9,554,796 B2 | 1/2017 | Kostrzewski |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,572,573 B2 | 2/2017 | Scheib et al. |
| 9,572,574 B2 | 2/2017 | Shelton, IV et al. |
| 9,572,577 B2 | 2/2017 | Lloyd et al. |
| 9,585,550 B2 | 3/2017 | Abel et al. |
| 9,585,657 B2 | 3/2017 | Shelton, IV et al. |
| 9,585,660 B2 | 3/2017 | Laurent et al. |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,075 B2 | 3/2017 | Shelton, IV et al. |
| 9,597,080 B2 | 3/2017 | Milliman et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |

(56) References Cited

U.S. PATENT DOCUMENTS

| | | |
|---|---|---|
| 9,615,826 B2 | 4/2017 | Shelton, IV et al. |
| 9,615,892 B2 | 4/2017 | Piferi et al. |
| 9,629,623 B2 | 4/2017 | Lytle, IV et al. |
| 9,629,626 B2 | 4/2017 | Soltz et al. |
| 9,629,628 B2 | 4/2017 | Aranyi |
| 9,629,629 B2 | 4/2017 | Leimbach et al. |
| 9,629,631 B2 | 4/2017 | Nicholas et al. |
| 9,629,814 B2 | 4/2017 | Widenhouse et al. |
| 9,636,112 B2 | 5/2017 | Penna et al. |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,655,614 B2 | 5/2017 | Swensgard et al. |
| 9,655,624 B2 | 5/2017 | Shelton, IV et al. |
| 9,662,131 B2 | 5/2017 | Omori et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,681,870 B2 | 6/2017 | Baxter, III et al. |
| 9,681,873 B2 | 6/2017 | Smith et al. |
| 9,687,230 B2 | 6/2017 | Leimbach et al. |
| 9,687,231 B2 | 6/2017 | Baxter, III et al. |
| 9,687,236 B2 | 6/2017 | Leimbach et al. |
| 9,690,362 B2 | 6/2017 | Leimbach et al. |
| 9,693,777 B2 | 7/2017 | Schellin et al. |
| 9,700,309 B2 | 7/2017 | Jaworek et al. |
| 9,700,317 B2 | 7/2017 | Aronhalt et al. |
| 9,700,321 B2 | 7/2017 | Shelton, IV et al. |
| 9,700,326 B2 | 7/2017 | Morriss et al. |
| 9,706,991 B2 | 7/2017 | Hess et al. |
| 9,724,091 B2 | 8/2017 | Shelton, IV et al. |
| 9,724,094 B2 | 8/2017 | Baber et al. |
| 9,724,100 B2 | 8/2017 | Scheib et al. |
| 9,730,692 B2 | 8/2017 | Shelton, IV et al. |
| 9,733,663 B2 | 8/2017 | Leimbach et al. |
| 9,737,301 B2 | 8/2017 | Baber et al. |
| 9,737,335 B2 | 8/2017 | Butler et al. |
| 9,743,928 B2 | 8/2017 | Shelton, IV et al. |
| 9,743,929 B2 | 8/2017 | Leimbach et al. |
| 9,750,499 B2 | 9/2017 | Leimbach et al. |
| 9,750,502 B2 | 9/2017 | Scirica et al. |
| 9,750,503 B2 | 9/2017 | Milliman |
| 9,757,123 B2 | 9/2017 | Giordano et al. |
| 9,757,124 B2 | 9/2017 | Schellin et al. |
| 9,757,128 B2 | 9/2017 | Baber et al. |
| 9,757,130 B2 | 9/2017 | Shelton, IV |
| 9,757,133 B2 | 9/2017 | Latimer et al. |
| 9,770,245 B2 | 9/2017 | Swayze et al. |
| 9,775,608 B2 | 10/2017 | Aronhalt et al. |
| 9,775,613 B2 | 10/2017 | Shelton, IV et al. |
| 9,782,169 B2 | 10/2017 | Kimsey et al. |
| 9,788,834 B2 | 10/2017 | Schmid et al. |
| 9,788,836 B2 | 10/2017 | Overmyer et al. |
| 9,795,382 B2 | 10/2017 | Shelton, IV |
| 9,795,384 B2 | 10/2017 | Weaner et al. |
| 9,801,626 B2 | 10/2017 | Parihar et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,814,460 B2 | 11/2017 | Kimsey et al. |
| 9,815,213 B2 | 11/2017 | Duey |
| 9,820,738 B2 | 11/2017 | Lytle, IV et al. |
| 9,826,976 B2 | 11/2017 | Parihar et al. |
| 9,826,977 B2 | 11/2017 | Leimbach et al. |
| 9,833,236 B2 | 12/2017 | Shelton, IV et al. |
| 9,833,241 B2 | 12/2017 | Huitema et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,848,873 B2 | 12/2017 | Shelton, IV |
| 9,848,875 B2 | 12/2017 | Aronhalt et al. |
| 9,861,359 B2 | 1/2018 | Shelton, IV et al. |
| 9,861,361 B2 | 1/2018 | Aronhalt et al. |
| 9,861,382 B2 | 1/2018 | Smith et al. |
| 9,867,612 B2 | 1/2018 | Parihar et al. |
| 9,867,618 B2 | 1/2018 | Hall et al. |
| 9,872,684 B2 | 1/2018 | Hall et al. |
| 9,877,721 B2 | 1/2018 | Schellin et al. |
| 9,877,722 B2 | 1/2018 | Schellin et al. |
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,924 B2 | 2/2018 | Ebersole et al. |
| 9,895,148 B2 | 2/2018 | Shelton, IV et al. |
| 9,901,342 B2 | 2/2018 | Shelton, IV et al. |
| 9,907,600 B2 | 3/2018 | Stulen et al. |
| 9,913,642 B2 | 3/2018 | Leimbach et al. |
| 9,913,646 B2 | 3/2018 | Shelton, IV |
| 9,918,704 B2 | 3/2018 | Shelton, IV et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,118 B2 | 4/2018 | Shelton, IV et al. |
| 9,943,309 B2 | 4/2018 | Shelton, IV et al. |
| 9,968,355 B2 | 5/2018 | Shelton, IV et al. |
| 9,974,529 B2 | 5/2018 | Shelton, IV et al. |
| 9,980,630 B2 | 5/2018 | Larkin et al. |
| 9,980,713 B2 | 5/2018 | Aronhalt et al. |
| 9,987,000 B2 | 6/2018 | Shelton, IV et al. |
| 9,987,001 B2 | 6/2018 | Williams |
| 9,993,248 B2 | 6/2018 | Shelton, IV et al. |
| 9,993,258 B2 | 6/2018 | Shelton, IV et al. |
| 9,999,408 B2 | 6/2018 | Boudreaux et al. |
| 10,004,497 B2 | 6/2018 | Overmyer et al. |
| 10,004,498 B2 | 6/2018 | Morgan et al. |
| 10,004,501 B2 | 6/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,028,761 B2 | 7/2018 | Leimbach et al. |
| 10,039,529 B2 | 8/2018 | Kerr et al. |
| 10,045,769 B2 | 8/2018 | Aronhalt et al. |
| 10,045,776 B2 | 8/2018 | Shelton, IV et al. |
| 10,045,779 B2 | 8/2018 | Savage et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,058,963 B2 | 8/2018 | Shelton, IV et al. |
| 10,064,621 B2 | 9/2018 | Kerr et al. |
| 10,071,452 B2 | 9/2018 | Shelton, IV et al. |
| 10,085,748 B2 | 10/2018 | Morgan et al. |
| 10,085,806 B2 | 10/2018 | Hagn et al. |
| 10,092,292 B2 | 10/2018 | Boudreaux et al. |
| 10,111,679 B2 | 10/2018 | Baber et al. |
| 10,117,649 B2 | 11/2018 | Baxter, III et al. |
| 10,123,798 B2 | 11/2018 | Baxter, III et al. |
| 10,130,352 B2 | 11/2018 | Widenhouse et al. |
| 10,130,359 B2 | 11/2018 | Hess et al. |
| 10,130,363 B2 | 11/2018 | Huitema et al. |
| 10,130,366 B2 | 11/2018 | Shelton, IV et al. |
| 10,135,242 B2 | 11/2018 | Baber et al. |
| 10,136,887 B2 | 11/2018 | Shelton, IV et al. |
| 10,136,890 B2 | 11/2018 | Shelton, IV et al. |
| 10,136,891 B2 | 11/2018 | Shelton, IV et al. |
| 10,149,680 B2 | 12/2018 | Parihar et al. |
| 10,149,682 B2 | 12/2018 | Shelton, IV et al. |
| 10,159,482 B2 | 12/2018 | Swayze et al. |
| 10,159,483 B2 | 12/2018 | Beckman et al. |
| 10,166,025 B2 | 1/2019 | Leimbach et al. |
| 10,172,611 B2 | 1/2019 | Shelton, IV et al. |
| 10,172,617 B2 | 1/2019 | Shelton, IV et al. |

(56) References Cited

U.S. PATENT DOCUMENTS

| | | |
|---|---|---|
| 10,178,992 B2 | 1/2019 | Wise et al. |
| 10,180,463 B2 | 1/2019 | Beckman et al. |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,188,393 B2 | 1/2019 | Smith et al. |
| 10,188,394 B2 | 1/2019 | Shelton, IV et al. |
| 10,194,913 B2 | 2/2019 | Nalagatla et al. |
| 10,201,364 B2 | 2/2019 | Leimbach et al. |
| 10,206,678 B2 | 2/2019 | Shelton, IV et al. |
| 10,213,198 B2 | 2/2019 | Aronhalt et al. |
| 10,226,250 B2 | 3/2019 | Beckman et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,058 B2 | 4/2019 | Omori et al. |
| 10,265,065 B2 | 4/2019 | Shelton, IV et al. |
| 10,307,157 B2 | 6/2019 | Miller et al. |
| 10,307,160 B2 | 6/2019 | Vendely et al. |
| 10,335,143 B2 | 7/2019 | Whitman et al. |
| 10,383,629 B2 | 8/2019 | Ross et al. |
| 10,390,829 B2 | 8/2019 | Eckert et al. |
| 10,426,477 B2 | 10/2019 | Harris et al. |
| 10,463,365 B2 | 11/2019 | Williams |
| 10,470,769 B2 | 11/2019 | Shelton, IV et al. |
| 2001/0025183 A1 | 9/2001 | Shahidi |
| 2001/0044656 A1* | 11/2001 | Williamson, IV ............ A61B 17/0469 623/2.11 |
| 2002/0095175 A1 | 7/2002 | Brock et al. |
| 2002/0103494 A1 | 8/2002 | Pacey |
| 2002/0117534 A1 | 8/2002 | Green et al. |
| 2003/0009193 A1 | 1/2003 | Corsaro |
| 2003/0039689 A1 | 2/2003 | Chen et al. |
| 2003/0096158 A1 | 5/2003 | Takano et al. |
| 2003/0181900 A1 | 9/2003 | Long |
| 2003/0190584 A1 | 10/2003 | Heasley |
| 2003/0236505 A1 | 12/2003 | Bonadio et al. |
| 2004/0054353 A1 | 3/2004 | Taylor |
| 2004/0068161 A1 | 4/2004 | Couvillon |
| 2004/0068224 A1 | 4/2004 | Couvillon et al. |
| 2004/0098040 A1 | 5/2004 | Taniguchi et al. |
| 2004/0102783 A1 | 5/2004 | Sutterlin et al. |
| 2004/0108357 A1 | 6/2004 | Milliman et al. |
| 2004/0147909 A1 | 7/2004 | Johnston et al. |
| 2004/0158230 A1 | 8/2004 | Hunn et al. |
| 2004/0158261 A1 | 8/2004 | Vu |
| 2004/0164123 A1 | 8/2004 | Racenet et al. |
| 2004/0167572 A1 | 8/2004 | Roth et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0254566 A1 | 12/2004 | Plicchi et al. |
| 2004/0260315 A1 | 12/2004 | Dell et al. |
| 2004/0267310 A1 | 12/2004 | Racenet et al. |
| 2005/0033226 A1 | 2/2005 | Kim |
| 2005/0051163 A1 | 3/2005 | Deem et al. |
| 2005/0059997 A1 | 3/2005 | Bauman et al. |
| 2005/0070929 A1 | 3/2005 | Dalessandro et al. |
| 2005/0080342 A1 | 4/2005 | Gilreath et al. |
| 2005/0085693 A1 | 4/2005 | Belson et al. |
| 2005/0125897 A1 | 6/2005 | Wyslucha et al. |
| 2005/0131390 A1 | 6/2005 | Heinrich et al. |
| 2005/0131457 A1 | 6/2005 | Douglas et al. |
| 2005/0139636 A1 | 6/2005 | Schwemberger et al. |
| 2005/0143756 A1 | 6/2005 | Jankowski |
| 2005/0143759 A1 | 6/2005 | Kelly |
| 2005/0154406 A1 | 7/2005 | Bombard et al. |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0236459 A1 | 10/2005 | Gresham |
| 2005/0245965 A1 | 11/2005 | Orban, III et al. |
| 2005/0246881 A1 | 11/2005 | Kelly et al. |
| 2005/0256452 A1 | 11/2005 | DeMarchi et al. |
| 2005/0263563 A1 | 12/2005 | Racenet et al. |
| 2005/0283188 A1 | 12/2005 | Loshakove et al. |
| 2006/0020258 A1 | 1/2006 | Strauss et al. |
| 2006/0025812 A1 | 2/2006 | Shelton |
| 2006/0041188 A1 | 2/2006 | Dirusso et al. |
| 2006/0049229 A1 | 3/2006 | Milliman et al. |
| 2006/0052669 A1 | 3/2006 | Hart |
| 2006/0052825 A1 | 3/2006 | Ransick et al. |
| 2006/0089535 A1 | 4/2006 | Raz et al. |
| 2006/0100643 A1 | 5/2006 | Laufer et al. |
| 2006/0149306 A1 | 7/2006 | Hart et al. |
| 2006/0161050 A1 | 7/2006 | Butler et al. |
| 2006/0161185 A1 | 7/2006 | Saadat et al. |
| 2006/0173470 A1 | 8/2006 | Oray et al. |
| 2006/0180634 A1 | 8/2006 | Shelton et al. |
| 2006/0185682 A1 | 8/2006 | Marczyk |
| 2006/0201989 A1 | 9/2006 | Ojeda |
| 2006/0211919 A1 | 9/2006 | Wilk |
| 2006/0235368 A1 | 10/2006 | Oz |
| 2006/0241651 A1 | 10/2006 | Wilk |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0271102 A1 | 11/2006 | Bosshard et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0027468 A1 | 2/2007 | Wales et al. |
| 2007/0043387 A1 | 2/2007 | Vargas et al. |
| 2007/0051375 A1 | 3/2007 | Milliman |
| 2007/0073341 A1 | 3/2007 | Smith et al. |
| 2007/0078484 A1 | 4/2007 | Talarico et al. |
| 2007/0080188 A1* | 4/2007 | Spence ............ A61B 17/0401 227/175.1 |
| 2007/0080814 A1 | 4/2007 | Ellsworth et al. |
| 2007/0084897 A1 | 4/2007 | Shelton et al. |
| 2007/0093869 A1 | 4/2007 | Bloom et al. |
| 2007/0102472 A1 | 5/2007 | Shelton |
| 2007/0106317 A1 | 5/2007 | Shelton et al. |
| 2007/0134251 A1 | 6/2007 | Ashkenazi et al. |
| 2007/0135803 A1 | 6/2007 | Belson |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0208359 A1 | 9/2007 | Hoffman |
| 2007/0225562 A1 | 9/2007 | Spivey et al. |
| 2007/0244471 A1 | 10/2007 | Malackowski |
| 2007/0246505 A1 | 10/2007 | Pace-Floridia et al. |
| 2007/0276409 A1 | 11/2007 | Ortiz et al. |
| 2007/0279011 A1 | 12/2007 | Jones et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0135600 A1 | 6/2008 | Hiranuma et al. |
| 2008/0140115 A1 | 6/2008 | Stopek |

(56) References Cited

U.S. PATENT DOCUMENTS

| | | |
|---|---|---|
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0200933 A1 | 8/2008 | Bakos et al. |
| 2008/0242939 A1 | 10/2008 | Johnston |
| 2008/0249536 A1 | 10/2008 | Stahler et al. |
| 2008/0255413 A1 | 10/2008 | Zemlok et al. |
| 2008/0262654 A1 | 10/2008 | Omori et al. |
| 2008/0294179 A1 | 11/2008 | Balbierz et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0005809 A1 | 1/2009 | Hess et al. |
| 2009/0012534 A1 | 1/2009 | Madhani et al. |
| 2009/0048589 A1 | 2/2009 | Takashino et al. |
| 2009/0078736 A1 | 3/2009 | Van Lue |
| 2009/0090763 A1 | 4/2009 | Zemlok et al. |
| 2009/0099876 A1 | 4/2009 | Whitman |
| 2009/0149871 A9 | 6/2009 | Kagan et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0242610 A1 | 10/2009 | Shelton, IV et al. |
| 2009/0255974 A1 | 10/2009 | Viola |
| 2009/0292283 A1 | 11/2009 | Odom |
| 2009/0308907 A1 | 12/2009 | Nalagatla et al. |
| 2010/0069942 A1 | 3/2010 | Shelton, IV |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0193566 A1 | 8/2010 | Scheib et al. |
| 2010/0222901 A1 | 9/2010 | Swayze et al. |
| 2010/0292540 A1 | 11/2010 | Hess et al. |
| 2010/0312261 A1 | 12/2010 | Suzuki et al. |
| 2011/0006101 A1 | 1/2011 | Hall et al. |
| 2011/0011916 A1 | 1/2011 | Levine |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0060363 A1 | 3/2011 | Hess et al. |
| 2011/0071356 A1 | 3/2011 | Edwards |
| 2011/0087276 A1 | 4/2011 | Bedi et al. |
| 2011/0091515 A1 | 4/2011 | Zilberman et al. |
| 2011/0114697 A1 | 5/2011 | Baxter, III et al. |
| 2011/0118706 A1 | 5/2011 | Gingras et al. |
| 2011/0125176 A1 | 5/2011 | Yates et al. |
| 2011/0147433 A1 | 6/2011 | Shelton, IV et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2012/0029272 A1 | 2/2012 | Shelton, IV et al. |
| 2012/0074200 A1 | 3/2012 | Schmid et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0109186 A1 | 5/2012 | Parrott et al. |
| 2012/0125792 A1 | 5/2012 | Cassivi |
| 2012/0175398 A1 | 7/2012 | Sandborn et al. |
| 2012/0199602 A1 | 8/2012 | Jordan et al. |
| 2012/0234895 A1 | 9/2012 | O'Connor et al. |
| 2012/0234897 A1 | 9/2012 | Shelton, IV et al. |
| 2012/0248169 A1 | 10/2012 | Widenhouse et al. |
| 2012/0283707 A1 | 11/2012 | Giordano et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2012/0303002 A1 | 11/2012 | Chowaniec et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026209 A1 | 1/2013 | Mozdzierz et al. |
| 2013/0026210 A1 | 1/2013 | Shelton, IV et al. |
| 2013/0030253 A1 | 1/2013 | Titus |
| 2013/0085339 A1 | 4/2013 | Jaworek et al. |
| 2013/0087597 A1 | 4/2013 | Shelton, IV et al. |
| 2013/0098970 A1 | 4/2013 | Racenet et al. |
| 2013/0116669 A1 | 5/2013 | Shelton, IV et al. |
| 2013/0153636 A1 | 6/2013 | Shelton, IV et al. |
| 2013/0153641 A1 | 6/2013 | Shelton, IV et al. |
| 2013/0175317 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0231667 A1 | 9/2013 | Taylor et al. |
| 2013/0233906 A1 | 9/2013 | Hess et al. |
| 2013/0256373 A1 | 10/2013 | Schmid et al. |
| 2013/0256379 A1 | 10/2013 | Schmid et al. |
| 2013/0256380 A1 | 10/2013 | Schmid et al. |
| 2013/0270322 A1 | 10/2013 | Scheib et al. |
| 2013/0324982 A1 | 12/2013 | Smith et al. |
| 2013/0331867 A1 | 12/2013 | Reeser et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005718 A1 | 1/2014 | Shelton, IV et al. |
| 2014/0014704 A1 | 1/2014 | Onukuri et al. |
| 2014/0014705 A1 | 1/2014 | Baxter, III |
| 2014/0039549 A1 | 2/2014 | Belsky et al. |
| 2014/0048580 A1 | 2/2014 | Merchant et al. |
| 2014/0107640 A1 | 4/2014 | Yates et al. |
| 2014/0151433 A1 | 6/2014 | Shelton, IV et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0166728 A1 | 6/2014 | Swayze et al. |
| 2014/0171966 A1 | 6/2014 | Giordano et al. |
| 2014/0175152 A1 | 6/2014 | Hess et al. |
| 2014/0188159 A1 | 7/2014 | Steege |
| 2014/0200561 A1 | 7/2014 | Ingmanson et al. |
| 2014/0224857 A1 | 8/2014 | Schmid |
| 2014/0243865 A1 | 8/2014 | Swayze et al. |
| 2014/0246475 A1 | 9/2014 | Hall et al. |
| 2014/0249557 A1 | 9/2014 | Koch, Jr. et al. |
| 2014/0263541 A1 | 9/2014 | Leimbach et al. |
| 2014/0263552 A1 | 9/2014 | Hall et al. |
| 2014/0263554 A1 | 9/2014 | Leimbach et al. |
| 2014/0284371 A1 | 9/2014 | Morgan et al. |
| 2014/0291378 A1 | 10/2014 | Shelton, IV et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0309666 A1 | 10/2014 | Shelton, IV et al. |
| 2015/0012006 A1 | 1/2015 | Hausen et al. |

(56) References Cited

U.S. PATENT DOCUMENTS

| | | |
|---|---|---|
| 2015/0053737 A1 | 2/2015 | Leimbach et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0282810 A1 | 10/2015 | Shelton, IV et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297229 A1 | 10/2015 | Schellin et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0313594 A1 | 11/2015 | Shelton, IV et al. |
| 2016/0066913 A1 | 3/2016 | Swayze et al. |
| 2016/0089146 A1 | 3/2016 | Harris et al. |
| 2016/0113653 A1 | 4/2016 | Zingman |
| 2016/0120544 A1 | 5/2016 | Shelton, IV et al. |
| 2016/0135796 A1 | 5/2016 | Hundertmark et al. |
| 2016/0143637 A1 | 5/2016 | Nering et al. |
| 2016/0249910 A1 | 9/2016 | Shelton, IV et al. |
| 2016/0249916 A1 | 9/2016 | Shelton, IV et al. |
| 2016/0256071 A1 | 9/2016 | Shelton, IV et al. |
| 2016/0256154 A1 | 9/2016 | Shelton, IV et al. |
| 2016/0256160 A1 | 9/2016 | Shelton, IV et al. |
| 2016/0256185 A1 | 9/2016 | Shelton, IV et al. |
| 2016/0367246 A1 | 12/2016 | Baxter, III et al. |
| 2016/0367254 A1 | 12/2016 | Baxter, III et al. |
| 2016/0367255 A1 | 12/2016 | Wise et al. |
| 2016/0374672 A1 | 12/2016 | Bear et al. |
| 2017/0007229 A1 | 1/2017 | Widenhouse et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0055986 A1 | 3/2017 | Harris et al. |
| 2017/0056000 A1 | 3/2017 | Nalagatla et al. |
| 2017/0056008 A1 | 3/2017 | Shelton, IV et al. |
| 2017/0056065 A1 | 3/2017 | Do et al. |
| 2017/0119386 A1 | 5/2017 | Scheib et al. |
| 2017/0119387 A1 | 5/2017 | Dalessandro et al. |
| 2017/0119388 A1 | 5/2017 | Kostrzewski |
| 2017/0119389 A1 | 5/2017 | Turner et al. |
| 2017/0119390 A1 | 5/2017 | Schellin et al. |
| 2017/0119392 A1 | 5/2017 | Shelton, IV et al. |
| 2017/0189018 A1 | 7/2017 | Harris et al. |
| 2017/0189019 A1 | 7/2017 | Harris et al. |
| 2017/0189020 A1 | 7/2017 | Harris et al. |
| 2017/0196566 A1 | 7/2017 | Sgroi |
| 2017/0224330 A1 | 8/2017 | Worthington et al. |
| 2017/0224331 A1 | 8/2017 | Worthington et al. |
| 2017/0224332 A1 | 8/2017 | Hunter et al. |
| 2017/0224334 A1 | 8/2017 | Worthington et al. |
| 2017/0224335 A1 | 8/2017 | Weaner et al. |
| 2017/0224342 A1 | 8/2017 | Worthington et al. |
| 2017/0224343 A1 | 8/2017 | Baxter, III et al. |
| 2017/0231623 A1 | 8/2017 | Shelton, IV et al. |
| 2017/0231626 A1 | 8/2017 | Shelton, IV et al. |
| 2017/0231627 A1 | 8/2017 | Shelton, IV et al. |
| 2017/0231628 A1 | 8/2017 | Shelton, IV et al. |
| 2017/0258540 A1 | 9/2017 | Blatt |
| 2017/0281155 A1 | 10/2017 | Shelton, IV et al. |
| 2017/0281161 A1 | 10/2017 | Shelton, IV et al. |
| 2017/0281162 A1 | 10/2017 | Shelton, IV et al. |
| 2017/0281163 A1 | 10/2017 | Shelton, IV et al. |
| 2017/0281164 A1 | 10/2017 | Harris et al. |
| 2017/0281165 A1 | 10/2017 | Harris et al. |
| 2017/0281166 A1 | 10/2017 | Morgan et al. |
| 2017/0281167 A1 | 10/2017 | Shelton, IV et al. |
| 2017/0281168 A1 | 10/2017 | Shelton, IV et al. |
| 2017/0281170 A1 | 10/2017 | Shelton, IV et al. |
| 2017/0281171 A1 | 10/2017 | Shelton, IV et al. |
| 2017/0281172 A1 | 10/2017 | Shelton, IV et al. |
| 2017/0281173 A1 | 10/2017 | Shelton, IV et al. |
| 2017/0281174 A1 | 10/2017 | Harris et al. |
| 2017/0281177 A1 | 10/2017 | Harris et al. |
| 2017/0281178 A1 | 10/2017 | Shelton, IV et al. |
| 2017/0281179 A1 | 10/2017 | Shelton, IV et al. |
| 2017/0281180 A1 | 10/2017 | Morgan et al. |
| 2017/0281183 A1 | 10/2017 | Miller et al. |
| 2017/0281184 A1 | 10/2017 | Shelton, IV et al. |
| 2017/0281185 A1 | 10/2017 | Miller et al. |
| 2017/0281186 A1 | 10/2017 | Shelton, IV et al. |
| 2017/0281187 A1 | 10/2017 | Shelton, IV et al. |
| 2017/0281188 A1 | 10/2017 | Shelton, IV et al. |
| 2017/0281189 A1 | 10/2017 | Nalagatla et al. |
| 2018/0325508 A1 | 11/2018 | Aronhalt et al. |
| 2019/0021718 A1 | 1/2019 | Aronhalt et al. |
| 2019/0029661 A1 | 1/2019 | Widenhouse et al. |
| 2019/0059934 A1 | 2/2019 | Williams |
| 2019/0183508 A1 | 6/2019 | Shelton, IV et al. |

FOREIGN PATENT DOCUMENTS

| | | |
|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CA | 2795323 A1 | 5/2014 |
| CN | 1163558 A | 10/1997 |
| CN | 2488482 Y | 5/2002 |
| CN | 1523725 A | 8/2004 |
| CN | 1545154 A | 11/2004 |
| CN | 2686539 Y | 3/2005 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101675898 A | 3/2010 |
| CN | 101683280 A | 3/2010 |
| CN | 102188270 A | 9/2011 |
| CN | 101534723 B | 1/2012 |
| CN | 202313540 U | 7/2012 |
| CN | 101541251 A | 11/2012 |
| CN | 101507633 B | 2/2013 |
| CN | 101023879 B | 3/2013 |
| CN | 101401736 B | 6/2013 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 U1 | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314827 B3 | 4/2004 |
| DE | 10314072 A1 | 10/2004 |
| DE | 202007003114 U1 | 6/2007 |
| EP | 0000756 A1 | 2/1979 |
| EP | 0122046 A1 | 10/1984 |
| EP | 0070230 B1 | 4/1985 |
| EP | 0156774 A2 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0178940 B1 | 1/1991 |

(56) References Cited

FOREIGN PATENT DOCUMENTS

| | | |
|---|---|---|
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0379721 B1 | 9/1993 |
| EP | 0277959 B1 | 10/1993 |
| EP | 0233940 B1 | 11/1993 |
| EP | 0261230 B1 | 11/1993 |
| EP | 0324636 B1 | 3/1994 |
| EP | 0591946 A1 | 4/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0639349 A2 | 2/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0676173 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0528478 B1 | 5/1996 |
| EP | 0711611 A2 | 5/1996 |
| EP | 0541987 B1 | 7/1996 |
| EP | 0667119 B1 | 7/1996 |
| EP | 0737446 A1 | 10/1996 |
| EP | 0741996 B1 | 11/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 B1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0484677 B2 | 7/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1486172 A1 | 12/2004 |
| EP | 1001710 B1 | 1/2005 |
| EP | 1496805 A2 | 1/2005 |
| EP | 1256318 B1 | 2/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |

(56) References Cited

FOREIGN PATENT DOCUMENTS

| | | | |
|---|---|---|---|
| EP | 0870473 | B1 | 9/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 0906764 | B1 | 12/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |
| EP | 1621141 | A2 | 2/2006 |
| EP | 1621145 | A2 | 2/2006 |
| EP | 1621151 | A2 | 2/2006 |
| EP | 1034746 | B1 | 3/2006 |
| EP | 1201196 | B1 | 3/2006 |
| EP | 1632191 | A2 | 3/2006 |
| EP | 1647231 | A1 | 4/2006 |
| EP | 1065981 | B1 | 5/2006 |
| EP | 1082944 | B1 | 5/2006 |
| EP | 1230899 | B1 | 5/2006 |
| EP | 1652481 | A2 | 5/2006 |
| EP | 1382303 | B1 | 6/2006 |
| EP | 1253866 | B1 | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1256317 | B1 | 12/2006 |
| EP | 1285633 | B1 | 12/2006 |
| EP | 1728473 | A1 | 12/2006 |
| EP | 1736105 | A1 | 12/2006 |
| EP | 1011494 | B1 | 1/2007 |
| EP | 1479346 | B1 | 1/2007 |
| EP | 1484024 | B1 | 1/2007 |
| EP | 1749485 | A1 | 2/2007 |
| EP | 1754445 | A2 | 2/2007 |
| EP | 1759812 | A1 | 3/2007 |
| EP | 1767157 | A1 | 3/2007 |
| EP | 1767163 | A1 | 3/2007 |
| EP | 1563792 | B1 | 4/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1790294 | A1 | 5/2007 |
| EP | 1563793 | B1 | 6/2007 |
| EP | 1800610 | A1 | 6/2007 |
| EP | 1300117 | B1 | 8/2007 |
| EP | 1813199 | A1 | 8/2007 |
| EP | 1813200 | A2 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1815950 | A1 | 8/2007 |
| EP | 1330991 | B1 | 9/2007 |
| EP | 1837041 | A1 | 9/2007 |
| EP | 0922435 | B1 | 10/2007 |
| EP | 1487359 | B1 | 10/2007 |
| EP | 1599146 | B1 | 10/2007 |
| EP | 1839596 | A1 | 10/2007 |
| EP | 1679096 | B1 | 11/2007 |
| EP | 1857057 | A2 | 11/2007 |
| EP | 1402821 | B1 | 12/2007 |
| EP | 1872727 | A1 | 1/2008 |
| EP | 1550410 | B1 | 2/2008 |
| EP | 1671593 | B1 | 2/2008 |
| EP | 1897502 | A1 | 3/2008 |
| EP | 1611856 | B1 | 4/2008 |
| EP | 1908417 | A2 | 4/2008 |
| EP | 1917929 | A1 | 5/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943959 | A1 | 7/2008 |
| EP | 1943962 | A2 | 7/2008 |
| EP | 1943964 | A1 | 7/2008 |
| EP | 1943976 | A2 | 7/2008 |
| EP | 1593337 | B1 | 8/2008 |
| EP | 1970014 | A1 | 9/2008 |
| EP | 1974678 | A2 | 10/2008 |
| EP | 1980213 | A2 | 10/2008 |
| EP | 1759645 | B1 | 11/2008 |
| EP | 1987780 | A2 | 11/2008 |
| EP | 1990014 | A2 | 11/2008 |
| EP | 1552795 | B1 | 12/2008 |
| EP | 1693008 | B1 | 12/2008 |
| EP | 1759640 | B1 | 12/2008 |
| EP | 1997439 | A2 | 12/2008 |
| EP | 2000102 | A2 | 12/2008 |
| EP | 2005894 | A2 | 12/2008 |
| EP | 2005901 | A1 | 12/2008 |
| EP | 2008595 | A2 | 12/2008 |
| EP | 1736104 | B1 | 3/2009 |
| EP | 1749486 | B1 | 3/2009 |
| EP | 1782743 | B1 | 3/2009 |
| EP | 2039302 | A2 | 3/2009 |
| EP | 2039308 | A2 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 2055243 | A2 | 5/2009 |
| EP | 1550409 | B1 | 6/2009 |
| EP | 1550413 | B1 | 6/2009 |
| EP | 1719461 | B1 | 6/2009 |
| EP | 1834594 | B1 | 6/2009 |
| EP | 1709911 | B1 | 7/2009 |
| EP | 2077093 | A2 | 7/2009 |
| EP | 1745748 | B1 | 8/2009 |
| EP | 2090231 | A1 | 8/2009 |
| EP | 2090237 | A1 | 8/2009 |
| EP | 2090241 | A1 | 8/2009 |
| EP | 2090245 | A1 | 8/2009 |
| EP | 2090254 | A1 | 8/2009 |
| EP | 2090256 | A2 | 8/2009 |
| EP | 2095777 | A2 | 9/2009 |
| EP | 2098170 | A2 | 9/2009 |
| EP | 2110082 | A1 | 10/2009 |
| EP | 2110083 | A2 | 10/2009 |
| EP | 2110084 | A2 | 10/2009 |
| EP | 2111803 | A2 | 10/2009 |
| EP | 1813208 | B1 | 11/2009 |
| EP | 1908426 | B1 | 11/2009 |
| EP | 2116195 | A1 | 11/2009 |
| EP | 2116197 | A2 | 11/2009 |
| EP | 1607050 | B1 | 12/2009 |
| EP | 1762190 | B8 | 12/2009 |
| EP | 1815804 | B1 | 12/2009 |
| EP | 1875870 | B1 | 12/2009 |
| EP | 1878395 | B1 | 1/2010 |
| EP | 2151204 | A1 | 2/2010 |
| EP | 1813211 | B1 | 3/2010 |
| EP | 2165656 | A2 | 3/2010 |
| EP | 2165660 | A2 | 3/2010 |
| EP | 1566150 | B1 | 4/2010 |
| EP | 1813206 | B1 | 4/2010 |
| EP | 1769754 | B1 | 6/2010 |
| EP | 1854416 | B1 | 6/2010 |
| EP | 1911408 | B1 | 6/2010 |
| EP | 2198787 | A1 | 6/2010 |
| EP | 1647286 | B1 | 9/2010 |
| EP | 1825821 | B1 | 9/2010 |
| EP | 1535565 | B1 | 10/2010 |
| EP | 1702570 | B1 | 10/2010 |

(56) References Cited

FOREIGN PATENT DOCUMENTS

| | | |
|---|---|---|
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 2253280 A1 | 11/2010 |
| EP | 1627605 B1 | 12/2010 |
| EP | 2027811 B1 | 12/2010 |
| EP | 2130498 B1 | 12/2010 |
| EP | 2263568 A2 | 12/2010 |
| EP | 1994890 B1 | 1/2011 |
| EP | 2005900 B1 | 1/2011 |
| EP | 2283780 A2 | 2/2011 |
| EP | 2286738 A2 | 2/2011 |
| EP | 1690502 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 1813205 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 1728475 B1 | 8/2011 |
| EP | 2353545 A1 | 8/2011 |
| EP | 2361562 A1 | 8/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2399538 A2 | 12/2011 |
| EP | 1785102 B1 | 1/2012 |
| EP | 1962711 B1 | 2/2012 |
| EP | 2090253 B1 | 3/2012 |
| EP | 2430986 A2 | 3/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2005895 B1 | 8/2012 |
| EP | 2090248 B1 | 8/2012 |
| EP | 2481359 A1 | 8/2012 |
| EP | 2486862 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 2526877 A1 | 11/2012 |
| EP | 1884206 B1 | 3/2013 |
| EP | 2090238 B1 | 4/2013 |
| EP | 1806103 B1 | 5/2013 |
| EP | 1982657 B1 | 7/2013 |
| EP | 2614782 A2 | 7/2013 |
| EP | 2090234 B1 | 9/2013 |
| EP | 2633830 A1 | 9/2013 |
| EP | 2090244 B1 | 10/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 1772105 B1 | 5/2014 |
| EP | 2759267 A2 | 7/2014 |
| EP | 2446835 B1 | 1/2015 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 930100110 A | 11/1993 |
| JP | S4711908 Y1 | 5/1972 |
| JP | S5033988 U | 4/1975 |
| JP | S56112235 A | 9/1981 |
| JP | S58500053 A | 1/1983 |
| JP | S58501360 A | 8/1983 |
| JP | S59174920 A | 10/1984 |
| JP | S60100955 A | 6/1985 |
| JP | S60212152 A | 10/1985 |
| JP | S6198249 A | 5/1986 |
| JP | S61502036 A | 9/1986 |
| JP | S62170011 U | 10/1987 |
| JP | S6359764 A | 3/1988 |
| JP | S63147449 A | 6/1988 |
| JP | S63203149 A | 8/1988 |
| JP | H02279149 A | 11/1990 |
| JP | H0312126 A | 1/1991 |
| JP | H04215747 A | 8/1992 |
| JP | H04131860 U | 12/1992 |
| JP | H0584252 A | 4/1993 |
| JP | H05123325 A | 5/1993 |
| JP | H05212039 A | 8/1993 |
| JP | H067357 A | 1/1994 |
| JP | H0630945 A | 2/1994 |
| JP | H0654857 A | 3/1994 |
| JP | H0626812 U | 4/1994 |
| JP | H06121798 A | 5/1994 |
| JP | H06125913 A | 5/1994 |
| JP | H06197901 A | 7/1994 |
| JP | H06237937 A | 8/1994 |
| JP | H06327684 A | 11/1994 |
| JP | H0731623 A | 2/1995 |
| JP | H0747070 A | 2/1995 |
| JP | H0751273 A | 2/1995 |
| JP | H07124166 A | 5/1995 |
| JP | H07163574 A | 6/1995 |
| JP | H07171163 A | 7/1995 |
| JP | H07255735 A | 10/1995 |
| JP | H07285089 A | 10/1995 |
| JP | H0833641 A | 2/1996 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08336540 A | 12/1996 |
| JP | H08336544 A | 12/1996 |
| JP | H09501081 A | 2/1997 |
| JP | H09501577 A | 2/1997 |
| JP | H09164144 A | 6/1997 |
| JP | H10113352 A | 5/1998 |
| JP | H10118090 A | 5/1998 |

(56) References Cited

FOREIGN PATENT DOCUMENTS

| | | |
|---|---|---|
| JP | H10151137 A | 6/1998 |
| JP | H10512469 A | 12/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000287987 A | 10/2000 |
| JP | 2000325303 A | 11/2000 |
| JP | 2001046384 A | 2/2001 |
| JP | 2001087272 A | 4/2001 |
| JP | 2001514541 A | 9/2001 |
| JP | 2001276091 A | 10/2001 |
| JP | 2001286477 A | 10/2001 |
| JP | 2001517473 A | 10/2001 |
| JP | 2002051974 A | 2/2002 |
| JP | 2002085415 A | 3/2002 |
| JP | 2002143078 A | 5/2002 |
| JP | 2002204801 A | 7/2002 |
| JP | 2002528161 A | 9/2002 |
| JP | 2002314298 A | 10/2002 |
| JP | 2002369820 A | 12/2002 |
| JP | 2003000603 A | 1/2003 |
| JP | 2003500153 A | 1/2003 |
| JP | 2003504104 A | 2/2003 |
| JP | 2003135473 A | 5/2003 |
| JP | 2003148903 A | 5/2003 |
| JP | 2003164066 A | 6/2003 |
| JP | 2003521301 A | 7/2003 |
| JP | 2003523251 A | 8/2003 |
| JP | 2003523254 A | 8/2003 |
| JP | 2004147701 A | 5/2004 |
| JP | 2004162035 A | 6/2004 |
| JP | 2004229976 A | 8/2004 |
| JP | 2004524076 A | 8/2004 |
| JP | 2004531280 A | 10/2004 |
| JP | 2004532084 A | 10/2004 |
| JP | 2004532676 A | 10/2004 |
| JP | 2004329624 A | 11/2004 |
| JP | 2004337617 A | 12/2004 |
| JP | 2004344662 A | 12/2004 |
| JP | 2004344663 A | 12/2004 |
| JP | 2005028147 A | 2/2005 |
| JP | 2005028148 A | 2/2005 |
| JP | 2005028149 A | 2/2005 |
| JP | 2005505309 A | 2/2005 |
| JP | 2005505322 A | 2/2005 |
| JP | 2005505334 A | 2/2005 |
| JP | 2005080702 A | 3/2005 |
| JP | 2005103280 A | 4/2005 |
| JP | 2005103281 A | 4/2005 |
| JP | 2005103293 A | 4/2005 |
| JP | 2005511131 A | 4/2005 |
| JP | 2005511137 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005137919 A | 6/2005 |
| JP | 2005144183 A | 6/2005 |
| JP | 2005152416 A | 6/2005 |
| JP | 2005516714 A | 6/2005 |
| JP | 2005521109 A | 7/2005 |
| JP | 2005523105 A | 8/2005 |
| JP | 2005524474 A | 8/2005 |
| JP | 2005296412 A | 10/2005 |
| JP | 2005328882 A | 12/2005 |
| JP | 2005335432 A | 12/2005 |
| JP | 2005342267 A | 12/2005 |
| JP | 2006034975 A | 2/2006 |
| JP | 2006034977 A | 2/2006 |
| JP | 2006034978 A | 2/2006 |
| JP | 2006034980 A | 2/2006 |
| JP | 2006506106 A | 2/2006 |
| JP | 2006510879 A | 3/2006 |
| JP | 2006187649 A | 7/2006 |
| JP | 2006218297 A | 8/2006 |
| JP | 2006223872 A | 8/2006 |
| JP | 2006281405 A | 10/2006 |
| JP | 2006289064 A | 10/2006 |
| JP | 2006334412 A | 12/2006 |
| JP | 2006334417 A | 12/2006 |
| JP | 2006346445 A | 12/2006 |
| JP | 2007050253 A | 3/2007 |
| JP | 2007061628 A | 3/2007 |
| JP | 3906843 B2 | 4/2007 |
| JP | 2007083051 A | 4/2007 |
| JP | 2007098130 A | 4/2007 |
| JP | 2007105481 A | 4/2007 |
| JP | 2007117725 A | 5/2007 |
| JP | 2007130471 A | 5/2007 |
| JP | 3934161 B2 | 6/2007 |
| JP | 2007203049 A | 8/2007 |
| JP | 2007203051 A | 8/2007 |
| JP | 2007203057 A | 8/2007 |
| JP | 2007209751 A | 8/2007 |
| JP | 2007524435 A | 8/2007 |
| JP | 2007222615 A | 9/2007 |
| JP | 2007229448 A | 9/2007 |
| JP | 4001860 B2 | 10/2007 |
| JP | 2007325922 A | 12/2007 |
| JP | 2008068073 A | 3/2008 |
| JP | 2008206967 A | 9/2008 |
| JP | 2008212637 A | 9/2008 |
| JP | 2008212638 A | 9/2008 |
| JP | 2008220956 A | 9/2008 |
| JP | 2008259860 A | 10/2008 |
| JP | 2008264538 A | 11/2008 |
| JP | 2008283459 A | 11/2008 |
| JP | 2009502351 A | 1/2009 |
| JP | 2009506799 A | 2/2009 |
| JP | 2009507526 A | 2/2009 |
| JP | 2009072599 A | 4/2009 |
| JP | 2009090113 A | 4/2009 |
| JP | 2009106752 A | 5/2009 |
| JP | 2009189836 A | 8/2009 |
| JP | 2009189837 A | 8/2009 |
| JP | 2009189838 A | 8/2009 |
| JP | 2009536082 A | 10/2009 |
| JP | 2009261944 A | 11/2009 |
| JP | 2009539420 A | 11/2009 |
| JP | 2009291604 A | 12/2009 |
| JP | 2010504808 A | 2/2010 |
| JP | 2010504809 A | 2/2010 |
| JP | 2010504846 A | 2/2010 |
| JP | 2010505524 A | 2/2010 |
| JP | 2010069310 A | 4/2010 |
| JP | 2010088876 A | 4/2010 |
| JP | 2010098844 A | 4/2010 |
| JP | 4461008 B2 | 5/2010 |
| JP | 4549018 B2 | 9/2010 |
| JP | 2010540192 A | 12/2010 |
| JP | 4783373 B2 | 9/2011 |
| JP | 5140421 B2 | 2/2013 |
| JP | 5162595 B2 | 3/2013 |
| JP | 2013128791 A | 7/2013 |
| JP | 5333899 B2 | 11/2013 |
| KR | 20110003229 A | 1/2011 |
| RU | 1814161 C | 5/1993 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |

(56) References Cited

FOREIGN PATENT DOCUMENTS

| | | | |
|---|---|---|---|
| SU | 328636 | A | 9/1972 |
| SU | 674747 | A1 | 7/1979 |
| SU | 886900 | A1 | 12/1981 |
| SU | 1009439 | A | 4/1983 |
| SU | 1022703 | A1 | 6/1983 |
| SU | 1333319 | A2 | 8/1987 |
| SU | 1377053 | A1 | 2/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| SU | 1814161 | A1 | 5/1993 |
| WO | WO-8202824 | A1 | 9/1982 |
| WO | WO-8602254 | A1 | 4/1986 |
| WO | WO-9115157 | A1 | 10/1991 |
| WO | WO-9220295 | A1 | 11/1992 |
| WO | WO-9221300 | A1 | 12/1992 |
| WO | WO-9308755 | A1 | 5/1993 |
| WO | WO-9313718 | A1 | 7/1993 |
| WO | WO-9314690 | A1 | 8/1993 |
| WO | WO-9315648 | A1 | 8/1993 |
| WO | WO-9315850 | A1 | 8/1993 |
| WO | WO-9319681 | A1 | 10/1993 |
| WO | WO-9400060 | A1 | 1/1994 |
| WO | WO-9411057 | A1 | 5/1994 |
| WO | WO-9412108 | A1 | 6/1994 |
| WO | WO-9418893 | A1 | 9/1994 |
| WO | WO-9420030 | A1 | 9/1994 |
| WO | WO-9422378 | A1 | 10/1994 |
| WO | WO-9423659 | A1 | 10/1994 |
| WO | WO-9424943 | A1 | 11/1994 |
| WO | WO-9424947 | A1 | 11/1994 |
| WO | WO-9502369 | A1 | 1/1995 |
| WO | WO-9503743 | A1 | 2/1995 |
| WO | WO-9506817 | A1 | 3/1995 |
| WO | WO-9509576 | A1 | 4/1995 |
| WO | WO-9509577 | A1 | 4/1995 |
| WO | WO-9514436 | A1 | 6/1995 |
| WO | WO-9517855 | A1 | 7/1995 |
| WO | WO-9518383 | A1 | 7/1995 |
| WO | WO-9518572 | A1 | 7/1995 |
| WO | WO-9519739 | A1 | 7/1995 |
| WO | WO-9520360 | A1 | 8/1995 |
| WO | WO-9523557 | A1 | 9/1995 |
| WO | WO-9524865 | A1 | 9/1995 |
| WO | WO-9525471 | A3 | 9/1995 |
| WO | WO-9526562 | A1 | 10/1995 |
| WO | WO-9529639 | A1 | 11/1995 |
| WO | WO-9604858 | A1 | 2/1996 |
| WO | WO-9618344 | A2 | 6/1996 |
| WO | WO-9619151 | A1 | 6/1996 |
| WO | WO-9619152 | A1 | 6/1996 |
| WO | WO-9620652 | A1 | 7/1996 |
| WO | WO-9621119 | A1 | 7/1996 |
| WO | WO-9622055 | A1 | 7/1996 |
| WO | WO-9623448 | A1 | 8/1996 |
| WO | WO-9624301 | A1 | 8/1996 |
| WO | WO-9627337 | A1 | 9/1996 |
| WO | WO-9631155 | A1 | 10/1996 |
| WO | WO-9635464 | A1 | 11/1996 |
| WO | WO-9639085 | A1 | 12/1996 |
| WO | WO-9639086 | A1 | 12/1996 |
| WO | WO-9639087 | A1 | 12/1996 |
| WO | WO-9639088 | A1 | 12/1996 |
| WO | WO-9639089 | A1 | 12/1996 |
| WO | WO-9700646 | A1 | 1/1997 |
| WO | WO-9700647 | A1 | 1/1997 |
| WO | WO-9701989 | A1 | 1/1997 |
| WO | WO-9706582 | A1 | 2/1997 |
| WO | WO-9710763 | A1 | 3/1997 |
| WO | WO-9710764 | A1 | 3/1997 |
| WO | WO-9711648 | A2 | 4/1997 |
| WO | WO-9711649 | A1 | 4/1997 |
| WO | WO-9715237 | A1 | 5/1997 |
| WO | WO-9724073 | A1 | 7/1997 |
| WO | WO-9724993 | A1 | 7/1997 |
| WO | WO-9730644 | A1 | 8/1997 |
| WO | WO-9734533 | A1 | 9/1997 |
| WO | WO-9737598 | A1 | 10/1997 |
| WO | WO-9739688 | A2 | 10/1997 |
| WO | WO-9801080 | A1 | 1/1998 |
| WO | WO-9817180 | A1 | 4/1998 |
| WO | WO-9822154 | A2 | 5/1998 |
| WO | WO-9827880 | A1 | 7/1998 |
| WO | WO-9830153 | A1 | 7/1998 |
| WO | WO-9847436 | A1 | 10/1998 |
| WO | WO-9858589 | A1 | 12/1998 |
| WO | WO-9902090 | A1 | 1/1999 |
| WO | WO-9903407 | A1 | 1/1999 |
| WO | WO-9903408 | A1 | 1/1999 |
| WO | WO-9903409 | A1 | 1/1999 |
| WO | WO-9912483 | A1 | 3/1999 |
| WO | WO-9912487 | A1 | 3/1999 |
| WO | WO-9912488 | A1 | 3/1999 |
| WO | WO-9915086 | A1 | 4/1999 |
| WO | WO-9915091 | A1 | 4/1999 |
| WO | WO-9923933 | A2 | 5/1999 |
| WO | WO-9923959 | A1 | 5/1999 |
| WO | WO-9925261 | A1 | 5/1999 |
| WO | WO-9929244 | A1 | 6/1999 |
| WO | WO-9934744 | A1 | 7/1999 |
| WO | WO-9945849 | A1 | 9/1999 |
| WO | WO-9948430 | A1 | 9/1999 |
| WO | WO-9951158 | A1 | 10/1999 |
| WO | WO-0024322 | A1 | 5/2000 |
| WO | WO-0024330 | A1 | 5/2000 |
| WO | WO-0041638 | A1 | 7/2000 |
| WO | WO-0048506 | A1 | 8/2000 |
| WO | WO-0053112 | A2 | 9/2000 |
| WO | WO-0054653 | A1 | 9/2000 |
| WO | WO-0057796 | A1 | 10/2000 |
| WO | WO-0064365 | A1 | 11/2000 |
| WO | WO-0072762 | A1 | 12/2000 |
| WO | WO-0072765 | A1 | 12/2000 |
| WO | WO-0078222 | A1 | 12/2000 |
| WO | WO-0103587 | A1 | 1/2001 |
| WO | WO-0105702 | A1 | 1/2001 |
| WO | WO-0110482 | A1 | 2/2001 |
| WO | WO-0135845 | A1 | 5/2001 |
| WO | WO-0154594 | A1 | 8/2001 |
| WO | WO-0158371 | A1 | 8/2001 |
| WO | WO-0162158 | A2 | 8/2001 |
| WO | WO-0162161 | A1 | 8/2001 |
| WO | WO-0162162 | A1 | 8/2001 |
| WO | WO-0162163 | A1 | 8/2001 |
| WO | WO-0162164 | A2 | 8/2001 |
| WO | WO-0162169 | A2 | 8/2001 |
| WO | WO-0178605 | A2 | 10/2001 |
| WO | WO-0180757 | A2 | 11/2001 |
| WO | WO-0191646 | A1 | 12/2001 |
| WO | WO-0200121 | A1 | 1/2002 |
| WO | WO-0207608 | A2 | 1/2002 |
| WO | WO-0207618 | A1 | 1/2002 |
| WO | WO-0217799 | A1 | 3/2002 |
| WO | WO-0219920 | A1 | 3/2002 |
| WO | WO-0219932 | A1 | 3/2002 |
| WO | WO-0226143 | A1 | 4/2002 |
| WO | WO-0230297 | A2 | 4/2002 |
| WO | WO-0232322 | A2 | 4/2002 |
| WO | WO-0236028 | A1 | 5/2002 |
| WO | WO-0243571 | A2 | 6/2002 |
| WO | WO-02058568 | A1 | 8/2002 |
| WO | WO-02060328 | A1 | 8/2002 |
| WO | WO-02065933 | A2 | 8/2002 |
| WO | WO-02067785 | A2 | 9/2002 |
| WO | WO-02080781 | A2 | 10/2002 |
| WO | WO-02085218 | A2 | 10/2002 |
| WO | WO-02087586 | A1 | 11/2002 |
| WO | WO-02098302 | A1 | 12/2002 |
| WO | WO-03000138 | A2 | 1/2003 |
| WO | WO-03001329 | A2 | 1/2003 |
| WO | WO-03001986 | A2 | 1/2003 |
| WO | WO-03013363 | A1 | 2/2003 |

(56) References Cited

FOREIGN PATENT DOCUMENTS

| | | |
|---|---|---|
| WO | WO-03013372 A2 | 2/2003 |
| WO | WO-03015604 A2 | 2/2003 |
| WO | WO-03020106 A2 | 3/2003 |
| WO | WO-03020139 A2 | 3/2003 |
| WO | WO-03024339 A1 | 3/2003 |
| WO | WO-03030743 A2 | 4/2003 |
| WO | WO-03037193 A1 | 5/2003 |
| WO | WO-03055402 A1 | 7/2003 |
| WO | WO-03057048 A1 | 7/2003 |
| WO | WO-03057058 A1 | 7/2003 |
| WO | WO-03063694 A1 | 8/2003 |
| WO | WO-03077769 A1 | 9/2003 |
| WO | WO-03079911 A1 | 10/2003 |
| WO | WO-03082126 A1 | 10/2003 |
| WO | WO-03086206 A1 | 10/2003 |
| WO | WO-03088845 A2 | 10/2003 |
| WO | WO-03047436 A3 | 11/2003 |
| WO | WO-03090630 A2 | 11/2003 |
| WO | WO-03094743 A1 | 11/2003 |
| WO | WO-03094745 A1 | 11/2003 |
| WO | WO-03094746 A1 | 11/2003 |
| WO | WO-03094747 A1 | 11/2003 |
| WO | WO-03101313 A1 | 12/2003 |
| WO | WO-03105698 A2 | 12/2003 |
| WO | WO-03105702 A2 | 12/2003 |
| WO | WO-2004006980 A2 | 1/2004 |
| WO | WO-2004011037 A2 | 2/2004 |
| WO | WO-2004014238 A2 | 2/2004 |
| WO | WO-03079909 A3 | 3/2004 |
| WO | WO-2004019769 A1 | 3/2004 |
| WO | WO-2004019803 A1 | 3/2004 |
| WO | WO-2004021868 A2 | 3/2004 |
| WO | WO-2004028585 A2 | 4/2004 |
| WO | WO-2004030554 A1 | 4/2004 |
| WO | WO-2004032754 A2 | 4/2004 |
| WO | WO-2004032760 A2 | 4/2004 |
| WO | WO-2004032762 A1 | 4/2004 |
| WO | WO-2004032763 A2 | 4/2004 |
| WO | WO-2004032783 A1 | 4/2004 |
| WO | WO-2004034875 A2 | 4/2004 |
| WO | WO-2004047626 A1 | 6/2004 |
| WO | WO-2004047653 A2 | 6/2004 |
| WO | WO-2004049956 A2 | 6/2004 |
| WO | WO-2004050971 A2 | 6/2004 |
| WO | WO-2004052426 A2 | 6/2004 |
| WO | WO-2004056276 A1 | 7/2004 |
| WO | WO-2004056277 A1 | 7/2004 |
| WO | WO-2004062516 A1 | 7/2004 |
| WO | WO-2004064600 A2 | 8/2004 |
| WO | WO-2004078050 A2 | 9/2004 |
| WO | WO-2004078051 A2 | 9/2004 |
| WO | WO-2004078236 A2 | 9/2004 |
| WO | WO-2004086987 A1 | 10/2004 |
| WO | WO-2004096015 A2 | 11/2004 |
| WO | WO-2004096057 A2 | 11/2004 |
| WO | WO-2004103157 A2 | 12/2004 |
| WO | WO-2004105593 A1 | 12/2004 |
| WO | WO-2004105621 A1 | 12/2004 |
| WO | WO-2004112618 A2 | 12/2004 |
| WO | WO-2004112652 A2 | 12/2004 |
| WO | WO-2005027983 A2 | 3/2005 |
| WO | WO-2005037329 A2 | 4/2005 |
| WO | WO-2005042041 A1 | 5/2005 |
| WO | WO-2005044078 A2 | 5/2005 |
| WO | WO-2005055846 A1 | 6/2005 |
| WO | WO-2005072634 A2 | 8/2005 |
| WO | WO-2005078892 A1 | 8/2005 |
| WO | WO-2005079675 A2 | 9/2005 |
| WO | WO-2005087128 A1 | 9/2005 |
| WO | WO-2005096954 A2 | 10/2005 |
| WO | WO-2005112806 A2 | 12/2005 |
| WO | WO-2005112808 A1 | 12/2005 |
| WO | WO-2005115251 A1 | 12/2005 |
| WO | WO-2005115253 A2 | 12/2005 |
| WO | WO-2005117735 A1 | 12/2005 |
| WO | WO-2005122936 A1 | 12/2005 |
| WO | WO-2006023486 A1 | 3/2006 |
| WO | WO-2006023578 A2 | 3/2006 |
| WO | WO-2006027014 A1 | 3/2006 |
| WO | WO-2006028314 A1 | 3/2006 |
| WO | WO-2006044490 A2 | 4/2006 |
| WO | WO-2006044581 A2 | 4/2006 |
| WO | WO-2006044810 A2 | 4/2006 |
| WO | WO-2006049852 A2 | 5/2006 |
| WO | WO-2006051252 A1 | 5/2006 |
| WO | WO-2006059067 A1 | 6/2006 |
| WO | WO-2006083748 A1 | 8/2006 |
| WO | WO-2006085389 A1 | 8/2006 |
| WO | WO-2006092563 A1 | 9/2006 |
| WO | WO-2006092565 A1 | 9/2006 |
| WO | WO-2006115958 A1 | 11/2006 |
| WO | WO-2006125940 A1 | 11/2006 |
| WO | WO-2006132992 A2 | 12/2006 |
| WO | WO-2007002180 A2 | 1/2007 |
| WO | WO-2007016290 A2 | 2/2007 |
| WO | WO-2007018898 A2 | 2/2007 |
| WO | WO-2007059233 A2 | 5/2007 |
| WO | WO-2007074430 A1 | 7/2007 |
| WO | WO-2007089603 A2 | 8/2007 |
| WO | WO-2007098220 A2 | 8/2007 |
| WO | WO-2007121579 A1 | 11/2007 |
| WO | WO-2007131110 A2 | 11/2007 |
| WO | WO-2007137304 A2 | 11/2007 |
| WO | WO-2007139734 A2 | 12/2007 |
| WO | WO-2007142625 A2 | 12/2007 |
| WO | WO-2007145825 A2 | 12/2007 |
| WO | WO-2007146987 A2 | 12/2007 |
| WO | WO-2007147439 A1 | 12/2007 |
| WO | WO-2008020964 A2 | 2/2008 |
| WO | WO-2008021969 A2 | 2/2008 |
| WO | WO-2008039249 A1 | 4/2008 |
| WO | WO-2008039270 A1 | 4/2008 |
| WO | WO-2008045383 A2 | 4/2008 |
| WO | WO-2008057281 A2 | 5/2008 |
| WO | WO-2008070763 A1 | 6/2008 |
| WO | WO-2008089404 A2 | 7/2008 |
| WO | WO-2008101080 A1 | 8/2008 |
| WO | WO-2008101228 A2 | 8/2008 |
| WO | WO-2008103797 A2 | 8/2008 |
| WO | WO-2008109125 A1 | 9/2008 |
| WO | WO-2008124748 A1 | 10/2008 |
| WO | WO-2009022614 A1 | 2/2009 |
| WO | WO-2009023851 A1 | 2/2009 |
| WO | WO-2009033057 A2 | 3/2009 |
| WO | WO-2009039506 A1 | 3/2009 |
| WO | WO-2009046394 A1 | 4/2009 |
| WO | WO-2009067649 A2 | 5/2009 |
| WO | WO-2009091497 A2 | 7/2009 |
| WO | WO-2009120944 A2 | 10/2009 |
| WO | WO-2009137761 A2 | 11/2009 |
| WO | WO-2009143092 A1 | 11/2009 |
| WO | WO-2009143331 A1 | 11/2009 |
| WO | WO-2009150650 A2 | 12/2009 |
| WO | WO-2010028332 A2 | 3/2010 |
| WO | WO-2010030434 A1 | 3/2010 |
| WO | WO-2010050771 A2 | 5/2010 |
| WO | WO-2010054404 A1 | 5/2010 |
| WO | WO-2010063795 A1 | 6/2010 |
| WO | WO-2010093333 A1 | 8/2010 |
| WO | WO-2010098871 A2 | 9/2010 |
| WO | WO-2011008672 A2 | 1/2011 |
| WO | WO-2011013103 A1 | 2/2011 |
| WO | WO-2011044343 A2 | 4/2011 |
| WO | WO-2011060311 A2 | 5/2011 |
| WO | WO-2012006306 A2 | 1/2012 |
| WO | WO-2012021671 A1 | 2/2012 |
| WO | WO-2012040438 A1 | 3/2012 |
| WO | WO-2012044551 A1 | 4/2012 |
| WO | WO-2012044554 A1 | 4/2012 |
| WO | WO-2012044597 A1 | 4/2012 |
| WO | WO-2012044606 A2 | 4/2012 |
| WO | WO-2012044820 A1 | 4/2012 |
| WO | WO-2012044844 A2 | 4/2012 |
| WO | WO-2012044853 A1 | 4/2012 |

(56) References Cited

FOREIGN PATENT DOCUMENTS

| | | |
|---|---|---|
| WO | WO-2012058213 A2 | 5/2012 |
| WO | WO-2012068156 A2 | 5/2012 |
| WO | WO-2012127462 A1 | 9/2012 |
| WO | WO-2012143913 A2 | 10/2012 |
| WO | WO-2012148667 A2 | 11/2012 |
| WO | WO-2012148703 A2 | 11/2012 |
| WO | WO-2012160163 A1 | 11/2012 |
| WO | WO-2013009699 A2 | 1/2013 |
| WO | WO-2013036409 A1 | 3/2013 |
| WO | WO-2013043707 A2 | 3/2013 |
| WO | WO-2013043717 A1 | 3/2013 |
| WO | WO-2013043721 A2 | 3/2013 |
| WO | WO-2013062978 A2 | 5/2013 |
| WO | WO-2013/087092 A1 | 6/2013 |
| WO | WO-2013148762 A2 | 10/2013 |
| WO | WO-2013167427 A1 | 11/2013 |
| WO | WO-2014004199 A1 | 1/2014 |

OTHER PUBLICATIONS

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Covidien Brochure, "Endo GIA™ Reloads with Tri-Staple™ Technology," (2010), 1 page.

Covidien Brochure, "Endo GIA™ Reloads with Tri-Staple™ Technology and Endo GIA™ Ultra Universal Staplers," (2010), 2 pages.

Covidien Brochure, "Endo GIA™ Black Reload with Tri-Staple™ Technology," (2012), 2 pages.

Covidien Brochure, "Endo GIA™ Curved Tip Reload with Tri-Staple™ Technology," (2012), 2 pages.

Covidien Brochure, "Endo GIA™ Reloads with Tri-Staple™ Technology," (2010), 2 pages.

Covidien Brochure, "Endo GIA™ Ultra Universal Stapler," (2010), 2 pages.

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Byrne et al., "Molecular Imprinting Within Hydrogels," Advanced Drug Delivery Reviews, 54 (2002) pp. 149-161.

Qiu et al., "Environment-Sensitive Hydrogels for Drug Delivery," Advanced Drug Delivery Reviews, 53 (2001) pp. 321-339.

Hoffman, "Hydrogels for Biomedical Applications," Advanced Drug Delivery Reviews, 43 (2002) pp. 3-12.

Hoffman, "Hydrogels for Biomedical Applications," Advanced Drug Delivery Reviews, 54 (2002) pp. 3-12.

Peppas, "Physiologically Responsive Hydrogels," Journal of Bioactive and Compatible Polymers, vol. 6 (Jul. 1991) pp. 241-246.

Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.

Peppas, Editor "Hydrogels in Medicine and Pharmacy," vol. I, Fundamentals, CRC Press, 1986.

Matsuda, "Thermodynamics of Formation of Porous Polymeric Membrane from Solutions," Polymer Journal, vol. 23, No. 5, pp. 435-444 (1991).

Young, "Microcellular foams via phase separation," Journal of Vacuum Science & Technology A 4(3), (May/Jun. 1986).

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.

The Sodem Aseptic Battery Transfer Kit, Sodem Systems, 2000, 3 pages.

Chen et al., "Elastomeric Biomaterials for Tissue Engineering," Progress in Polymer Science 38 (2013), pp. 584-671.

Pitt et al., "Attachment of Hyaluronan to Metallic Surfaces," J. Biomed. Mater. Res. 68A: pp. 95-106, 2004.

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).

Solorio et al., "Gelatin Microspheres Crosslinked with Genipin for Local Delivery of Growth Factors," J. Tissue Eng. Regen. Med. (2010), 4(7): pp. 514-523.

http://ninpgan.net/publications/51-100/89.pdf; 2004, Ning Pan, on Uniqueness of Fibrous Materials, Design & Nature II. Eds: Colins, M. and Brebbia, C. WIT Press, Boston, 493-504.

Covidien iDrive™ Ultra in Service Reference Card, "iDrive™ Ultra Powered Stapling Device," (4 pages).

Covidien iDrive™ Ultra Powered Stapling System ibrochure, "The Power of iDrive™ Ultra Powered Stapling System and Tri-Staple™ Technology," (23 pages).

Seils et al., Covidien Summary: Clinical Study "UCONN Biodynamics: Final Report on Results," (2 pages).

Covidien "iDrive™ Ultra Powered Stapling System, a Guide for Surgeons," (6 pages).

Covidien "iDrive™ Ultra Powered Stapling System, Cleaning and Sterilization Guide," (2 pages).

Covidien Brochure "iDrive™ Ultra Powered Stapling System," (6 pages).

"Indian Standard: Automotive Vehicles—Brakes and Braking Systems (IS 11852-1:2001)", Mar. 1, 2001.

Zhang et al.; "Viscoelastic Properties of Wood Materials Characterized by Nanoindentation Experiments"; Dec. 20, 2011 (Year: 2011).

Batista et al.; "Evaluation of Weather Influence on Mechanical and Viscoelastic Properties of Polyetherimide/Carbon Fiber Composites"; Apr. 30, 2013 (Year: 2013).

L. Edward Parkman, III; "Viscoelastic Effects on a Polyetherimide Cylinder with Constant Radial Deformation"; May 2015; (Year: 2015).

* cited by examiner

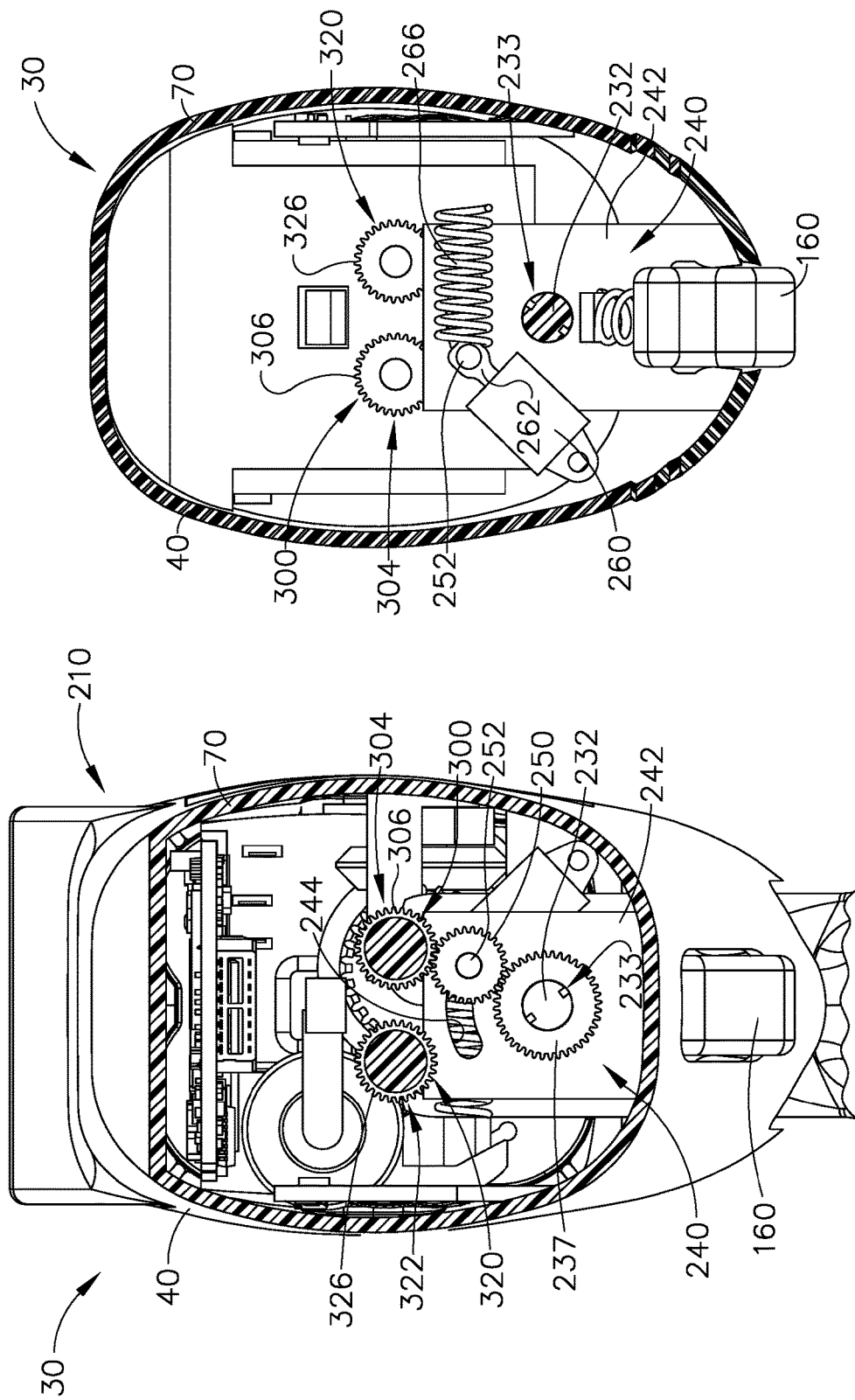

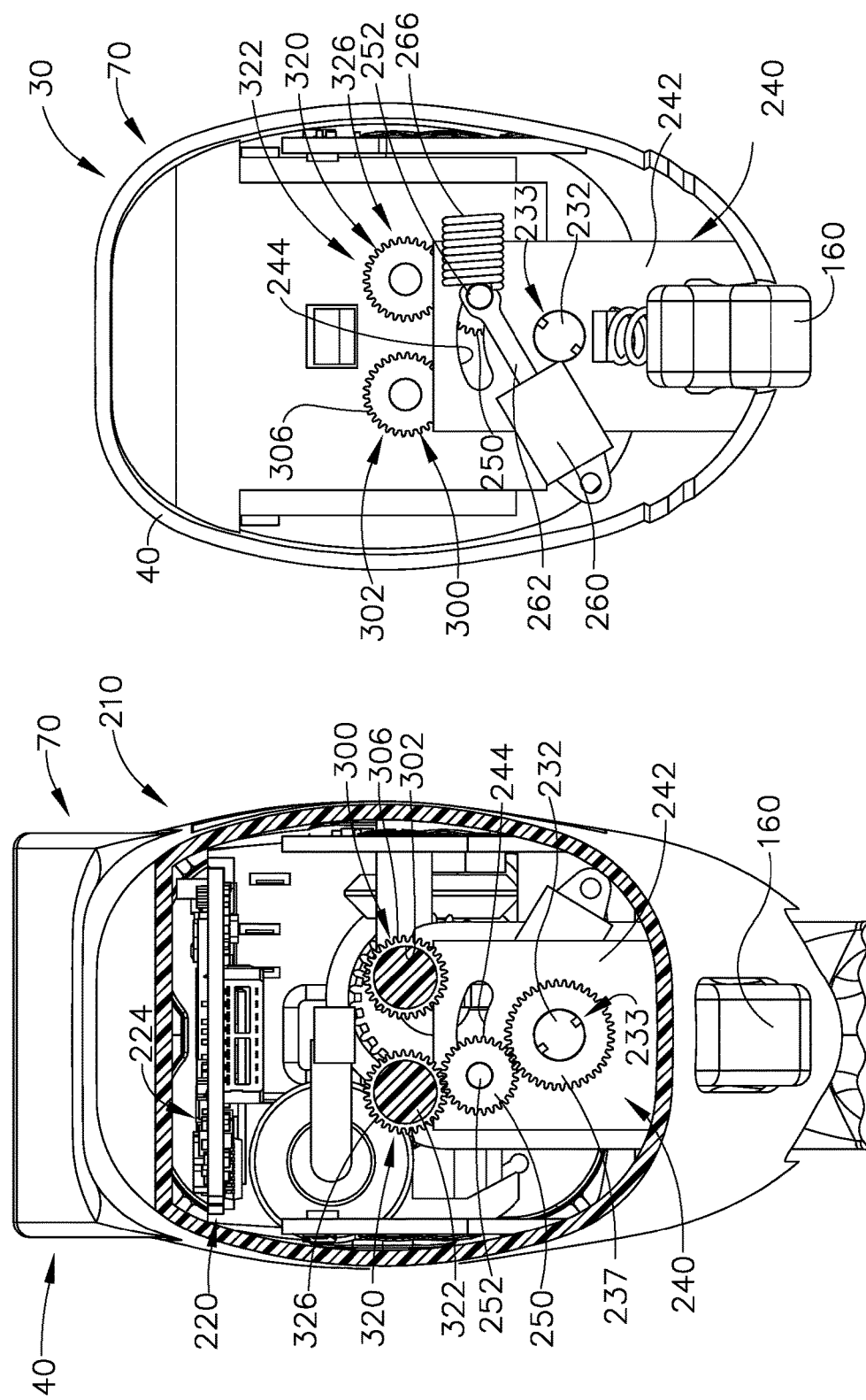

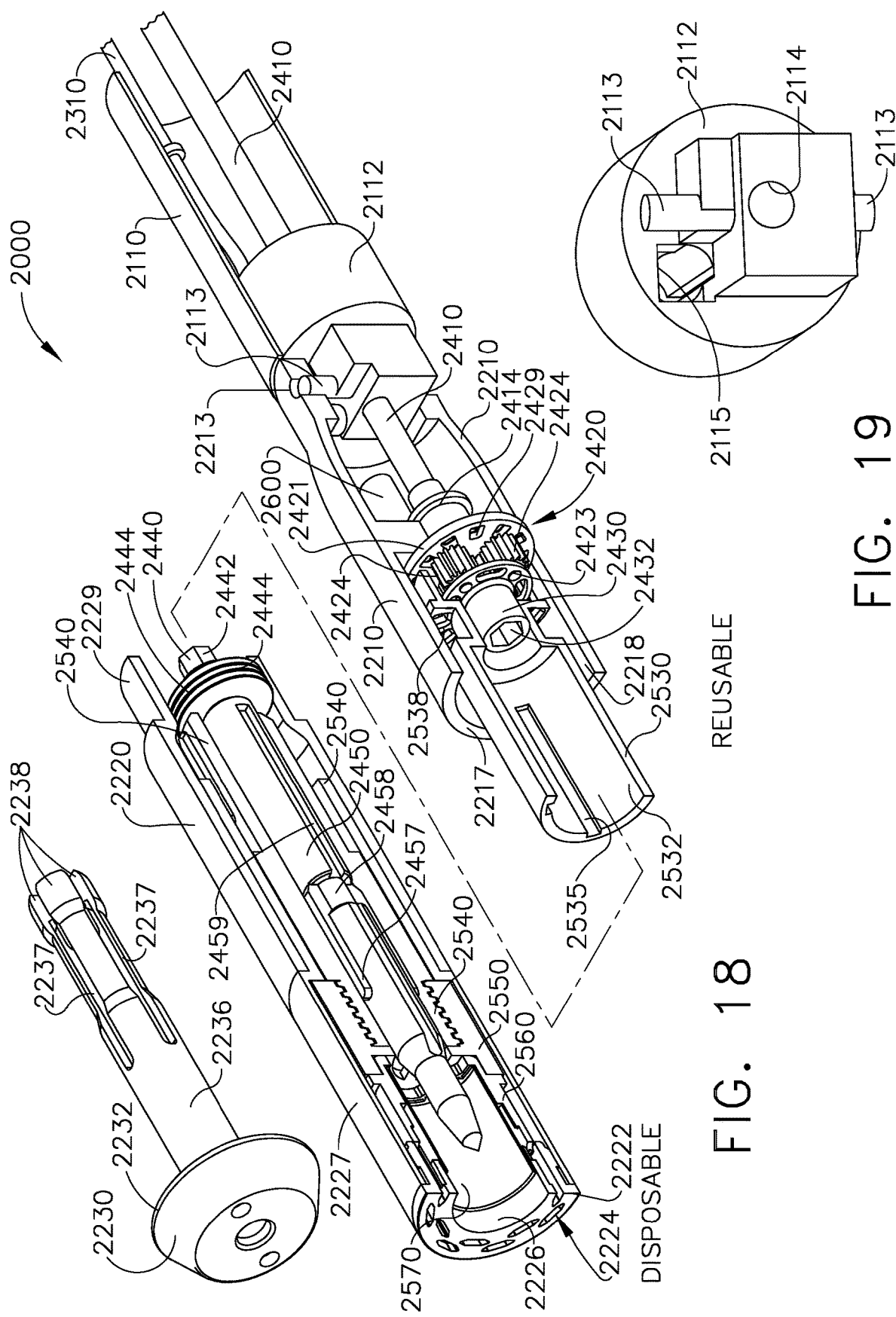

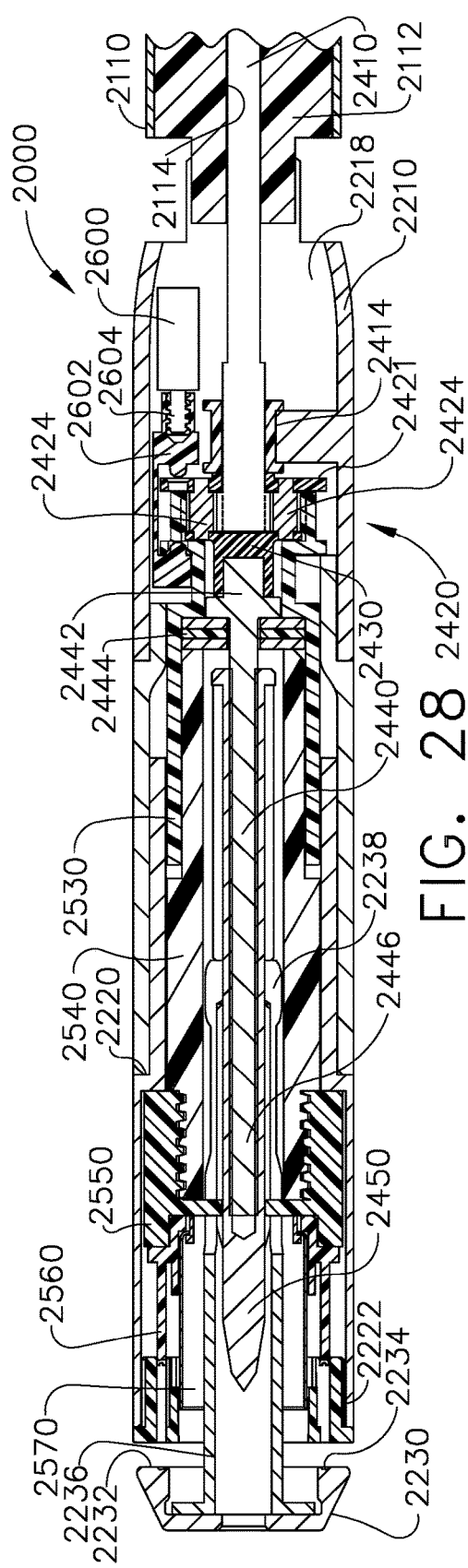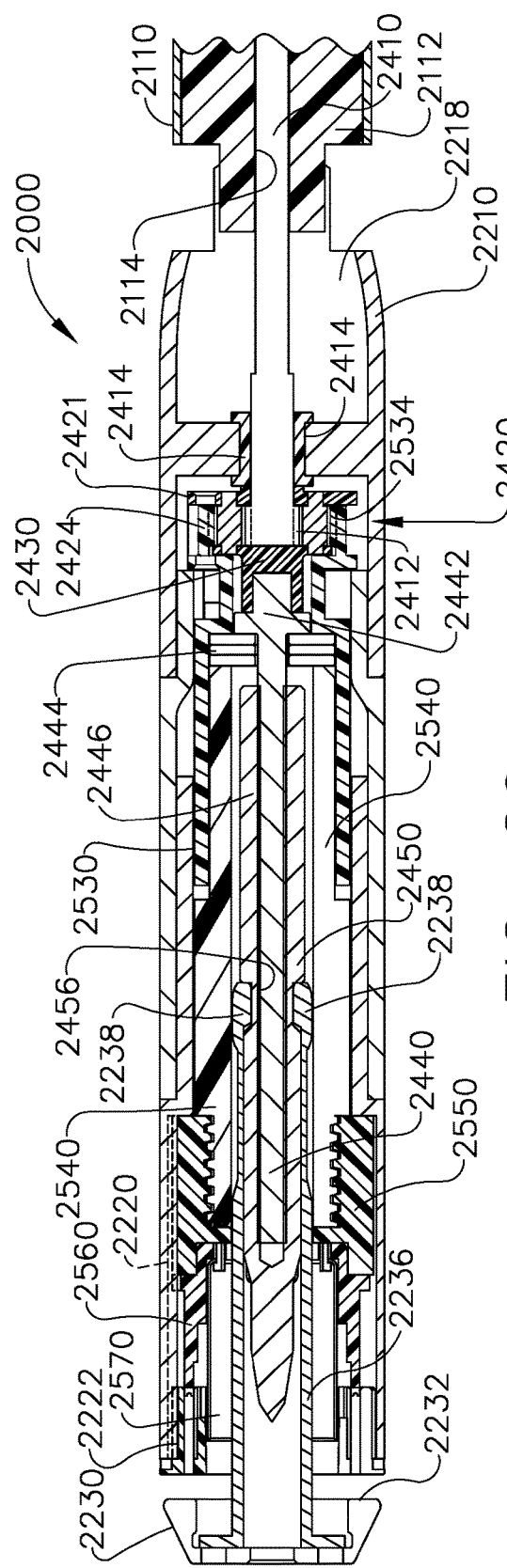

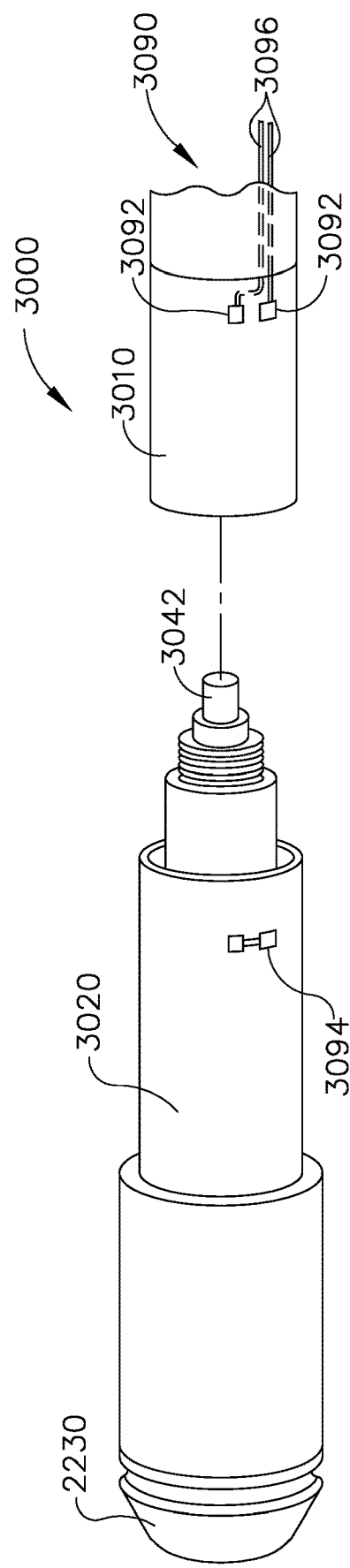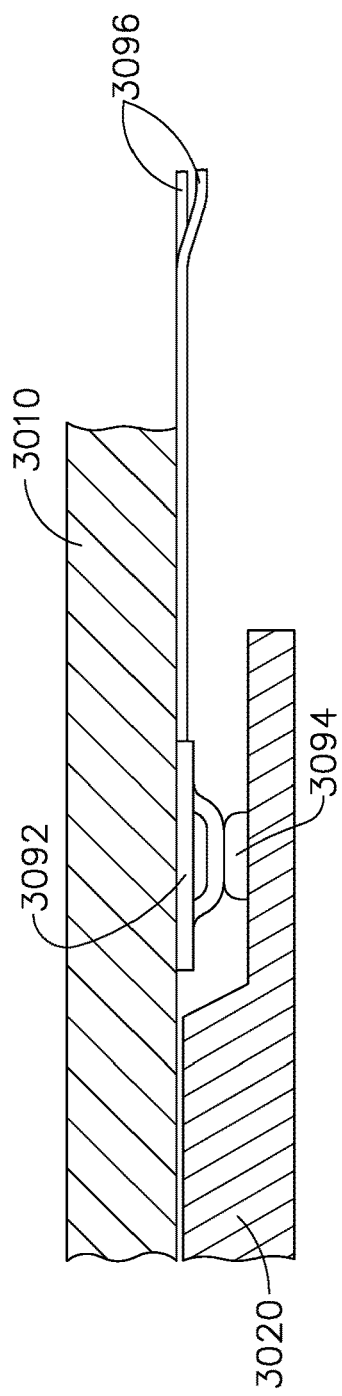
FIG. 39
FIG. 40

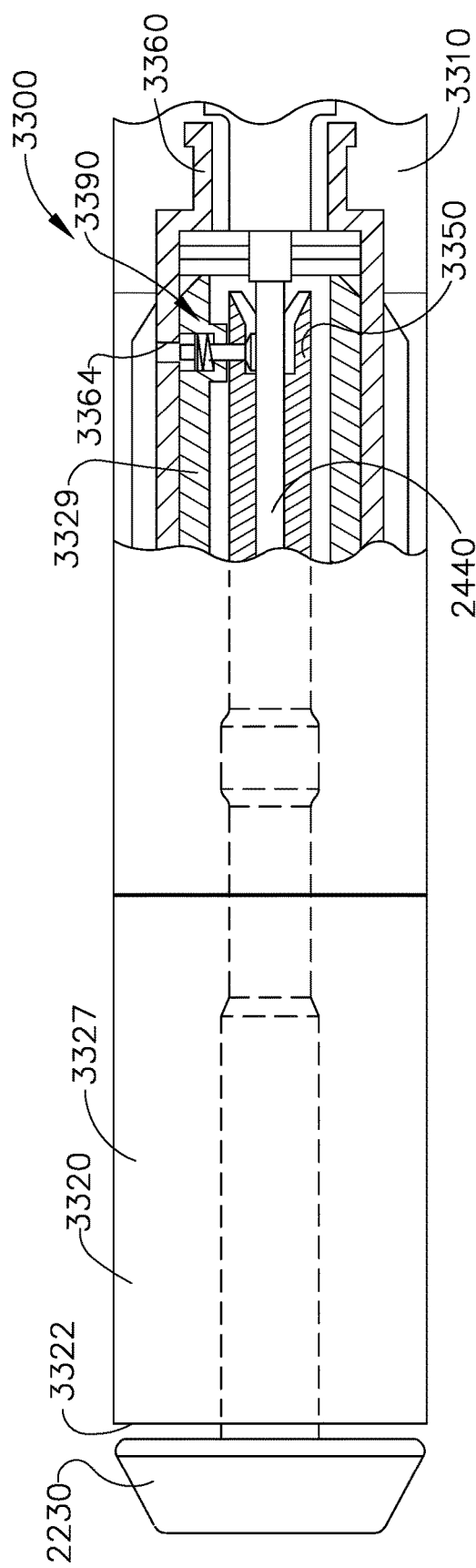
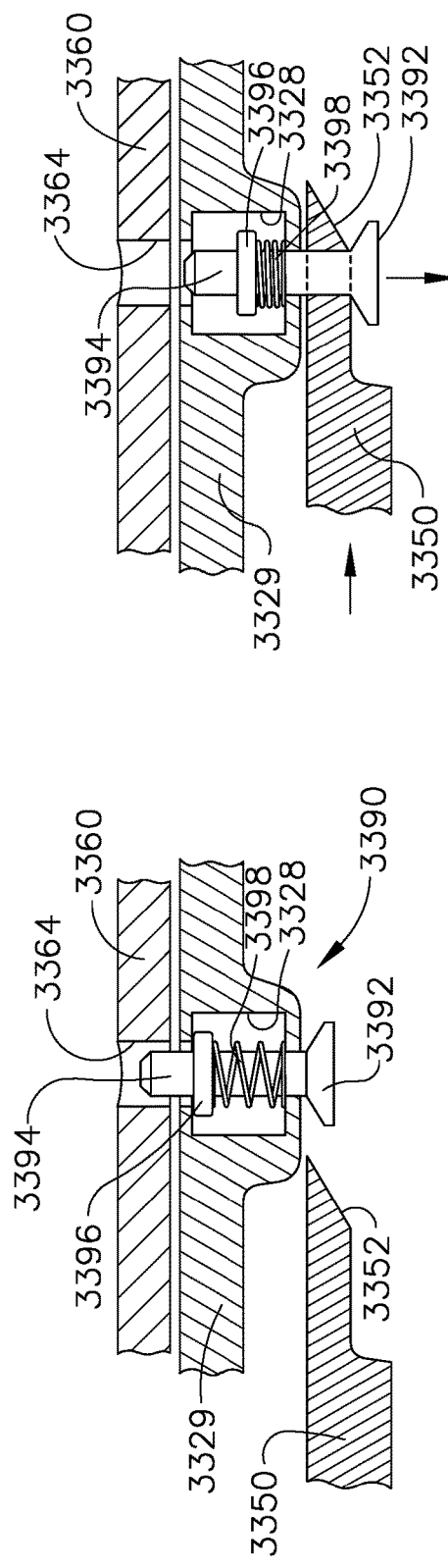
FIG. 46
FIG. 48
FIG. 47

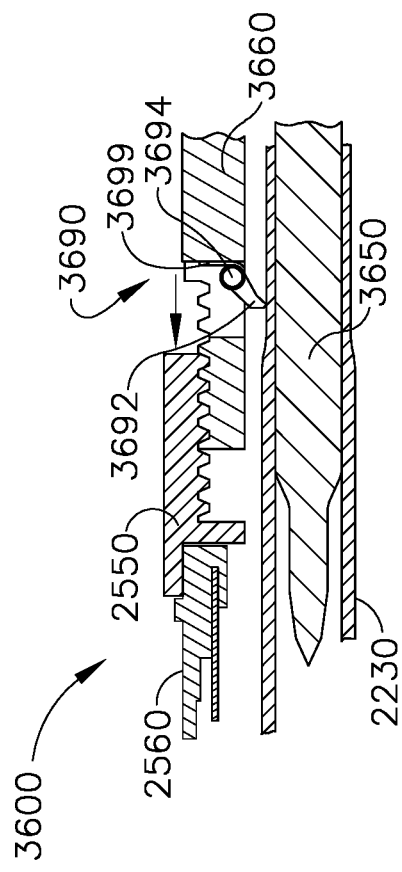
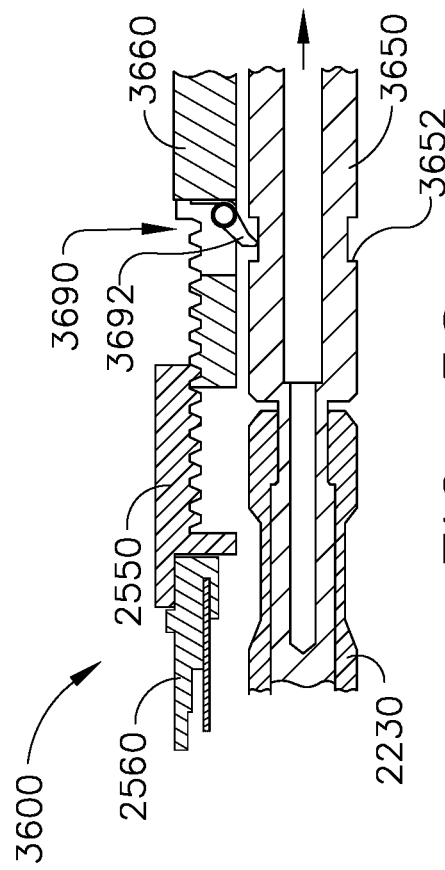
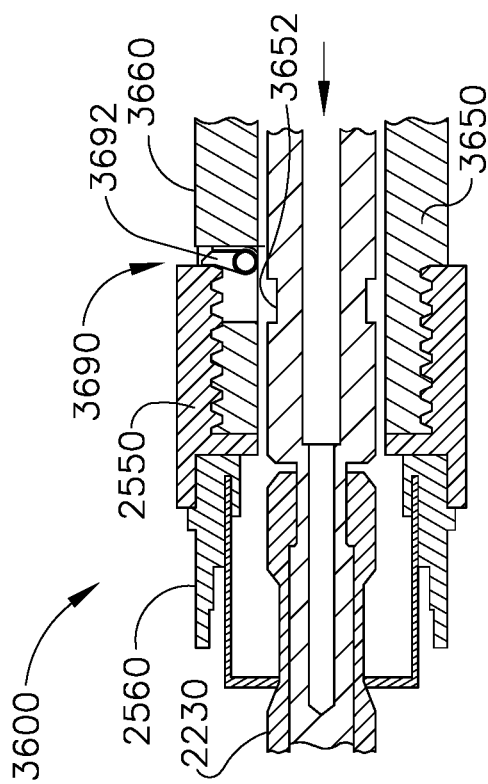
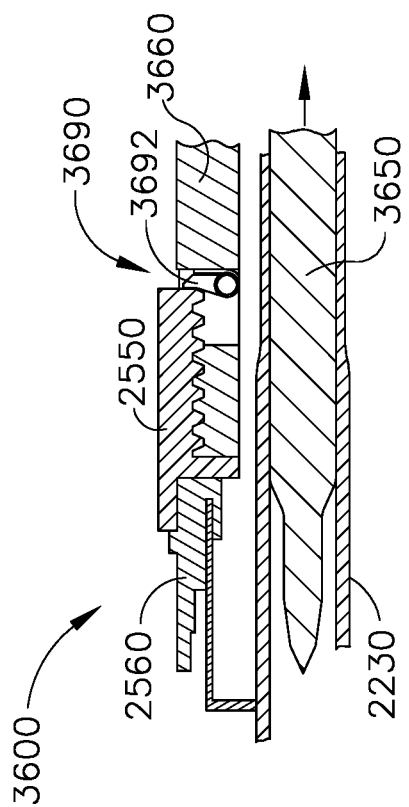
FIG. 55
FIG. 56
FIG. 57
FIG. 58

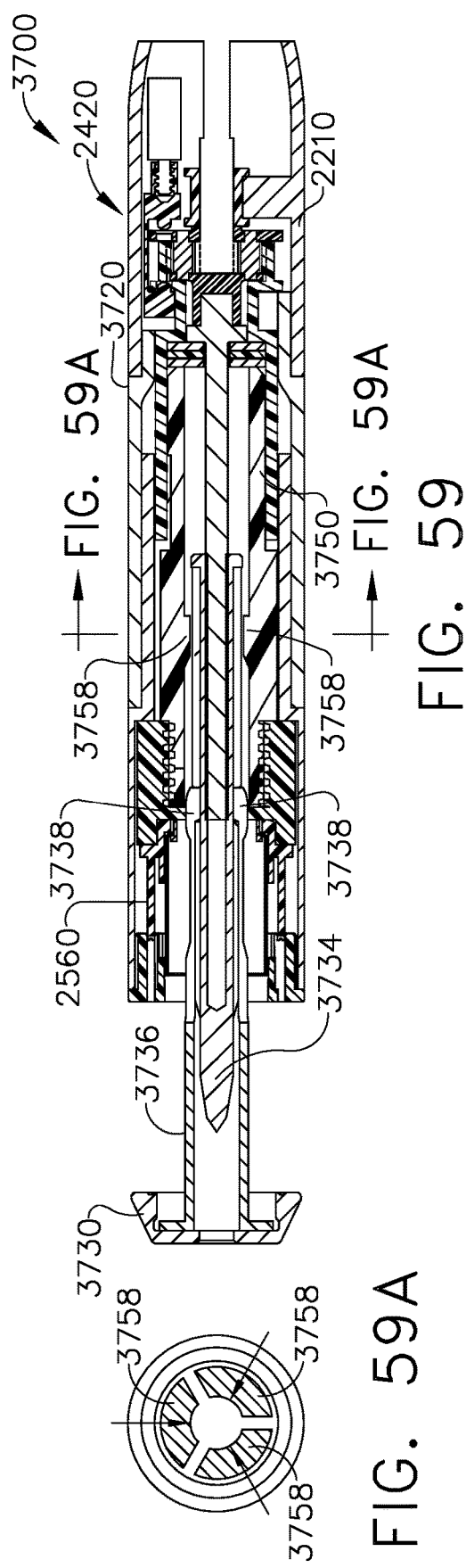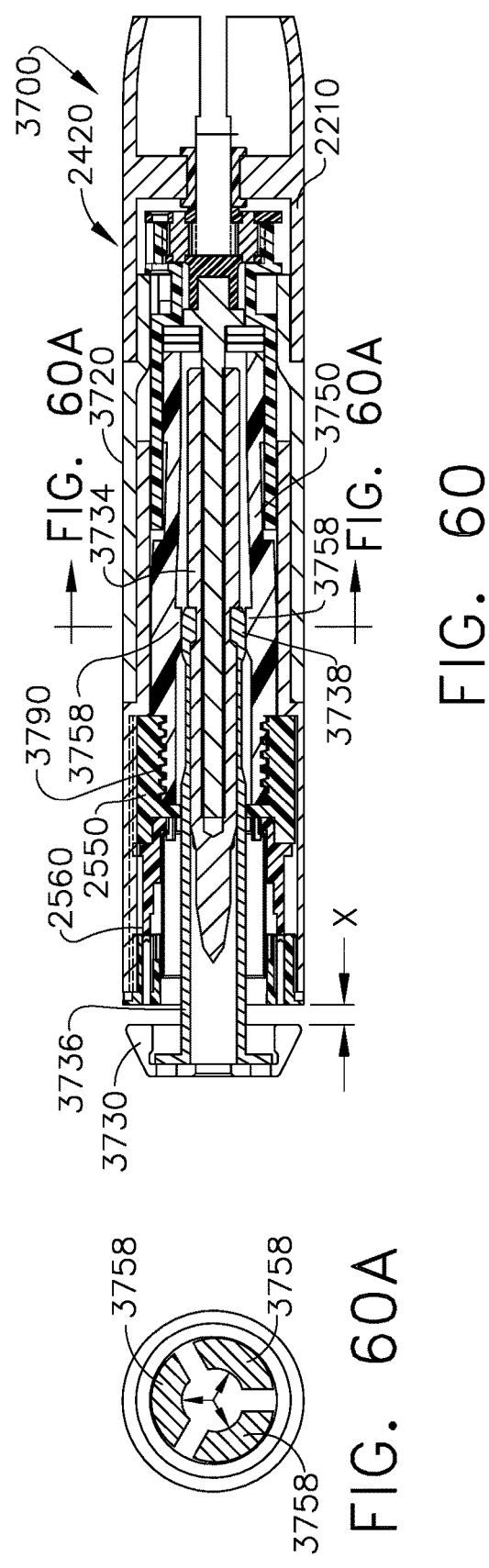

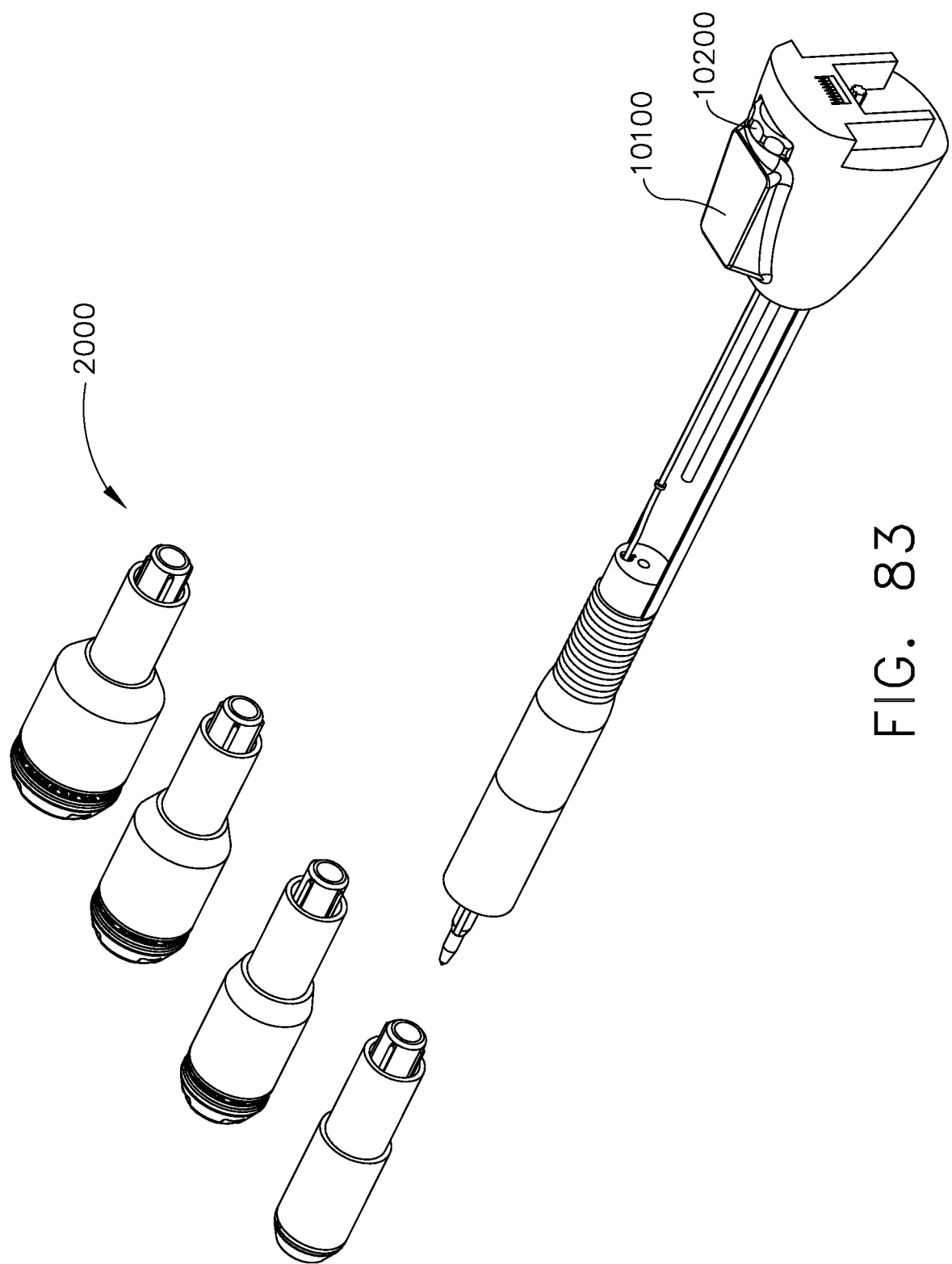

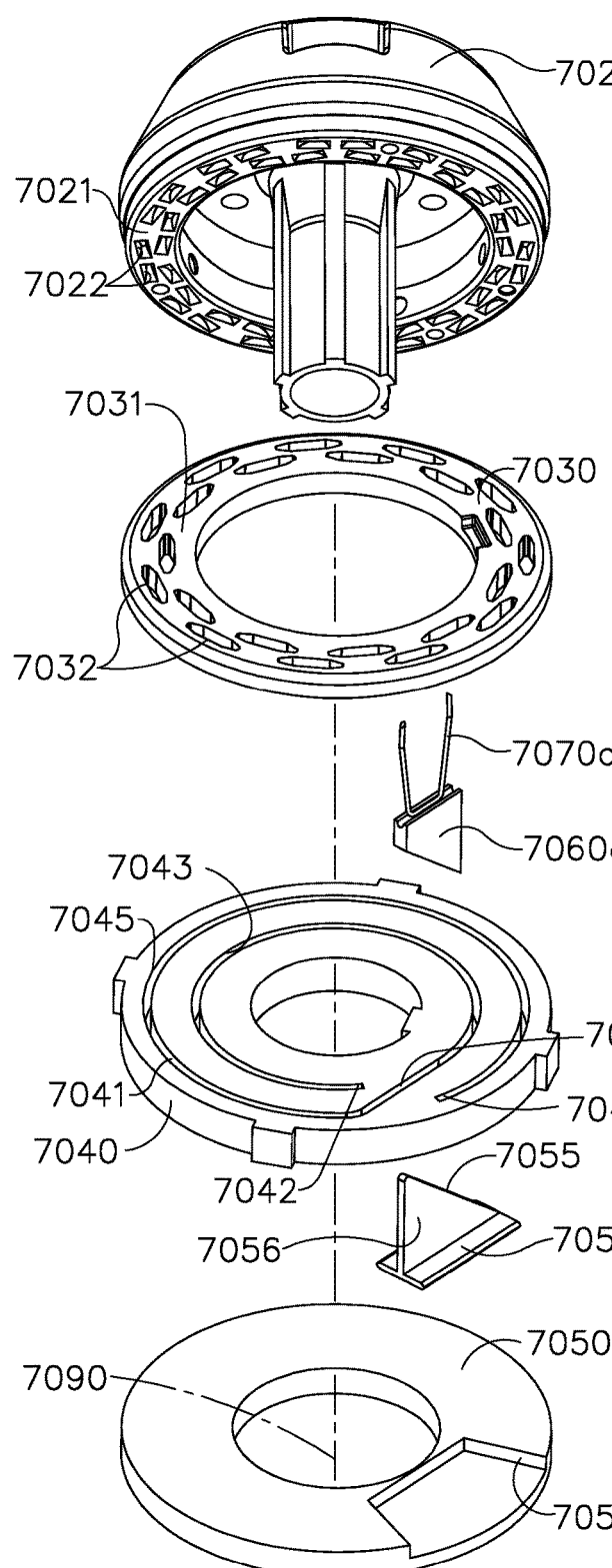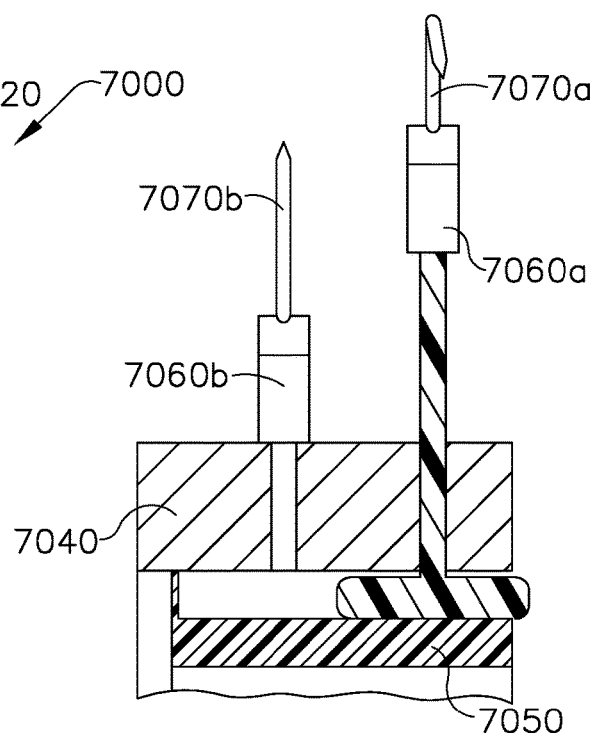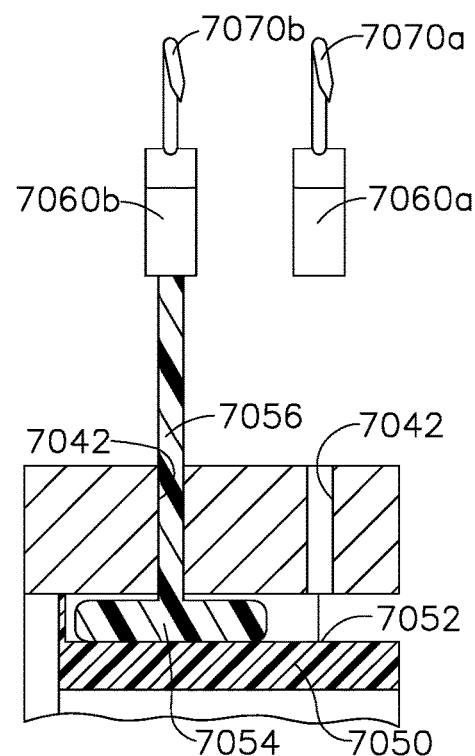

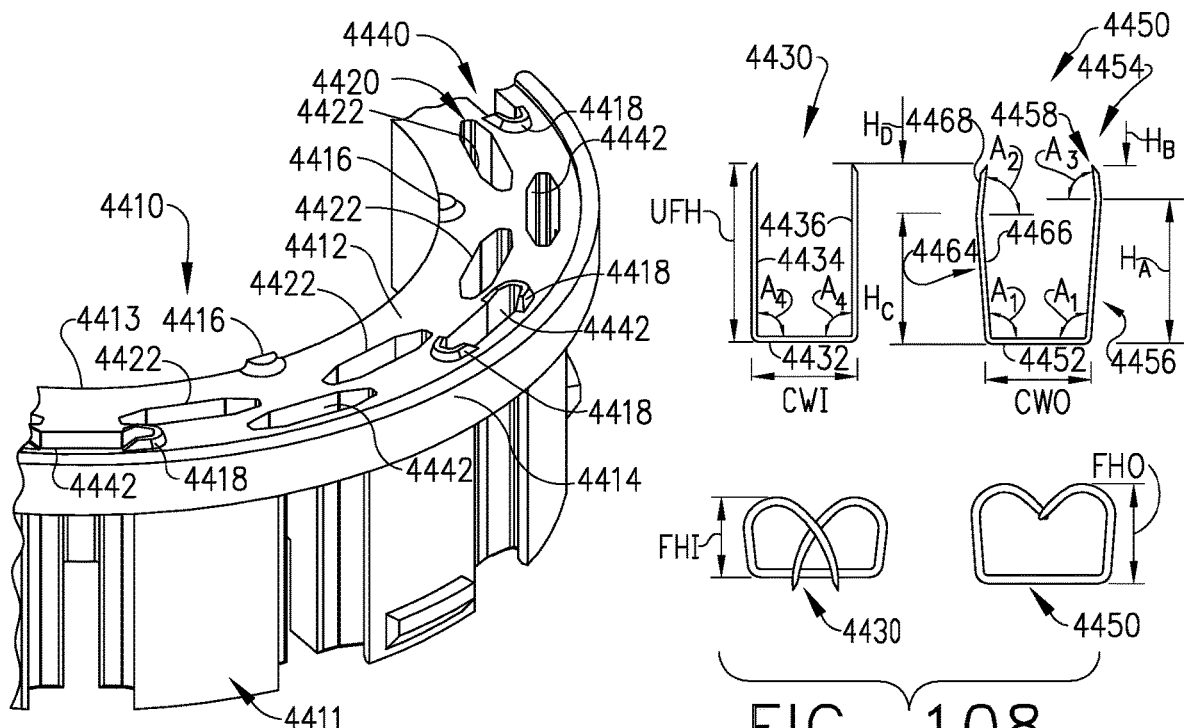
FIG. 107
FIG. 108
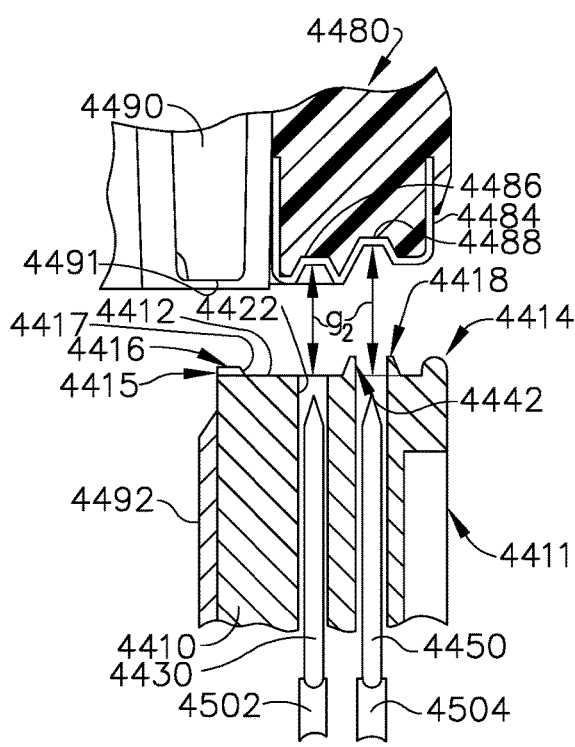
FIG. 109
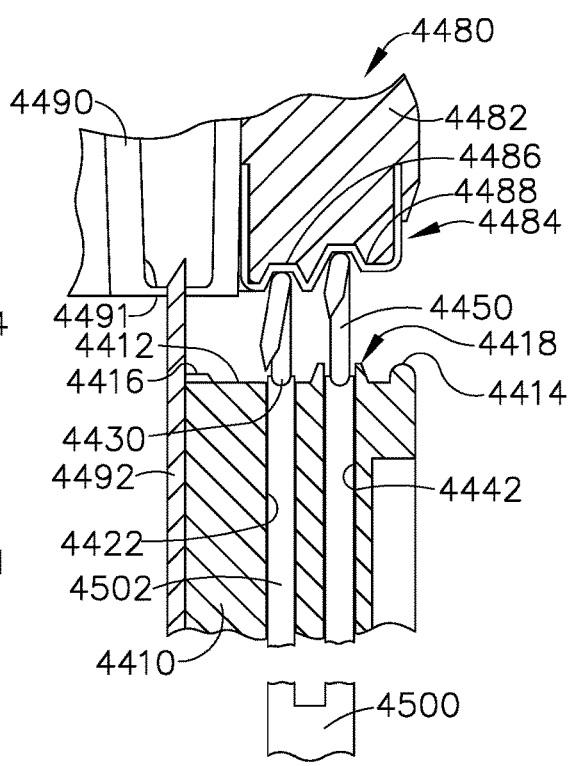
FIG. 110

CIRCULAR STAPLING SYSTEM COMPRISING ROTARY FIRING SYSTEM

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 6 is an end cross-sectional view of the handle assembly of FIGS. 2-5 taken along line 6-6 in FIG. 5;

FIG. 7 is another end cross-sectional view of the handle assembly of FIGS. 2-6 taken along line 7-7 in FIG. 5;

FIG. 8 is another end cross-sectional view of the handle assembly of FIGS. 2-7 showing a shifter gear in meshing engagement with a drive gear on a rotary drive socket;

FIG. 9 is another end cross-sectional view of the handle assembly of FIGS. 2-8 showing the position of a shifter solenoid when the shifter gear is in meshing engagement with the drive gear on the rotary drive socket;

FIG. 18 is a cross-sectional exploded view of the interchangeable tool assembly of FIG. 15;

FIG. 19 is a perspective view of an articulation block of the interchangeable tool assembly of FIG. 15;

FIG. 28 is a cross-sectional view of an end effector of the interchangeable tool assembly of FIG. 15 taken along line 28-28 in FIG. 26 illustrating the end effector in a clamped, but unfired condition;

FIG. 29 is a cross-sectional view of the end effector of the interchangeable tool assembly of FIG. 15 taken along line 29-29 in FIG. 26 illustrating the end effector in a clamped, but unfired condition;

FIG. 39 is a perspective view illustrating a staple cartridge and a shaft of a surgical stapling instrument in accordance with at least one embodiment;

FIG. 40 is a partial cross-sectional view of the staple cartridge assembled to the stapling instrument of FIG. 39;

FIG. 46 is a partial cross-sectional view of a surgical stapling instrument comprising a staple cartridge including staples removable stored therein, an anvil, a closure drive configured to move the anvil relative to the staple cartridge, and a firing drive configured to eject the staples from the staple cartridge;

FIG. 47 is a detail view of a lockout configured to prevent the firing drive from being actuated prior to the anvil being moved into a closed position;

FIG. 48 is a detail view of the lockout of FIG. 47 disengaged from the firing drive;

FIG. 55 is a partial cross-sectional view of a surgical stapling instrument comprising a staple cartridge including staples removable stored therein, an anvil, a closure drive configured to move the anvil relative to the staple cartridge, and a firing drive configured to eject the staples from the staple cartridge;

FIG. 56 is a partial cross-sectional view of the surgical stapling instrument of FIG. 55 illustrating the closure drive in a clamped configuration and the firing drive in an unfired configuration, wherein the firing drive is holding a lockout in an unreleased configuration;

FIG. 57 is a partial cross-sectional view of the surgical stapling instrument of FIG. 55 illustrating the firing drive in an at least partially-fired configuration and the lockout of FIG. 56 in a released configuration;

FIG. 58 is a partial cross-sectional view of the surgical stapling instrument of FIG. 55 illustrating the closure drive in an extended, or open, configuration and the lockout of FIG. 56 engaged with the closure drive to prevent the closure drive from being re-clamped;

FIG. 59 is a cross-sectional view of a surgical stapling instrument comprising a staple cartridge including staples removable stored therein, an anvil, a closure drive configured to move the anvil relative to the staple cartridge, and a firing drive configured to eject the staples from the staple cartridge which is illustrated in a disabled, or locked out, configuration;

FIG. 59A is a cross-sectional end view of the surgical stapling instrument of FIG. 59 taken along line 59A-59A in FIG. 59;

FIG. 60 is a cross-sectional view of the surgical stapling instrument of FIG. 59 illustrated in a clamped configuration in which the firing drive has been enabled;

FIG. 60A is a cross-sectional end view of the surgical stapling instrument of FIG. 59 taken along line 60A-60A in FIG. 60;

FIG. 83 is a perspective view of several end effectors depicted in FIG. 82;

FIG. 97 is an exploded view of an end effector in accordance with at least one embodiment configured to sequentially deploy a first annular row of staples and a second annular row of staples;

FIG. 98 is a partial cross-sectional view of the end effector of FIG. 97 illustrating a firing driver deploying a staple in the first row of staples;

FIG. 99 is a partial cross-sectional view of the end effector of FIG. 97 illustrating the firing driver of FIG. 98 deploying a staple in the second row of staples;

FIG. 107 is a perspective view of a portion of a surgical staple cartridge for use with a circular surgical stapling instrument in accordance with at least one embodiment;

FIG. 108 depicts a pair of staples in accordance with at least one embodiment in unformed and formed configurations;

FIG. 109 is a cross-sectional view of a portion of an anvil in relation to a portion of the surgical staple cartridge of FIG. 107 prior to actuation of the staple forming process;

FIG. 110 is another cross-sectional view of the anvil of FIG. 109 and the staple cartridge of FIG. 107 after the staples have been formed;

FIG. 116 is a cross-sectional view of a portion of an anvil in relation to a portion of a surgical staple cartridge;

FIG. 117 depicts three unformed surgical staples;

FIG. 118 illustrates a partial cross-sectional view of a staple cartridge of a circular stapler in accordance with at least one embodiment; and FIG. 119 illustrates a partial perspective view of a staple cartridge of a circular stapler in accordance with at least one embodiment.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
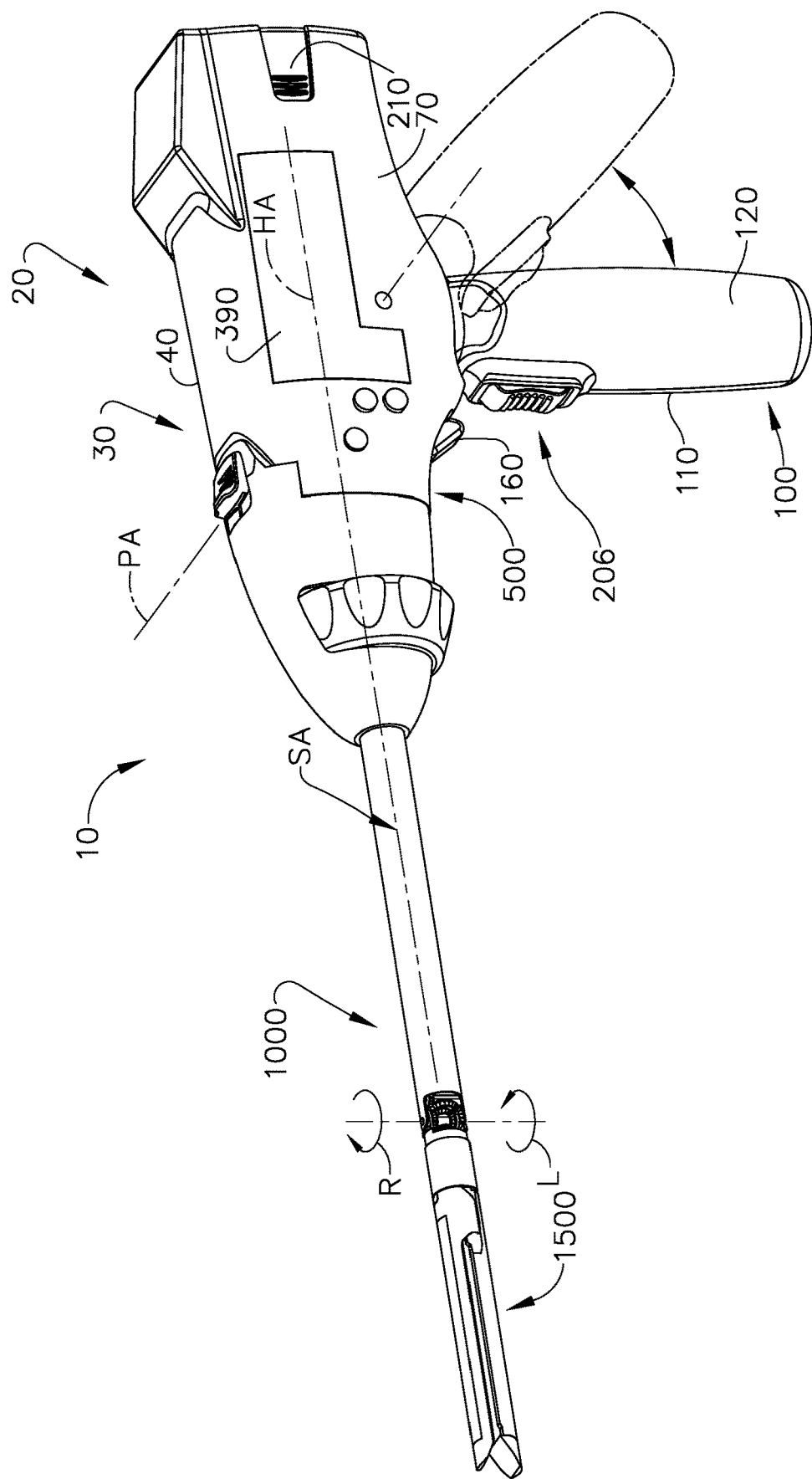
FIG. 1 is a perspective view of a surgical instrument including an interchangeable surgical tool assembly in accordance with at least one embodiment.

Applicant of the present application owns the following patent applications that were filed on Apr. 1, 2016 and which are each herein incorporated by reference in their respective entireties:

U.S. patent application Ser. No. 15/089,325, entitled METHOD FOR OPERATING A SURGICAL STAPLING SYSTEM, now U.S. Patent Application Publication No. 2017/0281171;

U.S. patent application Ser. No. 15/089,321, entitled MODULAR SURGICAL STAPLING SYSTEM COMPRISING A DISPLAY, now U.S. Pat. No. 10,271, 851;

U.S. patent application Ser. No. 15/089,326, entitled SURGICAL STAPLING SYSTEM COMPRISING A DISPLAY INCLUDING A RE-ORIENTABLE DISPLAY FIELD, now U.S. Patent Application Publication No. 2017/0281172;

U.S. patent application Ser. No. 15/089,263, entitled SURGICAL INSTRUMENT HANDLE ASSEMBLY WITH RECONFIGURABLE GRIP PORTION, now U.S. Patent Application Publication No. 2017/0281165;

U.S. patent application Ser. No. 15/089,262, entitled ROTARY POWERED SURGICAL INSTRUMENT WITH MANUALLY ACTUATABLE BAILOUT SYSTEM, now U.S. Patent Application Publication No. 2017/0281161;

U.S. patent application Ser. No. 15/089,277, entitled SURGICAL CUTTING AND STAPLING END EFFECTOR WITH ANVIL CONCENTRIC DRIVE MEMBER, now U.S. Patent Application Publication No. 2017/0281166;

U.S. patent application Ser. No. 15,089,283, entitled CLOSURE SYSTEM ARRANGEMENTS FOR SURGICAL CUTTING AND STAPLING DEVICES WITH SEPARATE AND DISTINCT FIRING SHAFTS, now U.S. Patent Application Publication No. 2017/0281167;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS, now U.S. Patent Application Publication No. 2017/0281168;

U.S. patent application Ser. No. 15/089,258, entitled SURGICAL STAPLING SYSTEM COMPRISING A SHIFTABLE TRANSMISSION, now U.S. Patent Application Publication No. 2017/0281178;

U.S. patent application Ser. No. 15/089,278, entitled SURGICAL STAPLING SYSTEM CONFIGURED TO PROVIDE SELECTIVE CUTTING OF TISSUE, now U.S. Patent Application Publication No. 2017/0281162;

U.S. patent application Ser. No. 15/089,284, entitled SURGICAL STAPLING SYSTEM COMPRISING A CONTOURABLE SHAFT, now U.S. Patent Application Publication No. 2017/0281186;

U.S. patent application Ser. No. 15/089,295, entitled SURGICAL STAPLING SYSTEM COMPRISING A TISSUE COMPRESSION LOCKOUT, now U.S. Patent Application Publication No. 2017/0281187;

U.S. patent application Ser. No. 15/089,300, entitled SURGICAL STAPLING SYSTEM COMPRISING AN UNCLAMPING LOCKOUT, now U.S. Patent Application Publication No. 2017/0281179;

U.S. patent application Ser. No. 15/089,196, entitled SURGICAL STAPLING SYSTEM COMPRISING A JAW CLOSURE LOCKOUT, now U.S. Patent Application Publication No. 15/089,196;

U.S. patent application Ser. No. 15/089,203, entitled SURGICAL STAPLING SYSTEM COMPRISING A JAW ATTACHMENT LOCKOUT, now U.S. Patent Application Publication No. 2017/0281184;

U.S. patent application Ser. No. 15/089,210, entitled SURGICAL STAPLING SYSTEM COMPRISING A SPENT CARTRIDGE LOCKOUT, now U.S. Patent Application Publication No. 2017/0281185;

U.S. patent application Ser. No. 15/089,324, entitled SURGICAL INSTRUMENT COMPRISING A SHIFTING MECHANISM, now U.S. Patent Application Publication No. 2017/0281170;

U.S. patent application Ser. No. 15/089,335, entitled SURGICAL STAPLING INSTRUMENT COMPRISING MULTIPLE LOCKOUTS, now U.S. Patent Application Publication No. 2017/0281155;

U.S. patent application Ser. No. 15/089,339, entitled SURGICAL STAPLING INSTRUMENT, now U.S. Patent Application Publication No. 2017/0281173;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS, now U.S. Patent Application Publication No. 2017/0281177;

U.S. patent application Ser. No. 15/089,304, entitled SURGICAL STAPLING SYSTEM COMPRISING A GROOVED FORMING POCKET, now U.S. Patent Application Publication No. 2017/0281188;

U.S. patent application Ser. No. 15/089,331, entitled ANVIL MODIFICATION MEMBERS FOR SURGICAL STAPLERS, now U.S. Patent Application Publication No. 2017/0281180;

U.S. patent application Ser. No. 15/089,336, entitled STAPLE CARTRIDGES WITH ATRAUMATIC FEATURES, now U.S. Patent Application Publication No. 2017/0281164;

U.S. patent application Ser. No. 15/089,312, entitled CIRCULAR STAPLING SYSTEM COMPRISING AN INCISABLE TISSUE SUPPORT, now U.S. Patent Application Publication No. 2017/0281189;

U.S. patent application Ser. No. 15/089,349, entitled CIRCULAR STAPLING SYSTEM COMPRISING LOAD CONTROL, now U.S. Patent Application Publication No. 2017/0281174;

The Applicant of the present application also owns the U.S. Patent Applications identified below which were filed on Dec. 31, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS;

U.S. patent application Ser. No. 14/984,525, entitled MECHANISMS FOR COMPENSATING FOR DRIVETRAIN FAILURE IN POWERED SURGICAL INSTRUMENTS; and U.S. patent application Ser. No. 14/984,552, entitled SURGICAL INSTRUMENTS WITH SEPARABLE MOTORS AND MOTOR CONTROL CIRCUITS.

The Applicant of the present application also owns the U.S. Patent Applications identified below which were filed on Feb. 9, 2016 which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR;

U.S. patent application Ser. No. 15/019,228, entitled SURGICAL INSTRUMENTS WITH MULTIPLE LINK ARTICULATION ARRANGEMENTS;

U.S. patent application Ser. No. 15/019,196, entitled SURGICAL INSTRUMENT ARTICULATION MECHANISM WITH SLOTTED SECONDARY CONSTRAINT;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY;

U.S. patent application Ser. No. 15/019,215, entitled SURGICAL INSTRUMENTS WITH NON-SYMMETRICAL ARTICULATION ARRANGEMENTS;

U.S. patent application Ser. No. 15/019,227, entitled ARTICULATABLE SURGICAL INSTRUMENTS WITH SINGLE ARTICULATION LINK ARRANGEMENTS;

U.S. patent application Ser. No. 15/019,235, entitled SURGICAL INSTRUMENTS WITH TENSIONING ARRANGEMENTS FOR CABLE DRIVEN ARTICULATION SYSTEMS;

U.S. patent application Ser. No. 15/019,230, entitled ARTICULATABLE SURGICAL INSTRUMENTS WITH OFF-AXIS FIRING BEAM ARRANGEMENTS; and U.S. patent application Ser. No. 15/019,245, entitled SURGICAL INSTRUMENTS WITH CLOSURE STROKE REDUCTION ARRANGEMENTS.

The Applicant of the present application also owns the U.S. Patent Applications identified below which were filed on Feb. 12, 2016 which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS;

U.S. patent application Ser. No. 15/043,259, entitled MECHANISMS FOR COMPENSATING FOR DRIVETRAIN FAILURE IN POWERED SURGICAL INSTRUMENTS;

U.S. patent application Ser. No. 15/043,275, entitled MECHANISMS FOR COMPENSATING FOR DRIVETRAIN FAILURE IN POWERED SURGICAL INSTRUMENTS; and U.S. patent application Ser. No. 15/043,289, entitled MECHANISMS FOR COMPENSATING FOR DRIVETRAIN FAILURE IN POWERED SURGICAL INSTRUMENTS.

Applicant of the present application owns the following patent applications that were filed on Jun. 18, 2015 and which are each herein incorporated by reference in their respective entireties:

U.S. patent application Ser. No. 14/742,925, entitled SURGICAL END EFFECTORS WITH POSITIVE JAW OPENING ARRANGEMENTS;

U.S. patent application Ser. No. 14/742,941, entitled SURGICAL END EFFECTORS WITH DUAL CAM ACTUATED JAW CLOSING FEATURES;

U.S. patent application Ser. No. 14/742,914, entitled MOVABLE FIRING BEAM SUPPORT ARRANGEMENTS FOR ARTICULATABLE SURGICAL INSTRUMENTS;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT;

U.S. patent application Ser. No. 14/742,885, entitled DUAL ARTICULATION DRIVE SYSTEM ARRANGEMENTS FOR ARTICULATABLE SURGICAL INSTRUMENTS; and U.S. patent application Ser. No. 14/742,876, entitled PUSH/PULL ARTICULATION DRIVE SYSTEMS FOR ARTICULATABLE SURGICAL INSTRUMENTS.

Applicant of the present application owns the following patent applications that were filed on Mar. 6, 2015 and which are each herein incorporated by reference in their respective entireties:

U.S. patent application Ser. No. 14/640,746, entitled POWERED SURGICAL INSTRUMENT;

U.S. patent application Ser. No. 14/640,795, entitled MULTIPLE LEVEL THRESHOLDS TO MODIFY OPERATION OF POWERED SURGICAL INSTRUMENTS;

U.S. patent application Ser. No. 14/640,832, entitled ADAPTIVE TISSUE COMPRESSION TECHNIQUES TO ADJUST CLOSURE RATES FOR MULTIPLE TISSUE TYPES;

U.S. patent application Ser. No. 14/640,935, entitled OVERLAID MULTI SENSOR RADIO FREQUENCY (RF) ELECTRODE SYSTEM TO MEASURE TISSUE COMPRESSION;

U.S. patent application Ser. No. 14/640,831, entitled MONITORING SPEED CONTROL AND PRECISION INCREMENTING OF MOTOR FOR POWERED SURGICAL INSTRUMENTS;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES;

U.S. patent application Ser. No. 14/640,817, entitled INTERACTIVE FEEDBACK SYSTEM FOR POWERED SURGICAL INSTRUMENTS;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE;

U.S. patent application Ser. No. 14/640,837, entitled SMART SENSORS WITH LOCAL SIGNAL PROCESSING;

U.S. patent application Ser. No. 14/640,765, entitled SYSTEM FOR DETECTING THE MIS-INSERTION OF A STAPLE CARTRIDGE INTO A SURGICAL STAPLER;

U.S. patent application Ser. No. 14/640,799, entitled SIGNAL AND POWER COMMUNICATION SYSTEM POSITIONED ON A ROTATABLE SHAFT; and U.S. patent application Ser. No. 14/640,780, entitled SURGICAL INSTRUMENT COMPRISING A LOCKABLE BATTERY HOUSING.

Applicant of the present application owns the following patent applications that were filed on Feb. 27, 2015, and which are each herein incorporated by reference in their respective entireties:

U.S. patent application Ser. No. 14/633,576, entitled SURGICAL INSTRUMENT SYSTEM COMPRISING AN INSPECTION STATION;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND;

U.S. patent application Ser. No. 14/633,560, entitled SURGICAL CHARGING SYSTEM THAT CHARGES AND/OR CONDITIONS ONE OR MORE BATTERIES;

U.S. patent application Ser. No. 14/633,566, entitled CHARGING SYSTEM THAT ENABLES EMERGENCY RESOLUTIONS FOR CHARGING A BATTERY;

U.S. patent application Ser. No. 14/633,555, entitled SYSTEM FOR MONITORING WHETHER A SURGICAL INSTRUMENT NEEDS TO BE SERVICED;

U.S. patent application Ser. No. 14/633,542, entitled REINFORCED BATTERY FOR A SURGICAL INSTRUMENT;

U.S. patent application Ser. No. 14/633,548, entitled POWER ADAPTER FOR A SURGICAL INSTRUMENT;

U.S. patent application Ser. No. 14/633,526, entitled ADAPTABLE SURGICAL INSTRUMENT HANDLE;

U.S. patent application Ser. No. 14/633,541, entitled MODULAR STAPLING ASSEMBLY; and U.S. patent application Ser. No. 14/633,562, entitled SURGICAL APPARATUS CONFIGURED TO TRACK AN END-OF-LIFE PARAMETER.

Applicant of the present application owns the following patent applications that were filed on Dec. 18, 2014 and which are each herein incorporated by reference in their respective entireties:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING;

U.S. patent application Ser. No. 14/574,483, entitled SURGICAL INSTRUMENT ASSEMBLY COMPRISING LOCKABLE SYSTEMS;

U.S. patent application Ser. No. 14/575,139, entitled DRIVE ARRANGEMENTS FOR ARTICULATABLE SURGICAL INSTRUMENTS;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE;

U.S. patent application Ser. No. 14/575,143, entitled SURGICAL INSTRUMENTS WITH IMPROVED CLOSURE ARRANGEMENTS;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS;

U.S. patent application Ser. No. 14/574,493, entitled SURGICAL INSTRUMENT ASSEMBLY COMPRISING A FLEXIBLE ARTICULATION SYSTEM; and U.S. patent application Ser. No. 14/574,500, entitled SURGICAL INSTRUMENT ASSEMBLY COMPRISING A LOCKABLE ARTICULATION SYSTEM.

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Patent Application Publication No. 2014/0246474;

U.S. patent application Ser. No. 13/782,460, entitled MULTIPLE PROCESSOR MOTOR CONTROL FOR MODULAR SURGICAL INSTRUMENTS, now U.S. Patent Application Publication No. 2014/0246478;

U.S. patent application Ser. No. 13/782,358, entitled JOYSTICK SWITCH ASSEMBLIES FOR SURGICAL INSTRUMENTS, now U.S. Patent Application Publication No. 2014/0246477;

U.S. patent application Ser. No. 13/782,481, entitled SENSOR STRAIGHTENED END EFFECTOR DURING REMOVAL THROUGH TROCAR, now U.S. Patent Application Publication No. 2014/0246479;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Patent Application Publication No. 2014/0246473; and U.S. patent application Ser. No. 13/782,536, entitled SURGICAL INSTRUMENT SOFT STOP, now U.S. Patent Application Publication No. 2014/0246476.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE, now U.S. Patent Application Publication No. 2014/0263542;

U.S. patent application Ser. No. 13/803,193, entitled CONTROL ARRANGEMENTS FOR A DRIVE MEMBER OF A SURGICAL INSTRUMENT, now U.S. Patent Application Publication No. 2014/0263537;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Patent Application Publication No. 2014/0263538;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Patent Application Publication No. 2014/0263565;

U.S. patent application Ser. No. 13/803,117, entitled ARTICULATION CONTROL SYSTEM FOR ARTICULATABLE SURGICAL INSTRUMENTS, now U.S. Patent Application Publication No. 2014/0263553;

U.S. patent application Ser. No. 13/803,130, entitled DRIVE TRAIN CONTROL ARRANGEMENTS FOR MODULAR SURGICAL INSTRUMENTS, now U.S. Patent Application Publication No. 2014/0263543; and U.S. patent application Ser. No. 13/803,159, entitled METHOD AND SYSTEM FOR OPERATING A SURGICAL INSTRUMENT, now U.S. Patent Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Patent Application Publication No. 2014/0263539.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Patent Application Publication No. 2015/0272581;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Patent Application Publication No. 2015/0272574;

U.S. patent application Ser. No. 14/226,075, entitled MODULAR POWERED SURGICAL INSTRUMENT WITH DETACHABLE SHAFT ASSEMBLIES, now U.S. Patent Application Publication No. 2015/0272579;

U.S. patent application Ser. No. 14/226,093, entitled FEEDBACK ALGORITHMS FOR MANUAL BAILOUT SYSTEMS FOR SURGICAL INSTRUMENTS, now U.S. Patent Application Publication No. 2015/0272569;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Patent Application Publication No. 2015/0272578;

U.S. patent application Ser. No. 14/226,097, entitled SURGICAL INSTRUMENT COMPRISING INTERACTIVE SYSTEMS, now U.S. Patent Application Publication No. 2015/0272570;

U.S. patent application Ser. No. 14/226,126, entitled INTERFACE SYSTEMS FOR USE WITH SURGICAL INSTRUMENTS, now U.S. Patent Application Publication No. 2015/0272572;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Patent Application Publication No. 2015/0277471;

U.S. patent application Ser. No. 14/226,076, entitled POWER MANAGEMENT THROUGH SEGMENTED CIRCUIT AND VARIABLE VOLTAGE PROTECTION, now U.S. Patent Application Publication No. 2015/0280424;

U.S. patent application Ser. No. 14/226,111, entitled SURGICAL STAPLING INSTRUMENT SYSTEM, now U.S. Patent Application Publication No. 2015/0272583; and U.S. patent application Ser. No. 14/226,125, entitled SURGICAL INSTRUMENT COMPRISING A ROTATABLE SHAFT, now U.S. Patent Application Publication No. 2015/0280384.

Applicant of the present application also owns the following patent applications that were filed on Sep. 5, 2014 and which are each herein incorporated by reference in their respective entireties:

U.S. patent application Ser. No. 14/479,103, entitled CIRCUITRY AND SENSORS FOR POWERED MEDICAL DEVICE, now U.S. Patent Application Publication No. 2016/0066912;

U.S. patent application Ser. No. 14/479,119, entitled ADJUNCT WITH INTEGRATED SENSORS TO QUANTIFY TISSUE COMPRESSION, now U.S. Patent Application Publication No. 2016/0066914;

U.S. patent application Ser. No. 14/478,908, entitled MONITORING DEVICE DEGRADATION BASED ON COMPONENT EVALUATION, now U.S. Patent Application Publication No. 2016/0066910;

U.S. patent application Ser. No. 14/478,895, entitled MULTIPLE SENSORS WITH ONE SENSOR AFFECTING A SECOND SENSOR'S OUTPUT OR INTERPRETATION, now U.S. Patent Application Publication No. 2016/0066909;

U.S. patent application Ser. No. 14/479,110, entitled USE OF POLARITY OF HALL MAGNET DETECTION TO DETECT MISLOADED CARTRIDGE, now U.S. Patent Application Publication No. 2016/0066915;

U.S. patent application Ser. No. 14/479,098, entitled SMART CARTRIDGE WAKE UP OPERATION AND DATA RETENTION, now U.S. Patent Application Publication No. 2016/0066911;

U.S. patent application Ser. No. 14/479,115, entitled MULTIPLE MOTOR CONTROL FOR POWERED MEDICAL DEVICE, now U.S. Patent Application Publication No. 2016/0066916; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entireties:

U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;

U.S. patent application Ser. No. 14/248,581, entitled SURGICAL INSTRUMENT COMPRISING A CLOSING DRIVE AND A FIRING DRIVE OPERA l'ED FROM THE SAME ROTATABLE OUTPUT, now U.S. Patent Application Publication No. 2014/0305989;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;

U.S. patent application Ser. No. 14/248,587, entitled POWERED SURGICAL STAPLER, now U.S. Patent Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entireties:

U.S. Provisional patent application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIG. 1 depicts a motor-driven surgical system 10 that may be used to perform a variety of different surgical procedures. In the illustrated embodiment, the motor driven surgical system 10 comprises a selectively reconfigurable housing or handle assembly 20 that is attached to one form of an interchangeable surgical tool assembly 1000. For example, the system 10 that is depicted in FIG. 1 includes an interchangeable surgical tool assembly 1000 that comprises a surgical cutting and fastening instrument which may be referred to as an endocutter. As will be discussed in further detail below, the interchangeable surgical tool assemblies may include end effectors that are adapted to support different sizes and types of staple cartridges and, have different shaft lengths, sizes, and types, etc. Such arrangements, for example, may utilize any suitable fastener, or fasteners, to fasten tissue. For instance, a fastener cartridge comprising a plurality of fasteners removably stored therein can be removably inserted into and/or attached to the end effector of a surgical tool assembly. Other surgical tool assemblies may be interchangeably employed with the handle assembly 20. For example, the interchangeable surgical tool assembly 1000 may be detached from the handle assembly 20 and replaced with a different surgical tool assembly that is configured to perform other surgical procedures. In other arrangements, the surgical tool assembly may not be interchangeable with other surgical tool assemblies and essentially comprise a dedicated shaft that is non-removably affixed or coupled to the handle assembly 20, for example. The surgical tool assemblies may also be referred to as elongate shaft assemblies. The surgical tool assemblies may be reusable or, in other configurations, the surgical tool assemblies may be designed to be disposed of after a single use.

As the present Detailed Description proceeds, it will be understood that the various forms of interchangeable surgical tool assemblies disclosed herein may also be effectively employed in connection with robotically-controlled surgical systems. Thus, the terms "housing" and "housing assembly" may also encompass a housing or similar portion of a robotic system that houses or otherwise operably supports at least one drive system that is configured to generate and apply at least one control motion which could be used to actuate the elongate shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operably control a surgical instrument. For example, the surgical tool assemblies disclosed herein may be employed with various robotic systems, instruments, components and methods such as, but not limited to, those disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719 which is hereby incorporated by reference herein in its entirety.

Figure 2:
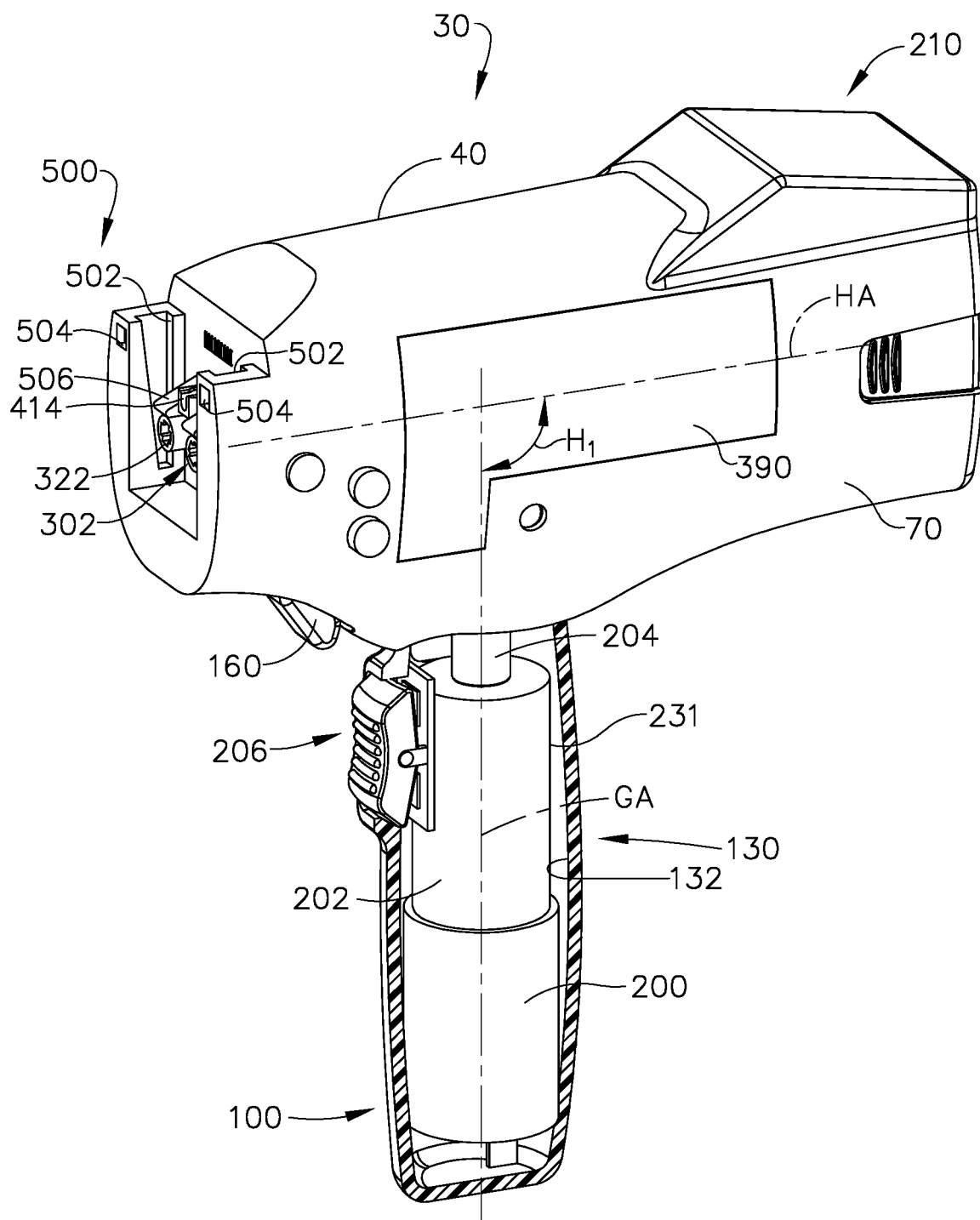
FIG. 2 is another perspective view of a handle assembly of the surgical instrument of FIG. 1, with a portion of the handle housing omitted to expose components housed therein.

Referring now to FIGS. 1 and 2, the housing assembly or handle assembly 20 comprises a primary housing portion 30 that may be formed from a pair of housing segments 40, 70 that may be fabricated from plastic, polymer materials, metal, etc. and be joined together by an appropriate fastener arrangement such as, for example, adhesive, screws, press-fit features, snap-fit features, latches, etc. As will be discussed in further detail below, the primary housing portion 30 operably supports a plurality of drive systems therein that are configured to generate and apply various control motions to corresponding portions of the interchangeable surgical tool assembly that is operably attached thereto. The handle assembly 20 further comprises a grip portion 100 that is movably coupled to the primary housing portion 30 and is configured to be gripped and manipulated by the clinician in various positions relative to the primary housing portion 30.

The grip portion 100 may be fabricated from a pair of grip segments 110, 120 that may be fabricated from plastic, polymer materials, metal, etc. and are joined together by an appropriate fastener arrangement such as, for example, adhesive, screws, press-fit features, snap-fit features, latches, etc. for assembly and maintenance purposes.

Figure 5:
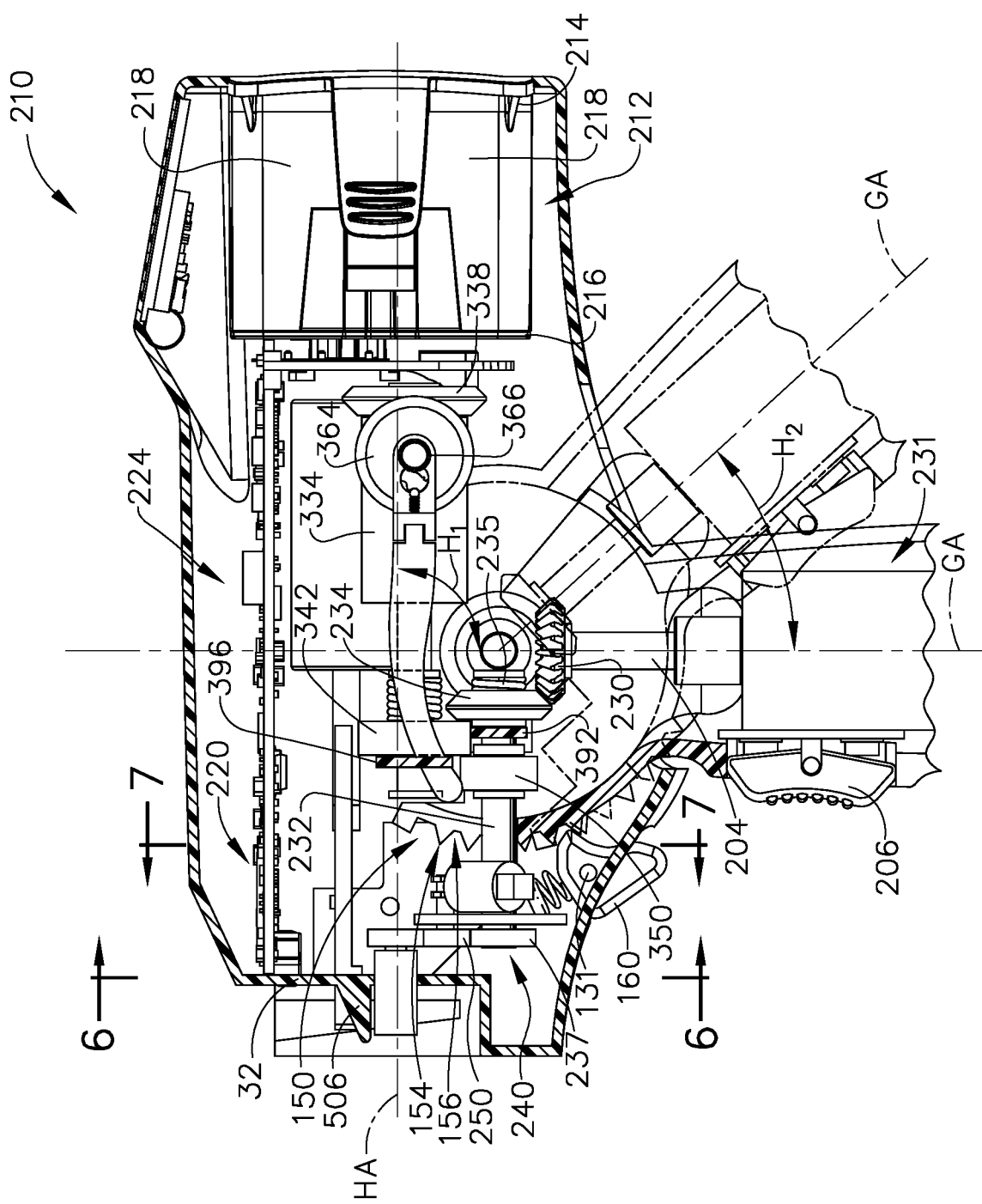
FIG. 5 is a partial cross-sectional side view of the handle assembly of FIGS. 2-4 with a grip portion of the handle assembly shown in solid lines in one position relative to a primary housing portion and in phantom lines in another position relative to the primary housing portion of the handle assembly.

As can be seen in FIG. 2, the grip portion 100 comprises a grip housing 130 that defines a hollow cavity 132 that is configured to operably support a drive motor and gearbox which will be discussed in further detail below. The upper portion 134 of the grip housing 130 is configured to extend through an opening 80 in the primary housing portion 30 and be pivotally journaled on a pivot shaft 180. The pivot shaft 180 defines a pivot axis designated as "PA". See FIG. 3. For reference purposes, the handle assembly 20 defines a handle axis designated as "HA" that may be parallel to the shaft axis "SA" of the elongate shaft assembly of the interchangeable surgical tool that is operably attached to the handle assembly 20. The pivot axis PA is transverse to the handle axis HA. See FIG. 1. Such arrangement enables the grip portion 100 to be pivoted relative to the primary housing portion 30 about the pivot axis PA to a position that is best suited for the type of interchangeable surgical tool assembly that is coupled to the handle assembly 20. The grip housing 130 defines a grip axis, generally designated as "GA". See FIG. 2. When the interchangeable surgical tool assembly that is coupled to the handle assembly 20 comprises an endocutter for example, the clinician might want to position the grip portion 100 relative to the primary housing portion 30 such that the grip axis GA is perpendicular or approximately perpendicular (angle "H1") to the handle axis HA (referred to herein as a "first grip position"). See FIG. 5. However, if the handle assembly 20 is being used to control an interchangeable surgical tool assembly that comprises a circular stapler for example, the clinician may wish to pivot the grip portion 100 relative to the primary housing portion 30 to a position wherein the grip axis GA is at a forty-five degree or approximately forty-five degree angle or other suitable acute angle (angle "H2") relative to the handle axis HA. This position is referred to herein as a "second grip position". FIG. 5 illustrates the grip portion 100 in phantom lines in the second grip position.

Figure 3:
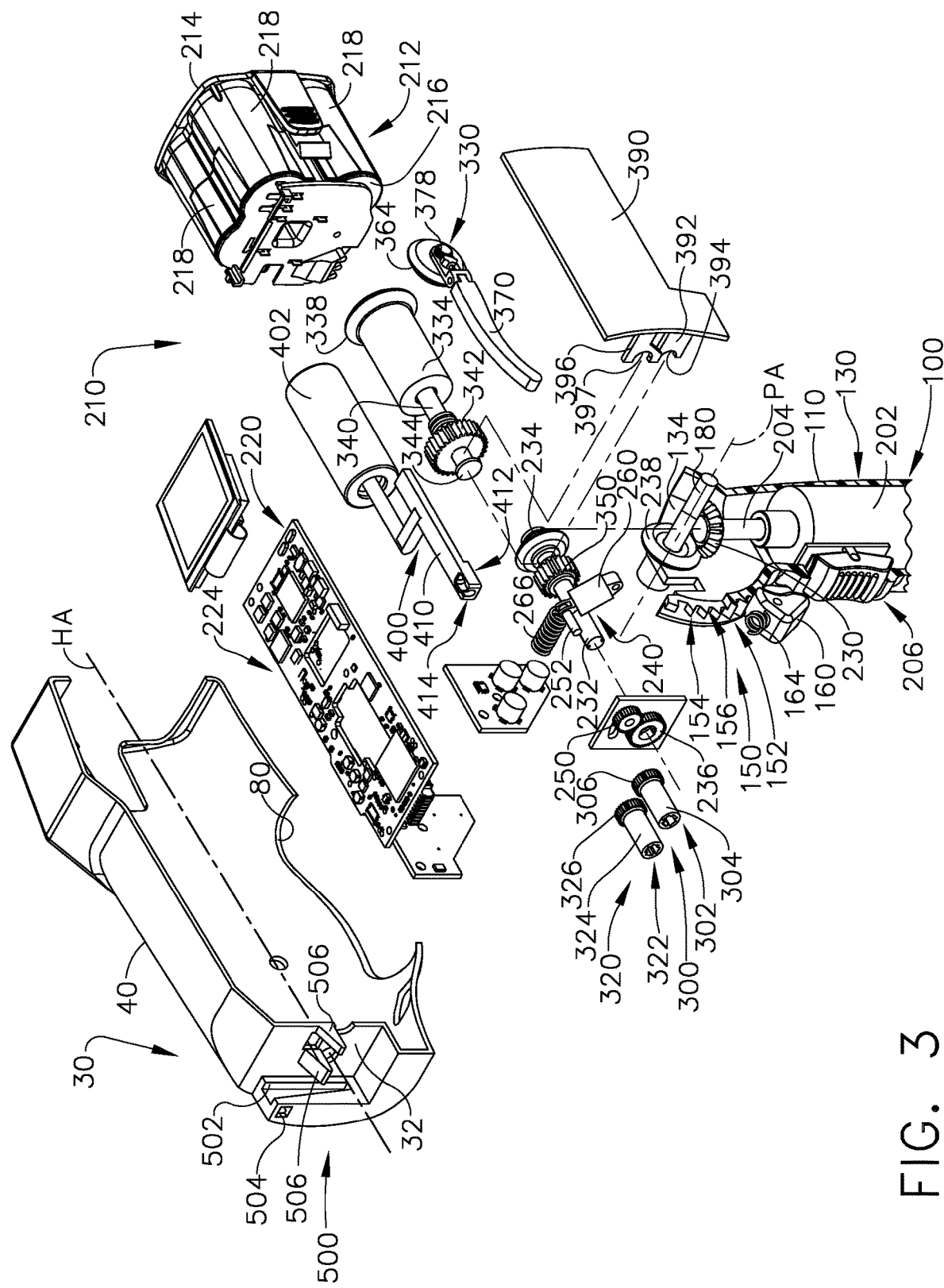
FIG. 3 is an exploded assembly view of portions of the handle assembly of the surgical instrument of FIGS. 1 and 2.
Figure 4:
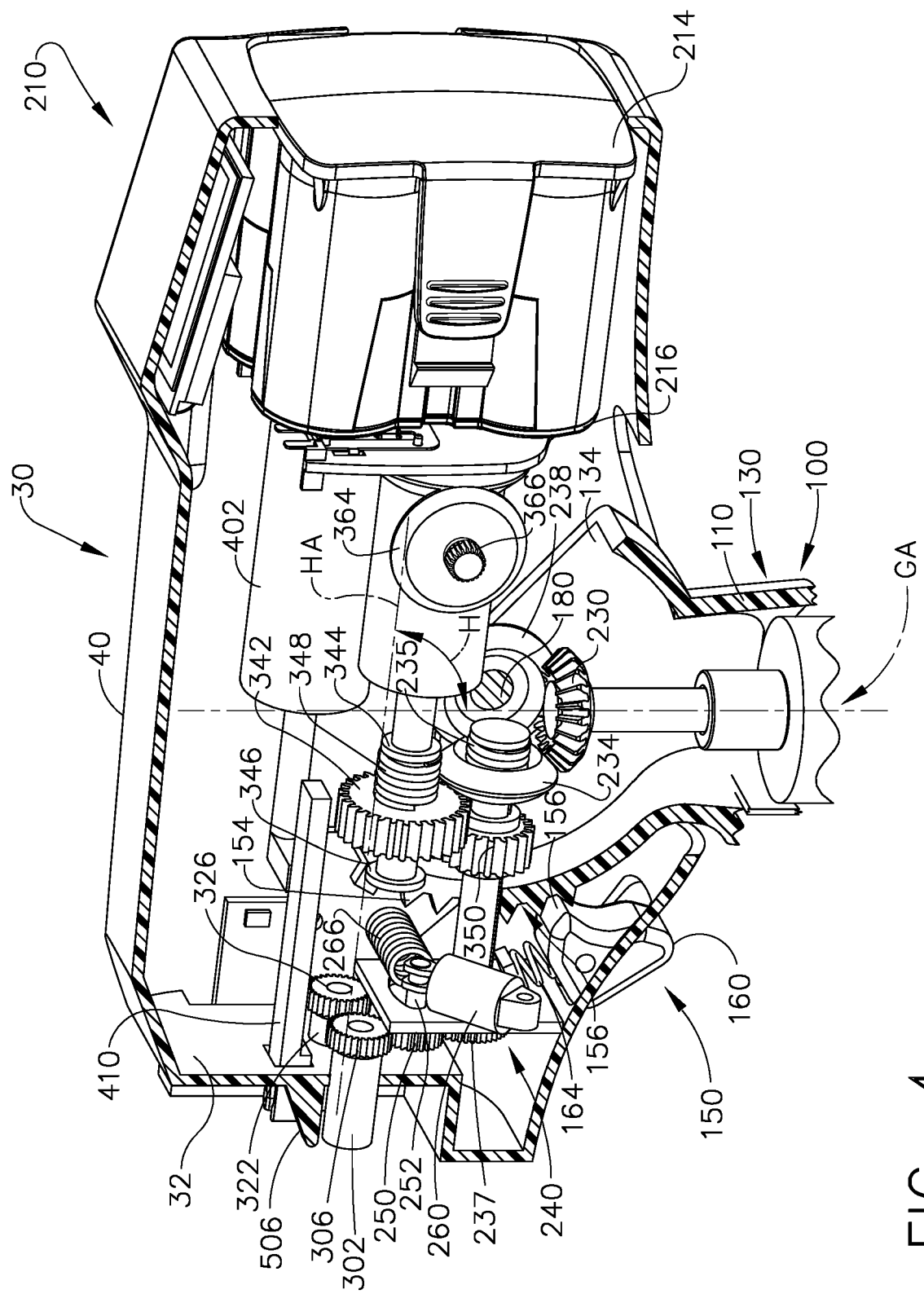
FIG. 4 is a cross-sectional perspective view of the handle assembly of FIGS. 2 and 3.

Referring now to FIGS. 3-5, the handle assembly 20 also includes a grip locking system, generally designated as 150, for selectively locking the grip portion 100 in the desired orientation relative to the primary housing portion 30. In one arrangement, the grip locking system 150 comprises an arcuate series 152 of pointed teeth 154. The teeth 154 are spaced from each other and form a locking groove 156 therebetween. Each locking groove 156 corresponds to a particular angular locking position for the grip portion 100. For example, in at least one arrangement, the teeth 154 and locking grooves or "locking locations" 156 are arranged to permit the grip portion 100 to be locked at 10-15 degree intervals between the first grip position and the second grip position. The arrangement may employ two stop positions which are tailored to the type of instrument (shaft arrangement) employed. For example, for an endocutter shaft arrangement, it may be approximately around ninety degrees to the shaft and for a circular stapler arrangement, the angle may be approximately forty-five degrees to the shaft while being swept forward towards the surgeon. The grip locking system 150 further includes a locking button 160 that has a locking portion that is configured to lockingly engage the locking grooves 156. For example, the locking button 160 is pivotally mounted in the primary handle portion 30 on a pivot pin 131 to permit the locking button 160 to pivot into engagement with a corresponding locking groove 156. A locking spring 164 serves to bias the locking button 160 into an engaged or locked position with the corresponding locking groove 156. The locking portion and the teeth configurations serve to enable the teeth 154 to slide past the locking portion when the clinician depresses the locking button 160. Thus, to adjust the angular position of the grip portion 100 relative to the primary housing portion 30, the clinician depresses the locking button 160 and then pivots the grip portion 100 to the desired angular position. Once the grip portion 100 has been moved to the desired position, the clinician releases the locking button 160. The locking spring 164 will then bias the locking button 160 toward the series of teeth 154 so that the locking portion enters the corresponding locking groove 156 to retain the grip portion 100 in that position during use.

The handle assembly 20 operably supports a first rotary drive system 300, a second rotary drive system 320 and a third axial drive system 400. The rotary drive systems 300, 320 are each powered by a motor 200 that is operably supported in the grip portion 100. As can be seen in FIG. 2, for example, the motor 200 is supported within the cavity 132 in the grip portion 100 and has a gear box assembly 202 that has an output drive shaft 204 protruding therefrom. In various forms, the motor 200 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 200 may be powered by a power source 210 that, in one form, may comprise a removable power pack 212. The power source 210 may comprise, for example, anyone of the various power source arrangements disclosed in further detail in U.S. Patent Application Publication No. 2015/0272575 and entitled SURGICAL INSTRUMENT COMPRISING A SENSOR SYSTEM, the entire disclosure of which is hereby incorporated by reference herein. In the illustrated arrangement, for example, the power pack 212 may comprise a proximal housing portion 214 that is configured for attachment to a distal housing portion 216. The proximal housing portion 214 and the distal housing portion 216 are configured to operably support a plurality of batteries 218 therein. Batteries 218 may each comprise, for example, a Lithium Ion ("LI") or other suitable battery. The distal housing portion 216 is configured for removable operable attachment to a handle circuit board assembly 220 which is also operably coupled to the motor 200. The handle circuit board assembly 220 may also be generally referred to herein as the "control system or CPU 224". A number of batteries 218 may be connected in series may be used as the power source for the handle assembly 20. In addition, the power source 210 may be replaceable and/or rechargeable. In other embodiments, the surgical instrument 10 may be powered by alternating current (AC) for example. The motor 200 may be controlled by a rocker switch 206 that is mounted to the grip portion 100.

Figure 14:
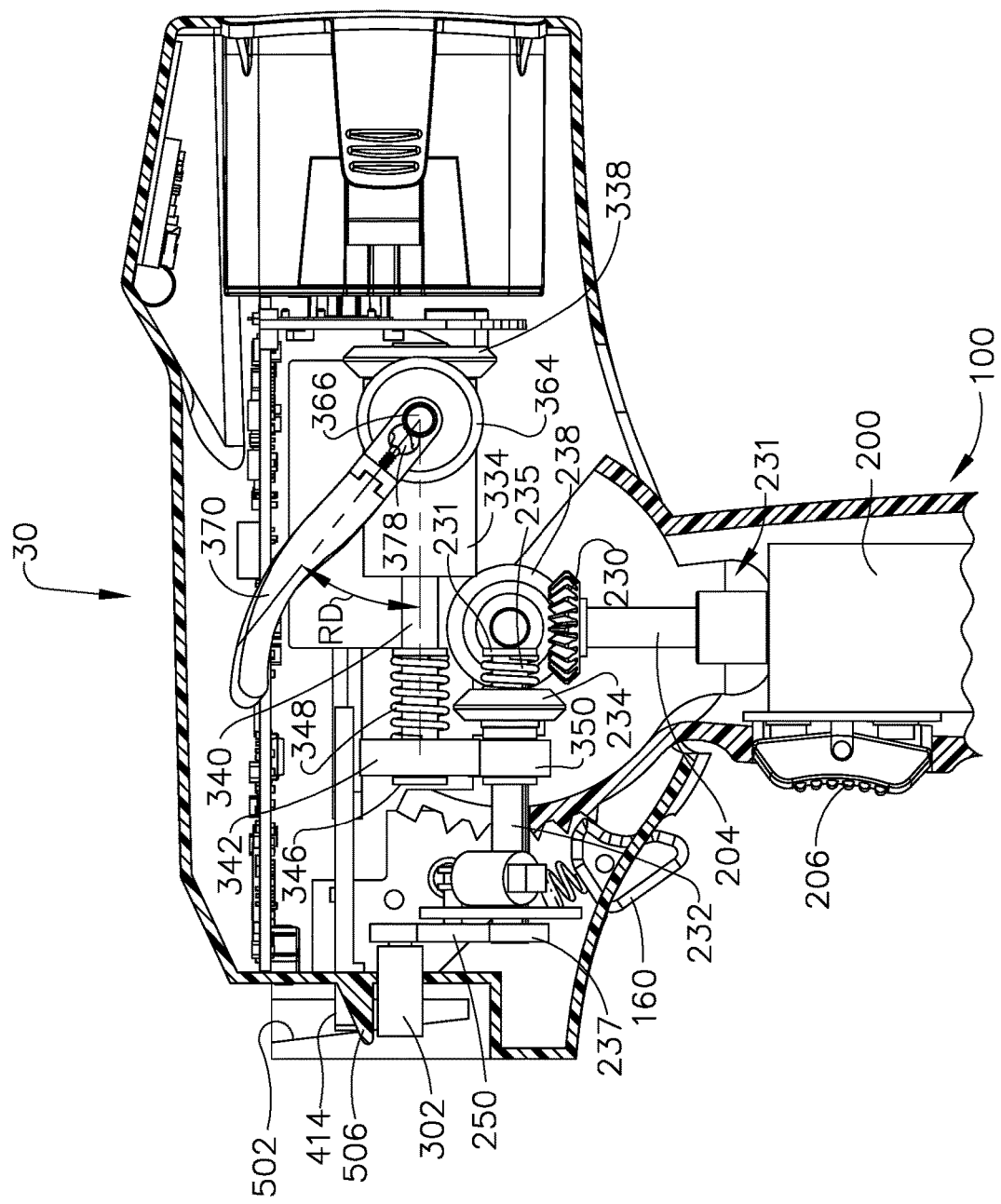
FIG. 14 is a cross-sectional elevation view of the handle assembly of FIG. 11.

As outlined above, the motor 200 is operably coupled to a gear box assembly 202 that includes an output drive shaft 204. Attached to the output drive shaft 204 is a driver bevel gear 230. The motor 200, the gear box assembly 202, the output drive shaft 204 and the driver bevel gear 230 may also be collectively referred to herein as a "motor assembly 231". The driver bevel gear 230 interfaces with a driven bevel gear 234 that is attached to a system drive shaft 232 as well as a pivot bevel gear 238 that is journaled on the pivot shaft 180. The driven bevel gear 234 is axially movable on the system drive shaft 232 between an engaged position wherein the driven bevel gear 234 is in meshing engagement with the driver bevel gear 230 (FIG. 5) and a disengaged position wherein the driven bevel gear 234 is out of meshing engagement with the drive bevel gear 230 (FIG. 14). A drive system spring 235 is journaled between the driven bevel gear 234 and a proximal end flange 236 that is formed on a proximal portion of the system drive shaft 232. See FIGS. 4 and 14. The drive system spring 235 serves to bias the driven bevel gear 234 out of meshing engagement with the driver bevel gear 230 as will be discussed in further detail below. The pivot bevel gear 238 facilitates pivotal travel of the output drive shaft 204 and driver bevel gear 230 with the grip portion 100 relative to the primary handle portion 30.

In the illustrated example, the system drive shaft 232 interfaces with a rotary drive selector system, generally designated as 240. In at least one form, for example, the rotary drive selector system 240 comprises a shifter gear 250 that is selectively movable between the first rotary drive system 300 and the second rotary drive system 320. As can be seen in FIGS. 6-9, for example, the drive selector system 240 comprises a shifter mounting plate 242 that is non-movably mounted within primary handle portion 30. For example, the shifter mounting plate 242 may be frictionally retained between mounting lugs (not shown) formed in the housing segments 40, 70 or be otherwise retained therein by screws, adhesive, etc. Still referring to FIGS. 6-9, the system drive shaft 232 extends through a hole in the shifter mounting plate 242 and has the central, or system, drive gear 237 non-rotatably attached thereto. For example the central drive gear 237 may be attached to the system drive shaft 232 by a keyway arrangement 233. See FIGS. 6-9. In other arrangements, the system drive shaft 232 may be rotatably supported in the shifter mounting plate 242 by a corresponding bearing (not shown) that is mounted thereto. In any event, rotation of the system drive shaft 232 will result in rotation of the central drive gear 234.

As can be seen in FIG. 3, the first drive system 300 includes a first drive socket 302 that is rotatably supported in a distal wall 32 formed in the primary handle portion 30. The first drive socket 302 may comprise a first body portion 304 that has a splined socket formed therein. A first driven gear 306 is formed on or is non-movably attached to the first body portion 304. The first body portion 304 may be rotatably supported in a corresponding hole or passage provided the distal wall 32 or it may be rotatably supported in a corresponding bearing (not shown) that is mounted in the distal wall 32. Similarly, the second rotary drive system 320 includes a second drive socket 322 that is also rotatably supported in the distal wall 32 of the primary handle portion 30. The second drive socket 322 may comprise a second body portion 324 that has a splined socket formed therein. A second driven gear 326 is formed on or is non-rotatably mounted to the second body portion 324. The second body portion 324 may be rotatably supported in a corresponding hole or passage provided the distal wall 32 or it may be rotatably supported in a corresponding bearing (not shown) that is mounted in the distal wall 32. The first and second drive sockets 302, 322 are spaced from each other on each lateral side of the handle axis HA. See FIG. 4, for example.

As indicated above, in the illustrated example, the rotary drive selector system 240 includes a shifter gear 250. As can be seen in FIGS. 6-9, the shifter gear 250 is rotatably mounted on an idler shaft 252 that is movably supported in an arcuate slot 244 in the shifter mounting plate 242. The shifter gear 250 is mounted so as to freely rotate on the idler shaft 252 and remain in meshing engagement with the central drive gear 234. The idler shaft 252 is coupled to an end of a shaft 262 of a shifter solenoid 260. The shifter solenoid 260 is pinned or otherwise mounted with the primary handle housing 30 such that when the shifter solenoid 260 is actuated, the shifter gear 250 is moved into meshing engagement with one of the first driven gear 306 or the second driven gear 326. For example, in one arrangement, when the solenoid shaft is 262 is retracted (FIGS. 6 and 7), the shifter gear 250 is in meshing engagement with the central drive gear 234 and the first driven gear 306 such that actuation of the motor 200 will result in rotation of the first drive socket 302. As can be seen in FIGS. 6 and 7, a shifter spring 266 may be employed to bias the shifter gear 250 into that first actuation position. Thus, should power be lost to the surgical instrument 10, the shifter spring 266 will automatically bias the shifter gear 250 into the first position. When the shifter gear 250 is in that position, subsequent actuation of the motor 200 will result in rotation of the first drive socket 302 of the first rotary drive system 300. When the shifter solenoid is actuated, the shifter gear 250 is moved into meshing engagement with the second driven gear 326 on the second drive socket 322. Thereafter, actuation of the motor 200 will result in actuation or rotation of the second drive socket 322 of the second rotary drive system 320.

As will be discussed in further detail below, the first and second rotary drive systems 300, 320 may be used to power various component portions of the interchangeable surgical tool assembly that is coupled thereto. As indicated above, in at least one arrangement, if during the actuation of the interchangeable surgical tool assembly, power was lost to the motor, the shifter spring 266 will bias the shifter gear 250 to the first position. Depending upon which component portion of the interchangeable surgical tool assembly was being operated, it may be necessary to reverse the application of the rotary drive motion to the first drive system 300 to enable the interchangeable surgical tool assembly to be removed from the patient. The handle assembly 20 of the illustrated example employs a manually actuatable "bailout" system, generally designated as 330, for manually applying a rotary drive motion to the first rotary drive system 300 in the above described scenario, for example.

Figure 10:
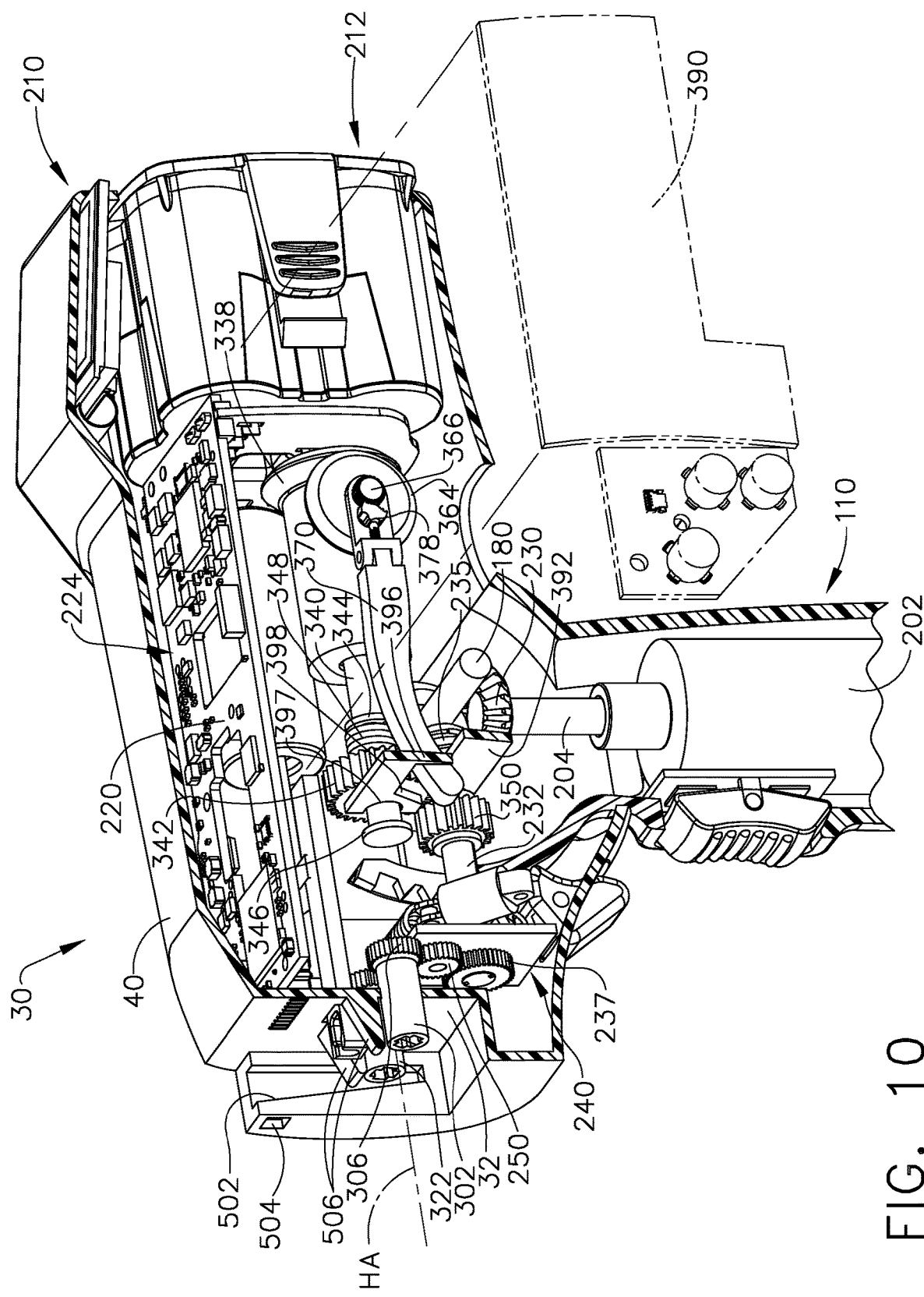
FIG. 10 is another perspective view of the handle assembly of FIGS. 2-9 with certain portions thereof shown in cross-section and with an access panel portion thereof shown in phantom.
Figure 11:
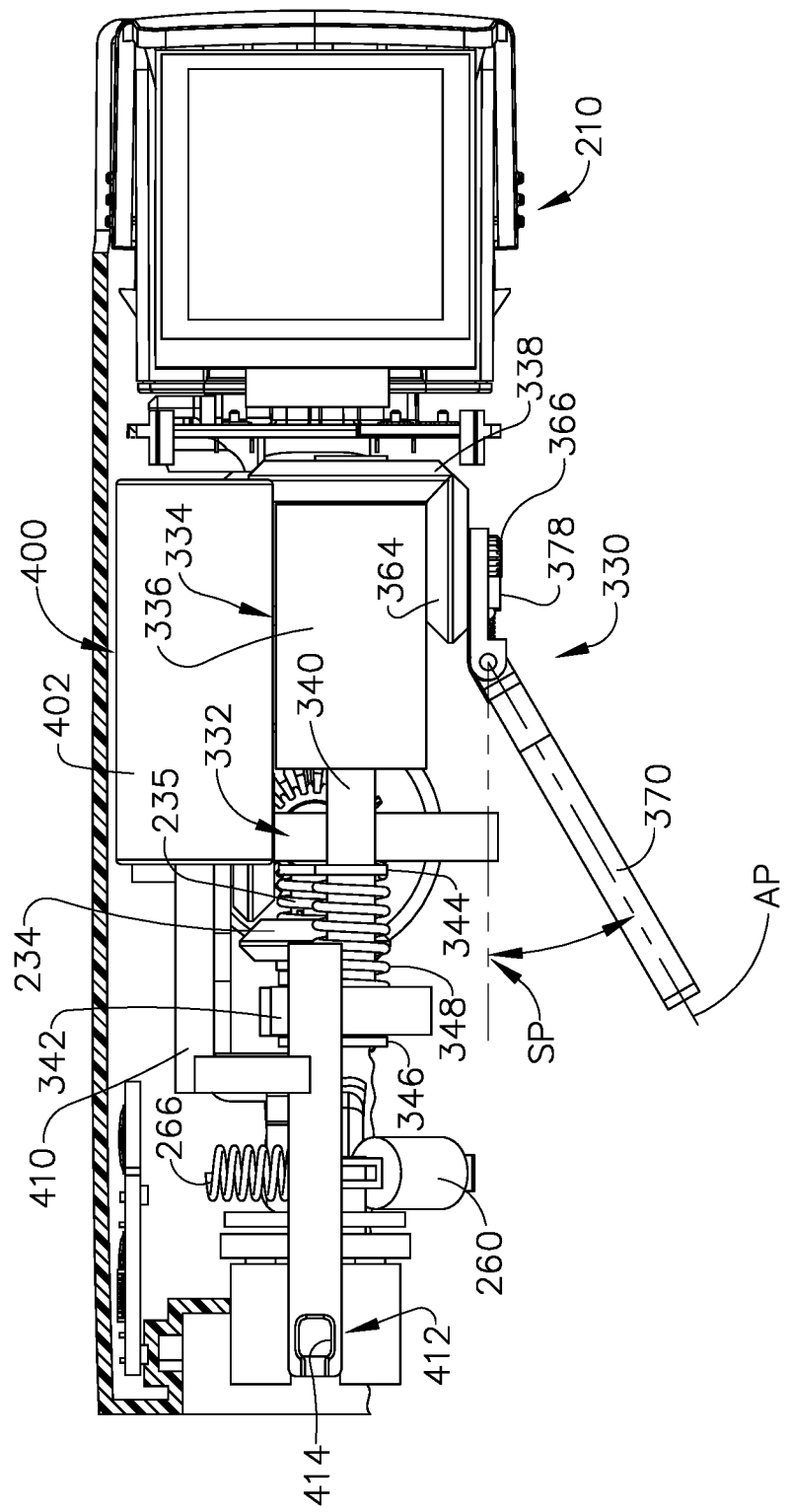
FIG. 11 is a top view of the handle assembly of FIGS. 2-11 with a bailout system shown in an actuatable position.

Referring now to FIGS. 3, 10 and 11, the illustrated bailout system 330 comprises a bailout drive train 332 that includes a planetary gear assembly 334. In at least one form, the planetary gear assembly 334 includes a planetary gear housing 336 that houses a planetary gear arrangement (not shown) that includes a planetary bevel gear 338. The planetary gear assembly 334 includes a bailout drive shaft 340 that is operably coupled to the planetary gear arrangement within the planetary gear housing 336. Rotation of the planetary bevel gear 338 rotates the planetary gear arrangement which ultimately rotates the bailout drive shaft 340. A bailout drive gear 342 is journaled on the bailout drive shaft 340 so that the bailout drive gear 342 can move axially on the bailout drive shaft 340, yet rotate therewith. The bailout drive gear 342 is movable between a spring stop flange 344 that is formed on the bailout drive shaft 340 and a shaft end stop 346 that is formed on the distal end of the bailout drive shaft 340. A bailout shaft spring 348 is journaled on the bailout drive shaft 340 between the bailout drive gear 342 and the spring stop flange 344. The bailout shaft spring 348 biases the bailout drive gear 342 distally on the bailout drive shaft 340. When the bailout drive gear 342 is in its distal-most position on the bail out drive shaft 340, it is in meshing engagement with a bailout driven gear 350 that is non-rotatably mounted to the system drive shaft 232. See FIG. 14.

Figure 12:
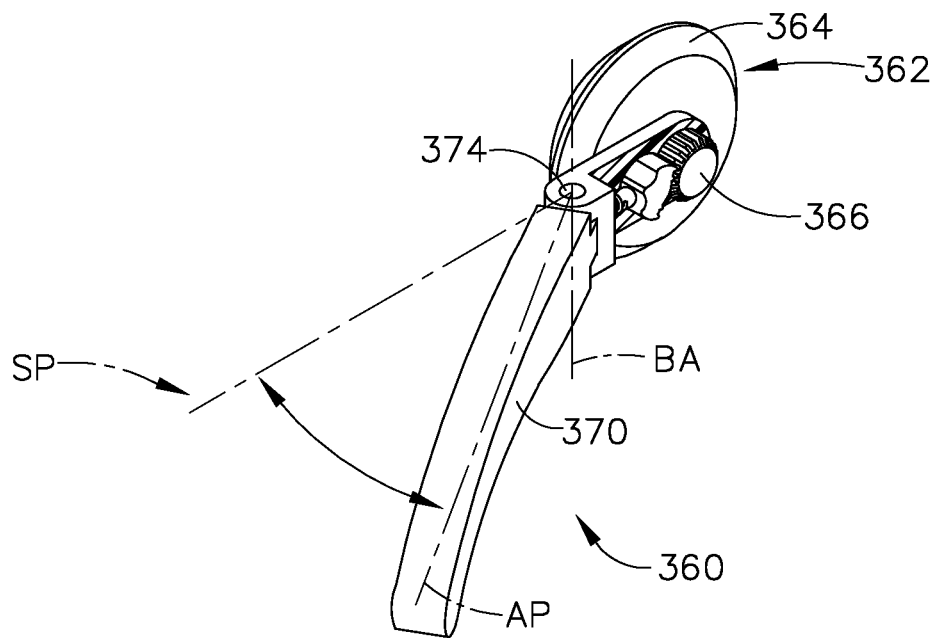
FIG. 12 is a perspective view of a bailout handle of the bailout system depicted in FIGS. 2-11.
Figure 13:
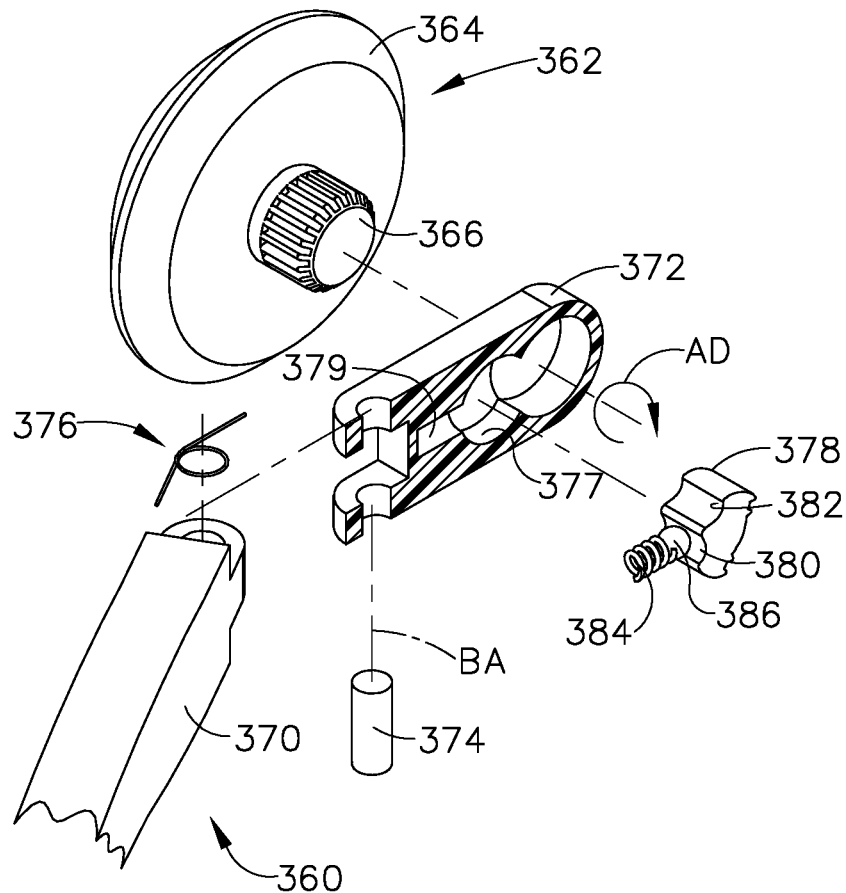
FIG. 13 is an exploded assembly view of portions of the bailout handle of FIG. 12 with portions thereof shown in cross-section.

Referring now to FIGS. 12 and 13, the bailout system 330 includes a bailout actuator assembly or bailout handle assembly 360 that facilitates the manual application of a bailout drive motion to the bailout drive train 332. As can be seen in those Figures, the bailout handle assembly 360 includes a bailout bevel gear assembly 362 that comprises a bailout bevel gear 364 and a ratchet gear 366. The bailout handle assembly 360 further includes a bailout handle 370 that is movably coupled to the bailout bevel gear assembly 362 by a pivot yoke 372 that is pivotally mounted on the ratchet gear 366. The bailout handle 370 is pivotally coupled to the pivot yoke 372 by a pin 374 for selective pivotal travel between a stored position "SP" and an actuation position "AP". See FIG. 12. A handle spring 376 is employed to bias the bailout handle 370 into the actuation position AP. In at least one arrangement, the angle between the axis SP representing the stored position and the axis AP representing the actuation position may be approximately thirty degrees, for example. See FIG. 13. As can also be seen in FIG. 13, the bailout handle assembly 360 further includes a ratchet pawl 378 that is rotatably mounted in a cavity or hole 377 in the pivot yoke 372. The ratchet pawl 378 is configured to meshingly engage the ratchet gear 366 when rotated in an actuation direction "AD" and then rotate out of meshing engagement when rotated in the opposite direction. A ratchet spring 384 and ball member 386 are movably supported in a cavity 379 in the pivot yoke 372 and serve to lockingly engage detents 380, 382 in the ratchet pawl 378 as the bailout handle 370 is actuated (ratcheted).

Referring now to FIGS. 3 and 10, the bailout system 330 further includes a bailout access panel 390 that is maneuverable between an open position and a closed position. In the illustrated arrangement, the bailout access panel 390 is configured to be removably coupled to the housing segment 70 of the primary housing portion 30. Thus, in at least that embodiment, when the bailout access panel 390 is removed or detached from the primary housing portion 30, it is said to be in an "open" position and when the bailout access panel 390 is attached to the primary housing portion 30 as illustrated, it is said to be in a "closed" position. Other embodiments are contemplated, however, wherein the access panel is movably coupled to the primary housing portion such that when the access panel is in the open position, it remains attached thereto. For example, in such embodiments, the access panel may be pivotally attached to the primary housing portion or slidably attached to the primary housing portion and be maneuverable between an open position and a closed position. In the illustrated example, the bailout access panel 390 is configured to snappingly engage corresponding portions of the housing segment 70 to removably retain it in a "closed" position. Other forms of mechanical fasteners such as screws, pins, etc. could also be used.

Regardless of whether the bailout access panel 390 is detachable from the primary housing portion 30 or it remains movably attached to the primary housing portion 30, the bailout access panel 390 includes a drive system locking member or yoke 392 and a bailout locking member or yoke 396 that each protrudes out from the backside thereof or are otherwise formed thereon. The drive system locking yoke 392 includes a drive shaft notch 394 that is configured to receive a portion of the system drive shaft 232 therein when the bailout access panel 390 is installed in the primary housing portion 30 (i.e., the bailout access panel is in the "closed" position). When the bailout access panel 390 is positioned or installed in the closed position, the drive system locking yoke 392 serves to bias the driven bevel gear 234 into meshing engagement with the driver bevel gear 230 (against the bias of the drive system spring 235). In addition, the bailout locking yoke 396 includes a bailout drive shaft notch 397 that is configured to receive a portion of the bailout drive shaft 340 therein when the bailout access panel 390 is installed or positioned in the closed position. As can be seen in FIGS. 5 and 10, the bailout locking yoke 396 also serves to bias the bailout drive gear 342 out of meshing engagement with the bailout driven gear 350 (against the bias of the bailout shaft spring 348). Thus, the bailout locking yoke 396 prevents the bailout drive gear 342 from interfering with rotation of the system drive shaft 232 when the bailout access panel 390 is installed or in the closed position. In addition, the bailout locking yoke 396 includes a handle notch 398 for engaging the bailout handle 370 and retaining it in the stored position SP.

FIGS. 4, 5 and 10 illustrate the configurations of the drive system components and the bailout system components when the bailout access panel 390 is installed or is in the closed position. As can be seen in those Figures, the drive system locking member 392 biases the driven bevel gear 234 into meshing engagement with the driver bevel gear 230. Thus, when the bailout access panel 390 is installed or is in the closed position, actuation of the motor 200 will result in the rotation of the driver bevel gear 230 and ultimately the system drive shaft 232. Also, when in that position, the bailout locking yoke 396 serves to bias the bailout drive gear 342 out of meshing engagement with the bailout driven gear 350 on the system drive shaft 232. Thus, when the bailout access panel 390 is installed or is in the closed position, the drive system is actuatable by the motor 200 and the bailout system 330 is disconnected or prevented from applying any actuation motion to the system drive shaft 232. To activate the bailout system 330, the clinician first removes the bailout access panel 390 or otherwise moves the bailout access panel 390 to the open position. This action removes the drive system locking member 392 from engagement with the driven bevel gear 234 which thereby permits the drive system spring 235 to bias the driven bevel gear 234 out of meshing engagement with the driver bevel gear 230. In addition, removal of the bailout access panel 390 or movement of the bailout access panel to an open position also results in the disengagement of the bailout locking yoke 396 with the bailout drive gear 342 which thereby permits the bailout shaft spring 348 to bias the bailout drive gear 342 into meshing engagement with the bailout driven gear 350 on the system drive shaft 232. Thus, rotation of the bailout drive gear 342 will result in rotation of the bailout driven gear 350 and the system drive shaft 232. Removal of the bailout access panel 390 or otherwise movement of the bailout access panel 390 to an open position also permits the handle spring 376 to bias the bailout handle 370 into the actuation position shown in FIGS. 11 and 14. When in that position, the clinician can manually ratchet the bailout handle 370 in the ratchet directions RD which results in the rotation of the of the ratchet bevel gear 364 (in a clockwise direction in FIG. 14, for example) which ultimately results in the application of a retraction rotary motion to the system drive shaft 232 through the bailout drive train 332. The clinician may ratchet the bailout handle 370 a number of times until the system drive shaft 232 has been sufficiently rotated a number of times to retract a component of the surgical end effector portion of the surgical tool assembly that is attached to the handle assembly 20. Once the bailout system 330 has been sufficiently manually actuated, the clinician may then replace the bailout access panel 390 (i.e., return the bailout access panel 390 to the closed position) to thereby cause the drive system locking member 392 to bias the driven bevel gear 234 into meshing engagement with the driver bevel gear 230 and the bailout locking yoke 396 to bias the bailout drive gear 342 out of meshing engagement with the bailout driven gear 350. As was discussed above, should power be lost or interrupted, the shifter spring 266 will bias the shifter solenoid 260 into the first actuation position. As such, actuation of the bailout system 330 will result in the application of reversing or retraction motions to the first rotary drive system 300.

As discussed above, a surgical stapling instrument can comprise a manually-actuated bailout system configured to retract a staple firing drive, for example. In many instances, the bailout system may need to be operated and/or cranked more than one time to fully retract the staple firing drive. In such instances, the user of the stapling instrument may lose track of how many times they have cranked the bailout and/or otherwise become confused as to how much further the firing drive needs to be retracted. Various embodiments are envisioned in which the stapling instrument comprises a system configured to detect the position of a firing member of the firing drive, determine the distance in which the firing member needs to be retracted, and display that distance to the user of the surgical instrument.

In at least one embodiment, a surgical stapling instrument comprises one or more sensors configured to detect the position of the firing member. In at least one instance, the sensors comprise Hall Effect sensors, for example, and can be positioned in a shaft and/or end effector of the stapling instrument. The sensors are in signal communication with a controller of the surgical stapling instrument which is, in turn, in signal communication with a display on the surgical stapling instrument. The controller comprises a microprocessor configured to compare the actual position of the firing member to a datum, or reference, position—which comprises a fully retracted position of the firing member—and calculate the distance, i.e., the remaining distance, between the actual position of the firing member and the reference position.

Further to the above, the display comprises an electronic display, for example, and the controller is configured to display the remaining distance on the electronic display in any suitable manner. In at least one instance, the controller displays a progress bar on the display. In such instances, an empty progress bar can represent that the firing member is at the end of its firing stroke and a full progress bar can represent that the firing member has been fully retracted, for example. In at least one instance, 0% can represent that the firing member is at the end of its firing stroke and 100% can represent that the firing member has been fully retracted, for example. In certain instances, the controller is configured to display how many actuations of the bailout mechanism are required to retract the firing member to its fully retracted position on the display.

Further to the above, the actuation of the bailout mechanism can operably disconnect a battery, or power source, of the surgical stapling instrument from an electric motor of the firing drive. In at least one embodiment, the actuation of the bailout mechanism flips a switch which electrically decouples the battery from the electric motor. Such a system would prevent the electric motor from resisting the manual retraction of the firing member.

The illustrated handle assembly 20 also supports a third axial drive system that is generally designated as 400. As can be seen in FIGS. 3 and 4, the third axial drive system 400, in at least one form, comprises a solenoid 402 that has a third drive actuator member or rod 410 protruding therefrom. The distal end 412 of the third drive actuator member 410 has a third drive cradle or socket 414 formed therein for receiving a corresponding portion of a drive system component of an interchangeable surgical tool assembly that is operably attached thereto. The solenoid 402 is wired to or otherwise communicates with the handle circuit board assembly 220 and the control system or CPU 224. In at least one arrangement, the solenoid 402 is "spring loaded" such that when the solenoid 402 is unactuated, the spring component thereof biases the third drive actuator 410 back to an unactuated starting position.

As indicated above, the reconfigurable handle assembly 20 may be advantageously employed to actuate a variety of different interchangeable surgical tool assemblies. To that end, the handle assembly 20 includes a tool mounting portion that is generally designated as 500 for operably coupling an interchangeable surgical tool assembly thereto. In the illustrated example, the tool mounting portion 500 includes two inwardly facing dovetail receiving slots 502 that are configured to engage corresponding portions of a tool attachment module portion of the interchangeable surgical tool assembly. Each dovetail receiving slot 502 may be tapered or, stated another way, be somewhat V-shaped. The dovetail receiving slots 502 are configured to releasably receive corresponding tapered attachment or lug portions that are formed on a portion of the tool attachment nozzle portion of the interchangeable surgical tool assembly. Each interchangeable surgical tool assembly may also be equipped with a latching system that is configured to releasable engage corresponding retention pockets 504 that are formed in the tool mounting portion 500 of the handle assembly 20.

The various interchangeable surgical tool assemblies may have a "primary" rotary drive system that is configured to be operably coupled to or interface with the first rotary drive system 310 as well as a "secondary" rotary drive system that is configured to be operably coupled to or interface with the second rotary drive system 320. The primary and secondary rotary drive systems may be configured to provide various rotary motions to portions of the particular type of surgical end effector that comprises a portion of the interchangeable surgical tool assembly. To facilitate operable coupling of the primary rotary drive system to the first rotary drive system and the secondary rotary drive system to the second rotary drive system 320, the tool mounting portion 500 of the handle assembly 20 also includes a pair of insertion ramps 506 that are configured to bias portions of the primary and secondary rotary drive systems of the interchangeable surgical tool assembly distally during the coupling process so as to facilitate alignment and operable coupling of the primary rotary drive system to the first rotary drive system 300 on the handle assembly 20 and the secondary rotary drive system to the second rotary drive system 320 on the handle assembly 20.

The interchangeable surgical tool assembly may also include a "tertiary" axial drive system for applying axial motion(s) to corresponding portions of the surgical end effector of the interchangeable surgical tool assembly. To facilitate operable coupling of the tertiary axial drive system to the third axial drive system 400 on the handle assembly 20, the third drive actuator member 410 is provided with a socket 414 that is configured to operably receive a lug or other portion of the tertiary axial drive system therein.

Figure 15:
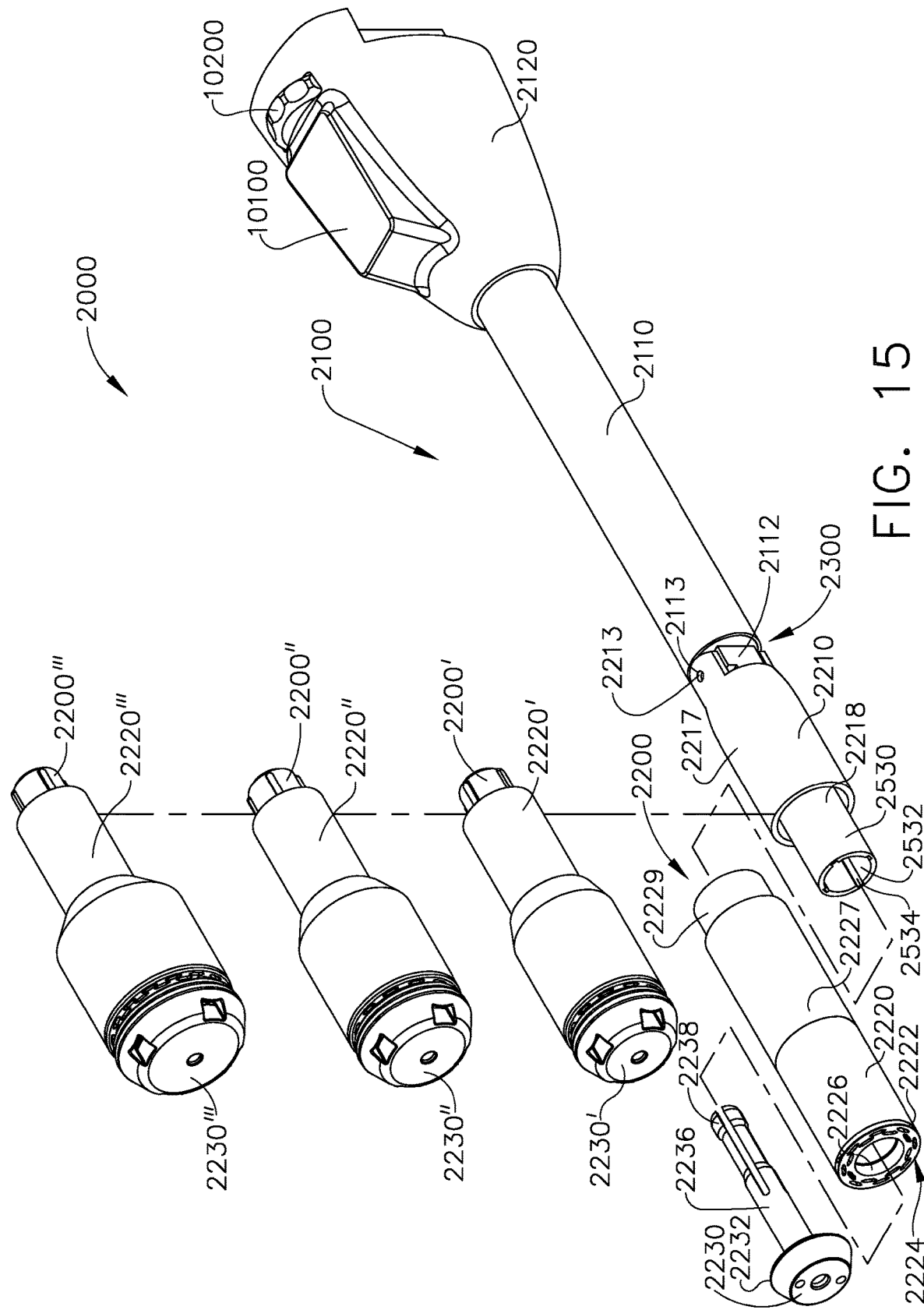
FIG. 15 illustrates an exploded view of an interchangeable tool assembly in accordance with at least one embodiment.
Figure 16:
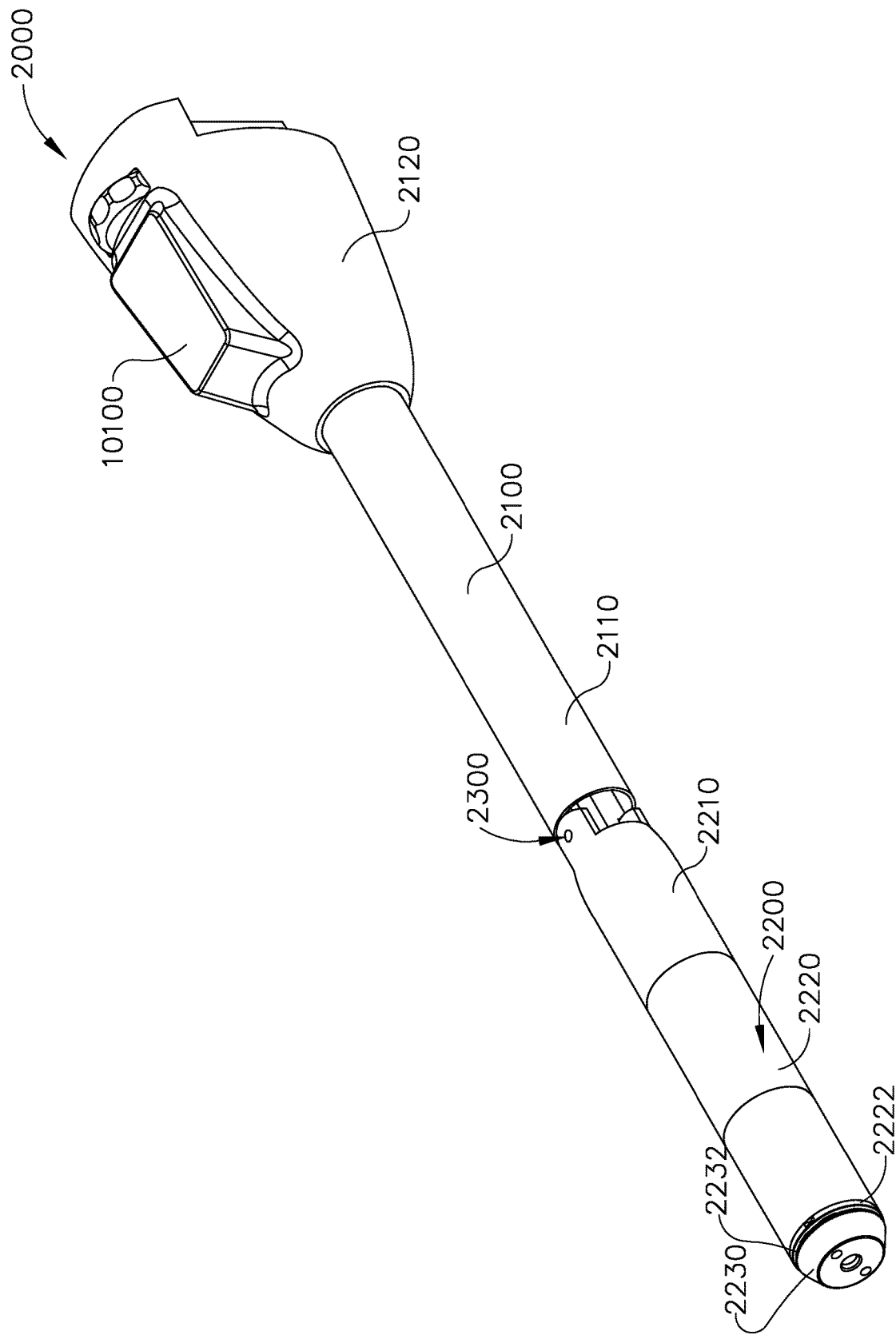
FIG. 16 is a perspective view of the interchangeable tool assembly of FIG. 15.
Figure 27:
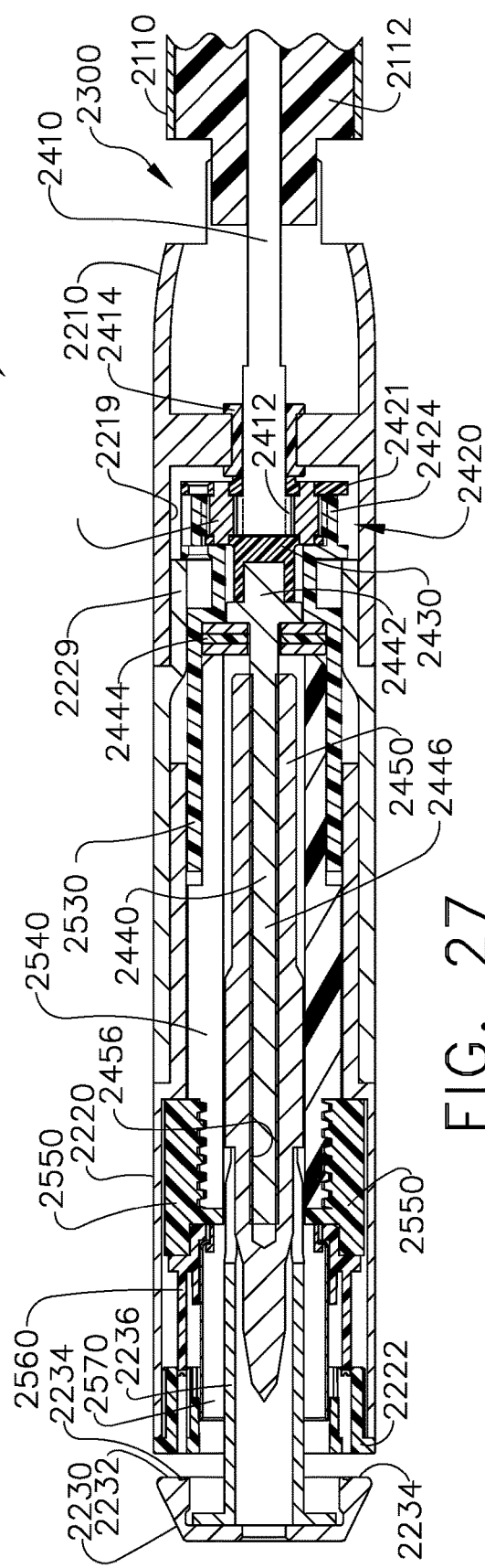
FIG. 27 is a cross-sectional view of an end effector of the interchangeable tool assembly of FIG. 15 taken along line 27-27 in FIG. 26 illustrating the end effector in a clamped, but unfired condition.

An interchangeable tool assembly 2000 is illustrated in FIG. 15. The interchangeable tool assembly 2000 is similar to the interchangeable tool assembly 1000 in many respects, but is different than the interchangeable tool assembly 1000 in certain other respects. For instance, the interchangeable assembly 2000 is a circular stapling assembly. Referring primarily to FIGS. 15 and 16, the circular stapling assembly 2000 comprises a shaft portion 2100 and an end effector 2200. The shaft portion 2100 comprises a proximal portion which is releasably attachable to the handle assembly 20, for example. The end effector 2200 comprises a first portion 2210 rotatably attached to the shaft portion 2100 about an articulation joint 2300. The end effector 2200 further comprises a second portion 2220 releasably attached to the first portion 2210. The second portion 2220 comprises a cartridge portion 2222 including an annular array of staple cavities 2224 defined therein and a staple stored in each staple cavity 2224. The second portion 2220 further comprises an anvil 2230 including a tissue compression surface 2232 and an annular array of forming pockets or forming pockets 2234 (FIG. 27) registered with the staple cavities 2224 which are configured to deform the staples when the staples are ejected from the staple cavities 2224.

Further to the above, referring again to FIGS. 15 and 16, the second portion 2220 of the end effector 2200 is selectively attachable to and selectively detachable from the first portion 2210 of the end effector 2200. The second portion 2220 comprises an outer housing 2227 including a proximal connector 2229 which is configured to be received within an aperture, or chamber, 2218 defined in a housing 2217 of the first portion 2210. The fit between the connector 2229 of the housing 2227 and the housing 2217 of the first portion 2210 is snug. A compression fit between the connector 2229 and the housing 2217 can prevent the second portion 2220 from being accidentally displaced longitudinally and/or rotationally relative to the first portion 2210. In various instances, a detent member can be utilized to releasably secure the second portion 2220 to the first portion 2210 of the end effector 2200.

Referring to FIGS. 15 and 35-38, the second portion 2220 of the end effector 2200 is interchangeable with other second portions such as a second portion 2220', a second portion 2220", a second portion 2220''', and/or another second portion 2220, for example. The second portions 2220', 2220", and 2220''' are similar to the second portion 2220 in many respects. For instance, each second portion 2220, 2220', 2220", and 2220''' includes a central aperture 2226 defined therein. That said, the second portions 2220', 2220", and 2220''' are different than the second portion 2220 in other respects. For instance, the second portion 2220' has a larger diameter than the second portion 2220. Moreover, the annular array of staple cavities 2224 defined in the second portion 2220' has a larger circumference than the annular array of staple cavities 2224 defined in the second portion 2220. Similarly, the second portion 2220" has a larger diameter than the second portion 2220' and the annular array of staple cavities 2224 defined in the second portion 2220" has a larger circumference than the annular array of staple cavities 2224 defined in the second portion 2220'. Also, similarly, the second portion 2220''' has a larger diameter than the second portion 2220" and the annular array of staple cavities 2224 defined in the second portion 2220''' has a larger circumference than the annular array of staple cavities 2224 defined in the second portion 2220".

Further to the above, the anvil 2230 is interchangeable with other anvils such as an anvil 2230', an anvil 2230", an anvil 2230''', and/or another anvil 2230, for example. The anvils 2230', 2230", and 2230''' are similar to the anvil 2230 in many respects. For instance, each anvil 2230, 2230', 2230", and 2230''' comprises a longitudinal shaft 2236 including connecting flanges 2238. That said, the anvils 2230', 2230", and 2230''' are different than the anvil 2230 in other respects. For instance, the anvil 2230' has a larger diameter than the anvil 2230. Moreover, the annular array of the forming pockets 2234 defined in the anvil 2230' has a larger circumference than the annular array of forming pockets 2234 defined in the anvil 2230 such that the forming pockets 2234 remain registered with the staple cavities 2224 defined in the second portion 2220'. Similarly, the anvil 2230" has a larger diameter than the anvil 2230' and the annular array of forming pockets 2234 defined in the anvil 2230" has a larger circumference than the annular array of forming pockets 2234 defined in the anvil 2230' such that the forming pockets 2234 remain registered with the staple cavities 2224 defined in the second portion 2220". Also, similarly, the anvil 2230''' has a larger diameter than the anvil 2230" and the annular array of forming pockets 2234 defined in the second portion 2220''' has a larger circumference than the annular array of forming pockets 2234 defined in the anvil 2230" such that the forming pockets 2234 remain registered with the staple cavities 2224 defined in the second portion 2220'''.

Figure 17:
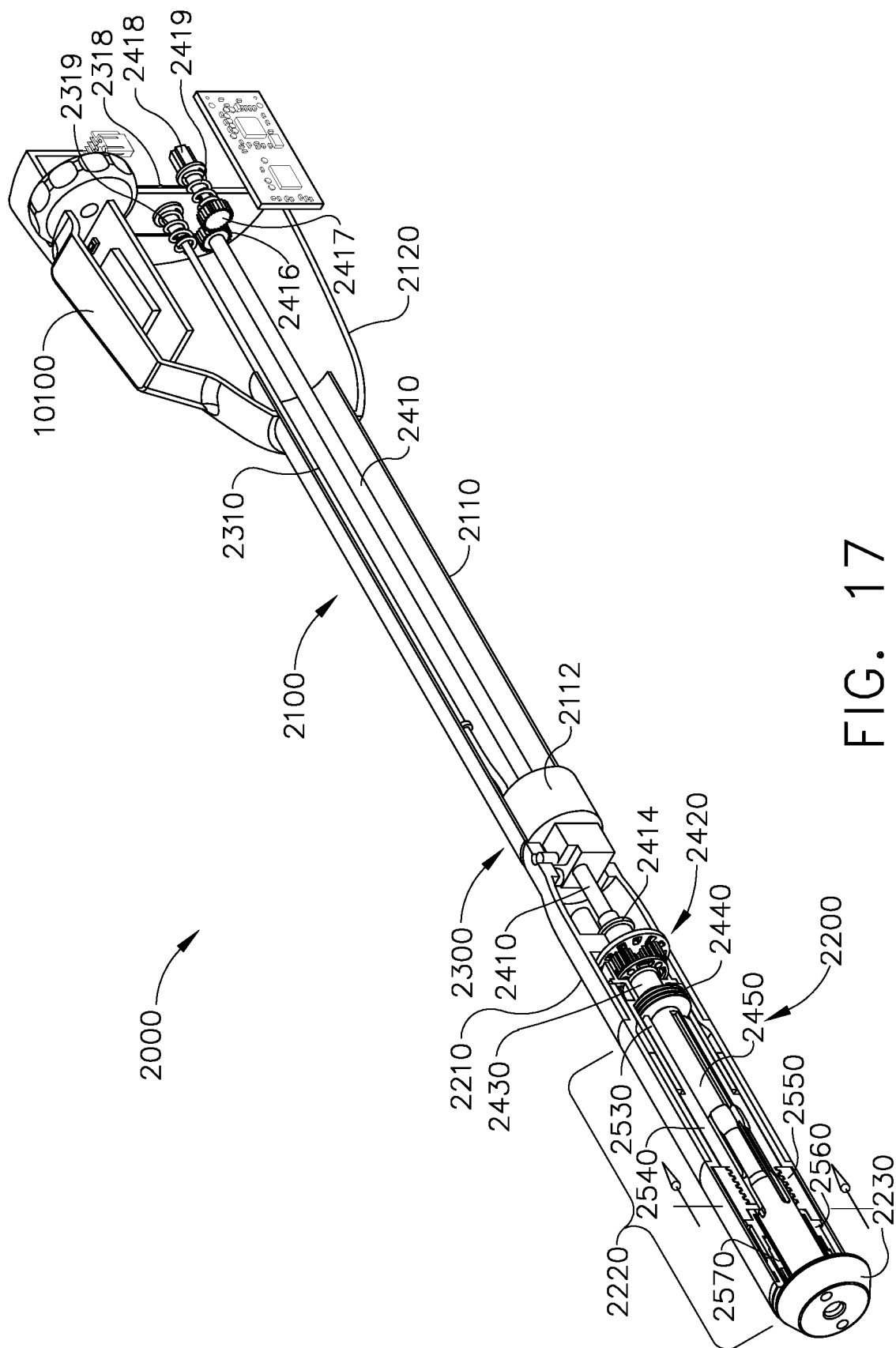
FIG. 17 is a cross-sectional perspective view of the interchangeable tool assembly of FIG. 15.

Referring primarily to FIG. 17, the shaft portion 2100 comprises a proximal connector 2120 and an elongate shaft portion 2110 extending distally from the proximal connector 2120. The proximal connector 2120 comprises a first input 2318 and a second input 2418. The first input 2318 is operably connected to an end effector articulation system and the second input 2418 is operably connected to an end effector clamping and staple firing system. The first input 2318 and the second input 2418 can be operated in any suitable order. For instance, the first input 2318 can be rotated in a first direction to articulate the end effector 2200 in a first direction and, correspondingly, rotated in a second direction to articulate the end effector 2200 in a second direction. Once the end effector 2200 has been suitably articulated, the second input 2428 can then be rotated to close the anvil 2230 and clamp tissue against the cartridge portion 2222 of the end effector 2200. As discussed in greater detail further below, the second input 2428 can then be operated to fire the staples from the staple cavities 2224 and incise tissue captured within the end effector 2200. In various alternative embodiments, the first input 2318 and the second input 2328 can be operated in any suitable order and/or at the same time.

Figure 20:
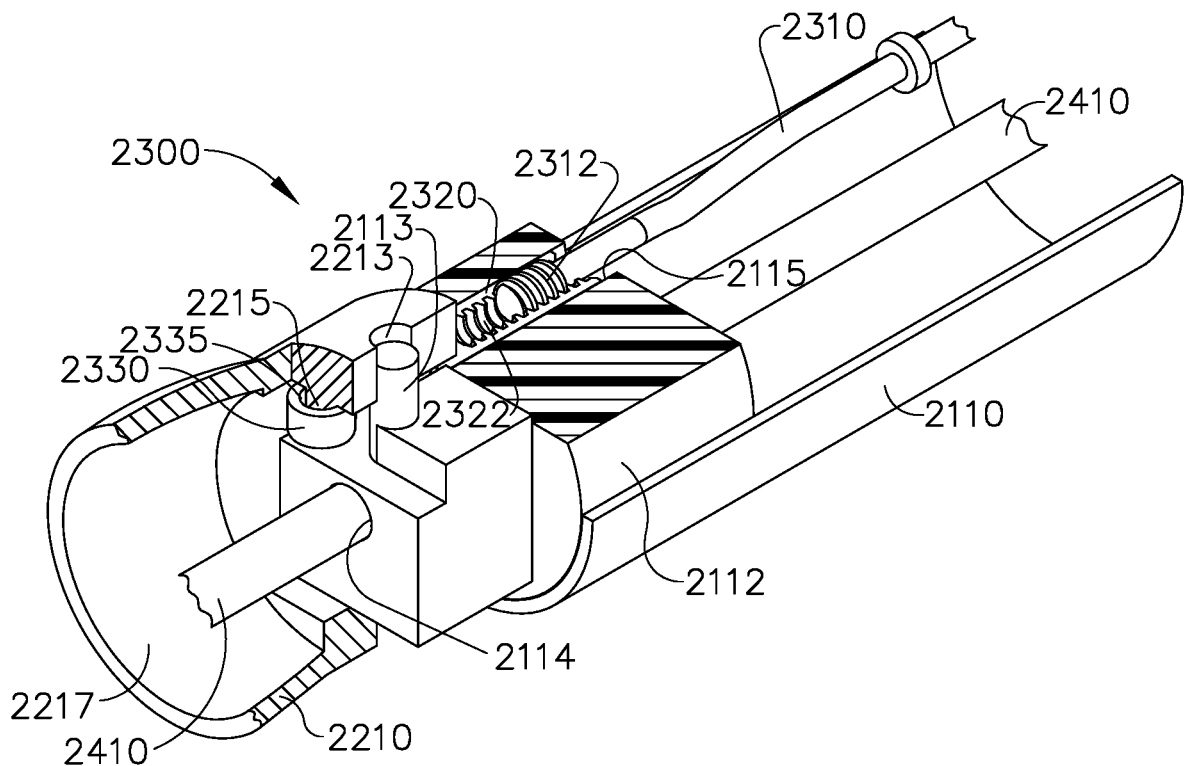
FIG. 20 is a cross-sectional perspective view of an articulation joint of the interchangeable tool assembly of FIG. 15 including the articulation block of FIG. 19.
Figure 21:
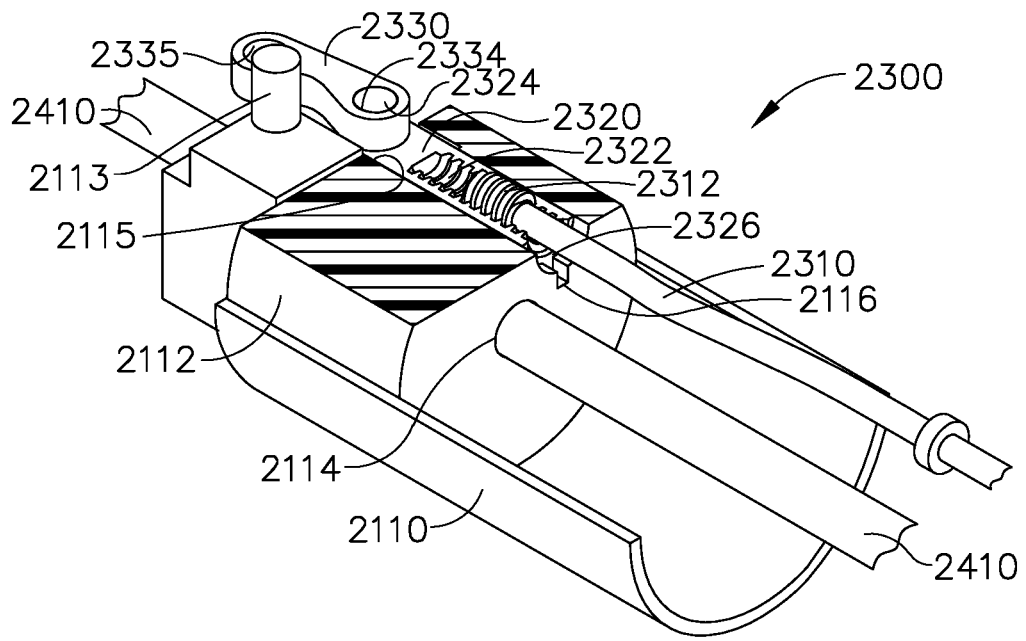
FIG. 21 is another cross-sectional perspective view of the articulation joint of FIG. 20.
Figure 31:
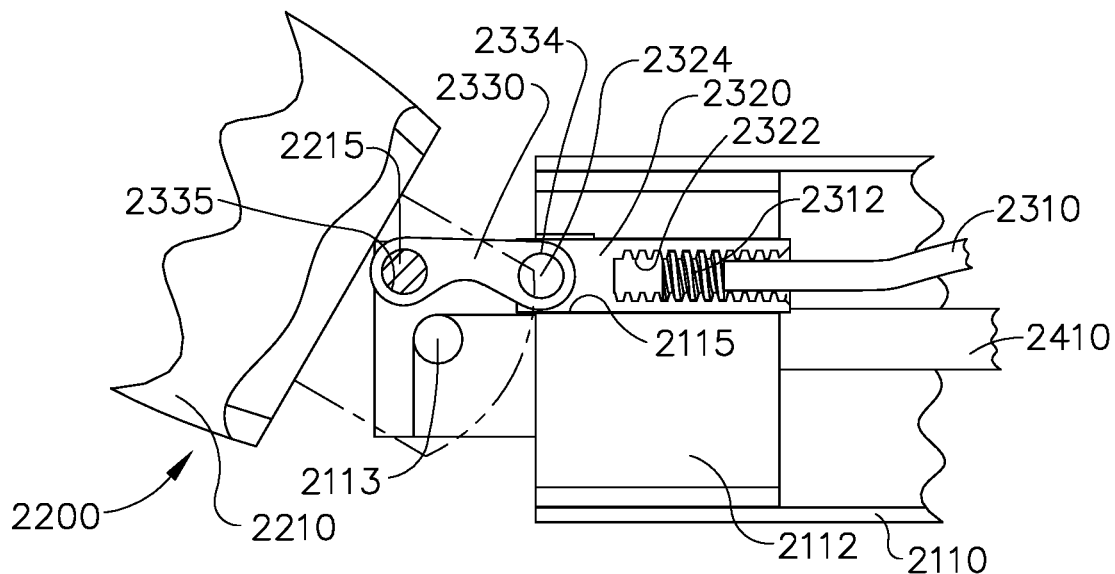
FIG. 31 illustrates the end effector of the interchangeable tool assembly of FIG. 15 articulated in a first direction.
Figure 32:
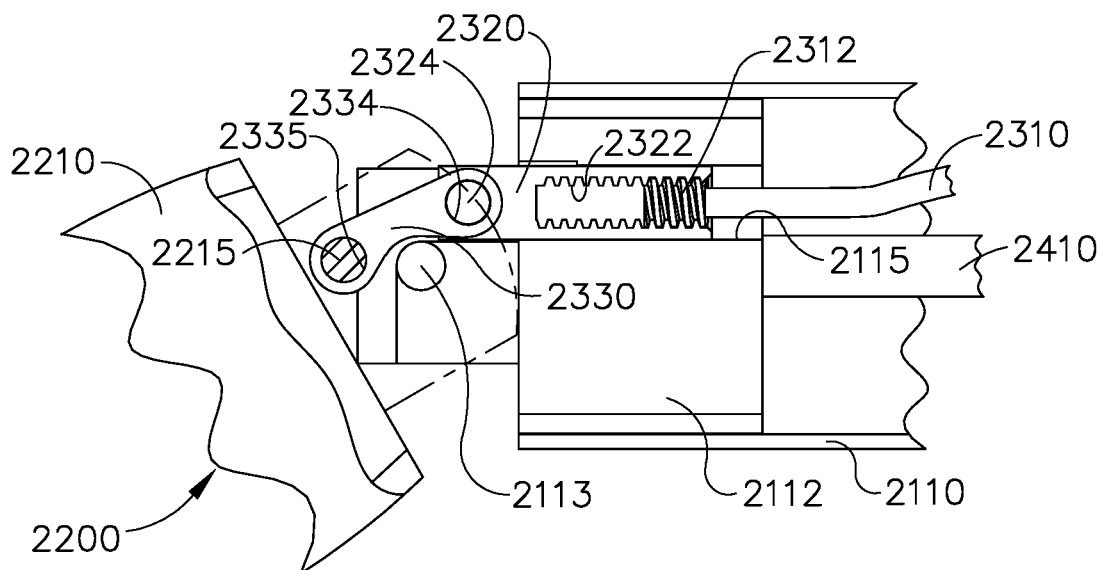
FIG. 32 illustrates the end effector of the interchangeable tool assembly of FIG. 15 articulated in a second direction.
Figure 33:
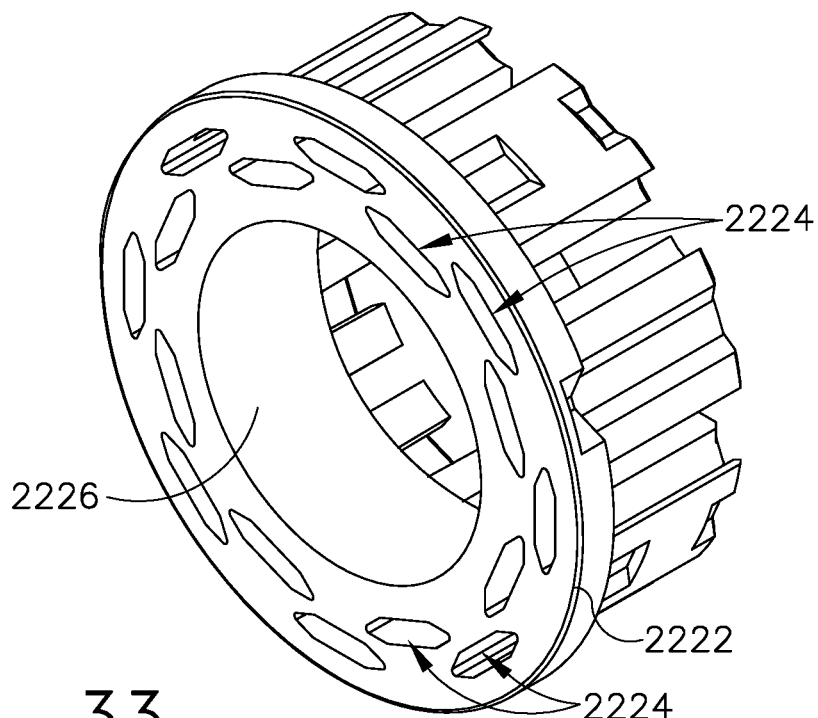
FIG. 33 is a perspective view of a cartridge body of the interchangeable tool assembly of FIG. 15.

The first input 2318 is mounted to a proximal end of an articulation shaft 2310 which is rotatably mounted in the shaft portion 2010. Referring primarily to FIGS. 20 and 21, the rotatable articulation shaft 2310 comprises a distal end and a worm gear 2312 mounted to the distal end. The worm gear 2312 is threadably engaged with an articulation slide 2320. More specifically, the articulation slide 2320 comprises a threaded aperture 2322 defined therein and the worm gear 2312 is threadably mated with the threaded aperture 2322. When the articulation shaft 2310 is rotated in a first direction, the worm gear 2312 pushes the articulation slide 2320 distally (FIG. 32). When the articulation shaft 2310 is rotated in a second, or opposite, direction, the worm gear 2312 pulls the articulation slide 2320 proximally (FIG. 31). The articulation slide 2320 is slidably supported by an articulation block 2112 fixedly mounted in the distal end of the elongate shaft portion 2110. The movement of the articulation slide 2320 is limited to proximal and distal movement by the articulation block 2112 by a guide slot 2315 defined in the articulation block 2112. The articulation slide 2320 further comprises a longitudinal key 2326 extending therefrom which is closely received in a longitudinal keyway 2116 defined in the bottom of the guide slot 2315 which limits the relative movement between the articulation slide 2320 and the articulation block 2112 to a longitudinal path.

Figure 24:
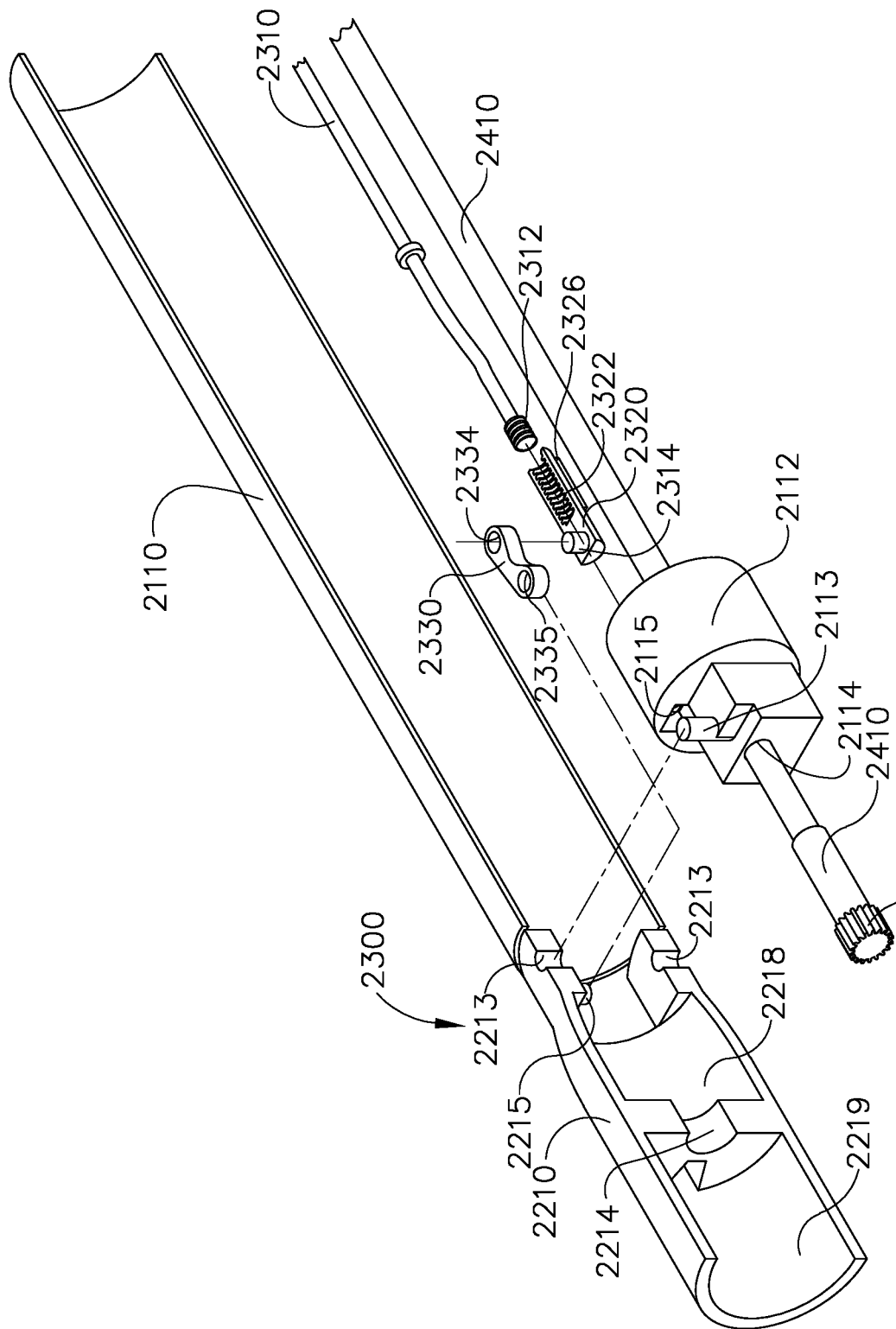
FIG. 24 is a partial exploded view of the articulation joint of FIG. 20.

Referring again to FIGS. 20, 21, and 24, the articulation slide 2320 is coupled to an articulation link 2330. The articulation slide 2320 comprises a drive pin 2324 extending therefrom which is positioned within a proximal aperture 2334 defined in the articulation link 2330. The drive pin 2324 is closely received within the aperture 2334 such that the drive pin 2324 and the sidewalls of the aperture 2334 co-operate to define an axis of rotation between the articulation slide 2320 and the articulation link 2330. The articulation link 2330 is also coupled to the housing 2217 of the end effector 2200. More specifically, the articulation link 2330 further comprises a distal aperture 2335 defined therein and the housing 2217 comprises a pin 2215 positioned in the distal aperture 2335. The pin 2215 is closely received within the aperture 2335 such that the pin 2215 and the sidewalls of the aperture 2335 co-operate to define an axis of rotation between the articulation link 2330 and the housing 2217.

Further to the above, referring to FIGS. 18-21 and 24, the end effector 2200 is rotatably coupled to the articulation block 2112 of the shaft 2100 about the articulation joint 2300. The housing 2217 of the end effector 2200 comprises apertures 2213 defined in opposite sides thereof and the articulation block 2112 comprises projections 2113 extending from opposite sides thereof which are positioned in the apertures 2213. The projections 2113 are closely received within the apertures 2213 such that the projections 2113 and the sidewalls of the apertures 2213 co-operate to define an articulation axis about which the end effector 2200 can be articulated. When the articulation shaft 2310 is rotated to drive the articulation slide 2320 distally, the articulation slide 2320 drives the proximal end of the articulation link 2330 distally. In response to the distal movement of the proximal end of the articulation link 2330, the articulation link 2330 rotates about the drive pin 2324 which rotates the end effector 2200 about the articulation joint 2300. When the articulation input 2310 is rotated to drive the articulation slide 2320 proximally, similar to the above, the articulation slide 2320 pulls the proximal end of the articulation link 2330 proximally. In response to the proximal movement of the proximal end of the articulation link 2330, the articulation link 2330 rotates about the drive pin 2324 which rotates the end effector 2200 about the articulation joint 2300. The articulation link 2330 provides at least one degree of freedom between the articulation slide 2320 and the housing 2217. As a result, the articulation link 2330 permits the end effector 2200 to be articulated through a wide range of articulation angles.

Figure 25:
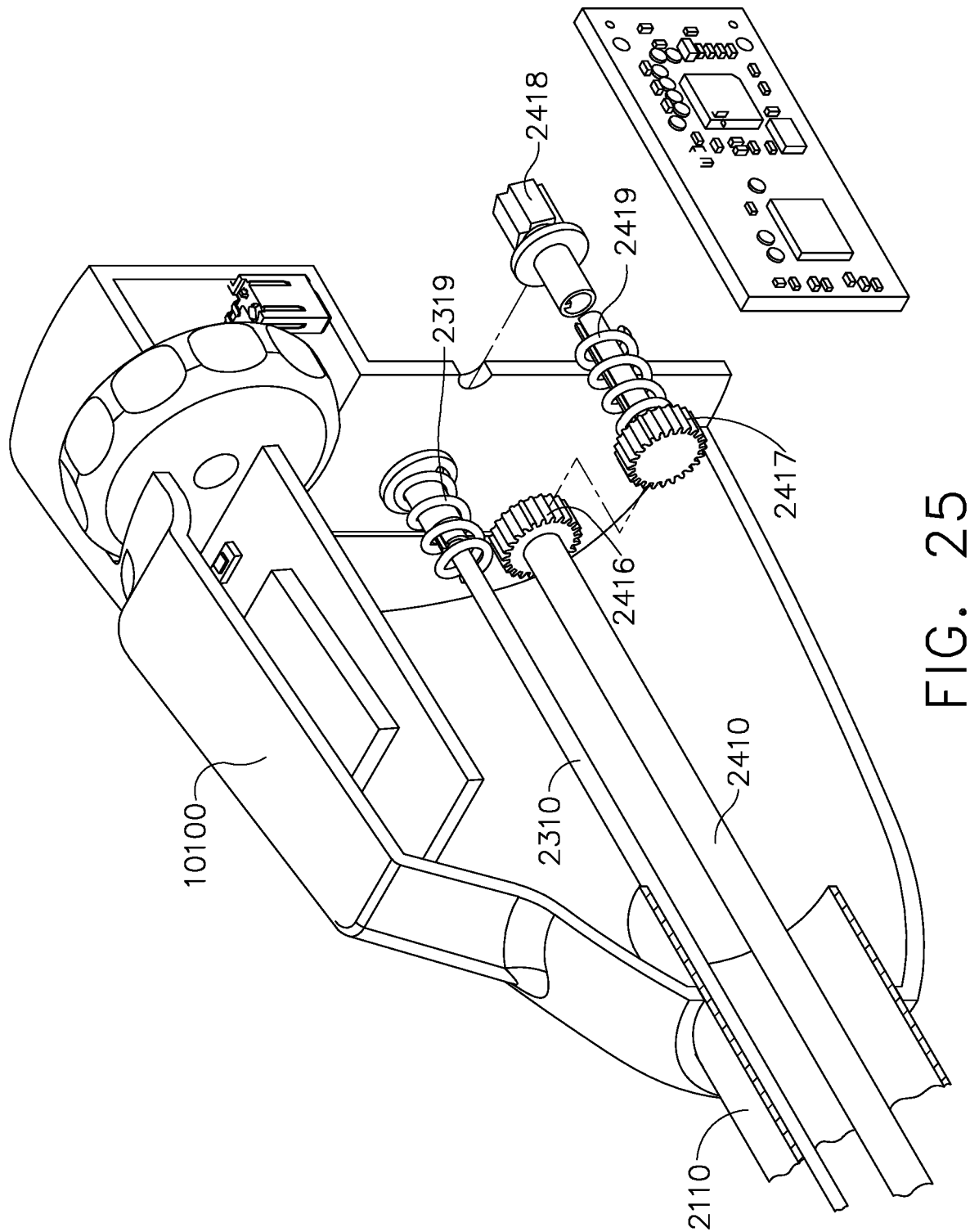
FIG. 25 is a cross-sectional perspective view of the proximal end of the interchangeable tool assembly of FIG. 15.
Figure 26:
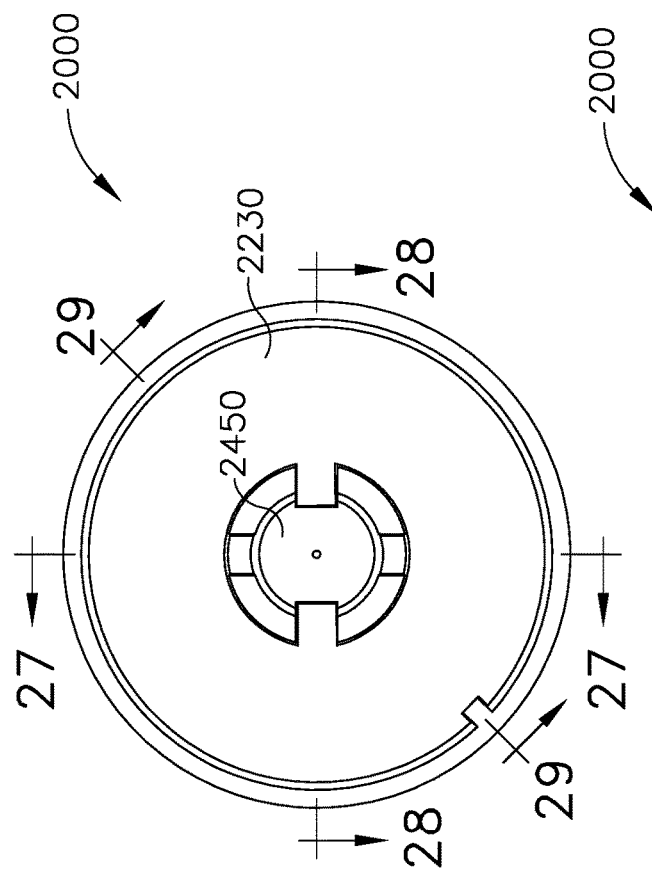
FIG. 26 is an end view of the interchangeable tool assembly of FIG. 15.

As discussed above, referring to FIGS. 17 and 25, the proximal connector 2120 of the interchangeable tool assembly 2000 comprises a second input 2418. The second input 2418 comprises a drive gear 2417 which is meshingly engaged with a drive gear 2416 mounted on a proximal end of a drive shaft 2410. The drive shaft 2410 extends through the shaft portion 2110 and an aperture 2114 defined in the articulation block 2112, as illustrated in FIG. 19. The aperture 2114 comprises a bearing and rotatably supports the drive shaft 2410. Alternatively, the aperture 2114 can comprise a clearance aperture. In either event, referring primarily to FIG. 22, the drive shaft 2410 extends through the articulation joint 2300 and into the chamber 2218 defined in the end effector housing 2217. The drive shaft 2410 is rotatably supported by a bearing 2414 mounted to the drive shaft 2410 which is captured within a recess 2214 defined in the housing 2217 of the end effector 2200. The drive shaft 2410 further comprises an output gear 2412 mounted to the distal end thereof such that the rotation of the drive shaft 2410 is transmitted to the output gear 2412.

Figure 22:
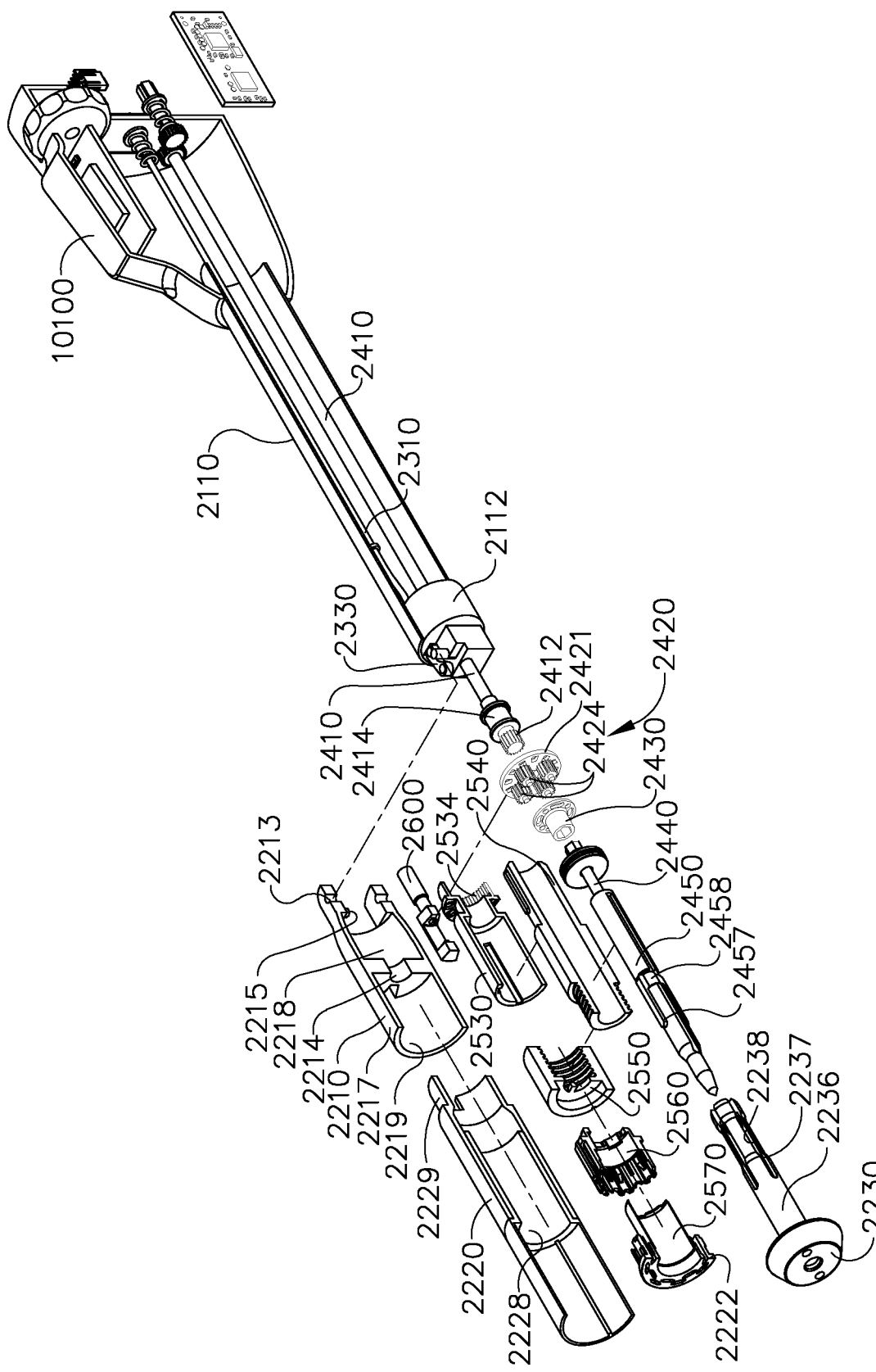
FIG. 22 is a partial exploded view of the interchangeable tool assembly of FIG. 15.
Figure 23:
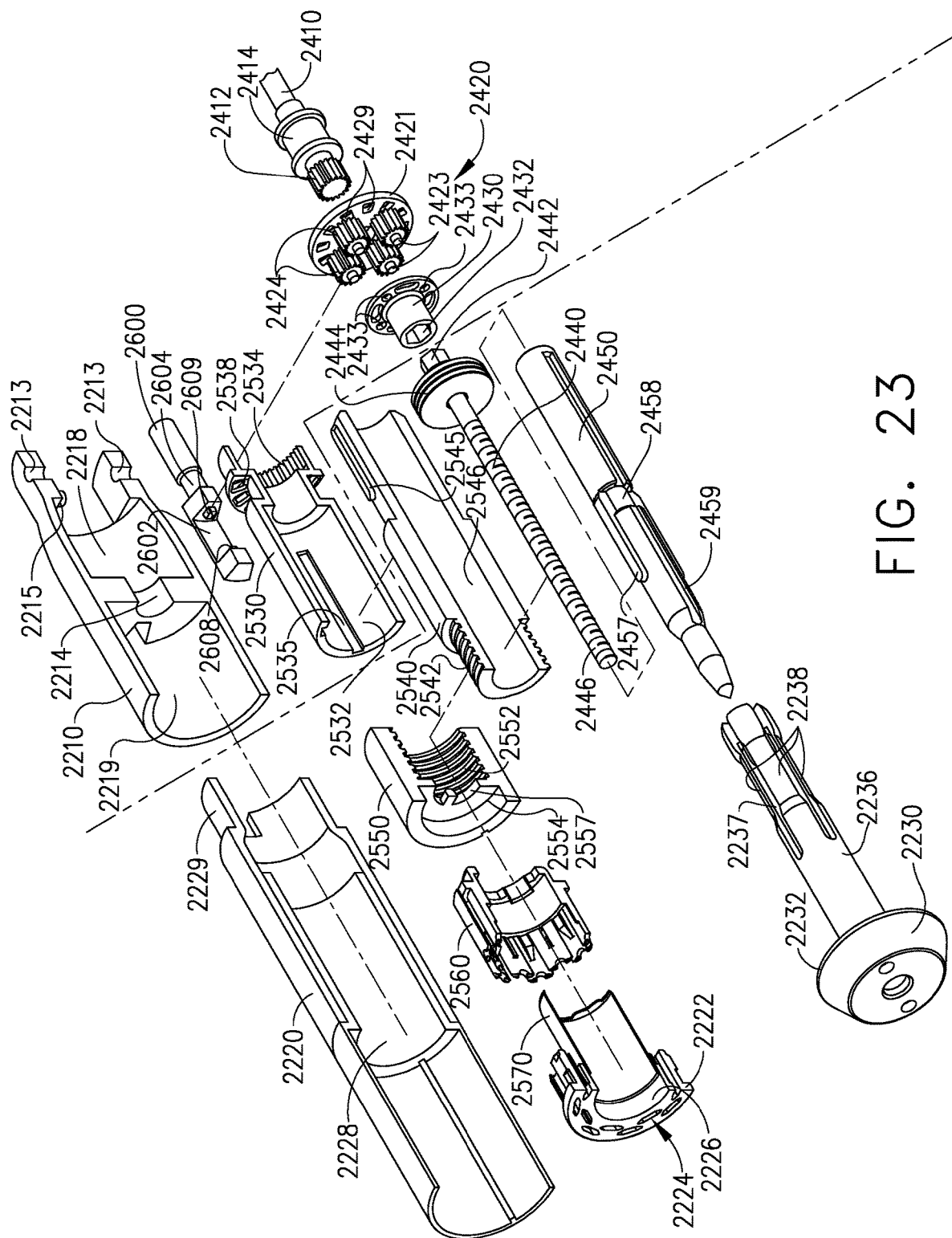
FIG. 23 is another partial exploded view of the interchangeable tool assembly of FIG. 15.

Referring primarily to FIGS. 18, 22, and 23, the output gear 2412 of the drive shaft 2410 is operably engaged with a transmission 2420. As discussed in greater detail below, the transmission 2420 is configured to shift the end effector 2200 between a first operating mode in which the drive shaft 2410 moves the anvil 2230 relative to the cartridge body 2222 and a second operating mode in which the drive shaft 2410 fires the staples from the staple cavities 2224 and incises the tissue captured between the anvil 2230 and the cartridge body 2222. The transmission 2420 comprises an orbit drive comprising a planetary plate 2421 and four planetary gears 2424 rotatably mounted to the planetary plate 2421. The planetary plate 2421 comprises a clearance aperture extending through the center thereof and the drive shaft 2410 extends through the clearance aperture. The planetary plate 2421 and the planetary gears 2424 are positioned in a chamber 2219 defined in the end effector housing 2217. Each planetary gear 2424 is rotatable about a gear pin 2423 extending from the planetary plate 2421. The gear pins 2423 are positioned along a circumference surrounding the clearance aperture. The output gear 2412 is meshingly engaged with the planetary gears 2424 and, as described in greater detail below, the drive shaft 2410 drives the planetary gears 2424.

Further to the above, the drive shaft 2410 extends trough the articulation joint 2300. In order for the output gear 2412 to remain properly engaged with the planetary gears 2424 when the end effector 2200 is articulated, the drive shaft 2410 is flexible. In at least one instance, the drive shaft 2410 is comprised of plastic, for example.

Figure 30:
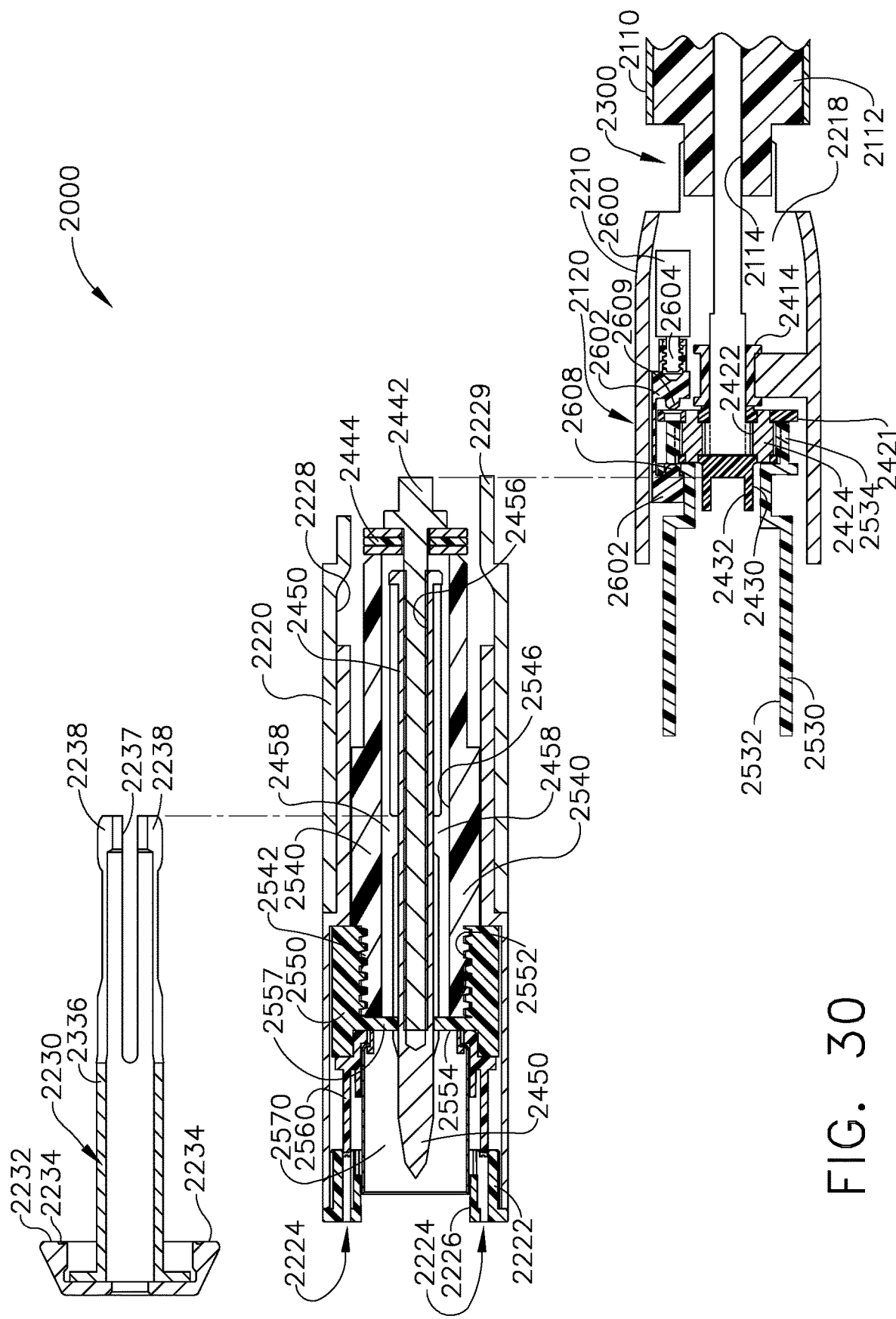
FIG. 30 is a cross-sectional view of the end effector of the interchangeable tool assembly of FIG. 15 illustrated in a disassembled condition.

As discussed above, the transmission 2420 comprises a first operating mode and a second operating mode. Referring primarily to FIGS. 23 and 28, the interchangeable tool assembly 2000 further comprises a shifter 2600 movable between a first position and a second position to switch the transmission 2420 between its first operating mode and its second operating mode. When the shifter 2600 is in its first position, as illustrated in FIGS. 28-30, the shifter 2600 is not engaged with the planetary plate 2421 of the transmission 2420 and, as a result, the planetary plate 2421 and the planetary gears 2424 are rotated by the drive shaft 2410. More specifically, the drive shaft 2410 rotates the planetary gears 2424 about their respective gear pins 2423 and the planetary gears 2424 rotate the planetary plate 2421 owing to reactionary forces between the planetary gears 2424 and an annular ring of teeth 2534 which extends around the planetary gears 2424, as described in greater detail further below. The planetary plate 2421 is operably coupled with an output coupling 2430 such that the rotation of the planetary plate 2421 is transmitted to the output coupling 2430. Referring primarily to FIG. 23, the output coupling 2430 comprises an array of apertures 2433 extending around the outer perimeter thereof wherein the gear pins 2423 extending from the planetary plate 2421 extend into, and are closely received by, the apertures 2433 defined in the output coupling 2430 such that there is little, if any, relative movement between the planetary plate 2421 and the output coupling 2430.

Referring primarily to FIGS. 18 and 23, the output coupling 2430 comprises a drive socket 2432. The drive socket 2432 comprises a substantially hexagonal aperture, for example; however, any suitable configuration could be utilized The drive socket 2432 is configured to receive a closure shaft 2440 extending through the second portion 2220 of the end effector 2200. The closure shaft 2440 comprises a proximal drive end 2442 which has a substantially-hexagonal shape that is closely received within the drive socket 2432 such that the rotation of the drive shaft 2410 is transferrable to the closure shaft 2440. The closure shaft 2440 is rotatably supported within the housing 2227 of the second portion 2220 by a bearing 2444. The bearing 2444 comprises a thrust bearing, for example; however, the bearing 2444 may comprise any suitable bearing.

Referring primarily to FIGS. 23 and 28-30, the closure shaft 2440 comprises a threaded portion 2446 that is threadably engaged with a threaded aperture 2456 defined in a trocar 2450. As discussed in greater detail further below, the anvil 2230 is attachable to the trocar 2450 which can be translated to move the anvil 2230 toward and/or away from the cartridge body 2222. Referring again to FIG. 18, the trocar 2450 comprises at least one longitudinal key slot 2459 defined therein which is configured to co-operate with at least one longitudinal key extending from an inner surface 2546 of the drive sleeve 2540. The drive sleeve 2540 is part of the staple firing system, discussed further below, and the reader should understand that the trocar 2450 and the drive sleeve 2540, one, slide relative to one another, and, two, co-operatively inhibit relative rotational movement therebetween. Owing to the threaded engagement between the closure shaft 2440 and the trocar 2450, the closure shaft 2440 can displace, or translate, the trocar 2450 distally when the closure shaft 2440 is rotated in a first direction and, correspondingly, displace, or translate, the trocar 2450 proximally when the closure shaft 2440 is rotated in a second, or opposite, direction.

As discussed above, the anvil 2230 is attachable to the trocar 2450. The anvil 2230 comprises connecting flanges 2238 which are configured to engage and grip the trocar 2450. The connecting flanges 2238 comprise cantilever beams which are connected to the shaft portion 2236 of the anvil 2230. Referring primarily to FIG. 23, the trocar 2450 comprises retention notches, or recesses, 2458 which are configured to releasably receive the connecting flanges 2238 when the anvil 2230 is assembled to the trocar 2450. The retention notches 2458 and the connecting flanges 2238 are configured to resist the inadvertent detachment of the anvil 2230 from the trocar 2450. The connecting flanges 2238 are separated by longitudinal slots 2237. The longitudinal slots 2237 are configured to receive longitudinal ribs 2457 extending from the trocar 2450 when the anvil 2230 is assembled to the trocar 2450. The ribs 2457 are closely received within the slots 2237 and, as a result, the anvil 2230 is inhibited from rotating relative to the trocar 2450.

Once the anvil 2230 has been suitably positioned relative to the cartridge portion 2222, as discussed above, the tool assembly 2000 can be shifted into its second operating mode. The shifter 2600 comprises an electrically-actuated motor, for example, which is utilized to shift the transmission 2420 of the end effector 2200. In various other embodiments, the shifter 2600 can comprise any suitable device which is electrically and/or manually actuated. The shifter 2600 is in signal communication with a processor of the surgical stapling instrument and in power communication with a battery of the surgical stapling instrument. In various instances, insulated electrical wires, for example, extend between the shifter 2600 and a handle of the surgical instrument such that the processor can communicate with the shifter 2600 and the battery can supply power to the shifter 2600. In various other instances, the shifter 2600 can comprise a wireless signal receiver and the processor can communicate wirelessly with the shifter 2600. In certain instances, power can be supplied wirelessly to the shifter 2600, such as through an inductive circuit, for example. In various instances, the shifter 2600 can comprise its own power source.

The shifter 2600 comprises a housing mounted in the chamber 2218 defined in the proximal end of the end effector 2200. The shifter 2600 comprises a clutch key, or toggle, 2602 and an output shaft 2604 movable between a first position and a second position relative to the shifter housing. The clutch key 2602 comprises a first lock tooth 2608 and a second lock tooth 2609 and, when the clutch key 2602 is in its first position, the first lock tooth 2608 is engaged with a firing tube 2530 of the staple firing system and, concurrently, the second lock tooth 2609 is disengaged from the planetary plate 2421 of the transmission 2420. More specifically, the first lock tooth 2608 is positioned in an aperture 2538, which is part of an annular array of apertures 2538 defined around the firing tube 2530, and the second lock tooth 2609 is not positioned in an aperture 2429, which is part of an annular array of apertures 2429 defined around the planetary plate 2421. As a result of the above, the shifter 2600 prevents the firing tube 2530 from rotating and, accordingly, locks out the staple firing system when the clutch key 2602 is in its first position. Although the staple firing system has been locked out by the shifter 2600 when the clutch key 2602 is in its first position, the drive shaft 2410 can rotate the planetary plate 2421 and operate the anvil closure system, as discussed above.

As illustrated primarily in FIG. 23, the firing tube 2530 comprises an inner annular rack of teeth 2534 defined in an inner sidewall 2532 thereof. The planetary gears 2424 are operably intermeshed with the rack of teeth 2534. When the shifter 2600 is in its first position, as illustrated in FIG. 28, the firing tube 2530 is held in position by the shifter 2600 and the planetary gears 2424 are rotatable relative to the firing tube 2530 and the rack of teeth 2534 by the drive shaft 2410. In such instances, the planetary gears 2424 are rotated about a longitudinal drive axis defined by the drive shaft 2410 and, at the same time, rotated about axes defined by their respective gear pins 2423. The reader should appreciate that the planetary gears 2424 are directly driven by the drive shaft 2410 and, owing to reactionary forces created between the planetary gears 2424 and the firing tube 2530, the planetary gears 2424 drive and rotate the planetary plate 2421. When the shifter 2600 is actuated to move the clutch key 2602 into its second position, the first lock tooth 2608 is disengaged from the firing tube 2530 and, concurrently, the second lock tooth 2609 is engaged with the planetary plate 2421. The planetary plate 2421 is held in position by the shifter 2600 when the clutch key 2602 is in its second position and, as a result, the closure drive has been locked out and cannot be operated to move the anvil 2230. When the drive shaft 2410 is rotated in such instances, the output gear 2412 drives and rotates the planetary gears 2424 relative to the planetary plate 2421 about their respective gear pins 2423. The planetary gears 2424 drive the firing tube 2530 via the rack of teeth 2534 and rotate the firing tube 2530 about its longitudinal axis.

Further to the above, and referring again to FIG. 23, the firing tube 2530 is operably coupled with the drive sleeve 2540 of the staple firing system. More specifically, the inner sidewall 2532 of the firing tube 2530 comprises longitudinal slots 2535 defined therein which are configured to closely receive longitudinal ribs 2545 defined on the drive sleeve 2540 such that the drive sleeve 2540 rotates with the firing tube 2530. The drive sleeve 2540 further comprises a threaded distal end 2542 which is threadably engaged with a drive collar 2550. More specifically, the drive collar 2550 comprises a threaded aperture 2552 which is threadably engaged with the threaded distal end 2542. The drive collar 2550 is positioned in an aperture 2228 defined in the housing of the end effector 2200 and is prevented from rotating within the aperture 2228 by a longitudinal rib and groove arrangement, for example. As a result of the above, the rotation of the drive sleeve 2540 translates the drive collar 2550 longitudinally. For instance, the drive collar 2550 is advanced distally if the drive sleeve 2540 is rotated in a first direction and retracted proximally if the drive sleeve 2540 is rotated in a second, or opposite, direction.

When the drive collar 2550 is pushed distally, as discussed above, the drive collar 2550 pushes a staple driver block 2560 and a cutting member 2570, such as a knife, for example, distally during a firing stroke of the staple firing system. More specifically, the drive collar 2550 pushes the staple driver block 2560 and the cutting member 2570 between a proximal, unfired position in which the staples are positioned in the staple cavities 2224 defined in the cartridge body portion 2222 and the cutting member 2570 is recessed below the deck surface of the cartridge body portion 2222 and a distal, fired position in which the staples have been deformed against the anvil 2230 and the tissue captured between the anvil 2230 and the cartridge body portion 2222 has been transected by the cutting member 2570. The drive collar 2550 comprises a drive recess 2554 which is configured to abut the staple driver block 2560 and the cutting member 2570 as the drive collar 2550 is advanced distally. The staple driver block 2560 comprises a plurality of staple cradles defined therein wherein each staple cradle is configured to support the base of a staple. The staple cradles are aligned with the staple cavities 2224 defined in the cartridge body portion 2222 and are arranged in at least two concentric rows.

The staple driver block 2560 and the cutting member 2570 are attached to the drive collar 2550 such that, when the drive collar 2550 is moved proximally away from the anvil 2230, the staple driver block 2560 and the cutting member 2570 are pulled proximally by the drive collar 2550. In at least one instance, the staple driver block 2560 and the cutting member 2570 comprise one or more hooks which extend into apertures 2557 defined in the drive collar 2550. In various instances, the staple driver block 2560 and the cutting member 2570 can be retracted such that they are completely retracted below the deck surface of the cartridge body portion 2222.

Further to the above, the end effector 2200 is operable in a third operating mode in which the clutch key 2602 of the shifter 2600 is operably engaged with the anvil closure system and the staple firing system at the same time. In this operating mode, the first lock tooth 2608 is engaged with the firing tube 2530 of the staple firing system and the second lock tooth 2609 is engaged with the planetary plate 2421 of the transmission 2420. In such instances, the first lock tooth 2608 is positioned in an aperture 2538 defined in the firing tube 2530 and the second lock tooth 2609 is positioned in an aperture 2429 defined in the planetary plate 2421. As a result of the above, the drive shaft 2410 moves the anvil 2230, the staple driver block 2560, and the cutting member 2570 relative to the cartridge body 2222 at the same time.

Referring again to FIG. 15, the user of the interchangeable tool assembly 2000 can select from a kit of second portions 2220, 2220', 2220", 2220''' and/or any other suitable second portion and assembly the selected second portion to the first portion 2210 of the end effector 2200. Referring primarily to FIG. 18, each second portion comprises a housing connector 2229 which engages the housing 2217 of the first portion 2210 when the second portion is assembled to the first portion 2210. In addition, each second portion comprises a closure shaft 2440 which operably engages the drive socket 2432 of the first portion 2210 when the second portion is assembled to the first portion 2210. Moreover, each second portion comprises a drive sleeve 2540 which operably engages the firing tube 2530 of the first portion 2210 when the second portion is assembled to the first portion 2210.

Figure 35:
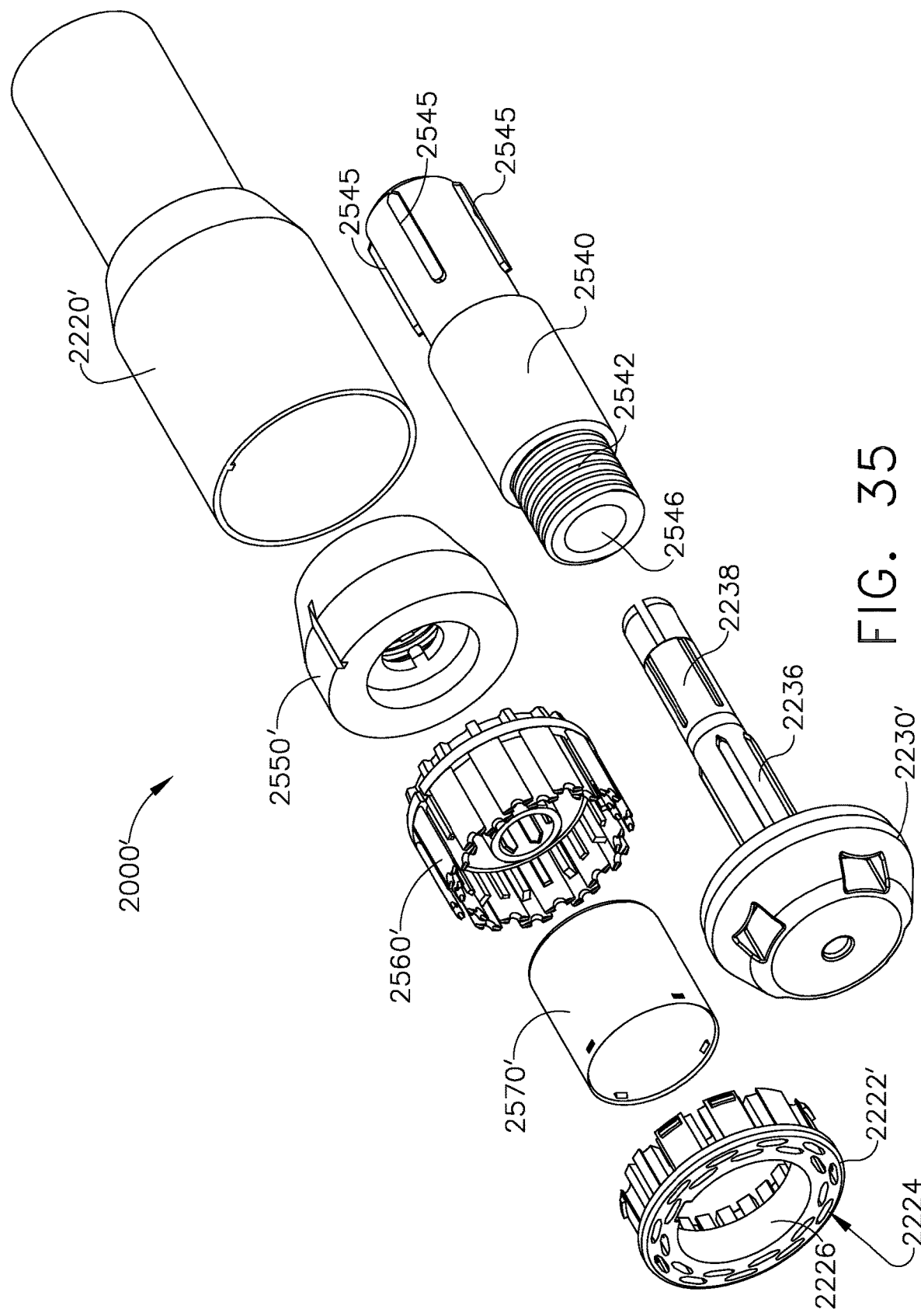
FIG. 35 is an exploded view of an end effector of an interchangeable tool assembly in accordance with at least one alternative embodiment.
Figure 36:
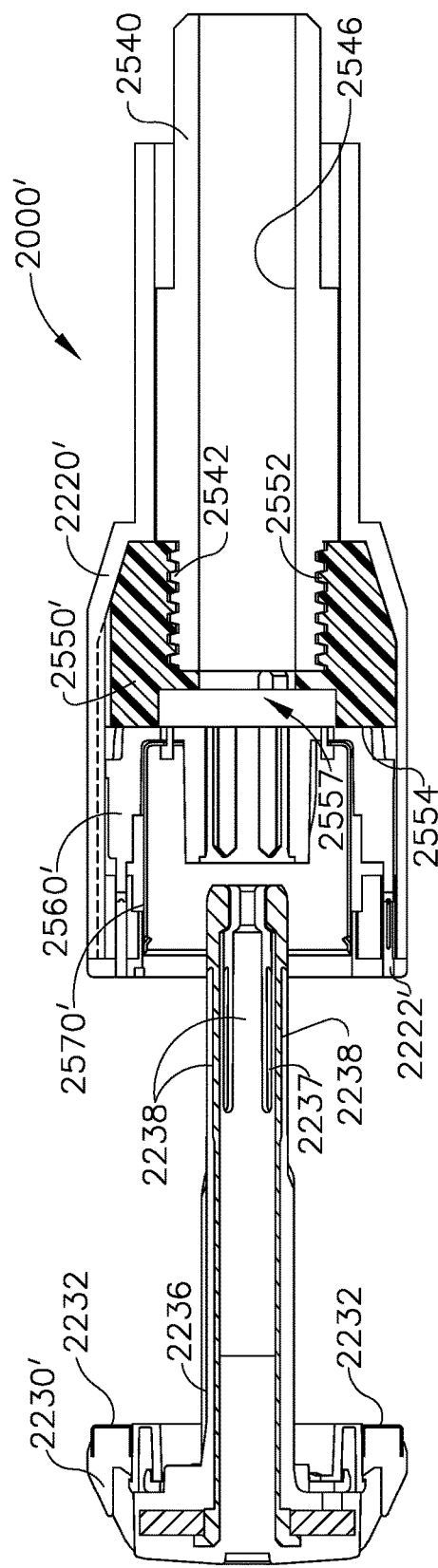
FIG. 36 is a disassembled view of the end effector of FIG. 35.
Figure 37:
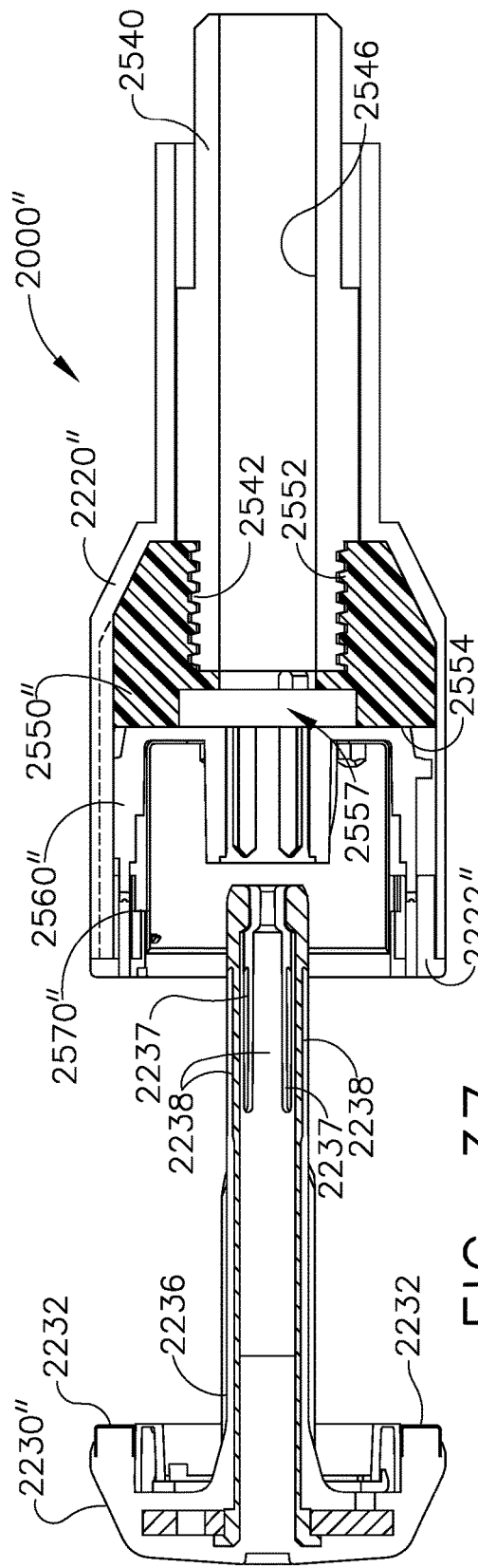
FIG. 37 is a disassembled view of an end effector of an interchangeable tool assembly in accordance with at least one alternative embodiment.
Figure 38:
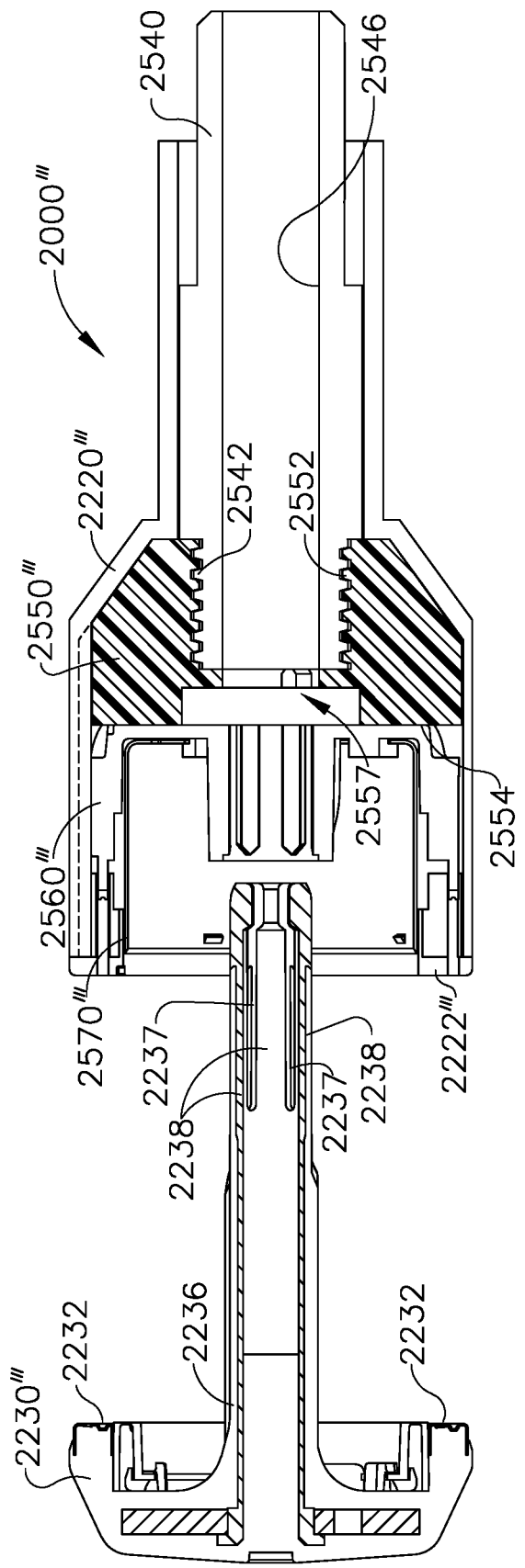
FIG. 38 is a disassembled view of an end effector of an interchangeable tool assembly in accordance with at least one alternative embodiment.

Further to the above, referring to FIGS. 35 and 36, a tool assembly 2000' is interchangeable with the tool assembly 2000. The tool assembly 2000' is similar to the tool assembly 2000 in many respects; however, the tool assembly 2000' is configured to apply circular staple lines having larger diameters than the circular staple lines applied by the tool assembly 2000. The tool assembly 2000' comprises, among other things, a wider second portion 2220', staple driver 2560', knife assembly 2570', cartridge body 2222', and anvil 2230'. Referring to FIG. 37, a tool assembly 2000" is interchangeable with the tool assembly 2000. The tool assembly 2000" is similar to the tool assemblies 2000 and 2000' in many respects; however, the tool assembly 2000" is configured to apply circular staple lines having larger diameters than the circular staple lines applied by the tool assembly 2000'. The tool assembly 2000" comprises, among other things, a wider second portion 2220", staple driver 2560", knife assembly 2570", cartridge body 2222", and anvil 2230". Referring to FIG. 38, a tool assembly 2000''' is interchangeable with the tool assembly 2000. The tool assembly 2000''' is similar to the tool assemblies 2000, 2000', and 2000" in many respects; however, the tool assembly 2000''' is configured to apply circular staple lines having larger diameters than the circular staple lines applied by the tool assembly 2000". The tool assembly 2000''' comprises, among other things, a wider second portion 2220''', staple driver 2560''', knife assembly 2570''', cartridge body 2222''', and anvil 2230'''.

In various embodiments, further to the above, a surgical instrument can have any suitable number of operating modes. In at least one embodiment, a surgical stapling instrument comprises a transmission which includes a first operating mode which fires the staples, a second operating mode which deploys the cutting member, and a third operating mode which both fires the staples and deploys the cutting member at the same time. In the first operating mode, the cutting member is not deployed. Moreover, the processor of such a surgical instrument can be programmed such that the instrument cannot be placed in the second operating mode without having first completed the first operating mode. As a result of the above, the user of the surgical instrument can decide whether or not to cut the tissue after the staples have been fired.

Figure 34:
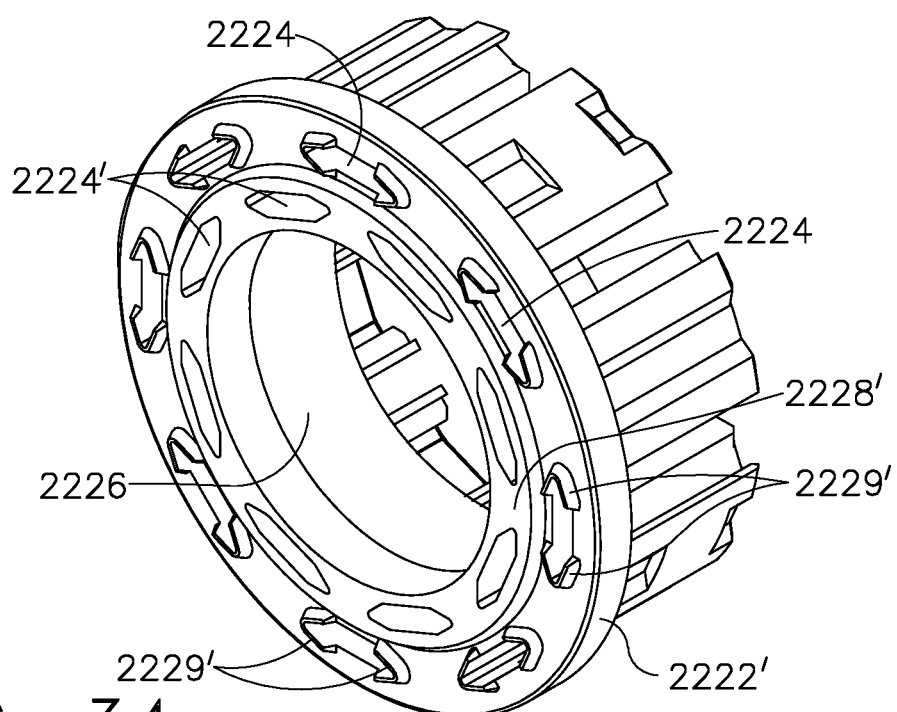
FIG. 34 is a perspective view of a cartridge body in accordance with at least one alternative embodiment.

An alternative embodiment of a staple cartridge body for use with a surgical stapler is illustrated in FIG. 34. A cartridge body 2222' comprises an annular outer row of staple cavities 2224 and an annular inner row of staple cavities 2224'. The staple cavities 2224 are defined in a first step of the cartridge body deck and the staple cavities 2224' are defined in a second step of the cartridge body deck. The second step extends above the first step. Stated another way, the first step has a first deck height and the second step has a second deck height which is taller than the first deck height. A deck wall separates the first step and the second step. In various embodiments, the deck wall is sloped. In certain embodiments, the deck wall is orthogonal to the first step and/or the second step.

The cartridge body 2222' further comprises cavity extensions 2229' extending from the first step of the deck. The cavity extensions 2229' surround the ends of the staple cavities 2224 and extend the staple cavities 2224 above the first step. The cavity extensions 2229' can at least partially control the staples above the first step as the staples are ejected from the staple cavities 2224. The cavity extensions 2229' are also configured to contact and compress tissue captured against the cartridge body 2222'. The cavity extensions 2229' can also control the flow of tissue relative to the cartridge body 2222'. For instance, the cavity extensions 2229' can limit the radial flow of the tissue. The cavity extensions 2229' can have any suitable configuration and can extend any suitable height from the first step. In at least one instance, the top surfaces of the cavity extensions 2229' are aligned with, or have the same height as, the second step, for example. In other instances, the cavity extensions 2229' can extend above or below the second step.

Further to the above, the staple cavities 2224 each comprise a first staple positioned therein having a first unformed height. The staple cavities 2224' each comprise a second staple positioned therein having a second unformed height which is different than the first unformed height. For instance, the first unformed height is taller than the second unformed height; however, the second unformed height could be taller than the first unformed height. In alternative embodiments, the first unformed staple height and the second unformed staple height is the same.

The first staples are deformed to a first deformed height and the second staples are deformed to a second deformed height which is different than the first deformed height. For instance, the first deformed height is taller than the second deformed height. Such an arrangement could improve blood flow into the stapled tissue. Alternatively, the second deformed height could be taller than the first deformed height. Such an arrangement could improve the pliability of the tissue along the inner transection line. In certain alternative embodiments, the first deformed height and the second deformed height is the same.

As discussed above, an interchangeable tool assembly can comprise, among other things, a shaft, an end effector, and a replaceable staple cartridge. The replaceable staple cartridge comprises a closure drive configured to move open and close the end effector to capture tissue within the end effector and a firing drive configured to staple and cut the tissue captured within the end effector. The closure drive and the firing drive of the end effector are operably coupled with a corresponding closure drive and firing drive of the shaft when the replaceable staple cartridge is assembled to the shaft. In the event that the replaceable staple cartridge is not properly assembled to the shaft, the replaceable staple cartridge may not operate in its intended manner. As described in greater detail below, the replaceable staple cartridge and/or the shaft can comprise a lockout which prevents the replaceable staple cartridge from being operated unless the replaceable staple cartridge is properly attached to the shaft.

Turning now to FIG. 39, an interchangeable tool assembly 3000 comprises a shaft 3010 and a replaceable staple cartridge 3020 Similar to the above, the replaceable staple cartridge 3020 comprises a closure drive input and a firing drive input which are operably coupled with a closure drive output and a firing drive output, respectively, when the staple cartridge 3020 is fully seated onto the shaft 3010. The operation of such closure and firing systems are not repeated herein for the sake of brevity.

The interchangeable tool assembly 3000 further comprises a lockout circuit 3090. The lockout circuit 3090 includes conductors 3096 and contacts 3092. A first contact 3092 is electrically coupled to a first conductor 3096 and a second contact 3092 is electrically coupled to a second conductor 3096. The first contact 3092 is not electrically coupled to the second contact 3092 prior to the staple cartridge 3020 being fully seated onto the shaft 3010. The staple cartridge 3020 comprises a contact bridge 3094 which engages and electrically couples the contacts 3092 when the staple cartridge 3020 is fully seated onto the shaft 3010. The contacts 3092 and the contact bridge 3094 are configured and arranged such that the contact bridge 3094 does not electrically couple the contacts 3092 when the staple cartridge 3020 is only partially seated onto the shaft 3010.

The interchangeable tool assembly 3000 is usable with a surgical instrument system which includes a manually-operable handle and/or a robotic system, for example. In various embodiments, the surgical instrument system includes an electric motor configured to drive the staple firing system of the tool assembly 3000 and, in addition, a controller configured to operate the electric motor. The lockout circuit of the tool assembly 3000 is in communication with the controller. When the controller detects that the contact bridge 3094 is not engaged with the contacts 3092, or that the lockout circuit is in an open condition, the controller prevents the electric motor from operating the staple firing system. In various instances, the controller is configured such that it does not supply power to the electric motor when the lockout circuit is in an open condition. In certain other instances, the controller is configured to supply power to the electric motor such that it can operate the closure system but not the firing system when the lockout circuit is in an open condition. In at least one such instance, the controller operates a transmission coupled to the electric motor such that the output of the electric motor is only directed to the closure system. When the controller detects that the contact bridge 3094 is engaged with the contacts 3092, or that the lockout circuit is in a closed condition, the controller allows the electric motor to operate the staple firing system.

When a surgical instrument system comprises a handle, further to the above, the controller can actuate a trigger lock which prevents a firing trigger of the handle from being actuated when the controller detects that the lockout circuit is in an open configuration. When the staple cartridge 3020 is fully seated onto the shaft 3010 and the lockout circuit is closed, the controller can retract the trigger lock and allow the firing trigger to be actuated. Such a system can be utilized with motorized and/or non-motorized firing drives. A non-motorized firing drive can be driven by a handcrank, for example.

As discussed above, an anvil 2230 can be assembled to the trocar shaft 2450 of the closure drive of the tool assembly 2000. The connecting flanges 2238 of the anvil 2230 are configured to engage a recess 2458 defined in the trocar shaft 2450 to connect the anvil 2230 thereto. Once the anvil 2230 has been assembled to the trocar shaft 2450, the trocar shaft 2450 and the anvil 2230 can be retracted, or pulled, toward the staple cartridge 2222 by the closure drive to compress tissue against the staple cartridge 2222. In some instances, however, the anvil 2230 may not be properly assembled to the trocar shaft 2450. The mis-assembly of the anvil 2230 to the trocar shaft 2450 can frequently occur when the trocar shaft 2450 is not sufficiently extended above the deck of the staple cartridge 2222 when a clinician attempts to assemble the anvil 2230 to the trocar shaft 2450.

Oftentimes, in such instances, the anvil 2230 is sufficiently attached to the trocar shaft 2450 such that the trocar shaft 2450 can move the anvil 2230 toward the staple cartridge 2222 but, when the anvil 2230 begins to compress the tissue against the staple cartridge 2222, the anvil 2230 can detach from the trocar shaft 2450.

Figures 41, 42:
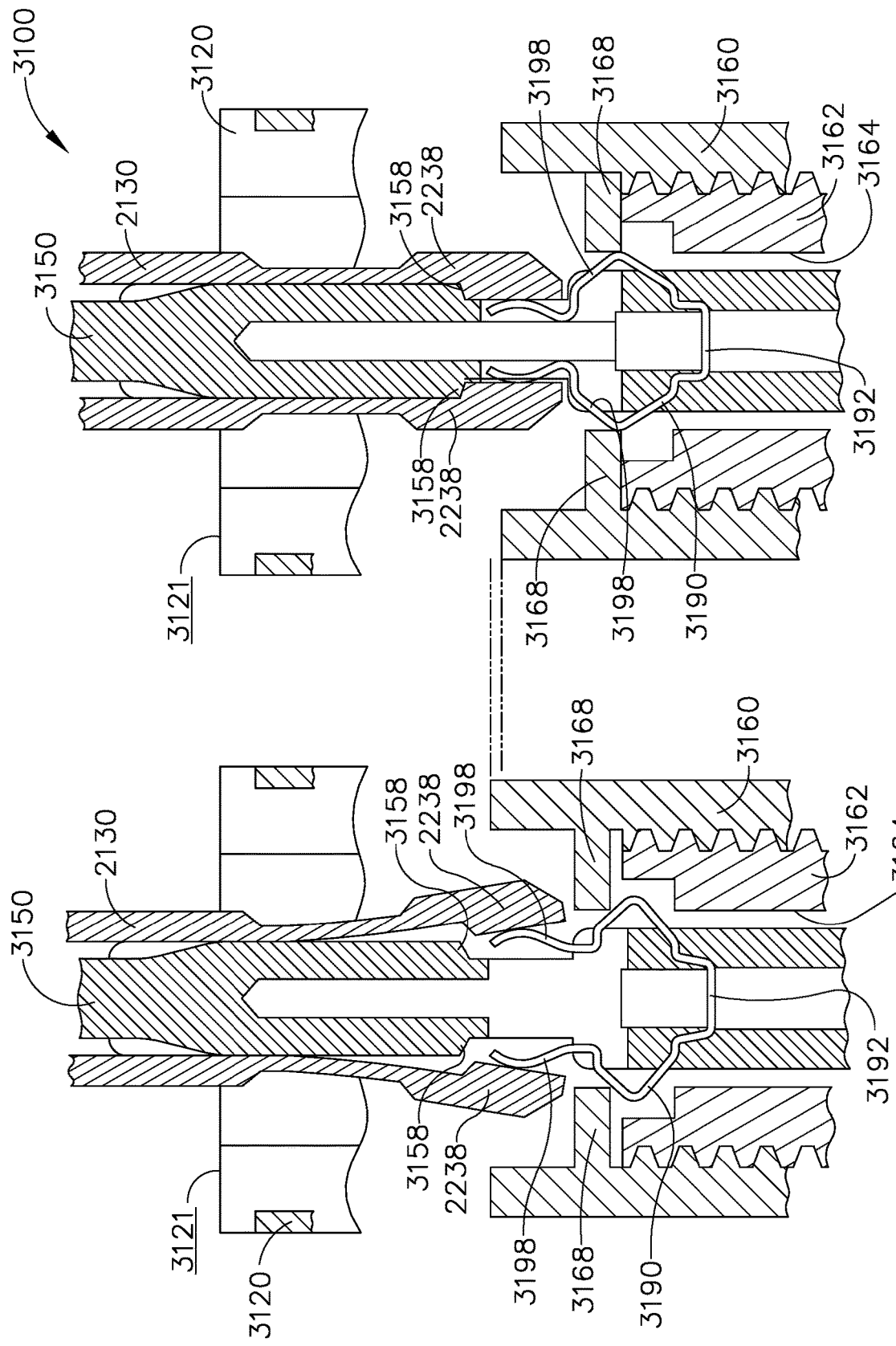
FIG. 41 is a partial cross-sectional view of a surgical stapling instrument comprising a closure drive, an anvil, and a lockout configured to prevent the anvil from being assembled to the closure drive if the closure drive is not in a fully-extended position.
FIG. 42 is a partial cross-sectional view of the surgical stapling instrument of FIG. 41 illustrating the anvil attached to the closure drive.

Turning now to FIGS. 41 and 42, an interchangeable tool assembly 3100 is depicted which is similar in many respects to the interchangeable tool assembly 2000 discussed above. The tool assembly 2000 comprises a cartridge body 3120 comprising a deck 3121 configured to support tissue when the tissue is compressed against the cartridge body 3120 by the anvil 2130. The tool assembly 3100 further comprises a closure drive configured to move the anvil 2130 relative to the cartridge body 3120. The closure drive comprises a trocar shaft 3150 which, similar to the above, includes a recess defined therein. The recess comprises a distal shoulder 3158 which is configured to retain the anvil 2130 to the trocar shaft 3150. In addition, the tool assembly 3100 further comprises a firing drive configured to eject staples from the cartridge body 3120. The firing drive comprises a rotatable shaft 3162 and a translatable collar 3160 threadably engaged with the rotatable shaft 3162 which is configured to eject staples from the cartridge body 3120. The rotatable shaft 3162 comprises a longitudinal aperture 3164 defined therein and the trocar shaft 3150 extends through the aperture 3164.

Further to the above, the closure drive further comprises a clip 3190 mounted to the trocar shaft 3150. The clip 3190 comprises a base 3192 mounted within a slot defined in the trocar shaft 3150. The clip 3190 further comprises compliant arms, or appendages, 3198 extending from the base 3192. The arms 3198 are movable between an extended position (FIG. 41) and a deflected position (FIG. 42). When the arms 3198 are in their deflected position, as illustrated in FIG. 42, the anvil 2130 can be locked to the trocar shaft 3150. The arms 3198 are held in their deflected position by the translatable collar 3160 of the firing drive when the trocar shaft 3150 has been sufficiently extended above the deck 3121 of the cartridge body 3120, as illustrated in FIG. 42. The translatable collar 3160 comprises an annular shoulder 3168 configured to resiliently bias the arms 3198 inwardly when the arms 3198 are brought into contact with the shoulder 3168.

When the trocar shaft 3150 is not in a sufficiently extended position above the cartridge deck 3121, the arms 3198 are not biased inwardly by the shoulder 3168. In such instances, the arms 3198 are in their extended position, as illustrated in FIG. 41. When the arms 3198 are in their extended position, the arms 3198 prevent the anvil 2130 from being attached to the trocar shaft 3150. More specifically, the arms 3198 prevent the connecting flanges 2138 of the anvil 2130 from being seated behind the shoulder 3158 defined in the trocar shaft 3150. In such instances, the arms 3198 prevent the anvil 2130 from being partially attached to the trocar shaft 3150 and, as a result, the clinician attempting to assemble the anvil 2130 to the trocar shaft 3150 cannot partially assemble the anvil 2130 to the trocar shaft 3150 and can avoid the issues discussed above. The reader should appreciate that the anvil 2130 is often assembled to the trocar shaft 3150 in situ, or within a patient, and the proper assembly of the anvil 2130 to the trocar shaft 3150 expedites the completion of the surgical technique being used. The system discussed above provides a lockout which prevents a partially assembled anvil from being compressed against the tissue.

Figure 43:
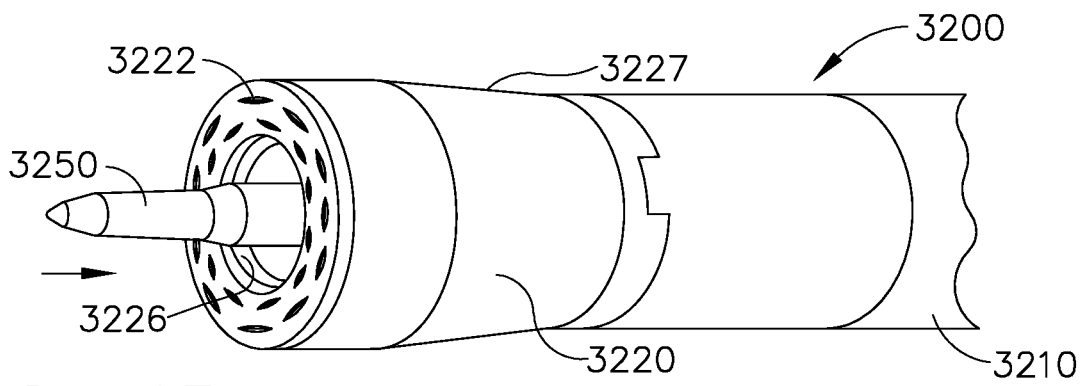
FIG. 43 is a partial perspective view of a surgical stapling instrument comprising a staple cartridge and a closure drive configured to move an anvil relative to the staple cartridge.
Figure 44:
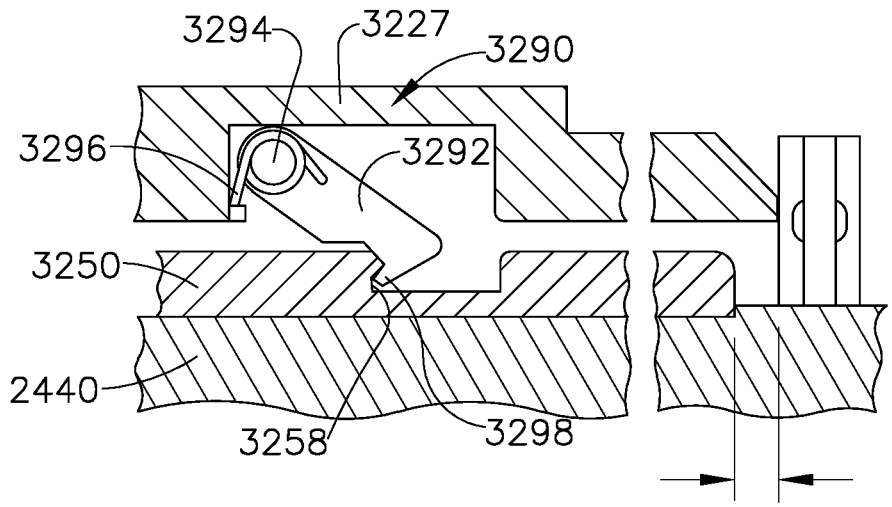
FIG. 44 is a partial cross-sectional view of the stapling instrument of FIG. 43 illustrating a lockout configured to prevent the closure drive from being retracted without the anvil being attached to the closure drive.
Figure 45:
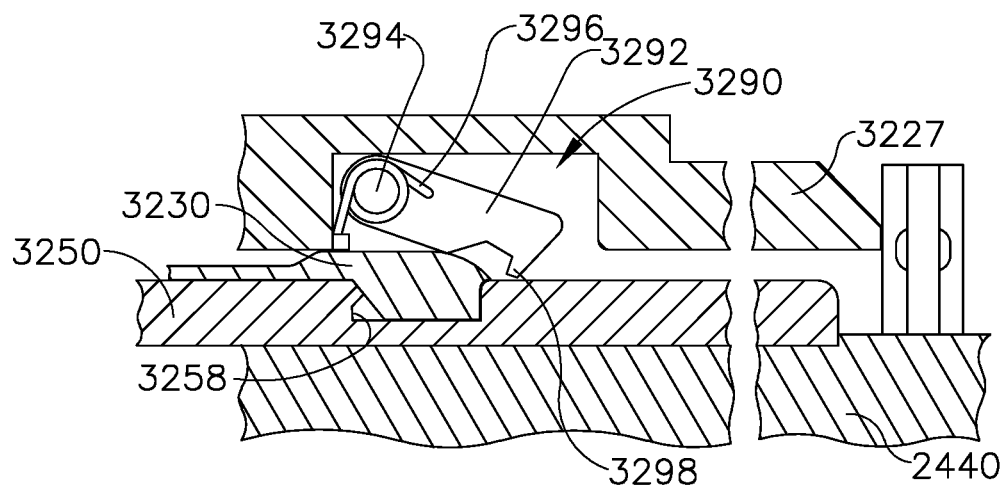
FIG. 45 is a partial cross-sectional view of the stapling instrument of FIG. 44 illustrating the anvil attached to the closure drive and the lockout disengaged from the closure drive.

Turning now to FIGS. 43-45, an interchangeable tool assembly 3200 comprises a lockout configured to prevent a closure drive from being retracted without an anvil attached thereto, as discussed in greater detail below. The tool assembly 3200 comprises a shaft 3210 and an end effector 3220. The end effector 3220 includes an outer housing 3227, a cartridge body 3222, and a longitudinal aperture 3226 defined therethrough. The tool assembly 3200 further comprises a closure drive including a trocar shaft 3250 and an anvil 3230 attachable to the trocar shaft 3250. Similar to the above, the closure drive is configured to move the anvil 3230 toward and away from the cartridge body 3222. The trocar shaft 3250 is movable between an extended position and a retracted position. FIGS. 44 and 45 both illustrate the trocar shaft 3250 in its extended position.

Further to the above, the tool assembly 3200 further comprises a retraction lock 3290 configured to prevent the trocar shaft 3250 from being moved from its extended position (FIGS. 44 and 45) toward its retracted position when the anvil 3230 is not assembled to the trocar shaft 3250. The retraction lock 3290 comprises a lock arm 3292 rotatably mounted to the housing 3227 about a projection, or pin, 3294. The retraction lock 3290 further comprises a spring 3296 engaged with the lock arm 3292 which is configured to bias the lock arm 3292 toward the trocar shaft 3250. The trocar shaft 3250 comprises a lock shoulder 3258 and, when the anvil 3230 is not assembled to the trocar shaft 3250 as illustrated in FIG. 44, the lock arm 3292 is configured to catch the lock shoulder 3258 and prevent the trocar shaft 3250 from being moved proximally. More specifically, the lock arm 3292 comprises a catch 3298 configured to slide under the lock shoulder 3258. When the anvil 3230 is assembled to the trocar shaft 3250, as illustrated in FIG. 45, the anvil 3230 contacts the lock arm 3292 and displaces the lock arm 3292 away from the lock shoulder 3258. At such point, the trocar shaft 3250 has been unlocked and can be moved toward the cartridge body 3222 into its retracted position.

Turning now to 46-48, an interchangeable tool assembly 3300 comprises a closure drive, a staple firing drive, and a lockout configured to prevent the staple firing drive from being operated until the anvil of the closure drive has been set to a proper tissue gap, as discussed in greater detail below. The tool assembly 3300 comprises a shaft 3310 and an end effector 3320. The end effector 3320 includes an inner frame 3329, an outer housing 3327, and a cartridge body 3322. Similar to the above, the closure drive includes a trocar shaft 3350 and an anvil 2230 attachable to the trocar shaft 3350. Also similar to the above, the trocar shaft 3350 is movable between an extended position (FIG. 47) and a retracted position (FIG. 48) to move the anvil 2230 toward and away from the cartridge body 3322. The firing drive includes a rotatable shaft 3360 which is configured to displace a firing drive distally to eject the staples stored in the cartridge body 3322.

Further to the above, the end effector 3320 comprises a firing drive lock 3390 movably mounted to the inner frame 3329. The firing drive lock 3390 comprises a lock pin 3394 and a lock spring 3398 positioned around the lock pin 3394. The lock pin 3394 comprises a head 3392 and a stop 3396. The lock spring 3398 is positioned intermediate the stop 3396 and a sidewall of a cavity 3328 defined in the inner frame 3329. When the trocar shaft 3350 is in an extended position, as illustrated in FIG. 47, the lock spring 3398 biases the lock pin 3394 into a lock aperture 3364 defined in the rotatable shaft 3360 of the staple firing drive. In such instances, the interaction between the lock pin 3394 and the sidewalls of the lock aperture 3364 prevent the shaft 3360 from being rotated to fire the staples from the cartridge body 3322. When the trocar shaft 3350 is sufficiently retracted, the trocar shaft 3350 engages the head 3392 of the lock pin 3394. The head 3392 comprises a cam surface defined thereon which is configured to be engaged by the trocar shaft 3350 to move the firing drive lock 3390 between a locked configuration (FIG. 47) and an unlocked configuration (FIG. 48). When the drive lock 3390 is in its unlocked configuration, the shaft 3360 of the firing drive can be rotated.

The firing drive lockout of the tool assembly 3300 requires the anvil 2230 to be moved into a predetermined position, or within a range of predetermined positions, before the staples can be fired. Moreover, the firing drive lockout of the tool assembly 3300 requires the tissue gap between the anvil 2230 and the cartridge body 3322 to be less than a certain distance before the staples can be fired. As a result, the position of the anvil 2230 and/or the closure system deactivates the staple firing lockout. Such an arrangement can assist in preventing the malformation of the staples and/or the undercompression of the tissue, among other things.

Figure 49:
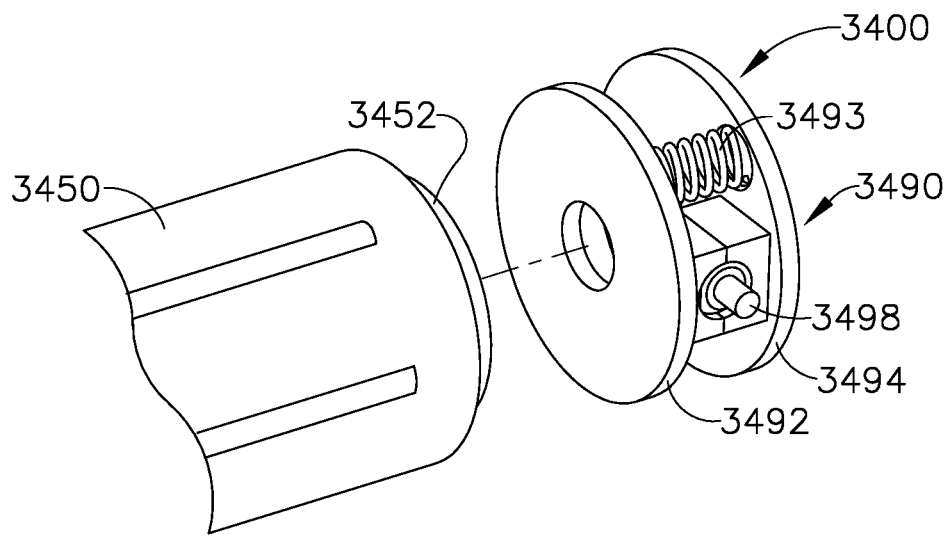
FIG. 49 is a partial perspective view of a surgical stapling instrument comprising a staple cartridge including staples removable stored therein, an anvil, a closure drive configured to move the anvil relative to the staple cartridge, and a firing drive configured to eject the staples from the staple cartridge.
Figure 50:
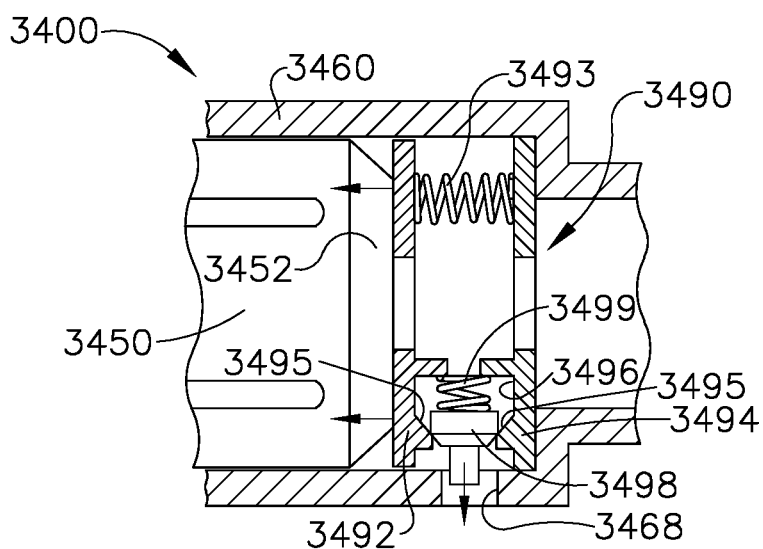
FIG. 50 is a detail view of a lockout of the surgical stapling instrument of FIG. 49 configured to prevent the firing drive from being actuated prior to the anvil applying a sufficient pressure to tissue captured between the anvil and the staple cartridge.
Figure 51:
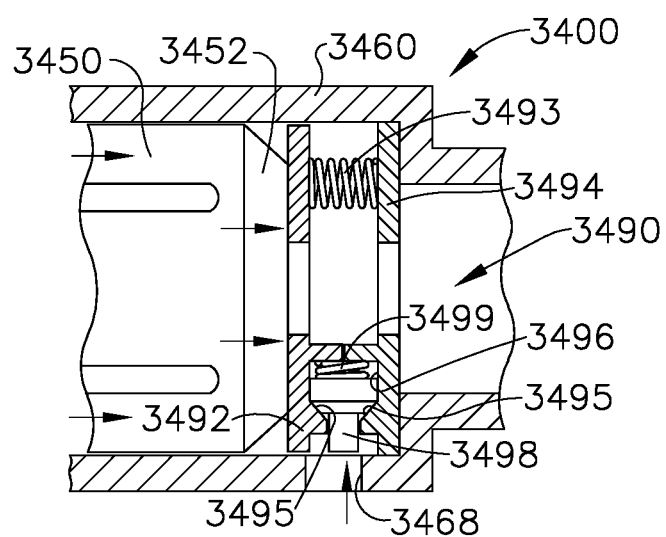
FIG. 51 is a detail view of the lockout of FIG. 50 disengaged from the firing drive.

Turning now to FIGS. 49-51, an interchangeable tool assembly 3400 comprises a closure drive configured to clamp tissue, a staple firing drive, and a firing drive lockout 3490 configured to prevent the staple firing drive from being operated prior to the closure drive applying a sufficient clamping pressure to the tissue. The closure drive comprises a trocar shaft 3450 and an anvil, such as anvil 2230, for example, attached to the trocar shaft 3450. Similar to the above, the trocar shaft 3450 is movable from an extended position (FIG. 50) to a retracted position (FIG. 51) to compress tissue against a cartridge body of the tool assembly 3400. The firing drive comprises a rotatable shaft 3460 configured to displace a staple driver distally and eject staples from the cartridge body.

The firing drive lockout 3490 is positioned intermediate the trocar shaft 3450 of the closure drive and the rotatable shaft 3460 of the firing drive. The firing drive lockout 3490 comprises a distal plate 3492, a proximal plate 3494, and a spring 3493 positioned intermediate the distal plate 3492 and the proximal plate 3494. The firing drive lockout 3490 further comprises a lock pin 3498 movable between a locked configuration (FIG. 50) in which the lock pin 3498 is engaged with the shaft 3460 and an unlocked configuration (FIG. 51) in which the lock pin 3498 is disengaged from the shaft 3460. The lock pin 3498 is positioned in a pin chamber 3496 defined between the distal plate 3492 and the proximal plate 3494. More specifically, the lock pin 3498 comprises a beveled head positioned intermediate a cam 3495 defined on the distal plate 3492 and a cam 3495 defined on the proximal plate 3494. When the trocar shaft 3450 is retracted proximally, the trocar shaft 3450 pushes the distal plate 3492 proximally and the cam 3495 defined on the distal plate 3492 engages the head of the lock pin 3498. In such instances, the cam 3495 defined on the distal plate 3492, in co-operation with the cam 3495 defined on the proximal plate 3494, displace the lock pin 3498 into its unlocked configuration, as illustrated in FIG. 51.

As discussed above, the cams 3495 of the firing drive lockout 3490 squeeze the head of the lock pin 3498 as the distal plate 3492 is moved toward the proximal plate 3494 by the trocar shaft 3450. More specifically, the cams 3495 drive the lock pin 3498 inwardly and out of engagement with the rotatable shaft 3460. The lock pin 3498 is positioned in a lock aperture 3468 defined in the shaft 3460 when the lock pin 3498 is in its locked configuration and, owing to the interaction between the lock pin 3498 and the sidewalls of the lock aperture 3468, the lock pin 3498 prevents the shaft 3460 from rotating. As a result, the staples cannot be fired from the cartridge body by the firing drive. When the lock pin 3498 is moved into is unlocked configuration, as discussed above, the lock pin 3498 is moved out of the lock aperture and the shaft 3460 can be rotated by the firing drive to fire the staples from the cartridge body. In various embodiments, the shaft 3460 can include a circumferential array of lock apertures 3468 defined in the shaft 3460, each of which is configured to receive the lock pin 3498 and lockout the firing drive. Referring again to FIGS. 49-51, the firing drive lockout 3490 further comprises a biasing member, such as a spring 3499, for example, which is configured to bias the lock pin 3498 into a lock aperture 3468.

Further to the above, the spring 3493 of the firing drive lockout 3490 is configured to resist the proximal movement of the trocar shaft 3450. The spring 3493 is a linear coil spring; however, any suitable spring could be used. Moreover, more than one spring could be used. In any event, the spring 3493, or spring system, has a stiffness which applies a spring force to the distal plate 3492 of the firing drive lockout 3490 as the trocar shaft 3450 is retracted. Stated another way, the force applied to the distal plate 3492 by the spring 3493 increases in proportion to the distance in which the trocar shaft 3450 is displaced proximally. The spring force generated by the spring 3493 opposes the clamping force that the anvil 2230 is applying to the tissue. As a result, the clamping force must overcome a certain, or predetermined, spring force being generated by the spring 3493 in order to sufficiently displace the distal plate 3492 and unlock the firing drive. In such instances, the tissue clamping force must meet a predetermined threshold before the firing drive lockout 3490 can be deactivated and the staple firing drive can be actuated.

Figure 53:
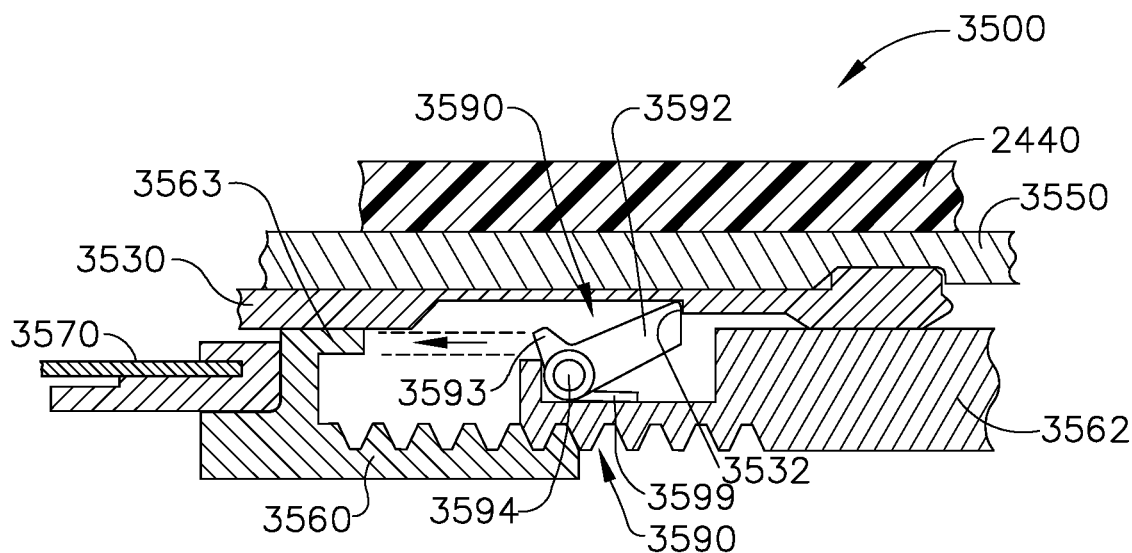
FIG. 53 is a detail view of a lockout of the surgical stapling instrument of FIG. 52 configured to prevent the anvil from being detached from the closure drive while a cutting member of the firing drive is exposed above the staple cartridge.
Figure 54:
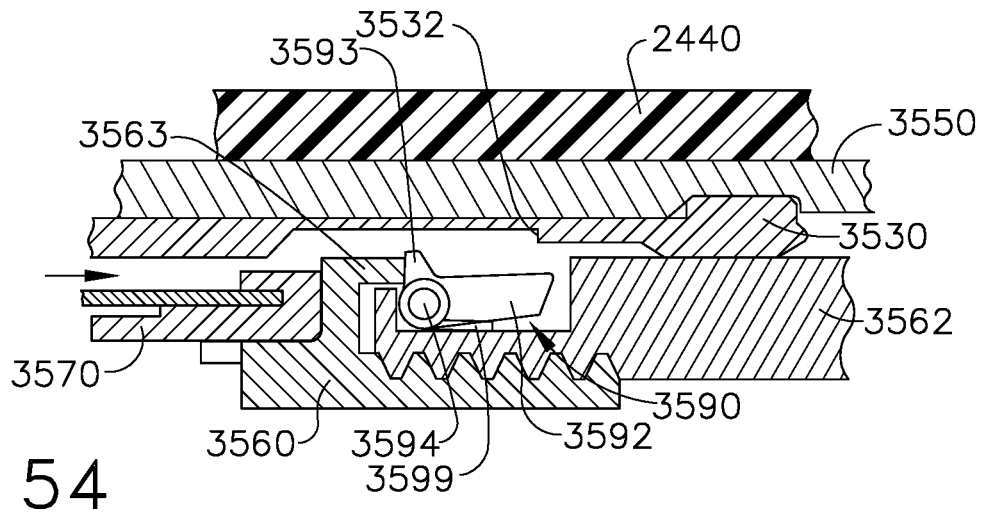
FIG. 54 is a detail view of the lockout of FIG. 53 disengaged from the anvil after the firing drive has been sufficiently retracted after a firing stroke.

As discussed in connection with various embodiments disclosed herein, a staple firing drive drives staples against an anvil to deform the staples to a desired formed height. In various instances, the staple firing drive is also configured to push a cutting member, such as a knife, for example, distally to cut tissue captured between the cartridge body and the anvil. In such instances, the knife is exposed above the deck of the cartridge body. That said, the anvil is positioned in close relationship to the cartridge body when the anvil is in its closed, or clamped, position and the knife is, for the most part, covered by the anvil even though the knife is exposed above the cartridge body. In the event that the anvil were to be moved to its open position and/or detached from the closure drive before the knife is retracted below the deck of the cartridge body, the knife would be uncovered and exposed. A tool assembly 3500 is illustrated in FIGS. 52-54 which comprises a lockout 3590 configured to prevent the anvil from being moved into its open position while the knife is exposed above the cartridge deck.

The tool assembly 3500 comprises a closure drive and a firing drive. The closure drive comprises a trocar shaft 3550 and an anvil 3530 releasably attachable to the trocar shaft 3550 Similar to the above, the trocar shaft 3550 is translatable proximally and distally by a rotatable closure shaft 2440 threadably engaged with the trocar shaft 3550. The firing drive comprises a rotatable shaft 3562 and a translatable collar 3560 threadably engaged with the rotatable shaft 3562 Similar to the above, the collar 3560 is translatable proximally and distally when the shaft 3562 is rotated in first and second directions, respectively. Also similar to the above, the collar 3560 of the firing drive is configured to advance and retract an array of staple drivers and a knife assembly 2570 toward and away from the anvil 3530.

Further to the above, the lockout 3590 comprises a lock arm 3592 rotatably mounted to the shaft 3562 of the firing drive about a pivot 3594. The lockout 3590 further comprises a biasing member, or spring, 3599 engaged with the lock arm 3592 which is configured to bias the lock arm 3592 into contact with the anvil 3530. In use, the anvil 3530 is assembled to the trocar shaft 3550 and the trocar shaft 3550 is then retracted to position the anvil 3530 in its closed, or clamped, position relative to the cartridge body. As the anvil 3530 is being retracted, the lock arm 3592 of the lockout 3590 slides against the outer surface of the anvil 3530 until the lock arm 3592 is aligned with a lock recess 3532 defined in the anvil 3530. At such point, the spring 3599 biases the lock arm 3592 into the lock recess 3532, as illustrated in FIG. 53. More specifically, the lock arm 3592 is positioned behind a lock shoulder which defines the lock recess 3532. The firing drive can then be operated to fire the staples and cut the tissue. In such instances, the cutting edge of the knife assembly 2570 is exposed above the cartridge body and, owing to the lockout 3590, the closure drive is locked out, or prevented from being opened, until the cutting edge of the knife assembly 2570 is no longer exposed.

Figure 52:
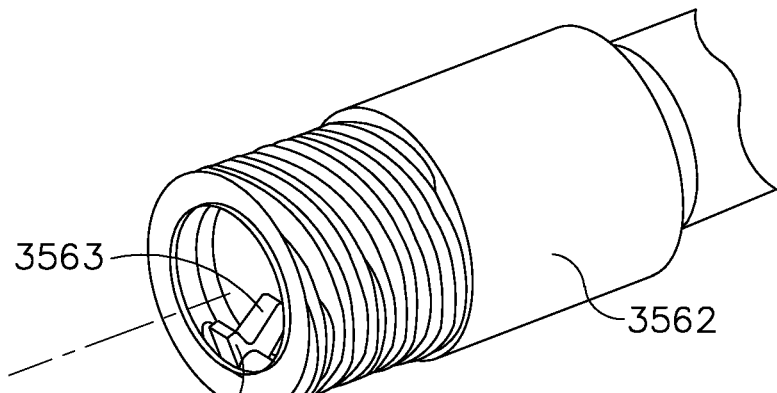
FIG. 52 is a partial perspective view of a surgical stapling instrument comprising a staple cartridge including staples removable stored therein, an anvil, a closure drive configured to move the anvil relative to the staple cartridge, and a firing drive configured to eject the staples from the staple cartridge.

Referring primarily to FIG. 52, the lock arm 3592 further comprises a reset tab 3593 extending therefrom. The collar 3560 of the firing drive further comprises a cam 3563 configured to engage the reset tab 3593 when the collar 3560 and the knife assembly 2570 are retracted proximally by the firing drive. The cam 3563 is configured to rotate the lock arm 3592 downwardly out of engagement with the lock shoulder defined in the lock recess 3532 and unlock the closure drive. The cam 3563 is configured to unlock the closure drive when the cutting edge of the knife assembly 2570 has been retracted below the cartridge deck; however, in other embodiments, the cam 3563 can unlock the closure drive when the cutting edge is flush with, or at least substantially flush with, the cartridge deck. In some embodiments, the closure drive may not be unlocked until the knife assembly 2570 has been completely retracted. Once the closure drive has been unlocked, the closure drive can be operated to move the anvil 3530 to an open, or unclamped, position once again.

Once the staples of an interchangeable tool assembly have been fired, according to various embodiments, the tool assembly may not be re-used. As discussed in greater detail below, a tool assembly can include a lockout configured to prevent the tool assembly from being re-clamped onto tissue after it has been used to staple tissue.

In at least one embodiment, referring now to FIGS. 55-58, an interchangeable tool assembly 3600 comprises a closure drive configured to position an anvil, such as anvil 2230, for example, relative to a staple cartridge and a firing drive configured to drive staples from the staple cartridge. Similar to the above, the anvil 2230 is attachable to a translatable trocar shaft 3650 of the closure drive. Also similar to the above, the firing drive comprises a rotatable shaft 3660, a translatable collar 2550 threadably engaged with the rotatable shaft 3660, and a staple firing driver 2560 displaceable by the rotatable shaft 3660. In use, the closure drive is operable to position the anvil 2230 in a clamped position relative to the staple cartridge and the firing driver is then operable to fire the staples into tissue captured between the anvil 2230 and the staple cartridge. Thereafter, the closure drive is operated to open the anvil 2230 and release the tissue.

Further to the above, the tool assembly 3600 comprises a lockout 3690 configured to prevent the anvil 2230 from being reclamped onto the tissue. The lockout 3690 comprises a lock arm 3692 rotatably mounted to the rotatable shaft 3660 which is held in an unlocked configuration by the firing drive as the closure drive moves the anvil 2230 between an open, unclamped position (FIG. 55) and a closed, clamped position (FIG. 56). The lock arm 3692 is held in its unlocked configuration between the rotatable shaft 3660 and the translatable collar 2550 as the trocar shaft 3650 and the anvil 2230 are moved relative to the firing drive to position the anvil 2230 relative to the staple cartridge. The arm 3692 is held in its unlocked configuration until the firing drive is operated, as illustrated in FIG. 55. As the shaft 3460 is rotated in a first direction, the collar 2550 is displaced distally and a spring 3699 of the lockout 3690 can bias the lock arm 3692 against the trocar shaft 3650. The trocar shaft 3650 rotates relative to the lock arm 3692 as the collar 2550 is displaced distally to fire the staples and then retracted proximally. The closure drive can then be operated to re-open the anvil 2230 to unclamp the tissue and/or detach the anvil 2230 from the trocar shaft 3650. As the anvil 2230 is being re-opened, the spring 3699 biases the lock arm 3692 into a lock recess 3652 defined in the trocar shaft 3650 and/or anvil 2230. Once the lock arm 3692 is positioned in the lock recess 3652, the lock arm 3692 prevents the trocar shaft 3650 from being retracted proximally. In the event that the closure drive is operated in an attempt to retract the trocars shaft 3650 the lock arm 3692 will abut a lock shoulder defined in the lock recess 3652 and prevent the retraction of the trocar shaft 3650 and anvil 2230. As a result, the lockout 3690 prevents the anvil 2230 from being re-clamped onto tissue after the tool assembly 3600 has undergone, or at least partially undergone, a firing cycle and the tool assembly 3600 cannot be used again. Moreover, the lockout 3690 can serve as a spent cartridge lockout.

Turning now to FIGS. 59 and 60, a tool assembly 3700 comprises a staple cartridge 3720 and an anvil 3730. The tool assembly 3700 further comprises a closure system configured to move the anvil 3730 toward the staple cartridge 3720 and, in addition, a firing system configured to eject, or fire, staples removably stored in the staple cartridge 3720. The anvil 3730 comprises a longitudinal shaft portion 3736 and attachment arms 3738 extending from the shaft portion 3736 which are configured to resiliently grip a closure actuator, or trocar, 3734 of the closure system. The closure actuator 3734 is retractable proximally by a closure drive to move the trocar 3734 between an open, unclamped position (FIG. 59) and a closed, clamped position (FIG. 60). When the closure system is in its open configuration, as illustrated in FIG. 59, the staple firing system is disabled and cannot be actuated to fire the staples stored in the staple cartridge 3720, as described in greater detail below.

Further to the above, the staple firing system comprises a rotatable firing shaft 3750 comprising a threaded distal end and, in addition, a translatable firing nut 2550 comprising a threaded aperture configured to receive the threaded distal end of the firing shaft 3750. Notably, referring to FIG. 59, a gap is present between the threaded distal end of the firing shaft 3750 and the threaded aperture defined in the firing nut 2550 when the anvil 3730 is in its open position. As a result, the firing shaft 3750 cannot displace the firing nut 2550 distally until the firing shaft 3750 is threadably engaged with the firing nut 2550.

As illustrated in FIG. 60, the attachment arms 3738 of the anvil 3730 are configured to engage the firing shaft 3750 and deflect the firing shaft 3750 outwardly when the anvil 3730 is moved into its closed position. Referring primarily to FIGS. 59A and 60A, the attachment arms 3738 are configured to engage inwardly-extending projections 3758 defined on the firing shaft 3750 and push the projections 3758 and the perimeter of the firing shaft 3750 outwardly. In such instances, the threaded distal end of the firing shaft 3750 is pushed into operative engagement with the threaded aperture of the firing nut 2550 at a thread interface 3790 and, at such point, the firing shaft 3750 can displace the firing nut 2550 distally to eject the staples from the staple cartridge 3720 when the firing shaft 3750 is rotated by a firing drive. When the anvil 3730 is re-opened, the firing shaft 3750 will return to its original configuration and become operably disengaged from the firing nut 2550.

As a result of the above, the tool assembly 3700 comprises a lockout which prevents the staples from being fired if the anvil 3730 is not attached to the closure system, if the anvil 3730 is improperly attached to the closure system, and/or if the anvil 3730 is not sufficiently closed.

Figure 61:
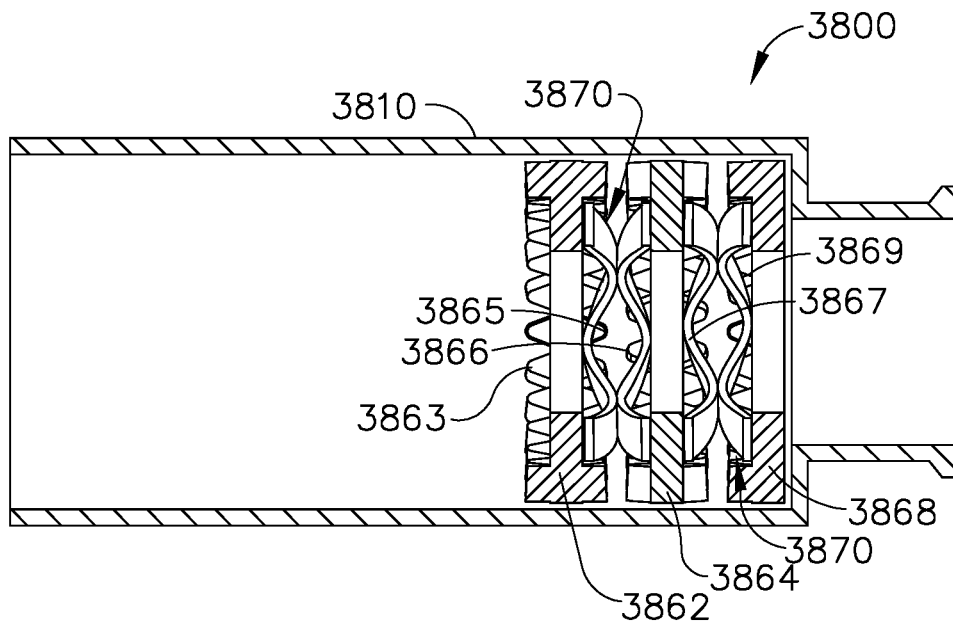
FIG. 61 is a partial cross-sectional view of a surgical stapling instrument comprising a staple cartridge including staples removable stored therein, an anvil, a closure drive configured to move the anvil relative to the staple cartridge, and a firing drive configured to eject the staples from the staple cartridge, wherein the closure drive is illustrated in an unclamped configuration and the firing drive is illustrated in an inoperable configuration.
Figure 62:
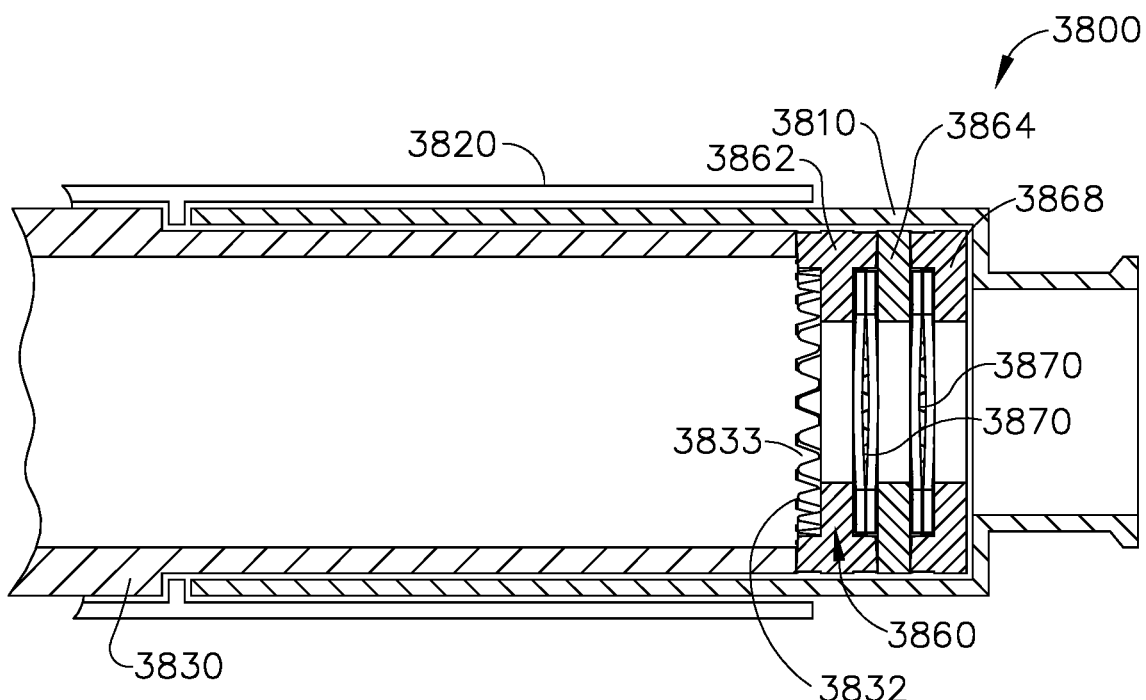
FIG. 62 is a partial cross-sectional view of the surgical stapling instrument of FIG. 61 with the closure drive illustrated in a clamped configuration and the firing drive is illustrated in an operable configuration.

Turning now to FIGS. 61 and 62, a tool assembly 3800 comprises a replaceable staple cartridge including staples removably stored therein, an anvil configured to deform the staples, a closure drive system configured to move the anvil relative to the staple cartridge, and a firing system configured to eject the staples from the staple cartridge. As discussed below, the tool assembly 3800 further comprises a lockout configured to prevent the firing system from being operated unless the staple cartridge is fully seated onto the tool assembly 3800.

The staple cartridge comprises a cartridge frame 3820 configured to engage a shaft frame 3810 of the tool assembly 3800. The staple cartridge further comprises a drive shaft 3830 which is inserted into the shaft frame 3810 when the staple cartridge is assembled to the tool assembly 3800. More particularly, referring primarily to FIG. 64, the drive shaft 3830 comprises a proximal end 3832 including an annular gear portion 3833 which is configured to engage and compress a transmission 3860 of the firing system when the staple cartridge is assembled to the tool assembly 3800. Referring primarily to FIG. 62, the transmission 3860 comprises a first portion 3862, a second portion 3864, and a third portion 3868 which, when pushed into operative engagement with each other, are able to transmit a rotary input motion to the drive shaft 3830.

Figure 63:
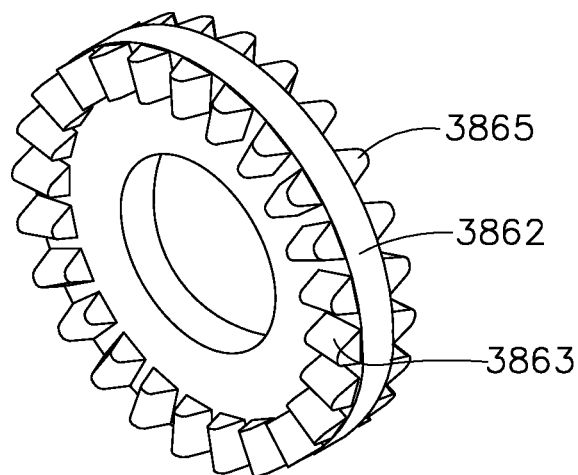
FIG. 63 is a perspective view of a rotatable intermediate drive member of the firing drive of the surgical instrument of FIG. 61.
Figure 64:
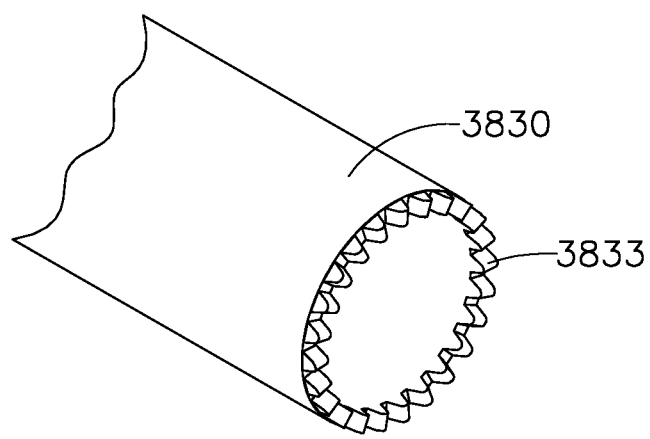
FIG. 64 is a partial perspective view of a rotatable firing shaft of the firing drive of the surgical instrument of FIG. 61.

Referring primarily to FIGS. 63 and 64, the annular gear portion 3833 of the drive shaft 3830 is configured to engage a corresponding gear portion 3863 defined on the distal side of the first transmission portion 3862 and, when the first transmission portion 3862 is pushed proximally by the drive shaft 3830, the first transmission portion 3862 can operably engage the second transmission portion 3864. More specifically, the first transmission portion 3862 comprises a proximal gear portion 3865 which engages a distal gear portion 3866 of the second transmission portion 3864 and, concurrently, pushes the second transmission portion 3864 proximally when the first transmission portion 3862 is pushed proximally by the drive shaft 3830. When the second transmission portion 3864 is pushed proximally by the first transmission portion 3862, similar to the above, the second transmission portion 3864 can operably engage the third transmission portion 3868. More specifically, the second transmission portion 3862 comprises a proximal gear portion 3867 which engages a distal gear portion 3869 of the third transmission portion 3864 when the first transmission portion 3862 and the second transmission portion 3864 are pushed proximally by the drive shaft 3830. The third transmission portion 3868 is operably coupled to an input shaft and supported from being displaced proximally by the input shaft and/or the shaft housing 3810.

Figure 65:
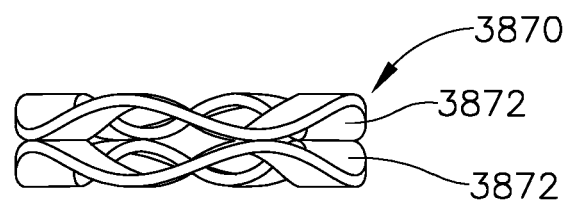
FIG. 65 is an elevational view of a spring system configured to bias the firing shaft of FIG. 64 out of engagement with the intermediate drive member of FIG. 63.

Referring primarily to FIG. 61, the transmission 3860 further comprises at least one spring member 3870 positioned intermediate the first transmission portion 3862 and the second transmission portion 3864. In at least one instance, the spring member 3870 can comprise one or more wave springs, for example. The spring member 3870 is configured to bias the first transmission portion 3862 and the second transmission portion 3864 apart from one another. In addition to or in lieu of the above, the transmission 3860 further comprises at least one spring member 3870 positioned intermediate the second transmission portion 3864 and the third transmission portion 3868 which, similar to the above, is configured to bias the second transmission portion 3864 and the third transmission portion 3868 apart from one another. Referring primarily to FIG. 65, each spring member 3870 comprises two disc springs 3872 which are configured to deflect when a compressive force is applied thereto; however, the springs members 3870 can comprise any suitable configuration.

Further to the above, and referring again to FIG. 61, the input shaft of the tool assembly 3800 can rotate the third transmission portion 3868; however, the rotation of the third transmission portion 3868 cannot be transmitted to the second transmission portion 3864 unless the spring member 3870 positioned intermediate the second transmission portion 3864 and the third transmission portion 3868 has been sufficiently compressed to connect the proximal gear portion 3867 of the second transmission portion 3864 with the distal gear portion 3869 of the third transmission portion 3868. Similarly, the second transmission portion 3864 cannot transmit rotary motion to the first transmission portion 3862 unless the spring member 3870 positioned intermediate the first transmission portion 3862 and the second transmission portion 3864 has been sufficiently compressed to connect the proximal gear portion 3865 of the first transmission portion 3862 and the distal gear portion 3866 of the second transmission portion 3864. As discussed above, the drive shaft 3830 engages the first transmission portion 3862 with the second transmission portion 3864 and engages the second transmission portion 3864 with the third transmission portion 3868 when the staple cartridge is fully seated onto the shaft frame 3810, as illustrated in FIG. 62. In such instances, the rotation of the input shaft can be transmitted to the drive shaft 3830. If the staple cartridge is not fully seated onto the shaft frame 3810, however, one or more of the transmission portions 3862, 3864, and 3868 are not operably engaged with each other and the rotation of the input shaft cannot be transmitted to the drive shaft 3830. Thus, the tool assembly 3800 assures that the staples stored within the staple cartridge cannot be ejected from the staple cartridge unless the staple cartridge is fully seated onto the shaft frame 3810.

Figure 66:
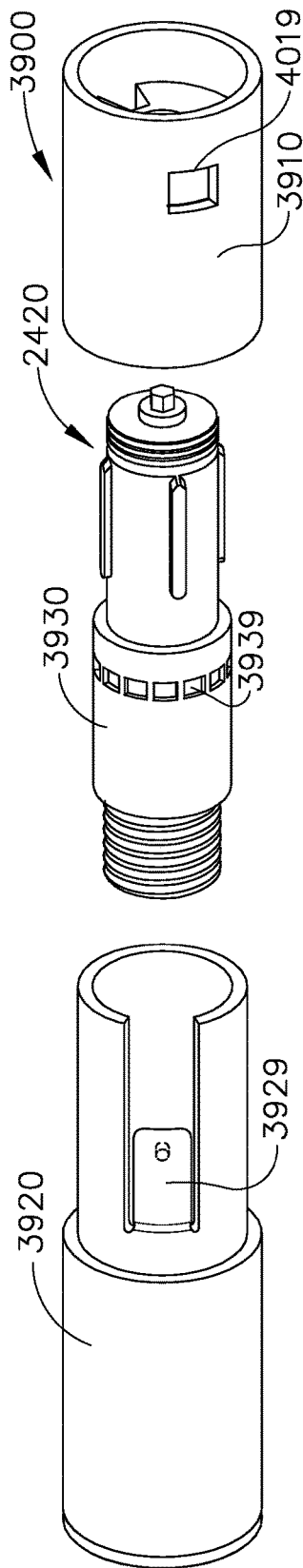
FIG. 66 is an exploded view of an end effector of a surgical stapling instrument comprising a staple cartridge in accordance with at least one embodiment.
Figure 67:
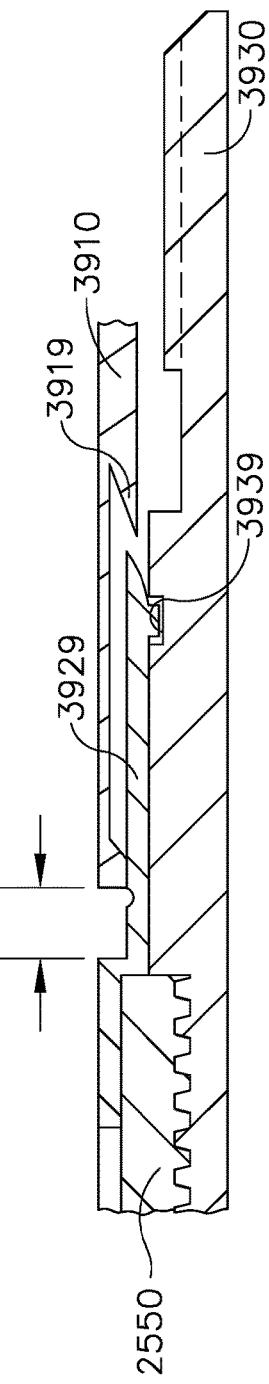
FIG. 67 is a partial cross-sectional view of the end effector of FIG. 66 illustrating a lockout configured to prevent the end effector from being operated if the staple cartridge is not fully assembled to the stapling instrument.
Figure 68:
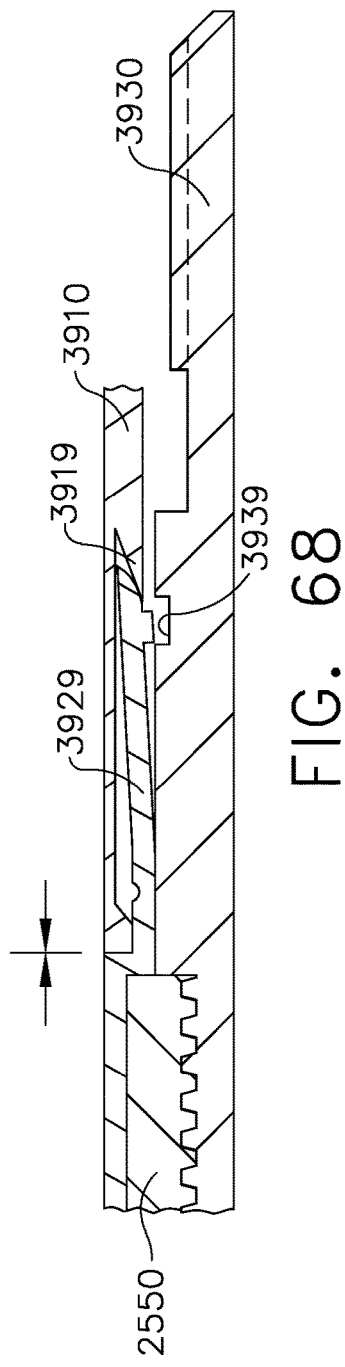
FIG. 68 is a partial cross-sectional view of the end effector of FIG. 66 illustrating the lockout in an unlocked configuration.

Turning now to FIGS. 66-68, a tool assembly 3900 comprises a shaft 3910 and a replaceable staple cartridge 3920. The replaceable staple cartridge 3920 comprises a closure drive configured to move an anvil relative to the staple cartridge 3920 and, in addition, a firing drive comprising a rotatable firing shaft 3930 configured to eject staples removably stored in the staple cartridge 3920 Similar to the above, the tool assembly 3900 comprises a lockout configured to prevent the firing drive from ejecting the staples from the staple cartridge 3920 unless the staple cartridge 3920 is fully, or sufficiently, seated onto the shaft 3910. More specifically, the lockout prevents the firing shaft 3930 from rotating within the staple cartridge 3920 unless the staple cartridge 3920 is fully, or sufficiently, seated onto the shaft 3910. In various instances, referring to FIG. 67, the firing shaft 3930 comprises an annular array of lock apertures 3939 defined in the outer perimeter thereof and the staple cartridge 3920 comprises at least one lock 3929 configured to releasably engage a lock aperture 3939 defined in the shaft 3930. The lock 3929 comprises a proximally-extending cantilever beam; however, any suitable configuration could be utilized. The lock 3929 further comprises a locking projection that extends into the lock aperture 3939 and prevents the firing shaft 3930 from rotating, or at least substantially rotating, relative to the body of the staple cartridge 3920. The lock 3929 is configured such that it is biased into engagement with a lock aperture 3939 defined in the firing shaft 3930 until the lock 3929 is lifted out of the lock aperture 3939 when the staple cartridge 3920 is fully, or sufficiently, assembled to the shaft 3910, as illustrated in FIG. 68. Referring to FIG. 68, the outer housing of the shaft 3910 comprises a wedge 3919 configured to lift the lock 3929 away from the firing shaft 3930 and disengage the lock 3929 from the lock aperture 3939. The wedge 3919 is configured such that it does not disengage the lock 3929 from the firing shaft 3930 unless the staple cartridge 3920 has been fully, or sufficiently, seated onto the shaft 3910, as illustrated in FIG. 68. FIG. 67 illustrates a scenario where the staple cartridge 3920 has not been fully, or sufficiently, seated onto the shaft 3910.

Figure 69:
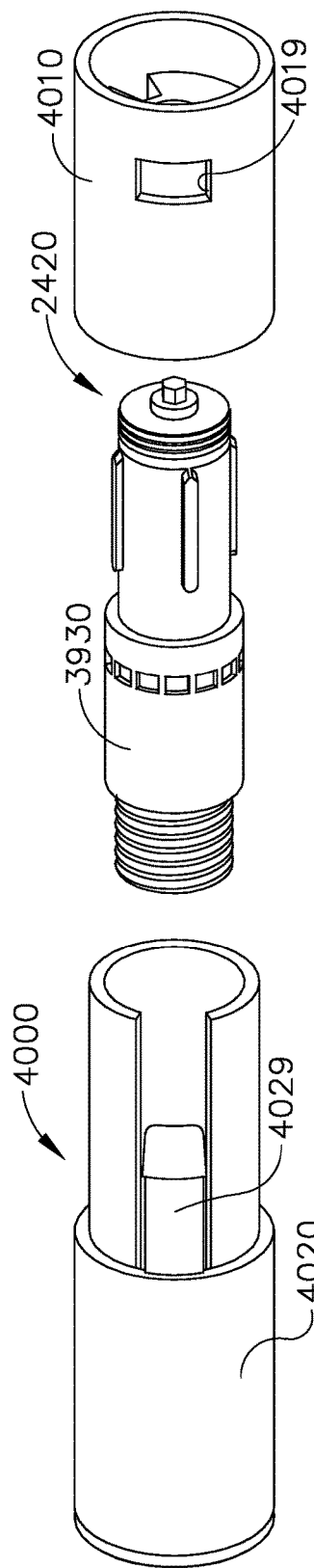
FIG. 69 is an exploded view of an end effector of a surgical stapling instrument comprising a staple cartridge in accordance with at least one embodiment.
Figure 70:
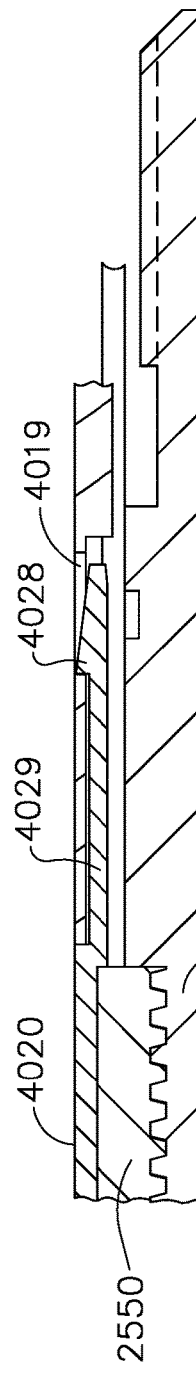
FIG. 70 is a partial cross-sectional view of the end effector of FIG. 69 illustrating a lock configured to releasably hold the staple cartridge to the stapling instrument.
Figure 71:
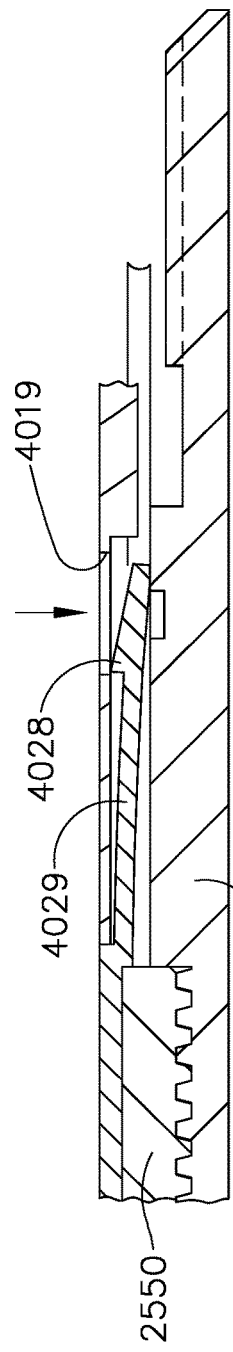
FIG. 71 is a partial cross-sectional view of the end effector of FIG. 69 illustrating the lock in an unlocked configuration.

Turning now to FIGS. 69-71, a tool assembly 4000 comprises a shaft 4010 and a replaceable staple cartridge 4020. The replaceable staple cartridge 4020 comprises a closure drive configured to move an anvil relative to the staple cartridge 4020 and, in addition, a firing drive comprising a rotatable firing shaft 3930 configured to eject staples removably stored in the staple cartridge 4020. The staple cartridge 4020 comprises a lock 4029 configured to releasably connect the staple cartridge 4020 to the shaft 4010. The lock 4029 comprises a proximally-extending cantilever and a lock shoulder 4028 extending therefrom. The lock 4029 is configured to deflect inwardly within the shaft 4010 as the staple cartridge 4020 is assembled to the shaft 4010 and then resiliently return to, or at least toward, its undeflected state when the lock shoulder 4028 of the lock 4029 becomes aligned with a window 4019 defined in the outer housing of the shaft 4010. In such instances, the lock shoulder 4028 enters into the window 4019 when the staple cartridge 4020 has been fully, or sufficiently, seated on the shaft 4010, as illustrated in FIG. 70. In order to unlock the staple cartridge 4020, a clinician can insert a tool or their finger, for example, into the window and depress the lock 4029 away from the window 4019. At such point, the staple cartridge 4020 can be removed from the shaft 4010 and, if the clinician so desires, and attach a new staple cartridge to the shaft 4010.

In addition to or in lieu of the above, a surgical stapling system can comprise an electrical lockout configured to prevent the closure drive of the stapling system from clamping the anvil onto the tissue and/or prevent the firing drive from performing its firing stroke when a staple cartridge has not been fully, or sufficiently, seated onto the shaft of the stapling system. In various instances, the stapling system can comprise a sensor configured to detect whether a staple cartridge has been fully, or sufficiently, seated on the shaft and, in addition, an electrical motor configured to operate the firing drive. In the event that the sensor detects that a staple cartridge has not been fully, or sufficiently, attached to the shaft, the motor can be electrically de-activated. In various instances, the stapling system comprises a controller, such as a microprocessor, for example, which is in communication with the sensor and the electric motor. In at least one instance, the controller is configured to, one, permit the electric motor to be operated if the sensor detects a properly seated staple cartridge on the shaft and, two, prevent the electric motor from being operated if the sensor detects an improperly seated staple cartridge on the shaft.

Figure 72:
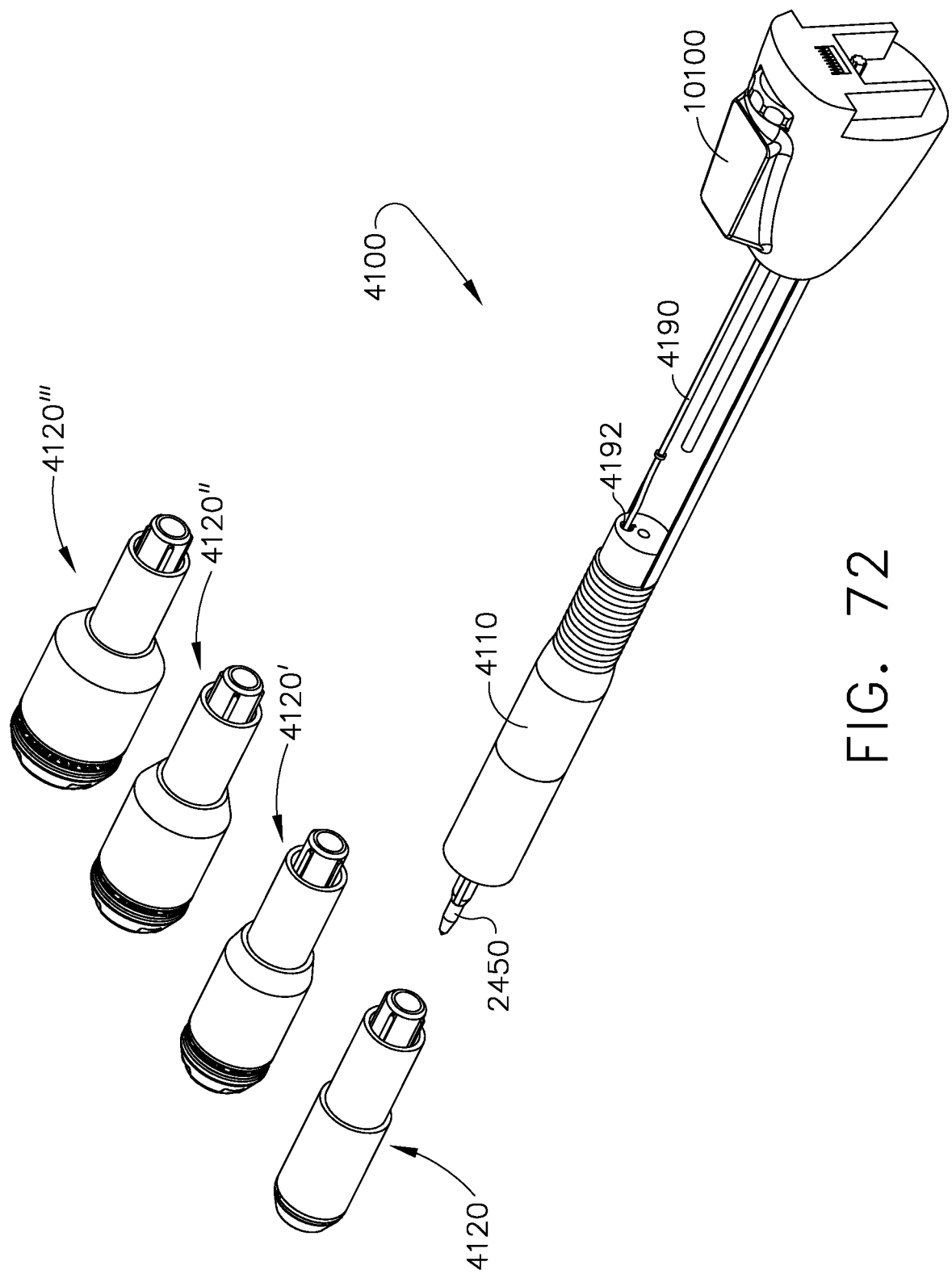
FIG. 72 illustrates a shaft of a surgical stapling instrument configured to be used with a staple cartridge selected from a plurality of circular staple cartridges.

Turning now to FIG. 72, a tool assembly kit 4100 comprises a shaft 4110 and a plurality of staple cartridges, such as 4120, 4120', 4120'', and 4120''', for example. Each staple cartridge 4120, 4120', 4120'', and 4120''' is configured to apply circular rows of staples having a different diameter. For example, the staple cartridge 4120''' is configured to apply staples in a pattern having a large diameter while the staple cartridge 4120 is configured to apply staples in a pattern having a small diameter. In various instances, different staple cartridges can deploy staples having different unformed heights. In at least one instance, staple cartridges that apply staples in larger patterns deploy staples having a larger undeformed height while staple cartridges that apply staples in smaller patterns deploy staples having a smaller undeformed height. In some instances, a staple cartridge can deploy staples having two or more unformed heights. In any event, a staple cartridge selected from the plurality of staple cartridges can be assembled to the shaft 4110.

Figure 73:
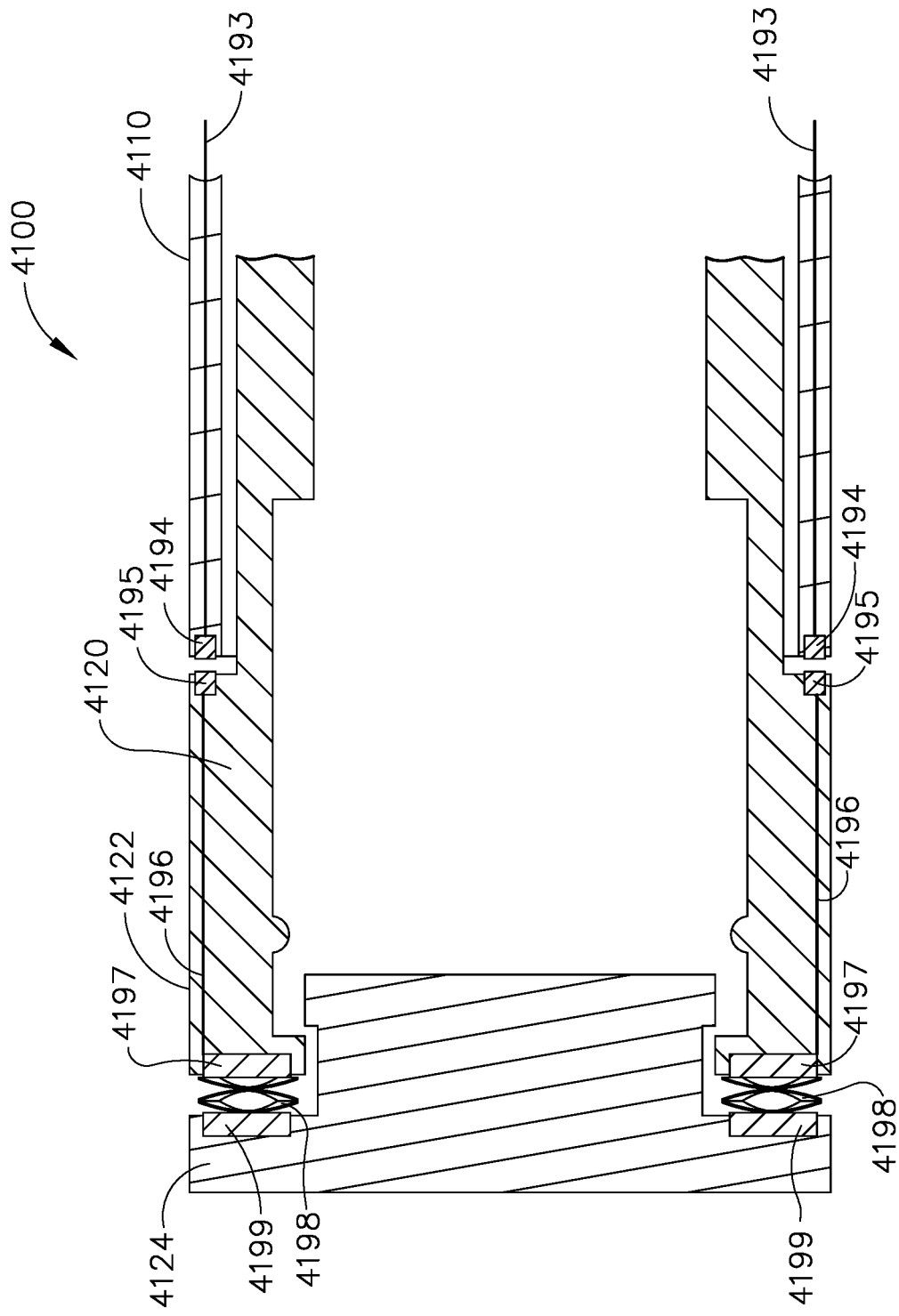
FIG. 73 is a cross-sectional view of a distal end of the stapling instrument of FIG. 72.

Referring to FIGS. 72 and 73, the tool assembly 4100 comprises a detection circuit 4190 configured to detect whether a staple cartridge is fully, or sufficiently, attached to the shaft 4110. The detection circuit 4190 is not entirely contained within the shaft 4110; rather, a staple cartridge must be properly assembled to the shaft 4110 to complete the detection circuit 4190. The detection circuit 4190 comprises conductors 4193 that extend through a passage 4192 defined in the frame of the shaft 4110 and/or along the outer housing of the shaft 4110. Referring primarily to FIG. 73, each conductor 4193 is electrically coupled to an electrical contact 4194 defined in the distal end of the housing. The staple cartridge 4120, for example, comprises corresponding electrical contacts 4195 which are positioned and arranged on the body 4122 of the staple cartridge 4120 such that the contacts 4195 engage the contacts 4194 on the shaft 4110. The staple cartridge 4120 further comprises conductors 4196 extending through and/or along the cartridge body 4122. Each conductor 4196 is electrically coupled with a contact 4195. In certain instances, the conductors 4196 are directly coupled to one another and, in such instances, the detection circuit 4190 is closed once the staple cartridge 4120 is properly assembled to the shaft 4110.

In certain instances, further to the above, the detection circuit 4190 of the tool assembly 4100 extends through a deck portion 4124 of the staple cartridge 4120. In at least one instance, the deck portion 4124 is movably attached to the cartridge body 4122. More specifically, in at least one such instance, spring members 4198 are positioned intermediate the cartridge body 4122 and the deck portion 4124 and are configured to permit the deck portion 4124 to move, or float, relative to the cartridge body 4122 when tissue is compressed against the deck portion 4124. In at least one instance, the spring members 4198 comprise one or more wave springs, for example. The spring members 4198 also form an electrically conductive pathway between the cartridge body 4122 and the deck portion 4124. More specifically, the spring members 4198 are positioned intermediate electrical contacts 4197 and 4199 defined on the cartridge body 4122 and the deck portion 4124, respectively. The conductors 4196 are electrically coupled to electrical contacts 4197 defined on the distal end of the cartridge body 4122 and the electrical contacts 4199 are electrically coupled to one another through a conductor in the deck portion 4125. As discussed above, the detection circuit 4190 is closed once the staple cartridge 4120 is properly assembled to the shaft 4110.

Figure 74:
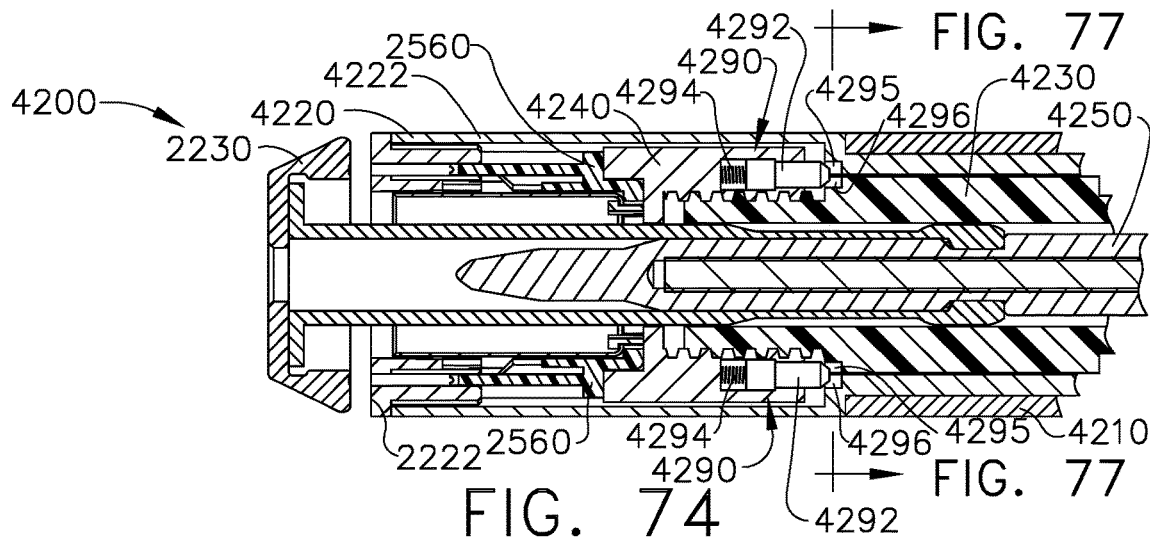
FIG. 74 is a partial cross-sectional view of a surgical stapling instrument comprising an unfired staple cartridge and a lockout system configured to prevent the staple cartridge from being re-fired after it has been previously fired by a firing drive of the surgical instrument.
Figure 75:
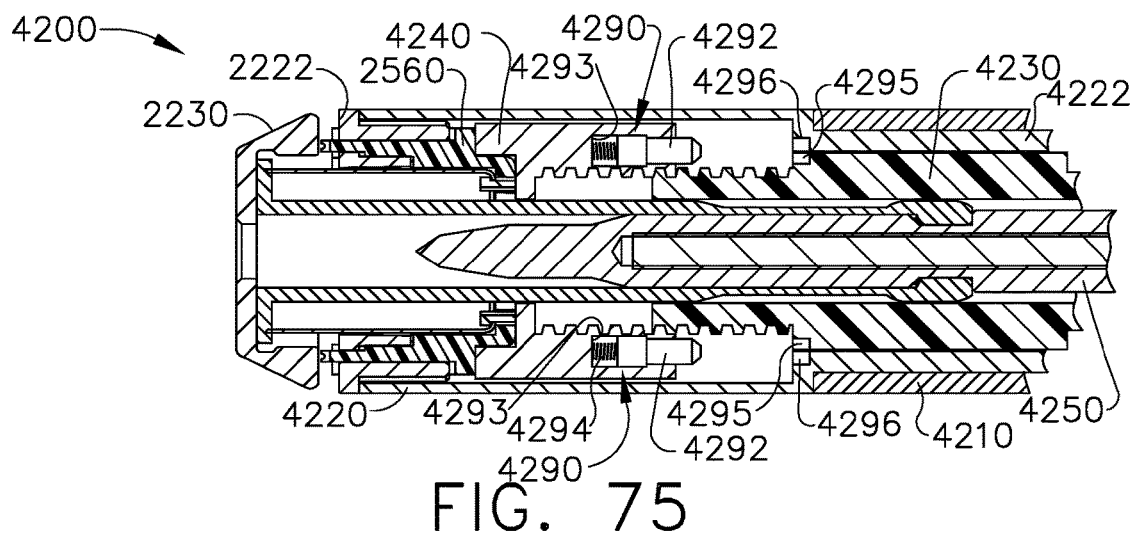
FIG. 75 is a partial cross-sectional view of the stapling instrument of FIG. 74 illustrated in a clamped configuration and the firing drive in a fired configuration.
Figure 76:
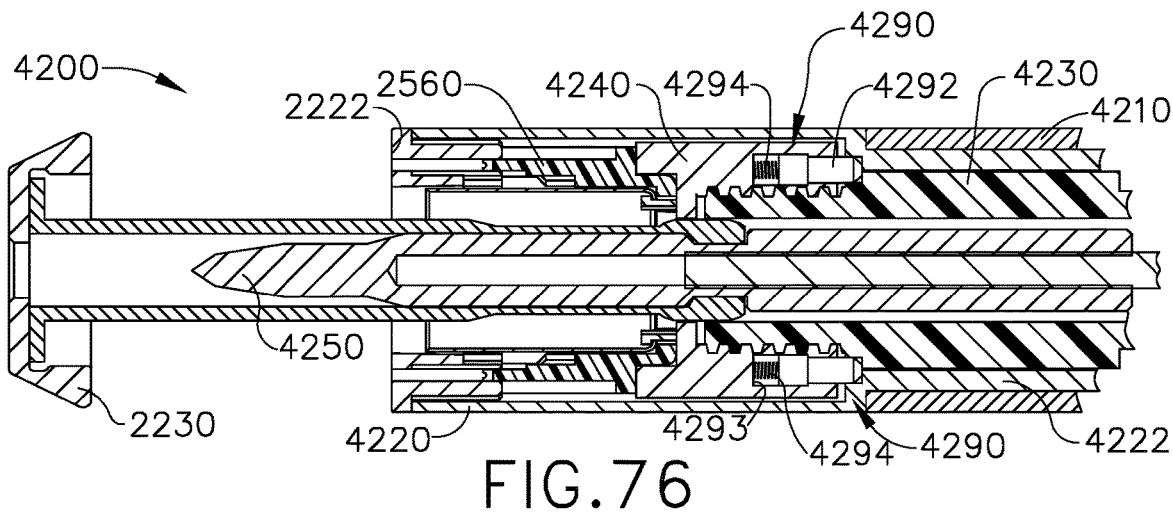
FIG. 76 is a partial cross-sectional view of the stapling instrument of FIG. 74 illustrated in an unclamped configuration and the firing drive in a retracted configuration.

Turning now to FIGS. 74-76, a tool assembly 4200 comprises a lockout configured to prevent a replaceable circular staple cartridge from being fired more than once, as described in greater detail further below. In use, a replaceable circular staple cartridge 4220 is assembled to a shaft 4210 of the tool assembly 4200. The tool assembly 4200 is then positioned in the surgical site and an anvil 2230 is assembled to the trocar 2450 of the closure drive. The closure drive is then used to move the anvil 2230 toward the staple cartridge 4220 to clamp the patient's tissue against the staple cartridge 4220 until the anvil 2230 reaches a closed, or clamped, position. This position of the anvil 2230 is illustrated in FIG. 74. At such point, the firing drive can be operated to deploy the staples removably stored in the staple cartridge 4220. The firing drive comprises, among other things, a rotatable drive shaft 4230 which is threadably engaged with a drive collar 4240 and, in addition, a staple firing driver 2560. The drive collar 4240 and the firing driver 2560 comprise separate components; however, the drive collar 4240 and the firing driver 2560 could be integrally formed in alternative embodiments. The firing drive is rotatable in a first direction during a firing stroke to push the drive collar 4240 and the staple firing driver 2560 distally between an unfired position (FIG. 74) and a fired position (FIG. 75) to eject the staples from the staple cartridge 4220. The drive collar 4240 and the staple driver 2560 are prevented from rotating within the staple cartridge 4220 and, as a result, the drive shaft 4230 rotates relative to the drive collar 4240 and the staple driver 2560.

Figure 78:
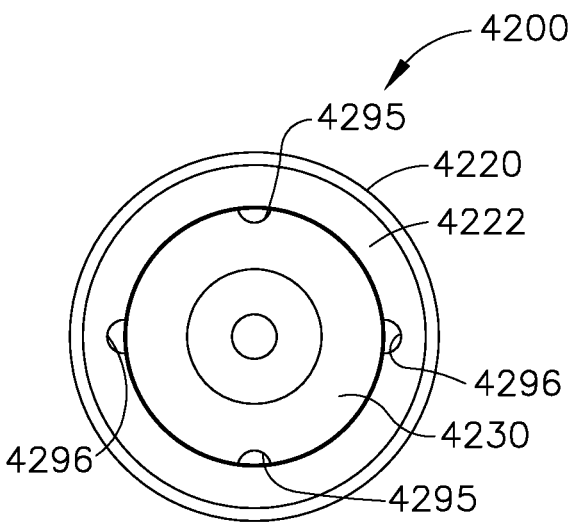
FIG. 78 is an end view of the firing drive and the frame of the stapling instrument of FIG. 74 illustrating the firing drive in a retracted configuration.

Further to the above, the drive collar 4240 comprises one or more lockouts 4290 extending proximally therefrom. Each lockout 4290 comprises a lockout pin 4292 slidably positioned within a pin aperture 4293 defined in the drive collar 4240. Each lockout 4290 further comprises a biasing member, such as a spring 4294, for example, configured to bias the pins 4292 proximally. When the firing drive is in its unfired configuration, as illustrated in FIG. 74, the lockouts 4290 are not engaged with the rotatable drive shaft 4230 and/or the frame 4222 of the staple cartridge 4220. As the drive collar 4240 and the staple driver 2560 are pushed distally by the drive shaft 4230, the lockout pins 4292 move away from the drive shaft 4230, as illustrated in FIG. 75. After the firing stroke has been completed and the staples have been sufficiently deformed against the anvil 2230, the drive shaft 4230 is rotated in an opposite direction to pull the drive collar 4240 and the staple driver 4260 proximally during a retraction stroke. In such instances, the lockouts 4290 are moved toward the drive shaft 4230. Notably, the retraction stroke is longer than the firing stroke and, as a result, the drive collar 4240 is moved proximally with respect to its original unfired position into a retracted position, as illustrated in FIG. 76. In this retracted position of the drive collar 4240, the lockouts 4290 have become engaged with the drive shaft 4230 and the frame 4222 of the staple cartridge 4220. More specifically, each lockout 4290 has entered into a lockout aperture defined between the drive shaft 4230 and the cartridge frame 4222. Referring now to FIG. 78, each lockout aperture is defined by an aperture wall 4295 in the drive shaft 4230 and an aperture wall 4296 in the frame 4222. Once the lockout pins 4292 have entered the lockout apertures, the drive collar 4240 cannot be rotated by the drive shaft 4230 and the firing system of the staple cartridge 4220 has become locked out. As a result, that particular staple cartridge 4220 cannot be used again and must be replaced with a new staple cartridge in order for the tool assembly 4200 to be used again.

The reader should appreciate, further to the above, that the lockout pins 4292 may or may not be partially positioned in the lockout apertures when the firing drive is in its unfired configuration as illustrated in FIG. 74. To the extent, however, that the lockout pins 4292 are partially positioned in the lockout apertures, in such instances, the pins 4292 can displace distally within the pin apertures 4293 defined in the drive collar 4240 when the firing drive shaft 4230 is rotated. As the reader should also appreciate, the lockout pins 4292 are seated deeply enough into the lockout apertures defined in the drive shaft 4230 when the drive collar 4240 is moved into its retracted position so as to prevent the pins 4292 from being displaced distally out of the lockout apertures if the firing drive shaft 4230 is rotated in its first direction once again.

Figure 77:
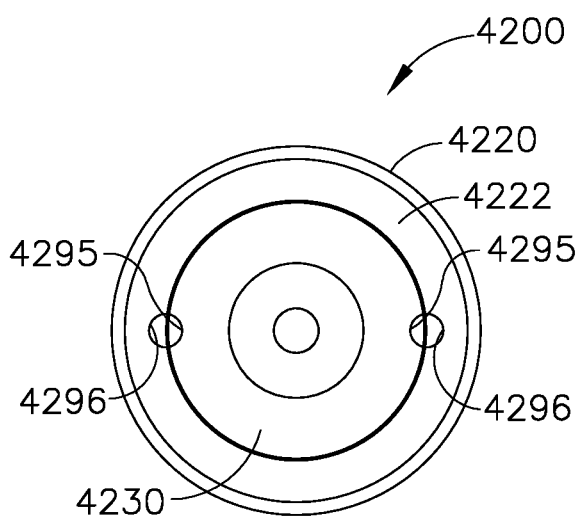
FIG. 77 is an end view of the firing drive and a frame of the stapling instrument of FIG. 74 illustrating the firing drive in an unfired configuration.

Referring again to FIG. 78, the sidewalls 4295 and 4296 of the lockout apertures are aligned with one another when the drive collar 4240 is in its retracted position. When the drive shaft 4230 is rotated, however, the sidewalls 4295 defined in the drive shaft 4230 will rotate out of alignment with the sidewalls 4296 defined in the cartridge frame 4222. In some instances, the sidewalls 4295 may momentarily rotate into re-alignment with the sidewalls 4296 as the firing drive 4230 is rotated. In any event, referring now to FIG. 77, the sidewalls 4295 are not aligned with the sidewalls 4296 when the firing system is in its unfired configuration. As a result, the lockout pins 4292 cannot enter into the lockout apertures when the firing system is in its unfired configuration and the staple cartridge 4220 cannot become unintentionally locked out.

Figure 80:
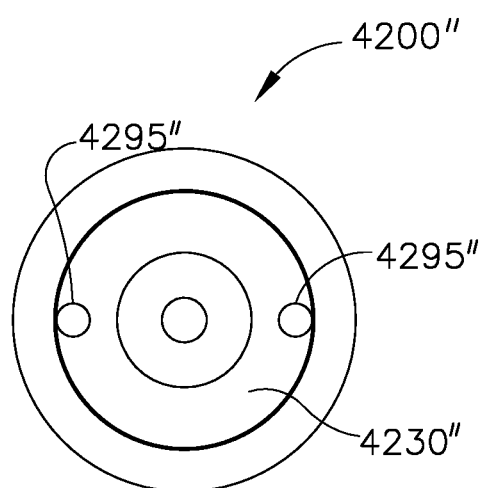
FIG. 80 is an end view of an alternative staple cartridge design that is usable with the stapling instrument of FIG. 74.

In at least one alternative embodiment, referring now to FIG. 80, one or more lockout apertures 4295" can be exclusively defined in a drive shaft 4230" of a tool assembly 4200". In such embodiments, the drive collar 4240 would not be able to rotate relative to the drive shaft 4230" once the lockout pins 4292 entered into the lockout apertures 4295". In effect, the drive collar 4240 and the drive shaft 4230" would become synchronously locked together, but not necessarily locked to the frame of the tool assembly 4200", which would prevent the drive shaft 4230" from rotating relative to the drive collar 2440 and displacing the drive collar 2440 distally.

Figure 79:
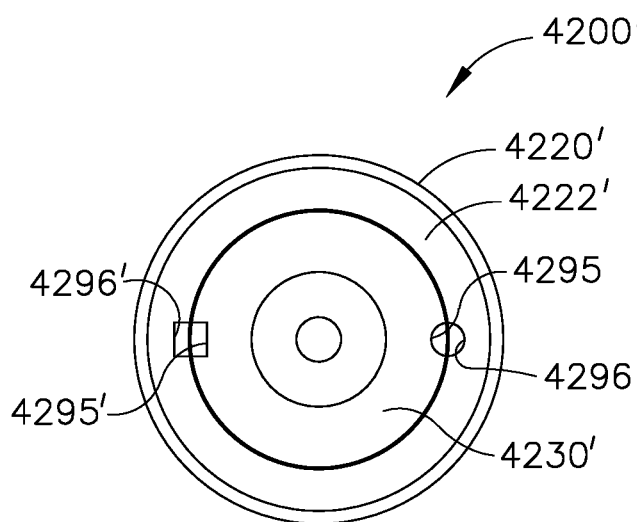
FIG. 79 is an end view of an alternative staple cartridge design that is usable with the stapling instrument of FIG. 74.

In at least one alternative embodiment, referring now to FIG. 79, each of the firing drive lockouts has a different configuration such that each lockout pin is uniquely indexed with its corresponding lockout aperture. For example, the tool assembly 4200' comprises a first lockout pin configured to enter a first lockout aperture defined by sidewalls 4295 and 4296 and a second lockout pin configured to enter a second lockout aperture defined by sidewalls 4295' and 4296'. The first lockout pin of the tool assembly 4200', however, is sized and configured such that it cannot enter into the second lockout aperture and, correspondingly, the second lockout pin is sized and configured such that it cannot enter into the first lockout aperture. Moreover, neither the first lockout pin nor the second lockout pin can enter an aperture formed by a combination of sidewalls 4295 and 4296' or an aperture formed by a combination of sidewalls 4295' and 4296.

Figure 81:
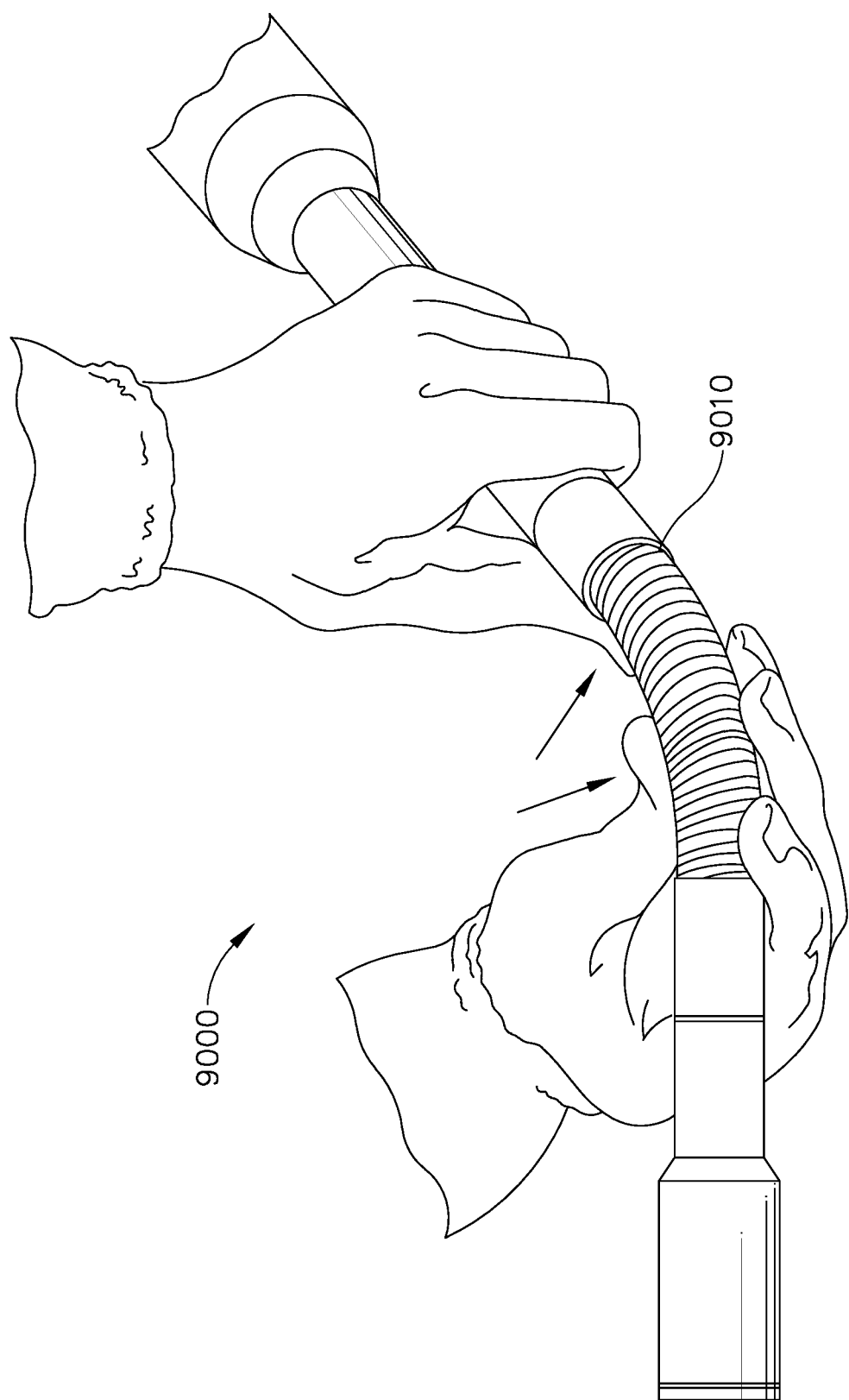
FIG. 81 is a perspective view of a surgical stapling instrument comprising a flexible shaft in accordance with at least one embodiment.

As discussed above, a stapling instrument configured to deploy circular rows of staples can comprise an articulation joint. The articulation joint is configured to permit an end effector of the stapling instrument to articulate relative to a shaft of the stapling instrument. Such a stapling instrument can assist a surgeon in positioning the end effector within the rectum and/or colon of a patient. In various embodiments, referring to FIG. 81, a stapling instrument configured to deploy circular rows of staples, such as stapling instrument 9000, for example, can be can comprise a contourable or adjustable frame 9010. The frame 9010 can be configured to be permanently deformed during use. In at least one such embodiment, the frame 9010 is comprised of a malleable metal, such as silver, platinum, palladium, nickel, gold, and/or copper, for example. In certain embodiments, the frame 9010 is comprised of a malleable plastic, for example. In at least one embodiment, the frame is comprised of a polymer including metal ions bonded with the polymer chains, such as ionic polymer-metal composites (IPMCs), for example. A voltage potential, or potentials, can be applied to the IPMC material in order to defect the shaft in a desired manner. In certain instances, the shaft is contourable along one radius of curvature while, in other instances, the shaft is contourable along more than one radius of curvature. The voltage potential, or potentials, can be modified to contour the shaft while the shaft is within the patient, for example. In certain embodiments, the contourable portion of the frame comprises a plurality of pivotable links In at least one embodiment, the contourable portion of the frame is comprised of a visco-elastic material.

Further to the above, the stapling instrument can further comprise a lock configured to releasably hold the contourable portion of the stapling instrument frame in its contoured configuration. In at least one instance, the stapling instrument frame comprises articulatable frame links and one or more longitudinal tension cables which can pull the frame links proximally and lock the frame links together. In certain instances, each frame link can comprise a longitudinal aperture extending therethrough which is configured to receive a distally movable rod. The rod is sufficiently flexible to pass through the longitudinal apertures, which may not be completely aligned with one another when the contourable portion has been contoured, yet sufficiently rigid to hold the stapling instrument in its contoured configuration.

Figure 82:
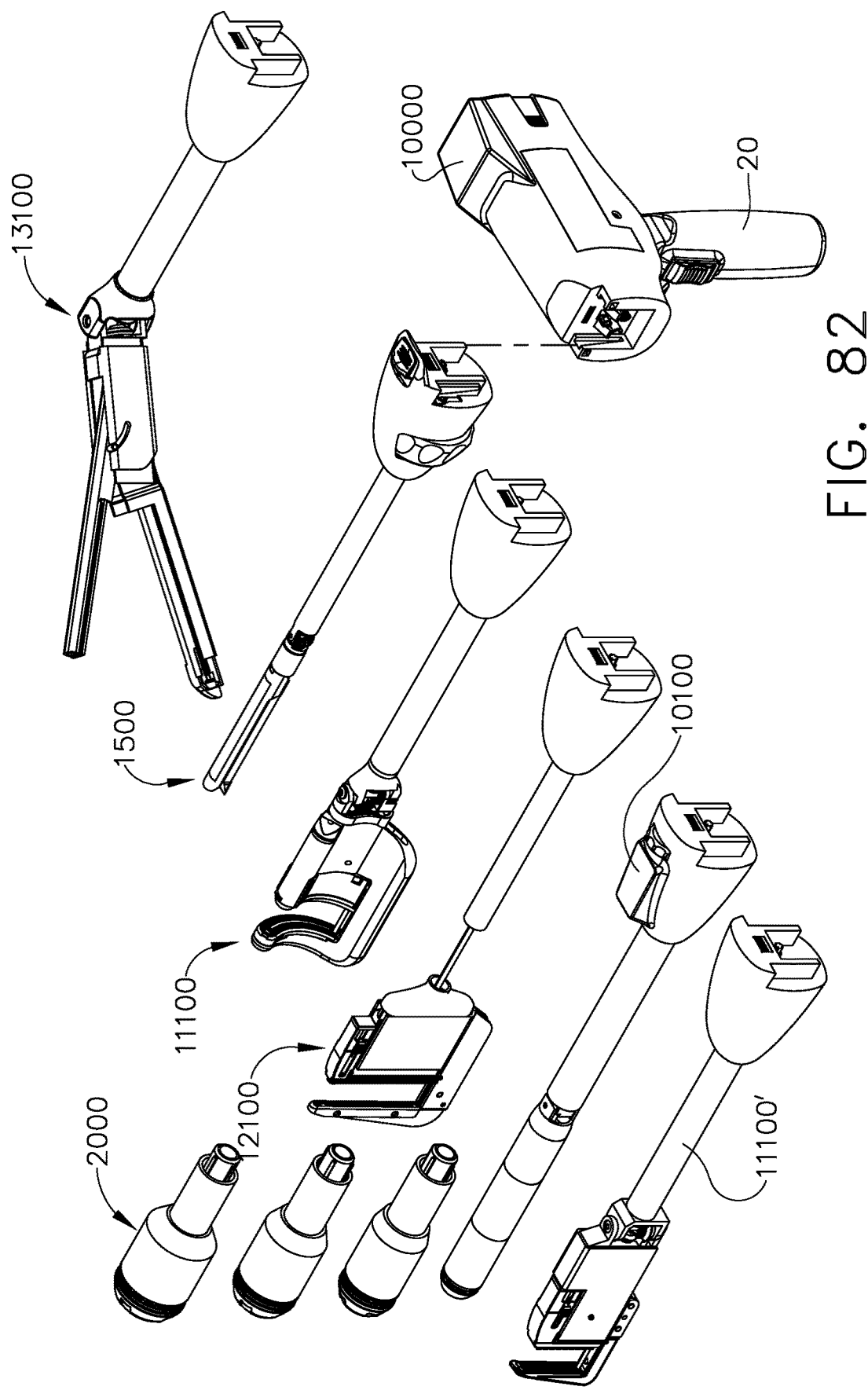
FIG. 82 is a schematic of a surgical instrument kit comprising a plurality of end effectors in accordance with at least one embodiment.

As discussed herein, a surgical instrument can be comprised of a plurality of modules that are assembled to one another. For instance, in at least one embodiment, a surgical instrument comprises a first module including a handle and a second module including a shaft assembly. The shaft assembly comprises an end effector configured to staple and/or incise the tissue of a patient; however, the shaft assembly can comprise any suitable end effector. In various instances, the end effector comprises a third module attachable to the shaft assembly. Referring now to FIGS. 82 and 83, a handle, such as the handle 20, for example, comprises a controller and a display 10000 in communication with the controller. The controller is configured to display data regarding the operation of the surgical instrument on the display 10000. The data displayed on the display 10000 relates information to a surgeon regarding at least one operating parameter of the first module and/or at least one operating parameter of the second module. For example, the controller can display data on the display 10000 regarding the progress of the staple firing stroke.

Further to the above, the shaft assembly comprises a second display. For example, the shaft assembly 2000 comprises a display 10100; however, any of the shaft assemblies disclosed herein can comprise a display such as display 10100, for example. The second module comprises its own controller configured to display data regarding the operation of the surgical instrument on the display 10100 Similar to the above, the data displayed on the display 10100 relates information regarding at least one operating parameter of the first module and/or at least one operating parameter of the second module. The controller of the second module is in signal communication with the controller of the first module; however, in other embodiments, the second module controller can operate independently of the first module controller. In certain alternative embodiments, the second module does not comprise a controller. In such embodiments, the controller of the first module is in signal communication with the first display 10000 and the second display 10100 and controls the data displayed on the first display 10000 and the second display 10100.

As discussed above, the tool assembly 2000 comprises an anvil and a staple cartridge. The handle 20 comprises an actuation system configured to move the anvil relative to the staple cartridge. The anvil is positionable in a range of positions relative to the staple cartridge to control the distance, or gap, between the anvil and the staple cartridge and, as a result, control the forming height of the staples when the staples are ejected from the staple cartridge. For instance, the anvil is positioned closer to the staple cartridge to deform the staples to a shorter formed height and positioned further away from the staple cartridge to deform the staples to a taller formed height. In any event, the second display 10100 of the tool assembly 2000 is configured to display the position of the anvil relative to the staple cartridge and/or display the height in which the staples will be or have been formed. In various embodiments, a shaft assembly can comprise an actuator configured to control a function of the end effector and a display which displays data regarding the end effector function which is adjacent to the actuator.

Referring to FIG. 1, a tool assembly 1500 comprises a shaft and an end effector extending from the shaft. The shaft comprises a shaft frame a longitudinal shaft axis. The end effector comprises an end effector frame and a longitudinal end effector axis. The end effector further comprises a distal head and a rotation joint which permits the distal head to rotate relative to the end effector frame about the longitudinal end effector axis. The distal head comprises a first jaw and a second jaw. The first jaw comprises a staple cartridge including staples removably stored therein, or a channel configured to receive such a staple cartridge, and the second jaw comprises an anvil configured to deform the staples. The second jaw is movable relative to the first jaw between an open position and a closed position; however, other embodiments are envisioned in which the first jaw is movable relative to the second jaw and/or both the first jaw and the second jaw are movable relative to each other.

In certain embodiments, a tool assembly can comprise an articulation joint in addition to the rotation joint. In at least one such embodiment, the rotation joint is distal with respect to the articulation joint. In such an embodiment, the rotation of the distal head does not affect the angle in which the end effector has been articulated. That said, other embodiments are envisioned in which the articulation joint is distal with respect to the rotation joint. Such embodiments can provide a wide sweep of the distal head. In either event, the longitudinal end effector axis is movable relative to the longitudinal shaft axis. In at least one instance, the longitudinal end effector axis is movable between a position in which it is collinear with the longitudinal shaft axis to a position in which it is transverse to the longitudinal shaft axis.

Further to the above, the distal head of the tool assembly 1500 is rotatable between an initial position and a rotated position. In at least one instance, the distal head is rotatable between a zero, or top-dead-center, position and a second position. In certain instances, the distal head is rotatable through an at least 360 degree range of motion. In other instances, the distal head is rotatable through a less than 360 degree range of rotation. In either event, the tool assembly 1500 and/or the handle 20 is configured to track the rotational position of the distal head. In various instances, the tool assembly 1500 and/or the handle 20 comprises an electric motor operably coupled with the distal head of the end effector and, in addition, an encoder configured to directly track the rotation of the distal head and/or indirectly track the rotation of the distal head by evaluating the rotational position of the shaft of the electric motor, for example. The controller of the handle 20 is in signal communication with the encoder and is configured to display the rotational position of the distal head on the display 10000, for example.

In at least one embodiment, the orientation and the arrangement of the data displayed on the display 10000 is static while the distal head of the end effector rotates. Of course, the data displayed on the display 10000 in such an embodiment would be updated by the surgical instrument controller; however, the data display is not re-oriented and/or re-arranged as the distal head rotates. Such an embodiment can provide a surgeon with the information necessary to properly utilize the surgical instrument in a static field. In at least one alternative embodiment, the data field on the display 10000 is dynamic In this context, the term dynamic means more than the data being updated on the display 10000; rather, the term dynamic means that the data is re-oriented and/or re-arranged on the display 10000 as the distal head is rotated. In at least one instance, the orientation of the data tracks the orientation of the distal head. For example, if the distal head is rotated 30 degrees, the data field on the display 10000 is rotated 30 degrees. In various instances, the distal head is rotatable 360 degrees and the data field is rotatable 360 degrees.

Further to the above, the data field can be oriented in any orientation that matches the orientation of the distal head. Such an embodiment can provide a surgeon with an accurate and intuitive sense of the orientation of the distal head. In certain embodiments, the controller orients the data field in an orientation selected from an array of discrete positions that most closely matches the orientation of the distal head. For instance, if the distal head has been rotated 27 degrees and the selectable discrete data field positions are 15 degrees apart, the controller can re-orient the data field 30 degrees from a datum orientation. Similarly, for example, if the distal head has been rotated 17 degrees and the selectable discrete data field positions are 5 degrees apart, the controller can re-orient the data field 15 degrees from the datum orientation. In at least one embodiment, the datum orientation is aligned with a feature of the surgical instrument itself. For example, the datum orientation of the handle 20 is aligned with an axis extending through a grip of the handle 20. In such an embodiment, the controller can disregard the orientation of the handle 20 with respect to its environment. In at least one alternative embodiment, however, the datum orientation is aligned with respect to the gravitational axis, for example.

Further to the above, the controller is configured to re-orient the entire data field displayed on the display 10000 with respect to the orientation of the distal head. In other embodiments, the controller is configured to re-orient only a portion of the data field displaced on the display 10000 with respect to the orientation of the distal head. In such an embodiment, a portion of the data field is held static with respect to the datum orientation while another portion of the data field is rotated with respect to the datum orientation. In certain embodiments, a first portion of the data field is rotated a first angle of rotation and a second portion of the data field is rotated a second angle of rotation in the same direction. For instance, the second portion can be rotated less than the first portion. In various embodiments, a first portion of the data field is rotated in a first direction and a second portion of the data field is rotated in a second, or opposite, direction.

Further to the above, the data field is re-oriented and/or re-arranged in real time, or at least substantially in real time, with the rotation of the distal head. Such an embodiment provides a very responsive data display. In other embodiments, the re-orientation and/or re-arrangement of the data field can lag the rotation of the distal head. Such embodiments can provide a data display with less jitter. In various embodiments, a first portion of the data field is re-oriented and/or re-arranged at a first speed and a second portion of the data field is re-oriented and/or re-arranged at a second, or different, speed. For instance, the second potion can be rotated at a slower speed.

As discussed above, the data field on the display 10000 is rotated as the distal head of the end effector is rotated. However, in other embodiments, the data field, or a portion of the data field, is translated as the distal head is rotated. As also discussed above, the controller of the surgical instrument is configured to re-orient and/or re-arrange the data field on the handle display 10000. However, the controller of the surgical instrument can re-orient and/or re-arrange the data field on a second display, such as a shaft display, for example.

Referring again to FIGS. 15 and 83, the tool assembly 2000 comprises an actuator 10200 configured to actuate the articulation drive system of the tool assembly 2000. The actuator 10200 is rotatable about a longitudinal axis which is parallel to, or at least substantially parallel to, a longitudinal axis of the shaft 2100, for example. The actuator 10200 is operably coupled to a rheostat, for example, which is in signal communication with a controller of the handle 20. When the actuator 10200 is rotated in a first direction about its longitudinal axis, the rheostat detects the rotation of the actuator 10200 and the controller operates the electric motor to articulate the end effector 2200 in a first direction. Similarly, when the actuator 10200 is rotated in a second, or opposite, direction about its longitudinal axis, the rheostat detects the rotation of the actuator 10200 and the controller operates the electric motor to articulate the end effector 2200 in a second, or opposite, direction. In various instances, the end effector 2200 can be articulated approximately 30 degrees from a longitudinal axis in a first direction and/or articulated approximately 30 degrees from the longitudinal axis in a second, or opposite, direction, for example.

As the reader should appreciate, further to the above, the tool assembly 2000 does not have an on-board electric motor configured to operate the articulation drive system; rather, the electric motor of the articulation drive system is in the handle, such as handle 20, for example, to which the tool assembly 2000 is attached. As a result, an actuator on the detachable shaft assembly controls the operation of the handle In other embodiments, the electric motor of the articulation driver system can be in the tool assembly 2000. In either event, the display 10100 is configured to display, in at least some manner, the articulation of the end effector 2200. As the reader should appreciate, the display 10100 is adjacent the actuator 10200 and, as a result, the surgeon is able to easily view the input and the output of the articulation drive system at the same time.

A surgical tool assembly comprising a contourable shaft, further to the above, can be advantageously shaped to fit within the rectum or colon of a patient, for example. Such a contourable shaft, however, cannot bear a significant amount of tensile and/or compressive loads. To compensate therefor, in various embodiments, only rotatable drive systems may extend through the contourable portion of the shaft. In such instances, the shaft need only resist the rotational reaction forces generated by the rotatable drive systems. In such embodiments, the rotational motion of the drive systems can be converted to linear motion, if necessary, distally with respect to the contourable shaft portion. Such longitudinal motions can generate tensile and/or compressive forces; however, such forces can be resolved, or balanced out, within the end effector, i.e., distally with respect to the contourable shaft portion. Such embodiments can also utilize an articulation joint positioned distally with respect to the contourable shaft portion. In such embodiments, the tool assembly may not utilize push-pull drive systems which traverse the contourable shaft portion.

Figure 84:
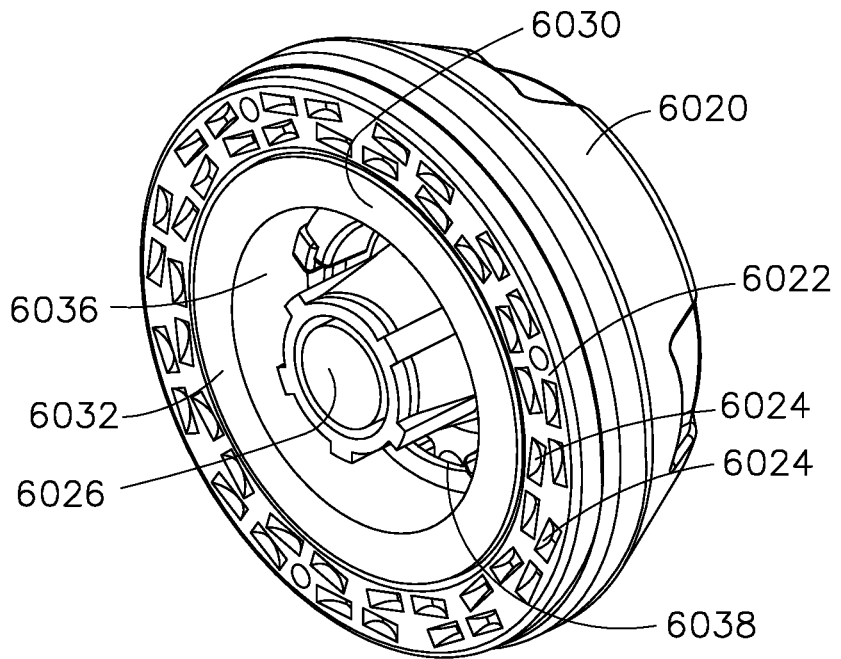
FIG. 84 is a perspective view of an anvil in accordance with at least one embodiment.
Figure 85:
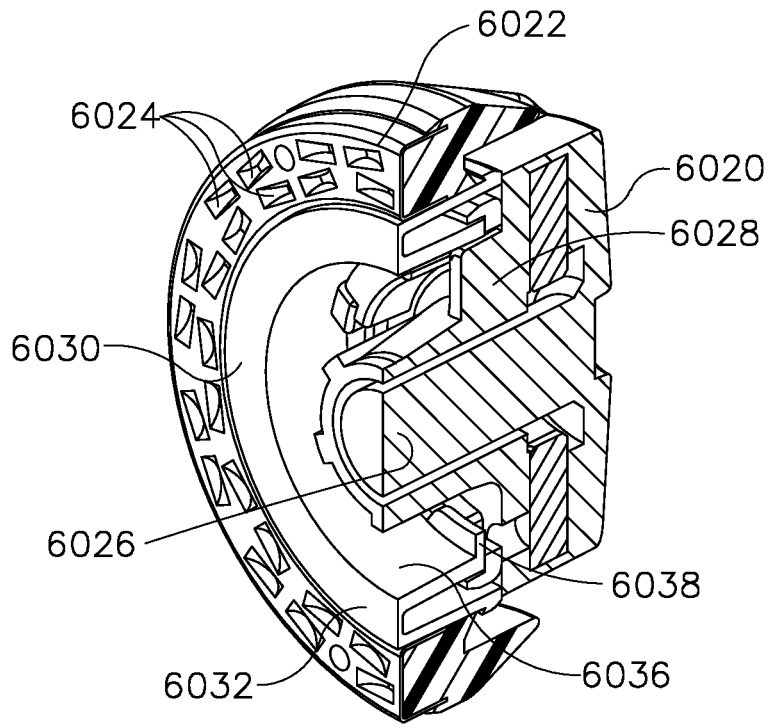
FIG. 85 is a cross-sectional view of the anvil of FIG. 84.

An anvil 6020 of a circular stapling instrument is illustrated in FIGS. 84 and 85. The anvil 6020 comprises a tissue compression surface 6022 and an annular array of staple forming pockets 6024 defined in the tissue compression surface 6022. The anvil 6020 further comprises a frame 6028, an attachment mount 6026, and a stem extending from the attachment mount 6026. The stem is configured to be releasably attached to a closure drive of the circular stapling instrument so that the anvil 6020 can be moved toward and away from a staple cartridge of the circular stapling instrument. The compression surface 6022, the attachment mount 6026, and the frame 6028 are comprised of stainless steel, for example; however, any suitable material, or materials, could be used.

Further to the above, the anvil 6020 comprises a tissue support 6030. The tissue support 6030 is positioned within an annular aperture defined within the tissue support surface 6022. The tissue support 6030 is snugly secured within the anvil 6020 such that there is little, if any, relative movement therebetween. The tissue support 6030 comprises an annular tissue support surface 6032 which is adjacent to the annular tissue compression surface 6022 of the anvil 6020. The tissue support 6030 further comprises an inner annular wall 6036 defined therein and, in addition, a bottom wall 6038 positioned adjacent the anvil frame 6028 of the anvil 6020.

Figure 86:
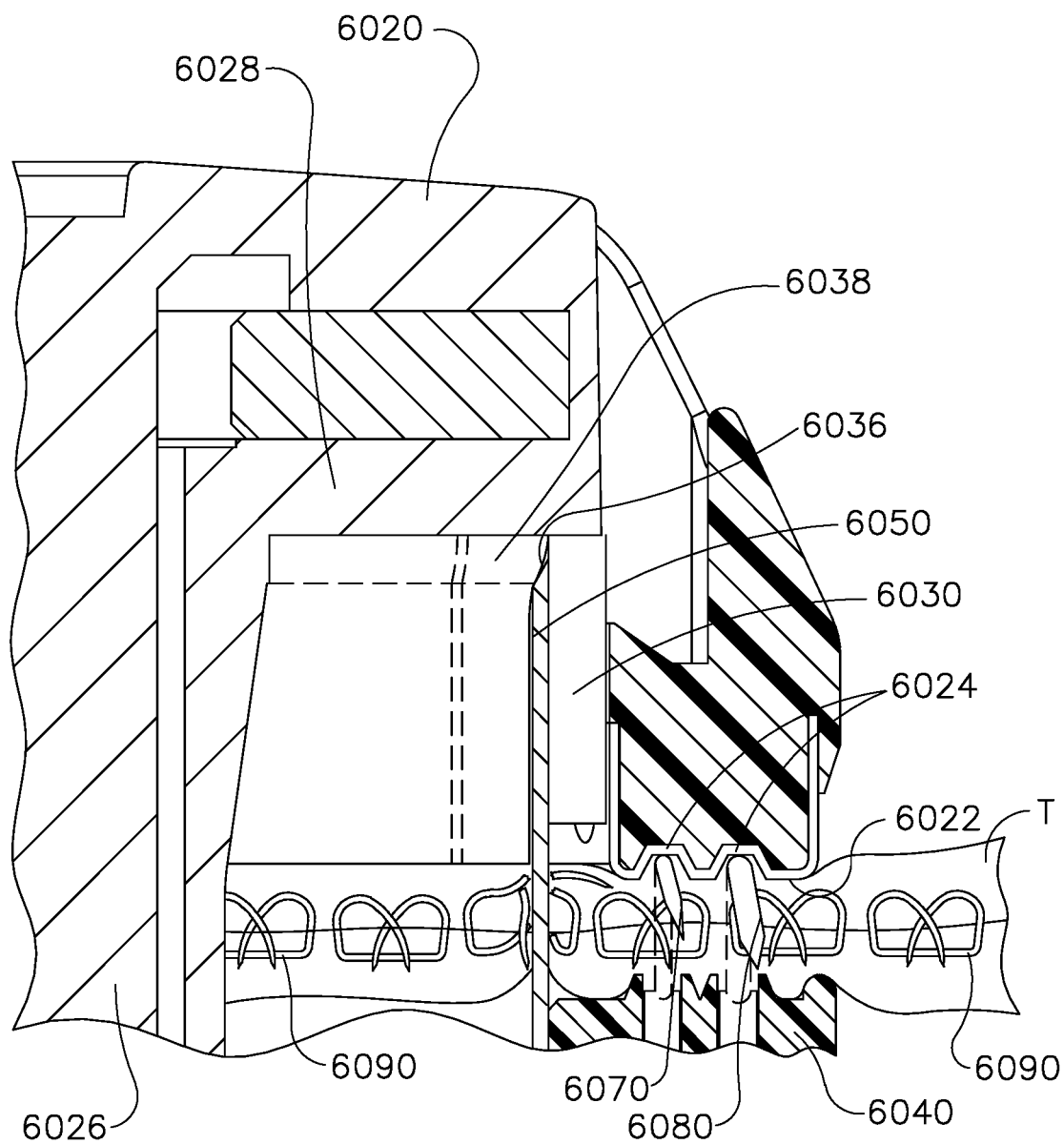
FIG. 86 is a partial cross-sectional view of an end effector including the anvil of FIG. 84 illustrated in a fired configuration.

Referring now to FIG. 86, the circular stapling instrument comprises a staple cartridge 6040 including a first annular row of staples 6070, a second annular row of staples 6080, and a firing drive configured to eject the staples 6070 and 6080 from the staple cartridge 6040 during a firing stroke of the firing drive. As illustrated in FIG. 86, the staples 6070 and 6080 are deformed by the forming pockets 6024 as they are ejected from the staple cartridge 6040. In various instances, the staples 6070 and the staples 6080 are deformed to the same height while, in other instances, the staples 6070 and the staples 6080 are deformed to different heights. For example, the staples 6070 can be deformed to a shorter deformed height than the staples 6080. In other examples, the staples 6080 are deformed to a shorter height than the staples 6070.

In addition to or in lieu of the above, the staples 6070 and the staples 6080 can have different unformed heights. For example, the staples 6070 can have a shorter unformed height than the staples 6080. In other examples, the staples 6080 have a shorter unformed height than the staples 6070. In certain instances, the staples 6070 and the staples 6080 have the same unformed height.

As the staples 6070 and 6080 are deformed against the anvil 6020 to staple the tissue T captured between the anvil 6020 and the staple cartridge 6040, further to the above, the stapling instrument can incise the tissue T. The firing drive, which ejects the staples from their staple cavities, drives a cutting member 6050 toward the tissue T and the anvil 6020. The distal edge of the cutting member 6050 transects the tissue T and then slides along the inner sidewall 6036 of the tissue support 6030 without transecting the inner sidewall 6036. The cutting edge of the cutting member 6050 is annular and it is aligned with the annular inner wall 6036 of the tissue support 6030. The cutting member 6050 is advanced into the anvil 6020 until the cutting member 6050 transects the bottom wall 6038, as illustrated in FIG. 86.

The firing drive experiences various loads when driving the staples 6070 and 6080 against the anvil 6020 and/or cutting the tissue. For instance, the firing drive may experience an increased load when transecting tissue that has been previously stapled, such as with staples 6090 (FIG. 86), for example. The transection of the bottom wall 6038 by the cutting member 6050, however, creates a sudden change or impulse in the force transmitted through the firing drive. This sudden change by the force can be sensed by the clinician using the surgical stapler and/or an electronic sensor system configured to detect load changes in the firing drive. The tissue support 6030 can be comprised of a material that can snap when the cutting member 6050 applies a load to the bottom wall 6038. In at least one instance, the tissue support 6030 is comprised of plastic, for example. In any event, the transection of the bottom wall 6038 can be detected and, once detected, the clinician and/or the electronic sensor system can determine that the cutting process has been completed.

The firing drive deforms the staples 6070, 6080 and incises the tissue with the cutting member 6050 at the same time; however, it is contemplated that the staple forming and tissue cutting steps could be staggered. In at least one instance, the tissue cutting step does not begin until the staple forming step has been completed.

It should be appreciated from FIG. 86 that, while surface 6032 can partially support the tissue T, the cutting member 6050 can push the tissue T into the cavity defined between the inner wall 6036 of the tissue support 6030 and the attachment mount 6026 when the cutting member 6050 is moved toward the bottom wall 6038. Stated another way, the cutting member 6050 can drag the tissue T along the wall 6036 before finally cutting it. In such instances, the incision made by the cutting member 6050 may not be precise. Discussed below are improvements to the embodiment disclosed in FIG. 86.

Figure 87:
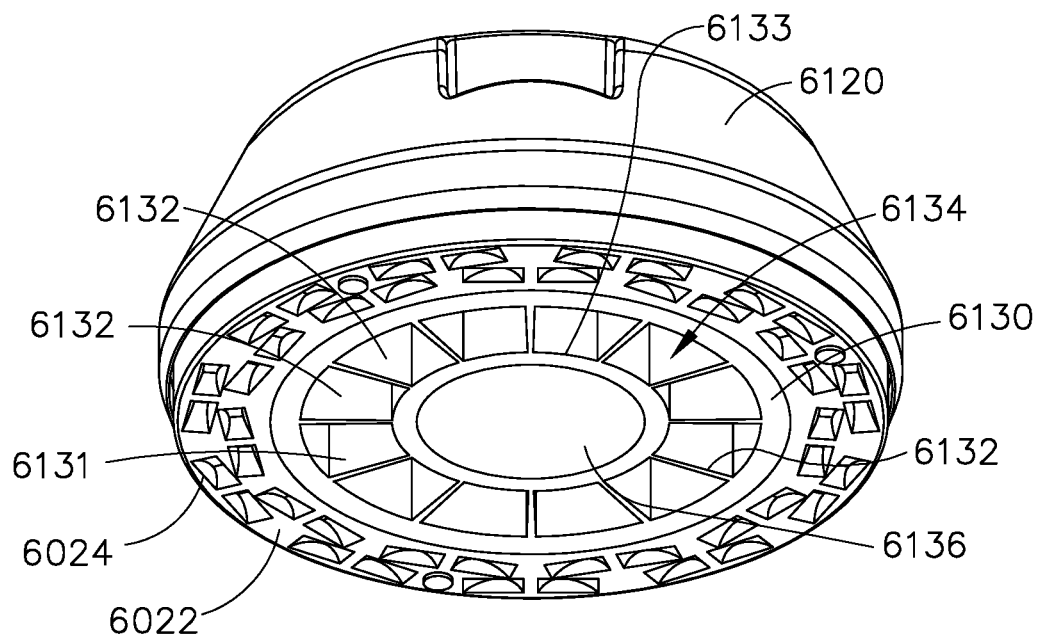
FIG. 87 is a perspective view of an anvil in accordance with at least one embodiment.
Figure 88:
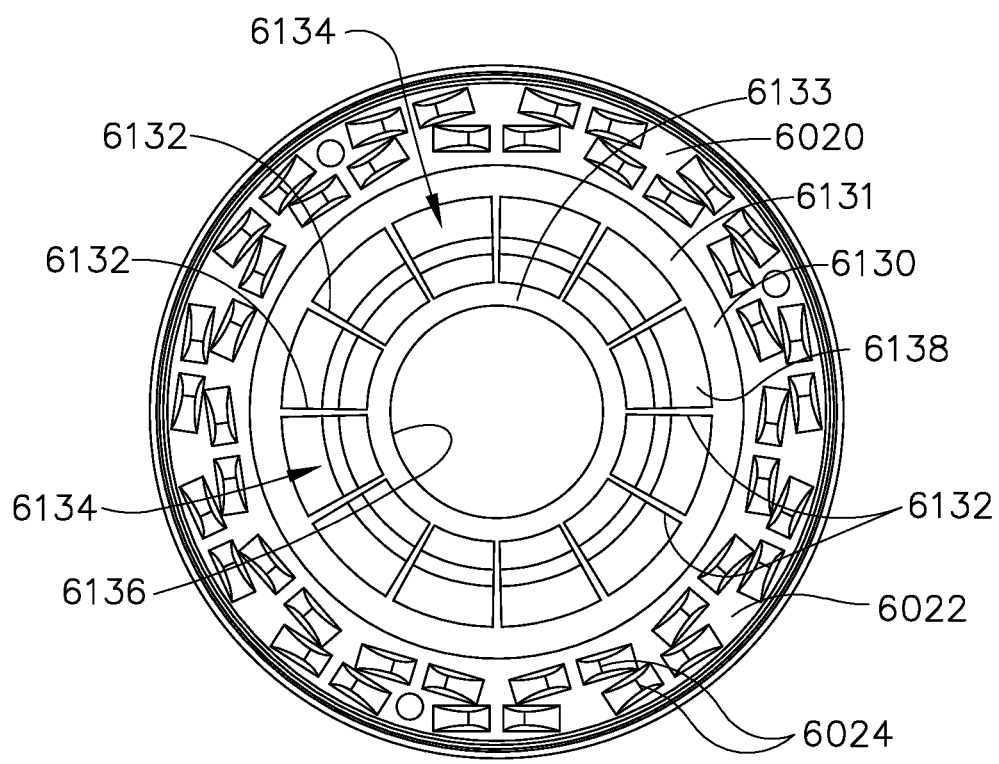
FIG. 88 is a plan view of the anvil of FIG. 87.

Turning now to FIGS. 87 and 88, the tissue support 6030 of anvil 6020 has been replaced with a tissue support 6130. The tissue support 6130 comprises a first, or outer, annular wall 6131 and a second, or inner, annular wall 6133. The inner wall 6133 defines an aperture 6136 configured to closely receive the attachment mount 6026. The outer wall 6131 and the inner wall 6133 are connected by lateral walls 6132. The lateral walls 6132 extend radially around a center of the tissue support 6130 between the inner wall 6133 and the outer wall 6131. The lateral walls 6132 are evenly spaced apart from one another; however, alternative embodiments are contemplated in which the lateral walls 6132 are not evenly spaced apart from one another. In either event, the lateral walls 6132 define an annular array of cavities 6134 in the tissue support 6130. In various instances, each cavity 6134 can be enclosed on every side but the side facing the tissue, for example. In other instances, the side of the cavity facing the tissue can be enclosed.

The outer wall 6131 and the inner wall 6133 of the tissue support 6130 are configured to support the tissue as the tissue is being transected by the cutting member 6050. The lateral walls 6132 also support the tissue and, in addition, block or resist the tissue from sliding relative to the outer wall 6131 and the inner wall 6133 as the tissue is being transected. It should be understood that the tissue can enter the cavities 6134 when the tissue is being transected; however, the relative movement between the tissue and the sidewalls can be greatly reduced. The composition and arrangement of the lateral walls 6132 can be selected to provide more support to the tissue or less support to the tissue depending on the amount of support that is desired. For instance, thicker lateral walls 6132 can provide more tissue support than thinner lateral walls 6132. Similarly, more lateral walls 6132 can provide more tissue support than thinner lateral walls 6132.

As the cutting member 6050 is moved through its cutting stroke, the cutting member 6050 cuts the tissue and transects the lateral walls 6132. The cutting member 6050 is annular and transects the lateral walls 6132 adjacent the outer wall 6131; however, a cutting member could transect the walls 6132 at any suitable location. In any event, the lateral walls 6132 support the tissue before, during, and after the tissue is cut and prevent, or at least reduce the possibility of, the tissue being dragged along the outer wall 6131 and/or the inner wall 6133 Similar to the tissue support 6030, the tissue support 6130 comprises a bottom wall 6138 that is transected at the end of the cutting stroke.

Figure 89:
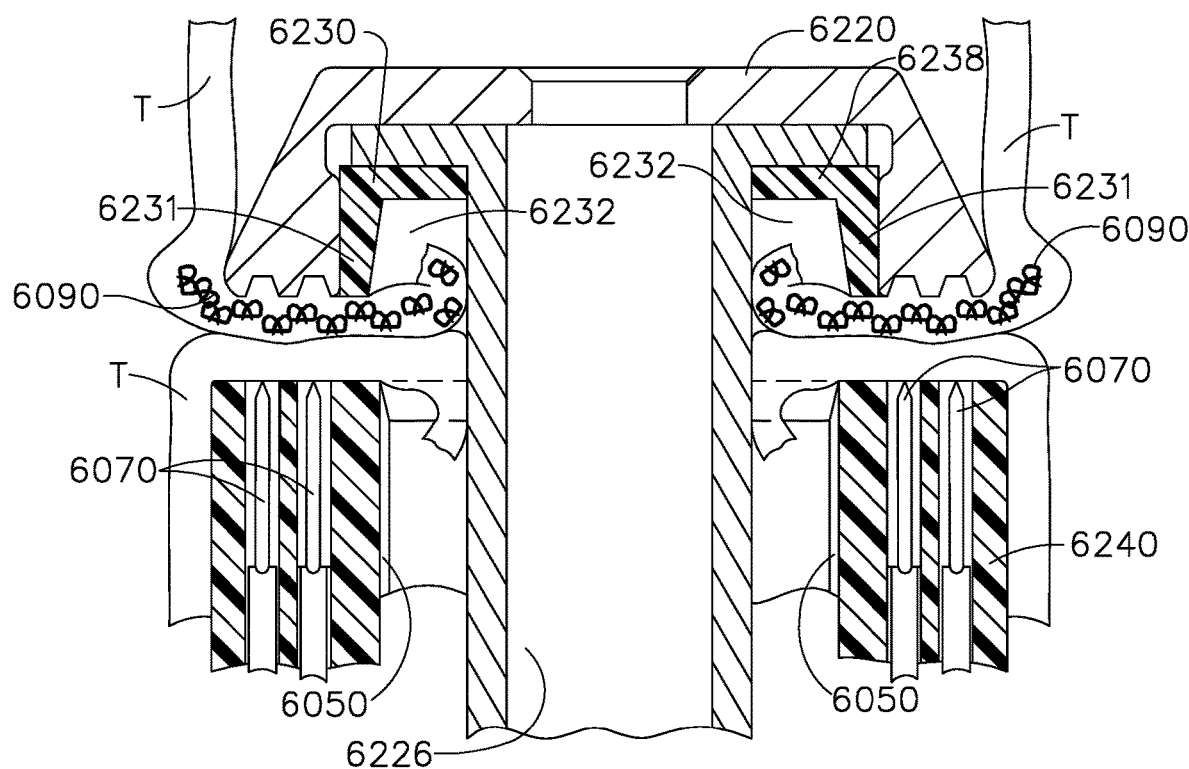
FIG. 89 is a cross-sectional view of an end effector in accordance with at least one embodiment illustrated in a clamped, unfired configuration.
Figure 90:
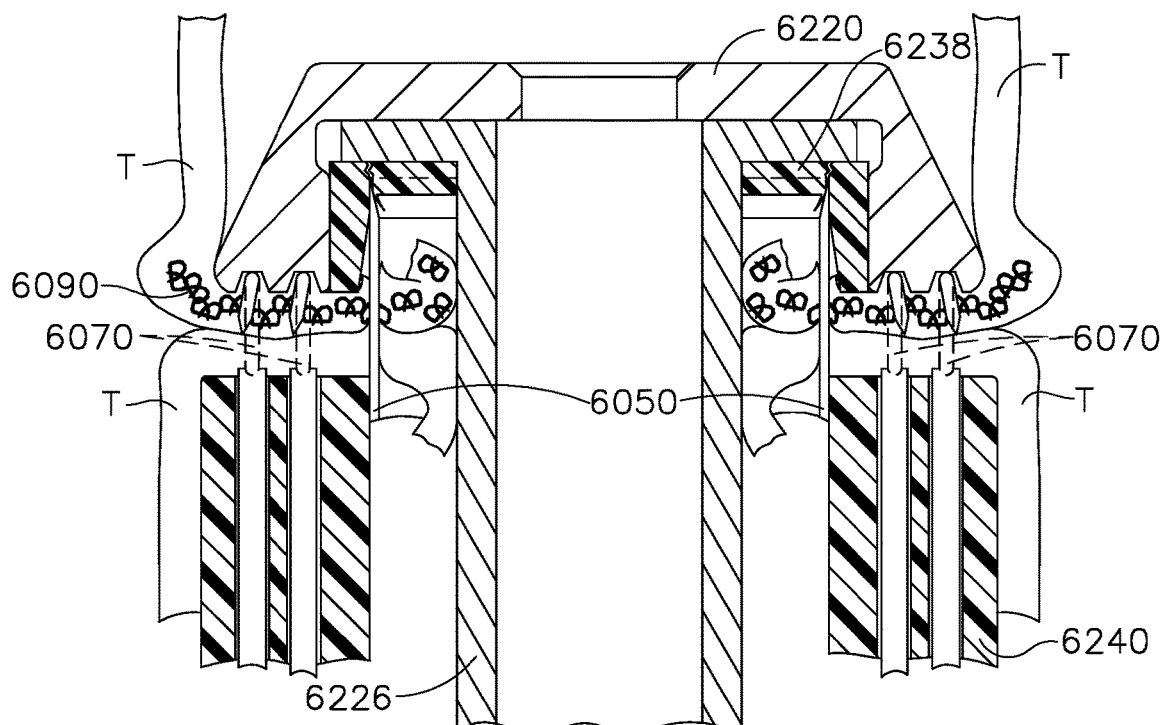
FIG. 90 is a cross-sectional view of the end effector of FIG. 89 illustrated in a fired configuration.

A surgical stapler comprising a staple cartridge 6240 and an anvil 6220 is disclosed in FIGS. 89 and 90. The staple cartridge 6240 is similar to the staple cartridge 6040 in many respects. The anvil 6220 is similar to the anvil 6020 and the anvil 6120 in many respects. The anvil 6220 comprises an attachment stem 6226 and an annular tissue support 6230 positioned around the attachment stem 6226. The tissue support 6230 comprises a central aperture configured to closely receive the stem 6226. The tissue support 6230 further comprises an annular outer wall 6231 positioned adjacent the tissue compression surface of the anvil 6220 and, in addition, lateral walls 6232 extending radially from the outer wall 6231. The tissue support 6230 does not comprise an inner annual wall and the inner ends of the lateral walls 6232 are free to deflect. The tissue support 6230 further comprises a bottom wall 6238 which is incised by the cutting member 6050, similar to the above.

Figure 91:
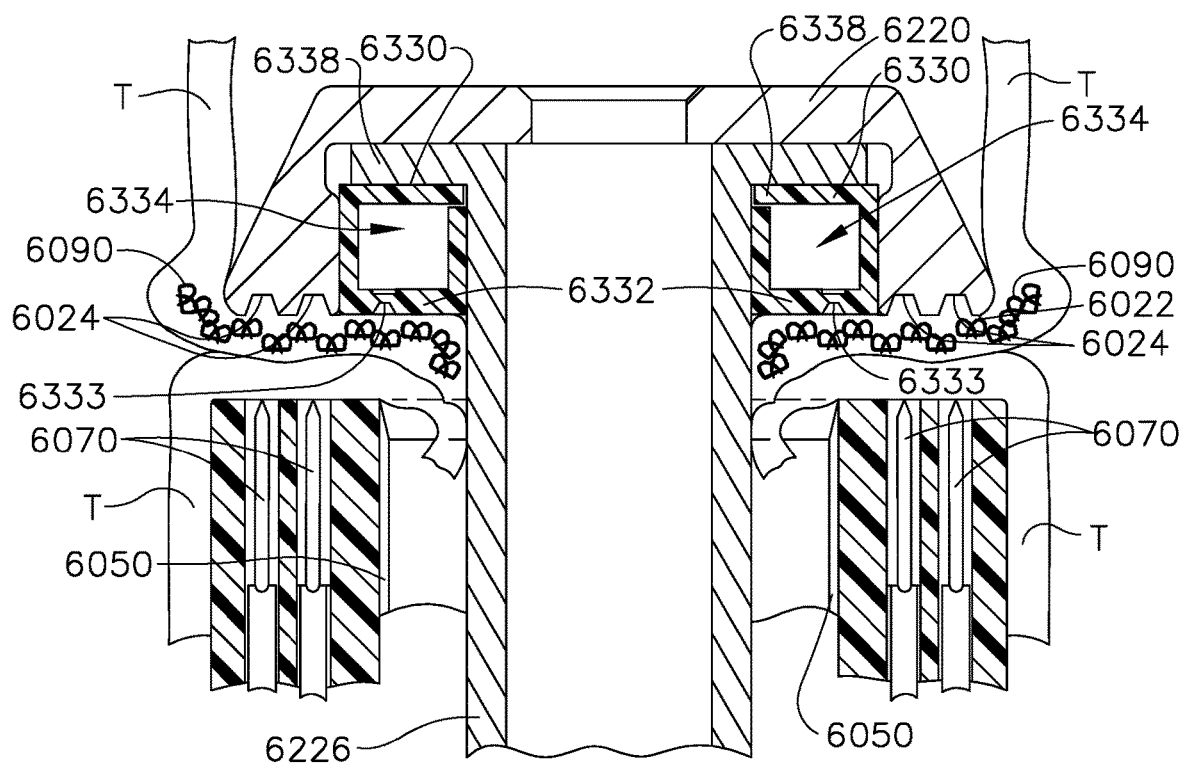
FIG. 91 is a cross-sectional view of an end effector in accordance with at least one alternative embodiment illustrated in a clamped, unfired configuration.
Figure 92:
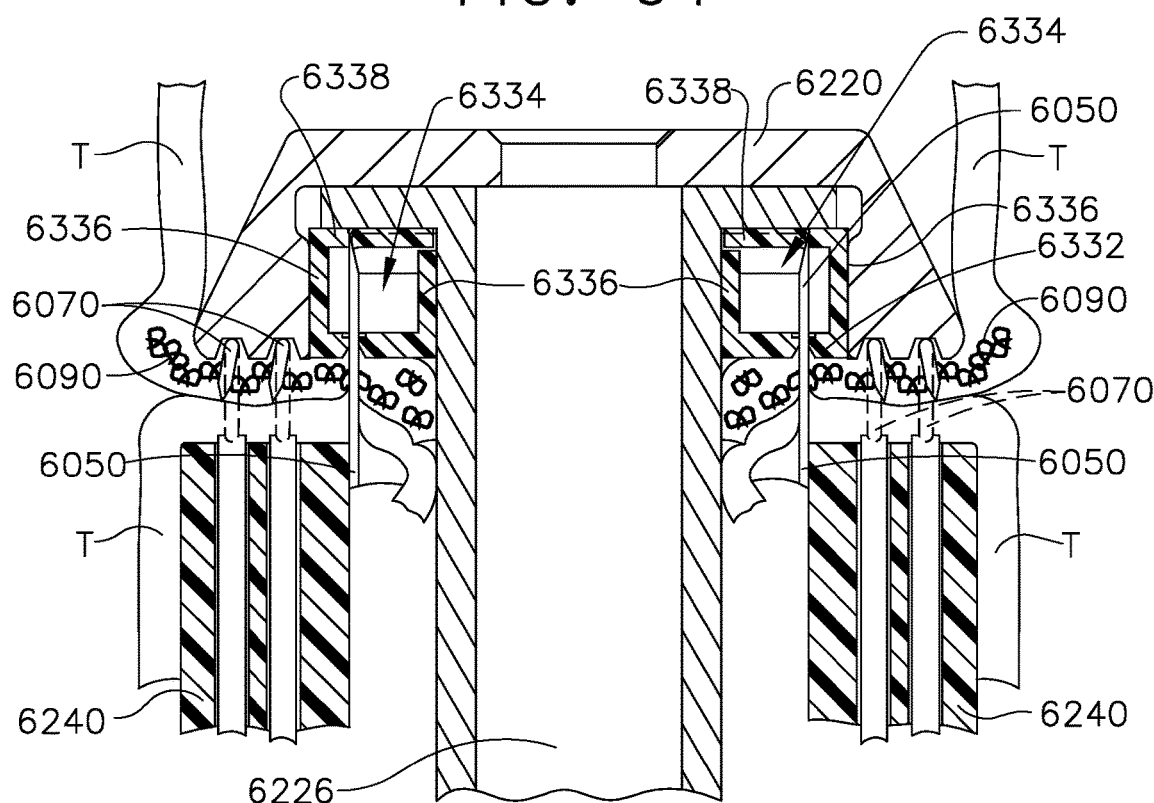
FIG. 92 is a cross-sectional view of the end effector of FIG. 91 illustrated in a fired configuration.

A surgical stapler comprising the staple cartridge 6240 and the anvil 6220 is illustrated in FIGS. 91 and 92. The reader should appreciate, however, that the tissue support 6230 of the anvil 6220 has been replaced with a tissue support 6330. The tissue support 6330 comprises an annular central aperture configured to closely receive the stem 6226. The tissue support 6330 further comprises a top wall 6332, a bottom wall 6338, and sidewalls 6336 extending between the top wall 6332 and the bottom wall 6338. The top wall 6332 and the bottom wall 6338 are parallel, or at least substantial parallel; however, embodiments are envisioned in which the walls 6332 and 6338 are not parallel. The sidewalls 6336 are parallel, or at least substantial parallel; however, embodiments are envisioned in which the sidewalls 6336 are not parallel.

The walls 6332, 6336, and 6338 define an annular cavity 6334 therebetween. The cavity 6334 is enclosed, or at least substantially enclosed, on all sides. The cavity 6334 extends uninterrupted around the stem 6226; however, other embodiments are envisioned in which the cavity 6334 is interrupted by sidewalls and/or changes in geometry, for example.

Similar to the above, the tissue support 6330 is configured to support the tissue as the tissue is being transected by the cutting member 6050. The tissue support 6330 is closely received within the anvil 6220 such that the tissue support 6330 does not move, or at least substantially move, relative to the anvil 6220. Moreover, the tissue support 6330 comprises a rigid box-shaped cross-section such that the deflection of the tissue support 6330 is minimized or insubstantial while the cutting member 6050 is transecting the tissue. As illustrated in FIG. 91, a gap is present between the bottom wall 6338 and the inner side wall 6336. Such a gap can provide some flexibility in the tissue support 6330; however, other embodiments are envisioned in which no such gaps are present. The tissue support 6330 is comprised of plastic, for example; however, in various embodiments, the tissue support 6330 can be comprised of a flexible and/or elastomeric material, for example.

The cutting member 6050 transects the tissue support 6330 during its cutting stroke. As illustrated in FIG. 92, the cutting member 6050 transects the top wall 6332 after transecting the tissue and then enters into the cavity 6334. The top wall 6332 comprises an annular notch 6333 defined therein which is aligned with the annular cutting edge of the cutting member 6050. The notch 6333 reduces the cross-section of the top wall 6332 and facilitates the incision of the top wall 6332. The cutting member 6050 can also transect the bottom wall 6338 during its cutting stroke. As the reader should appreciate, the transection of the top wall 6332 and the bottom wall 6338 of the tissue support 6330 can create force pulses in the firing drive of the stapling instrument. The top wall 6332 and the bottom wall 6338 can be structurally configured to provide different pulses so that the clinician and/or electronic sensor system of the surgical instrument can discern the difference between the pulses and not incorrectly interpret the incision of the top wall 6332 as the end of the firing/cutting stroke.

Referring again to FIGS. 91 and 92, the top wall 6332 of the tissue support 6330 is aligned, or at least substantially aligned, with the tissue compression surface 6022 of the anvil 6220. In addition to or in lieu of the above, the top wall 6332 can be recessed with respect to the tissue compression surface 6022 and/or extend above the tissue compression surface 6022. The top wall 6332 of the tissue support extends above the forming surfaces 6024 of the anvil 6220. In addition to or in lieu of the above, the top wall 6332 can be recessed with respect to the forming surfaces 6024 and/or aligned with the forming surfaces 6024.

Figure 93:
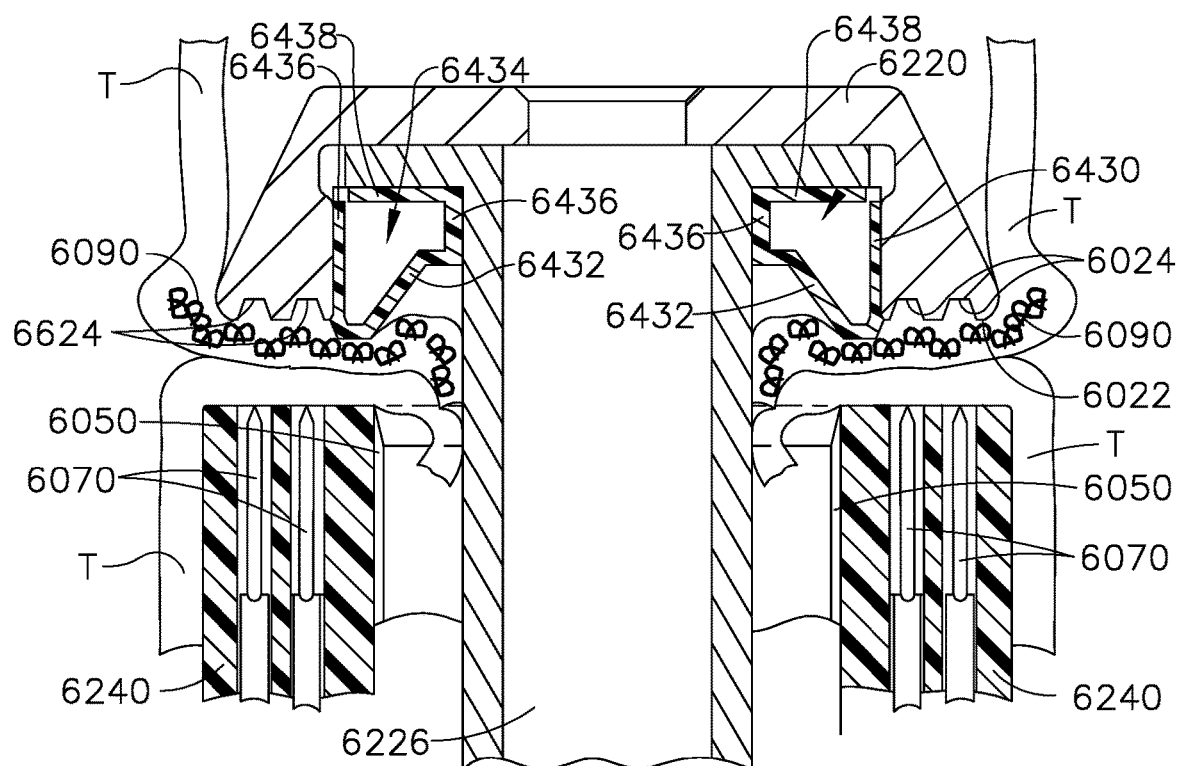
FIG. 93 is a cross-sectional view of an end effector in accordance with at least one alternative embodiment illustrated in a clamped, unfired configuration.
Figure 94:
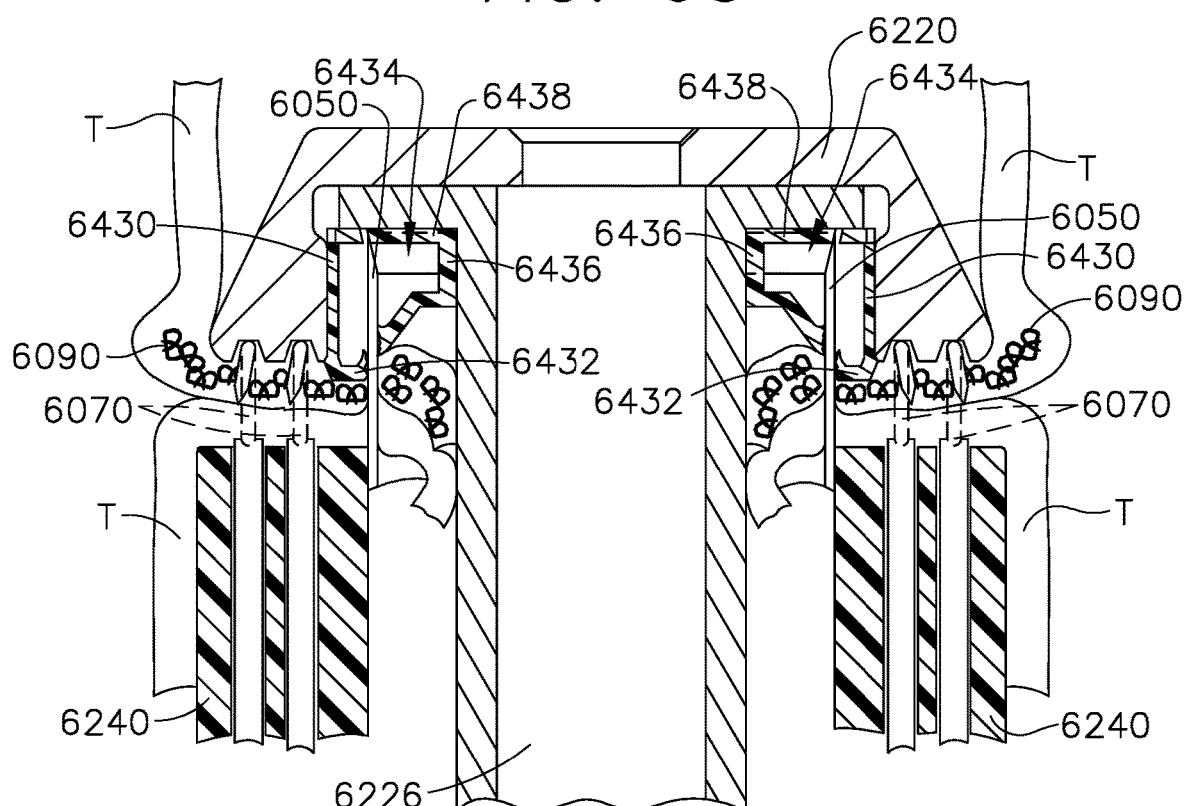
FIG. 94 is a cross-sectional view of the end effector of FIG. 91 illustrated in a fired configuration.

A surgical stapler comprising the staple cartridge 6240 and the anvil 6220 is illustrated in FIGS. 93 and 94. The reader should appreciate, however, that the tissue support 6230 of the anvil 6220 has been replaced with a tissue support 6430. The tissue support 6430 comprises an annular central aperture configured to closely receive the stem 6226. The tissue support 6430 further comprises a top wall 6432, a bottom wall 6438, and sidewalls 6436 extending between the top wall 6432 and the bottom wall 6438. The walls 6432, 6436, and 6438 define an annular cavity 6434 therebetween. The cavity 6434 is enclosed, or at least substantially enclosed, on all sides. The cavity 6434 extends uninterrupted around the stem 6226; however, other embodiments are envisioned in which the cavity 6434 is interrupted by sidewalls and/or changes in geometry, for example.

Similar to the above, the tissue support 6430 is configured to support the tissue as the tissue is being transected by the cutting member 6050. The tissue support 6430 is closely received within the anvil 6220 such that the tissue support 6430 does not move, or at least substantially move, relative to the anvil 6220. Moreover, the tissue support 6430 comprises a rigid polygonal cross-section such that the deflection of the tissue support 6430 is minimized or insubstantial while the cutting member 6050 is transecting the tissue. As illustrated in FIG. 93, a gap is present between the bottom wall 6438 and the inner side wall 6436. Such a gap can provide some flexibility in the tissue support 6430; however, other embodiments are envisioned in which no such gaps are present. The tissue support 6430 is comprised of plastic, for example; however, in various embodiments, the tissue support 6430 can be comprised of a flexible and/or elastomeric material, for example.

As illustrated in FIGS. 93 and 94, the inner sidewall 6436 is shorter than the outer sidewall 3436; however, other embodiments are envisioned in which the outer sidewall 6436 is shorter than the inner sidewall 6436. Moreover, the top wall 6432 is not parallel to the bottom wall 6438. More specifically, the top wall 6432 comprises an inclined portion which extends transversely to the bottom wall 6438 and/or other portions of the top wall 6432.

The cutting member 6050 transects the tissue support 6430 during its cutting stroke. As illustrated in FIG. 94, the cutting member 6050 transects the top wall 6432 after transecting the tissue and then enters into the cavity 6434. The cutting member 6050 can also transect the bottom wall 6438 during its cutting stroke.

As discussed above, the tissue supports disclosed herein are configured to support tissue as the tissue is being incised by a cutting member. Oftentimes, the tissue being incised by the cutting member has been previously stapled, i.e., stapled during an earlier step in the surgical procedure, for example. In various instances, such staples may also be incised by the cutting member even though they are comprised of metal, such as titanium and/or stainless steel, for example. In other instances, such staples may not be incised by the cutting member; rather, they may be pushed into the material comprising the tissue support. Whether or not the staples are incised by the cutting member, the tissue supports disclosed herein, in various instances, comprise a sufficient strength and/or stiffness that prevents a staple trapped against the tissue support by the cutting member from creating more than localized plastic deformation in the tissue support. In at least one such instance, the localized plastic deformation is limited to less than one characteristic length (CL) of the staple in any direction with respect to the staple. In at least one instance, the material of the tissue support can be selected such that the staple trapped against the tissue support may only create a zone of plastic deformation in the tissue support that has a diameter of less than 2*CL, for example. In other instances, the material of the tissue support can be selected such that the staple trapped against the tissue support may only create a zone of plastic deformation in the tissue support that has a diameter of less than 1.5*CL, for example. A characteristic length of a staple can be the width of the staple crown, or backspan, and/or the formed height of the staple legs in their deformed configuration, for example. Moreover, the tissue supports disclosed herein can be comprised of a material which is sufficiently hard enough to support the staples as they are being incised by the cutting member. In at least one instance, the hardness of the material comprising the tissue support is equal to or greater than the hardness of the material comprising the staples being incised against the tissue support. In certain instances, the hardness of the material comprising the tissue support is less than the hardness of the material comprising the staples being incised; however, the structural design of the tissue support is sufficient to prevent the tissue support from plastically stretching beyond an acceptable zone of plastic deformation. In certain instances, the energy needed to incise the tissue and the formed staples in the tissue is less than the energy needed to incise the tissue support. In various instances, the material comprising the tissue support may be resistant to being gouged by the staples. In at least one instance, a biocompatible lubricant may be placed on and/or impregnated within the tissue support to prevent the staples from catching on the tissue support.

In various instances, the tissue compression surface of an anvil and the tissue contacting surface of a tissue support are flat, or at least substantially flat. Such an arrangement can distribute the force applied by the anvil onto the tissue over a large area. Other embodiments are envisioned in which the tissue compression surface of the anvil and/or the tissue contacting surface of the tissue support are not flat. In certain instances, the tissue compression surface of an anvil and/or the tissue contacting surface of a tissue support comprise tissue gripping members, or spikes, extending therefrom which are configured to engage and grip tissue. Such tissue gripping members can reduce relative movement, or slipping, between the tissue and the anvil, for example. In at least one instance, the density of the tissue gripping members on the tissue compression surface of the anvil and the tissue contacting surface of the tissue support is the same. In other instances, the density of the tissue gripping members on the tissue contacting surface of the tissue support is higher than the density of the tissue gripping members on the compression surface of the anvil. As the tissue support is positioned radially inwardly with respect to the compression surface of the anvil, the tissue gripping members can prevent the tissue from flowing or sliding radially inwardly in such an instance.

Figure 95:
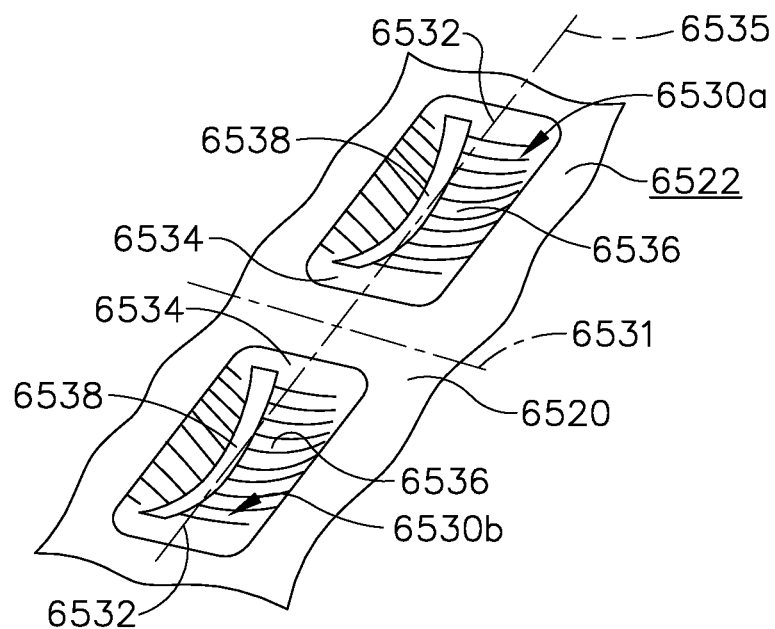
FIG. 95 is a perspective view of a staple forming pocket in accordance with at least one embodiment.

An anvil 6520 is disclosed in FIG. 95. The anvil 6520 comprises a tissue compression surface 6522 and, in addition, forming pockets defined in the tissue compression surface 6522 which are configured to deform staples into a desired configuration when the staples are ejected from their staple cartridge. Each forming pocket comprises a pair of cups, wherein each pair of cups is configured to deform the legs of a staple. For example, a pair of forming cups can include a first forming cup 6530*a* configured to deform the first leg of a staple and a second forming cup 6530*b* configured to deform the second leg of the staple. The first forming cup 6530*a* and the second forming cup 6530*b* are mirror images of one another with respect an axis 6531 extending between the first forming cup 6530*a* and the second forming cup 6530*b*; however, other arrangements can be utilized The first forming cup 6530*a* comprises a first, or outer, end 6532 and a second, or inner, end 6534. The first forming cup 6530*a* further comprises a bottom, or bathtub, surface 6536 extending between the outer end 6532 and the inner end 6534. The first end 6532 is configured to receive the leg of a staple and begin the forming process of the leg. The first end 6532 comprises a curved surface configured to deflect the staple leg toward the second end 6534. The bottom surface 6536 comprises a curved, or concave, surface configured to at least partially turn the staple leg back toward the staple cartridge. The second end 6534 comprises a curved surface which is configured to guide the staple leg out of the forming cup 6530*a*.

The second forming cup 6530*b* comprises a similar construction to that of the first forming cup 6530*a* and is configured to deform a second leg of the staple. As a result of the above, the first forming cup 6530*a* guides the first leg of the staple toward the second leg and the second forming cup 6530*b* guides the second leg of the staple toward the first leg. In various instances, the first forming cup 6530*a* and the second forming cup 6530*b* co-operate to deform the staple into a B-shaped configuration, for example; however, the forming cups can be configured to deform a staple into any suitable configuration.

Figure 96:
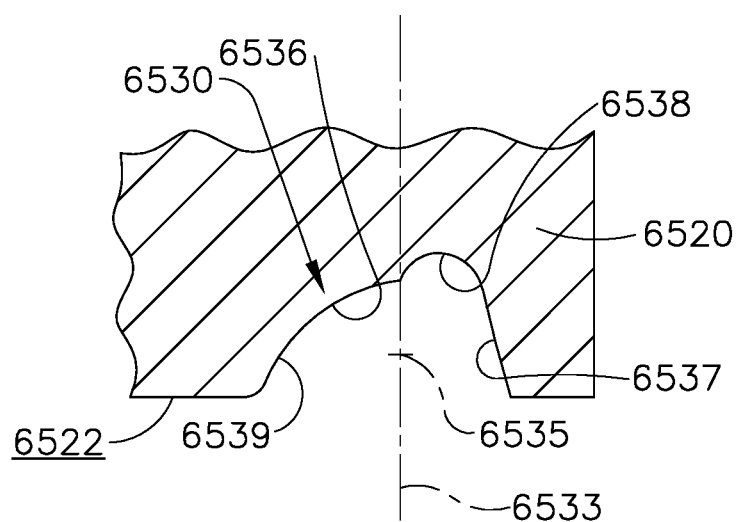
FIG. 96 is a cross-sectional view of the staple forming pocket of FIG. 95.

Referring primarily to FIG. 96, each forming cup 6530 (6530*a* and 6530*b*) comprises a first lateral sidewall 6537 and a second lateral sidewall 6539 extending between the first end 6532 and the second end 6534. In various instances, the first lateral sidewall 6537 and the second lateral sidewall 6539 are mirror images of one another with respect to a longitudinal axis 6533 extending through the center of the forming cup 6530. In other instances, the first lateral sidewall 6537 and the second lateral sidewall 6539 are not mirror images of each other. In either event, the sidewalls 6537, 6539 are sloped or inclined so as to guide the staple leg toward the center of the forming cup, i.e., toward the axis 6533, for example.

Each forming cup 6530 comprises a groove or channel 6538 defined in the bottom surface 6536 thereof. The groove 6538 extends longitudinally between the first end 6532 and the second end 6534 of the forming cup 6530. The groove 6538 extends parallel to, and laterally offset with respect to, a central longitudinal axis 6535 of the forming cup 6530. The groove 6538 is wider than the leg of the staple that is deformed by the forming cup 6530; however, other embodiments are envisioned in which the groove 6538 is narrower than the leg of the staple. In either event, the groove 6538 is configured to guide the staple leg along a predetermined path within the forming cup 6530.

In various instances, the grooves of the forming cups 6530 are configured to twist the legs of the staple while the legs are being deformed. In at least one instance, a staple is planar, or at least substantially planar, before it is deformed. In at least one such instance, the legs and the base of the staple lie in the same plane which is aligned with the longitudinal axis 6535 when the staple is ejected from the staple cartridge. The first ends 6532 and the bottom surfaces 6536 are sloped and/or otherwise configured to guide the legs toward the grooves 6538 when the staple legs enter into the forming cups 6530. Once the staple legs enter into the grooves 6538, the grooves 6538 will twist the staple legs out of plane with the base of the staple. As a result of the above, the unformed staple configuration is planar but the formed staple configuration is non-planar Other embodiments are envisioned, however, in which a staple has a non-planar configuration before and after it has been deformed.

The grooves 6538 of the forming cups 6530, for a given set of forming cups 6530, are positioned on the same side of the longitudinal axis 6535 and are configured to twist both of the staple legs to the same side of the staple base. Other embodiments, however, are envisioned in which a first staple leg is twisted to one side of the staple base and a second staple leg is twisted to another side of the staple base. In at least one such embodiment, a first groove 6538 is positioned on a first side of the longitudinal axis 6535 that is configured to twist a first staple leg to a first side of the staple base while a second groove 6538 is positioned on a second side of the longitudinal axis 6535 that is configured to twist a second staple leg to a second side of the staple base.

The grooves 6538 of the forming cups 6530, for a given set of forming cups 6530, are collinear, or at least substantially collinear. Other embodiments, however, are envisioned in which the grooves 6538 are positioned on the same side of the longitudinal axis 6535 but are not collinear with each other. In at least one such instance, the grooves 6538 are parallel to each other while, in other such instances, the grooves 6538 are not parallel to each other.

Referring primarily to FIG. 96, the groove 6538 is deeper than the bottom surface 6536 of the forming cup 6530. Other embodiments, however, are envisioned in which the groove and the bottom surface of a forming cup have the same depth.

In various instances, the forming cups 6530 are arranged in longitudinal rows when the anvil 6520 is part of a longitudinal end effector configured to apply longitudinal rows of staples. In at least one such instance, the grooves 6538 of the forming cups are arranged such all of the staples deployed by the end effector are bent out of plane in the same direction. In other instances, the grooves 6538 are arranged in a first longitudinal row of forming cups 6530 to bend the staple legs in a first direction and a second longitudinal row of forming cups 6530 to bend the staple legs in a second, or different, direction. In certain instances, the grooves 6538 are arranged to bend the legs of a first staple in a staple row in a first direction and a second staple in the staple row in a second, or opposite, direction.

In various instances, the forming cups 6530 are arranged in annular rows when the anvil 6520 is part of an annular end effector configured to apply annular rows of staples. In at least one such instance, the grooves 6538 are positioned radially outwardly with respect to the center longitudinal axes 6535 of the forming cups 6530. In other instances, the groove 6538 are positioned radially inwardly with respect to the center longitudinal axes 6535 of the forming cups 6530. In certain instances, the grooves 6538 are positioned radially outwardly in a first annular row of forming cups 6530 and radially inwardly in a second annular row of forming cups 6530.

Further to the above, the forming pockets of an anvil can comprise any suitable configuration. In at least one instance, a forming pocket can comprise two forming cups which are mirror images of each other with respect to a central axis. Each forming cup comprises a triangular configuration having an outer end and an inner end. The inner ends of a pair of forming cups are adjacent to each other. The outer ends of the forming cups are wider than the inner ends and are configured to receive the legs of a staple. Each forming cup further comprises a bottom, or bathtub, surface extending between the outer end and the inner end and, in addition, a longitudinal groove defined in the bottom surface configured to guide the staple leg within the forming cup. In at least one instance, the longitudinal groove is centered in the bottom surface of the forming cup.

An end effector 7000 of a circular stapling assembly is disclosed in FIGS. 97-99. The end effector 7000 comprises a staple cartridge including a deck 7030 and a cartridge body 7040. The deck 7030 comprises a tissue compression surface 7031 and staple cavities 7032 defined in the compression surface 7031. The staple cavities 7032 are arranged in a first, or inner, annular row and a second, or outer, annular row. Each staple cavity 7032 in the inner row comprises a first staple 7070*a* removably stored therein and each staple cavity 7032 in the outer row comprises a second staple 7070*b* removably stored therein.

The end effector 7000 further comprises staple drivers which are configured to push the staples out of the staple cartridge. For instance, the staple cartridge comprises a first annular row of staple drivers 7060*a* configured to eject the first row of staples 7070*a* and a second annular row of staple drivers 7060*b* configured to eject the second row of staples

7070b cartridge body 7040. The staple drivers 7060a and 7060b are positioned within and/or aligned with the staple cavities 7032 defined in the deck 7030. The staple drivers 7060a and 7060b are slidable within the staple cavities 7032 to eject the staples 7070a and 7070b, respectively, from the staple cavities 7032.

The end effector 7000 further comprises an anvil 7020. The anvil 7020 comprises a tissue compression surface 7021 and staple forming pockets 7022 defined in the compression surface 7021. The staple forming pockets 7022 are arranged in a first, or inner, annular row and a second, or outer, annular row. The staple forming pockets 7022 are aligned with the staple cavities 7032 such that the staples 7070a, 7070b contact the staple forming pockets 7022 when the staples 7070a, 7070b are ejected from the staple cavities 7032.

The end effector 7000 further comprises a firing member 7056 configured to lift the staple drivers 7060a and 7060b within the staple cavities 7032 to eject the staples 7070a and 7070b, respectively, from the staple cavities 7032. The firing member 7056 comprises a base 7054 and a ramp 7055. The base 7054 is slidably positioned within a recess 7052 defined in a firing drive 7050. The ramp 7055 is slidably positioned within a slot 7041 defined in the cartridge body 7040. As described in greater detail below, the ramp 7055 is configured to slide within the slot 7041 and progressively contact the staple drivers 7060a, 7060b to eject the staples 7070a, 7070b from the staple cavities 7032.

Further to the above, the firing member 7056 is movable through a firing stroke to eject the staples 7070a, 7070b from the staple cavities 7032. During the firing stroke, the firing member 7056 is moved along a curved, or arcuate, path which is defined by the slot 7041. Referring primarily to FIG. 97, the slot 7041 comprises a first end 7042 and a second end 7049 and a continuous path therebetween. The ramp 7055 of the firing member 7056 is positioned in the first end 7042 at the beginning of the firing stroke and the second end 7049 at the end of the firing stroke. The first end 7042 of the slot 7041 is aligned with the inner row of staple cavities 7032 and the second end 7049 of the slot 7041 is aligned with the outer row of staple cavities 7032. The slot 7041 further comprises a first circumferential portion 7043 that extends around a central longitudinal axis 7090 extending through the end effector 7000. The first circumferential portion 7043 of the slot 7041 is aligned with and extends under the staple drivers 7060a in the inner row of staple cavities 7032. The ramp 7055 of the firing member sequentially engages the staple drivers 7060a to sequentially fire the staples 7070a as the firing member 7056 moves through the first circumferential portion 7043 of the slot 7041.

The first circumferential portion 7043 is defined by a constant, or at least substantially constant, radius of curvature about the longitudinal axis 7090; however, other embodiments are envisioned in which the radius of curvature of the first circumferential portion 7043 is not constant. In at least one such instance, the first circumferential portion 7043 comprises a spiral. Stated another way, in such an instance, the first circumferential portion 7043 recedes away from the longitudinal axis 7090 as it extends around the longitudinal axis 7090.

The second circumferential portion 7045 of the slot 7041 is aligned with and extends under the staple drivers 7060b in the outer row of staple cavities 7032. The ramp 7055 of the firing member sequentially engages the staple drivers 7060b to sequentially fire the staples 7070b as the firing member 7056 moves through the second circumferential portion 7045 of the slot 7041. The second circumferential portion 7045 is defined by a constant, or at least substantially constant, radius of curvature about the longitudinal axis 7090; however, other embodiments are envisioned in which the radius of curvature of the second circumferential portion 7045 is not constant. In at least one such instance, the second circumferential portion 7045 comprises a spiral. Stated another way, in such an instance, the second circumferential portion 7045 recedes away from the longitudinal axis 7090 as it extends around the longitudinal axis 7090.

Further to the above, the slot 7041 comprises a transition portion 7044 intermediate the first circumferential portion 7043 and the second circumferential portion 7045. During the firing stroke, the ramp 7055 slides sequentially through the first circumferential portion 7043, the transition portion 7044, and then the second circumferential portion 7045. The transition portion 7044 permits the firing member 7056 to shift between the first radius of curvature of the first staple row and the second radius of curvature of the second staple row. In certain embodiments, a transition portion 7044 between the first circumferential portion 7043 and the second circumferential portion 7045 may be unnecessary. In at least one such instance, the first circumferential portion 7043 can comprise a first spiral configuration and the second circumferential portion 7045 can comprise a second spiral configuration which is aligned such that the end of the first spiral configuration is aligned with the beginning of the second spiral configuration, for example.

The firing member 7056 is driven along its firing path by a firing drive 7050. The firing drive 7050 is driven about the longitudinal axis 7090 by a handcrank and/or electric motor, for example. The firing drive 7050 comprises a drive recess 7052 defined therein. The base 7054 of the firing member 7056 is positioned in the drive recess 7052. The drive recess 7052 is larger than the base 7054 of the firing member 7056 such that the base 7054 can move, or float, within the drive recess 7052. The drive recess 7052 is defined by sidewalls which limit the movement of the base 7054 within the recess 7052. When the firing drive 7050 is rotated about the longitudinal axis 7090, a sidewall of the drive recess 7052 contacts the base 7054 and pushes the drive member 7056 through the slot 7051. As discussed above, the slot 7051 has one or more changes in its radius of curvature and, when the firing member 7056 moves through such changes, the base 7054 of the firing member 7056 can slide within the drive recess.

As described above, the staples in the first, or inner, row of staples are deployed sequentially and, then, the staples in the second, or outer, row of staples are deployed sequentially. Such an embodiment can control the inner periphery of the colon before stapling outwardly, for example. In other embodiments, the staples in the outer row of staples are deployed sequentially and, then, the staples in the inner row of staples are deployed sequentially. Such an embodiment can establish a boundary in the colon tissue before stapling inwardly, for example.

In various instances, further to the above, the first staples 7070a and the second staples 7070b have the same unformed height. In at least one such instance, the first staples 7070a and the second staples 7070b are formed to the same formed height. In other such instances, the first staples 7070a are formed to a first formed height and the second staples 7070b can be formed to a second formed height which is different than the first formed height. In at least one such instance, the first formed height of the inner row of staples is shorter than the second formed height of the outer row of staples. Such an arrangement can provide for a more gradual transition between the stapled tissue and the unstapled tissue, for example. In other instances, the first formed height of the inner row of staples is taller than the second formed height of the outer row of staples. Such an arrangement can allow the innermost tissue of a stapled bowel, for example, to be more flexible, for example.

In certain instances, further to the above, the first staples 7070a have a first unformed height and the second staples 7070b have a second unformed height which is different than the first unformed height. In at least one such instance, the first staples 7070a and the second staples 7070b are formed to the same formed height. In other such instances, the first staples 7070a are formed to a first formed height and the second staples 7070b are formed to a second formed height which is different than the first formed height.

The end effector 7000 has two annular rows of staples; however, an end effector can have any suitable number of annular staple rows. For example, an end effector can have three annular rows of staples. In at least one such instance, the staples in a first annular row can have a first unformed staple height, the staples in a second annular row can have a second unformed staple height, and the third staples in a third annular row can have a third unformed staple height. Moreover, in at least one such instance, the staples in a first annular row can have a first deformed staple height, the staples in a second annular row can have a second deformed staple height, and the third staples in a third annular row can have a third deformed staple height.

A firing drive 7150 is depicted in FIGS. 100-105. The firing drive 7150 comprises a rotatable drive shaft 7152 that is rotatable about a longitudinal axis. The firing drive 7150 further comprises a three-stage sequential driver assembly comprising a first, or inner, driver 7154a, a second, or intermediate, driver 7154b, and a third, or outer, driver 7154c. The drive shaft 7152 comprises a drive pin 7151 extending therefrom. The drive pin 7151 extends through a drive slot in each of the drivers 7154a, 7154b, and 7154c. For instance, the first driver 7154a comprises a first drive slot 7153a defined therein, the second driver 7154b comprises a second drive slot 7153b defined therein, and the third driver 7154c comprises a third drive slot 7153c defined therein. The drive slots 7153a, 7153b, and 7153c do not have the same configuration; however, the drive slots 7153a, 7153b, and 7153c have overlapping configurations that are aligned, or at least substantially aligned, with each other at the drive pin 7151. For instance, the drive pin 7151 is in an unfired position in FIG. 100 and the drive slots 7153a, 7153b, and 7153c are aligned with the drive pin 7151.

Figure 100:
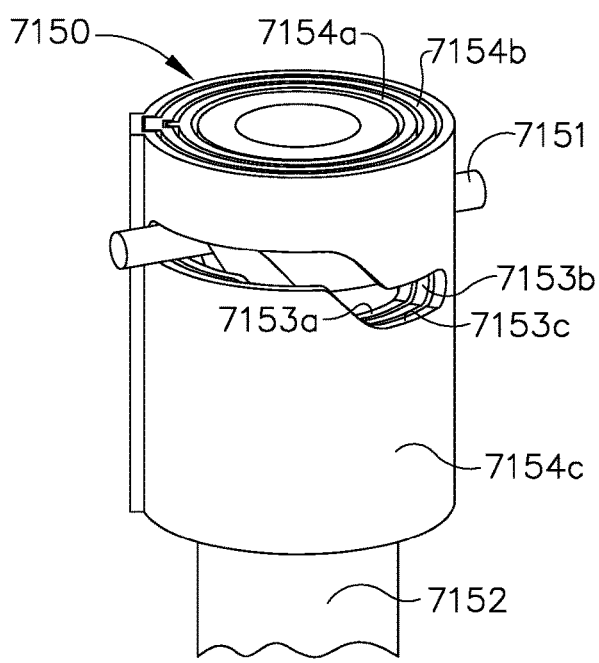
FIG. 100 is a partial perspective view of a firing drive configured to sequentially drive a first driver for firing a first row of staples, a second driver for firing a second row of staples, and then a third driver for driving a cutting member.
Figure 101:
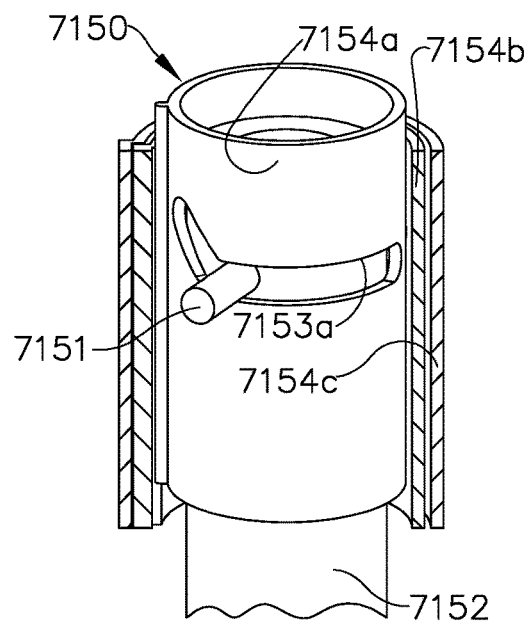
FIG. 101 is a partial perspective view of the firing drive of FIG. 100 illustrating the first driver in a fired position.

Further to the above, FIG. 100 illustrates drivers 7154a, 7154b, and 7154c in an unfired position. When the drive shaft 7152 is rotated through a first portion of its firing stroke, referring now to FIG. 101, the drive pin 7151 is rotated through a circumferential path where the drive pin 7151 engages a sidewall of the drive slot 7153a and pushes, or cams, the first driver 7154a distally. Notably, the drive pin 7151 has not driven the drivers 7154b and 7154c distally during the first portion of the firing stroke. As can be seen in FIG. 100, the drive slots 7153b and 7153c are aligned with the circumferential path of the drive pin 7151 throughout the first portion of the firing stroke. The first driver 7154a is configured to fire a first annular row of staples when the first driver 7154a is displaced distally.

Figure 102:
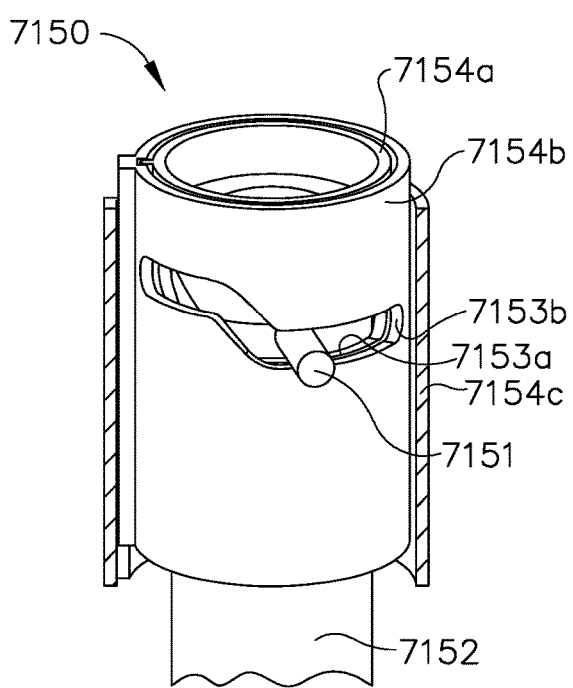
FIG. 102 is a partial perspective view of the firing drive of FIG. 100 illustrating the second driver in a fired position.

When the drive shaft 7152 is rotated through a second portion of its firing stroke, referring now to FIG. 102, the drive pin 7151 is rotated through a circumferential path where the drive pin 7151 engages a sidewall of the drive slot 7153b and pushes, or cams, the second driver 7154b distally. Notably, the drive pin 7151 has not driven the driver 7154c distally during the second portion of the firing stroke Similar to the above, the drive slots 7153a and 7153c are aligned with the circumferential path of the drive pin 7151 throughout the second portion of the firing stroke. The second driver 7154b is configured to fire a second annular row of staples when the second driver 7154b is displaced distally.

Figure 103:
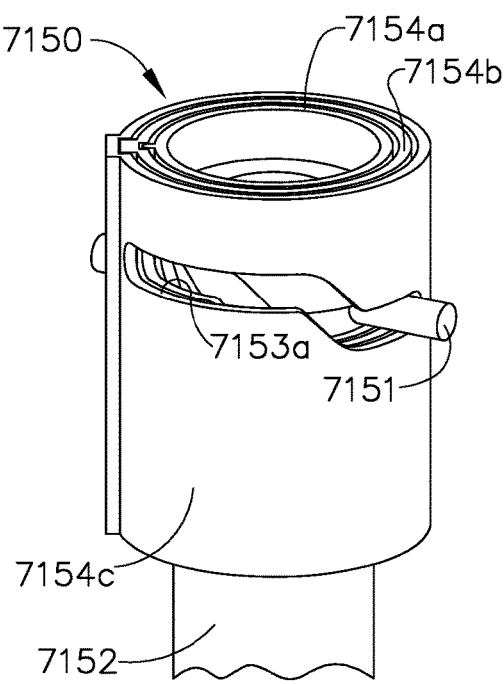
FIG. 103 is a partial perspective view of the firing drive of FIG. 100 illustrating the third driver in a fired position.

When the drive shaft 7152 is rotated through a third portion of its firing stroke, referring now to FIG. 103, the drive pin 7151 is rotated through a circumferential path where the drive pin 7151 engages a sidewall of the drive slot 7153c and pushes, or cams, the third driver 7154c distally Similar to the above, the drive slots 7153a and 7153b are aligned with the circumferential path of the drive pin 7151 throughout the third portion of the firing stroke. The third driver 7154c is configured to deploy a cutting member when the third driver 7154c is displaced distally; however, in certain embodiments, the third driver 7154c can deploy a third row of staples, for example.

As a result of the above, there is no overlap between the first staple firing stage, the second staple firing stage, and the tissue cutting stage. They are timed sequentially. Accordingly, the forces required to deform the staples and cut the tissue are spread out throughout the firing stroke. Moreover, the firing drive 7150 cannot cut the tissue until the tissue has been stapled. Various alternative embodiments are envisioned in which there is some overlap between the first staple firing stage, the second staple firing stage, and/or the tissue cutting stage. In at least one such embodiment, the configurations of the drive slots 7153a, 7153b, and 7153c can be adapted such that there is a partial overlap in the movement of the first driver 7154a and the second driver 7154b and/or a partial overlap in the movement of the second driver 7154b and the third driver 7154c.

Figures 104, 105:
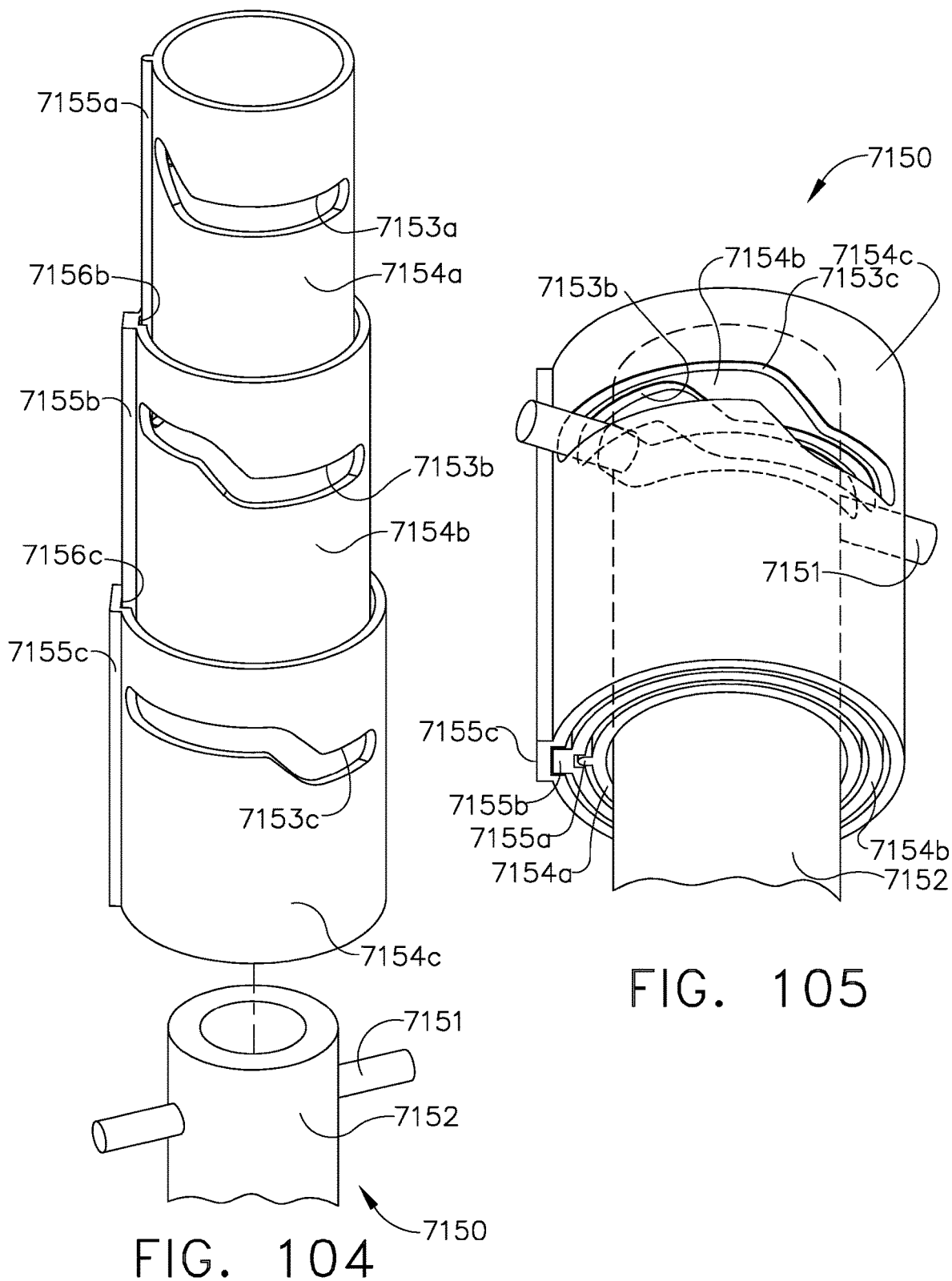
FIG. 104 is an exploded view of the firing drive of FIG. 100.
FIG. 105 is a partial perspective view of the firing drive of FIG. 100 in the configuration of FIG. 103.

Referring primarily to FIGS. 103 and 104, the drivers 7154a, 7154b, and 7154c comprise co-operating features which prevent, or at least inhibit, the drivers 7154a, 7154b, and 7154c from rotating relative to one another. For instance, the first driver 7154a comprises a longitudinal key 7155a positioned in a longitudinal slot 7156b defined in the second driver 7154b. The key 7155a and the slot 7156b are configured to permit the first driver 7154a to slide longitudinally relative to the second driver 7154b but block rotational movement between the first driver 7154a and the second driver 7154b. Similarly, the second driver 7154b comprises a longitudinal key 7155b positioned in a longitudinal slot 7156c defined in the third driver 7154c. The key 7155b and the slot 7156c are configured to permit the second driver 7154b to slide longitudinally relative to the third driver 7154c but block rotational movement between the second driver 7154b and the third driver 7154c.

In order to retract the drivers 7154a, 7154b, and 7154c, the drive shaft 7152 is rotated in an opposite direction. In such instances, the drive shaft 7152 sequentially engages a sidewall of the drive slot 7153c, a sidewall of the drive slot 7153b, and then a sidewall of the drive slot 7153a to return the third driver 7154c, the second driver 7154b, and the first driver 7154a back to their unfired positions (FIG. 100).

Figure 106:
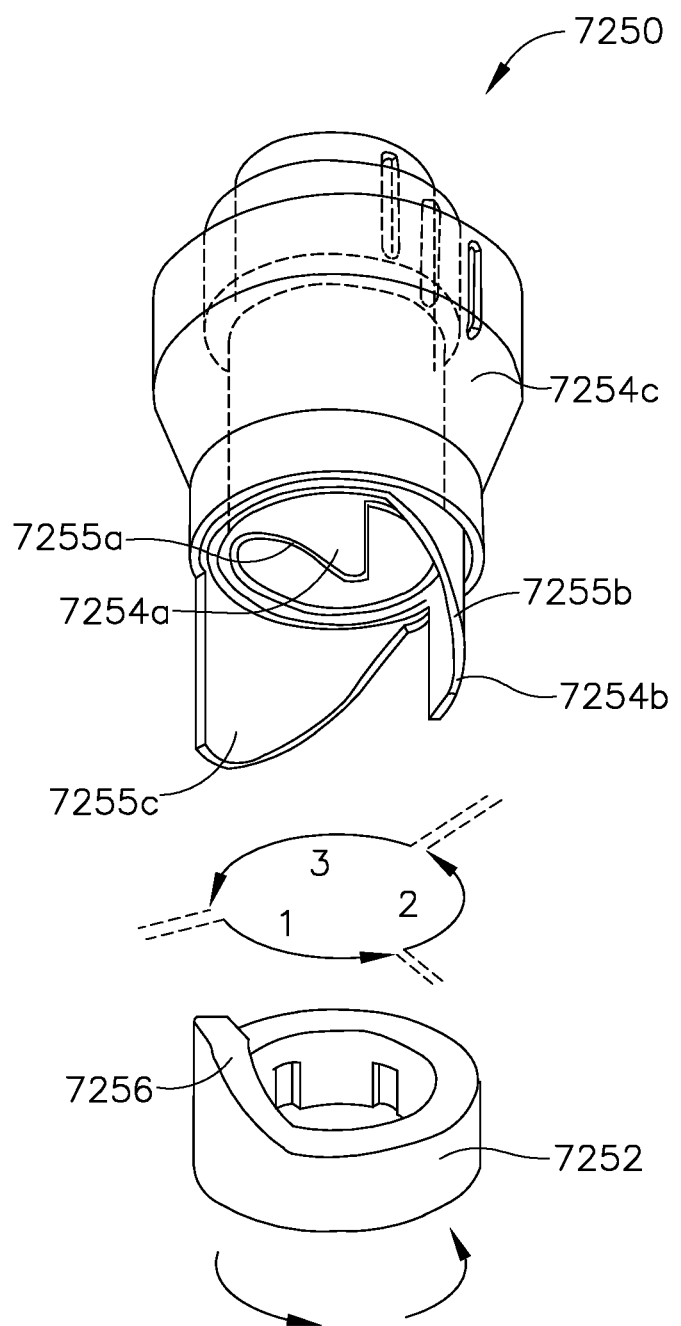
FIG. 106 is an exploded view of a firing drive in accordance with at least one alternative embodiment.

A firing drive 7250 is illustrated in FIG. 106. The firing drive 7250 operates in a similar manner to that of the firing drive 7150. The firing drive 7250 comprises a drive shaft 7252 which is rotatable about a longitudinal axis. The drive shaft 7252 comprises a cam surface, or ramp, 7256 which is rotated through several stages of a firing stroke. The firing drive 7250 further comprises a first driver 7254a, a second driver 7254b, and a third driver 7254c which are engaged by the cam 7256 of the drive shaft 7252 when the firing drive 7250 is rotated. In the first stage of the firing stroke, the cam 7256 engages a cam surface 7255a defined on the first driver 7254a and drives the first driver 7254a distally. In the second stage of the firing stroke, the cam 7256 engages a cam surface 7255b defined on the second driver 7254b and drives the second driver 7254b distally and, in the third stage of the firing stroke, the cam 7256 engages a cam surface 7255c defined on the third driver 7254c and drives the third driver 7254c distally.

The first cam surface 7255a is shorter than the second cam surface 7255b and, as a result, the first driver 7254a has a shorter firing stroke than the second driver 7254b. Similarly, the second cam surface 7255b is shorter than the third cam surface 7255c and, as a result, the second driver 7254b has a shorter firing stroke than the third driver 7254c. Such an arrangement may be useful to form different rows of staples to different formed heights, for example. In other embodiments, the drivers 7254a, 7254b, and 7254c may have any suitable firing stroke. In at least one embodiment, the drivers 7254a, 7254b, and 7254c have the same firing stroke, for example. Such an arrangement may be useful to form different rows of staples to the same formed height, for example.

FIG. 107 is a perspective view of a portion of a staple cartridge 4410 for use with a circular surgical stapling instrument in accordance with at least one embodiment. A variety of circular surgical stapling instruments are known. For example, U.S. patent application Ser. No. 14/836,110, filed Aug. 26, 2015, entitled SURGICAL STAPLING CONFIGURATIONS FOR CURVED AND CIRCULAR STAPLING INSTRUMENTS, which is hereby incorporated by reference in its entirety, discloses various circular surgical stapling instrument arrangements. U.S. patent application Ser. No. 14/498,070, filed Sep. 26, 2014, entitled CIRCULAR FASTENER CARTRIDGES FOR APPLYING RADIALLY EXPANDING FASTENER LINES, the entire disclosure of which is hereby incorporated by reference herein also discloses various circular surgical stapler arrangements. As discussed in those references, a circular surgical stapler generally comprises a frame assembly that comprises an attachment portion that is configured to operably couple an anvil to the circular surgical stapler.

In general, the anvil includes an anvil head that supports an annular line or lines of staple-forming pockets. An anvil stem or trocar portion is attached to the anvil head and is configured to be removably coupled to the anvil attachment portion of the circular stapling instrument. Various circular surgical stapling instruments include means for selectively moving the anvil toward and away from the surgical staple cartridge such that the target tissue may be clamped between the anvil and the deck of the surgical staple cartridge. The surgical staple cartridge removably stores a plurality of surgical staples therein that are arranged in one or more annular arrays that correspond to the arrangement of staple forming pockets provided in the anvil. The staples are removably stored within corresponding staple cavities that are formed in the staple cartridge and are supported on corresponding portions of a selectively movable pusher assembly that is operably received within the circular stapler. The circular stapler further includes an annular knife or cutting member that is configured to incise the tissue that is clamped between the anvil and the staple cartridge.

Referring again to FIG. 107, the staple cartridge 4410 comprises a cartridge body 4411 that defines an annular cartridge deck surface 4412. The cartridge body 4411 comprises an inner annular row 4420 of spaced inner staple cavities 4422 and an outer annular row 4440 of spaced outer staple cavities 4442. The inner staple cavities 4422 are staggered relative to the outer spaced staple cavities 4442 as can be seen in FIG. 107. Supported within each inner staple cavity 4422 is an inner surgical staple 4430 and supported within each outer staple cavity 4442 is an outer surgical staple 4450. The outer staples 4450 in the outer annular row 4440 may have different characteristics than the inner staples 4430 in the inner annular row 4420. For example, as illustrated in the embodiment of FIG. 108, the outer staples 4450 have an unformed "gullwing" configuration. In particular, each outer staple 4450 includes a pair of legs 4454, 4464 that extend from a staple crown 4452. Each leg 4454, 4464 includes a vertical portion 4456, 4466, respectively that extends from the crown 4452. The vertical portions 4456, 4466 may be parallel to each other in one embodiment. However, in the illustrated arrangement, the vertical portions 4456, 4466 are not parallel to each other. For example, the angle $A_1$ between the crown 4452 and the vertical portions 4456, 4466 in the illustrated arrangement is greater than ninety degrees. See FIG. 108. Further details regarding the staple configuration may be found in U.S. patent application Ser. No. 14/319,008, filed Jun. 30, 2014, entitled FASTENER CARTRIDGE COMPRISING NON-UNIFORM FASTENERS, U.S. Patent Application Publication No. 2015/0297232, the entire disclosure of which is hereby incorporated by reference herein. However, other the vertical portions 4456, 4466 may be arranged at other angles with respect to the crown 4452. One advantage of having the vertical leg portions 4456, 4466 oriented at angles greater than ninety degrees relative to the crown 4452 is that such arrangement may assist in the temporary retention of the staple within its corresponding staple cavity.

At least one leg 4454, 4464 includes an inwardly extending end portion. In the embodiment depicted in FIG. 108 for example, each leg 4454, 4464 includes an inwardly extending leg portion. In the illustrated arrangement, leg portion 4458 extends inwardly from the vertical leg portion 4456 and the leg portion 4468 extends inwardly from the vertical leg portion 4466. As can be seen in FIG. 108, the leg portion 4458 is shorter than the leg portion 4468. Stated another way, the distance $H_A$ between the staple crown 4452 and the point where the leg portion 4458 angles inward from the vertical leg portion 4456 is greater than the distance $H_C$ between the staple crown 4452 and the point where the leg portion 4468 angles inward from the vertical leg portion 4466. Thus, distance $H_B$ in at least one embodiment is shorter than the length $H_D$. The angle $A_2$ at which the leg portion 4458 angles relative to the vertical leg portion 4556 may be equal to the angle $A_3$ at which the leg portion 4468 angles relative to the vertical leg portion 4466 or angles $A_2$ and $A_3$ may be different from each other. Further details regarding the staple configuration may be found in U.S. patent application Ser. No. 14/319,008, filed Jun. 30, 2014, entitled FASTENER CARTRIDGE COMPRISING NON-UNIFORM FASTENERS, U.S. Patent Application Publication No. 2015/0297232, which has been herein incorporated by reference.

In at least one embodiment, each inner surgical staple 4430 may have the configuration illustrated in FIG. 108. As can be seen in FIG. 108, the inner surgical staple 4430 has a crown 4432 and two vertical legs 4434, 4436 extending therefrom. The vertical legs 4434, 4436 may extend relatively perpendicularly from the crown 4432 or they may extend at angles $A_4$ that may be greater than ninety degrees. Such arrangement may assist in the temporary retention of the staples 4430 within their corresponding staple cavity 4422. However, vertical legs 4434, 4436 may extend from the crown 4432 at different angles. In some embodiments, angles $A_4$ are equal to each other. In other embodiments, angles $A_4$ are different from each other. In the illustrated embodiment, the inner staples 4430 and the outer staples 4450 each have the same unformed height UFH. The inner and outer staples 4430, 4450 are formed from conventional surgical staple wire. In at least one embodiment, the diameter of the staple wire used to form the outer staples 4450 is greater than the diameter of the staple wire used to form the inner staples 4430. In other embodiments, the inner and outer staples may have the same diameters and be formed from wires with other diameters. In some arrangements, the inner and outer staples may be formed from the same type of staple wire. Thus, in such arrangement, the wire diameters of the inner and outer staples would be the same. In yet another embodiment, however, the inner and outer staples may have the same unformed shapes/configurations, yet be formed from two different staple wires that have different wire diameters. Also in at least one arrangement, the crown width $CW_O$ of each outer staple 4450 is larger than the crown width $CW_1$ of each inner staple 4430. Further details regarding the staple configuration may be found in U.S. patent application Ser. No. 14/319,008, filed Jun. 30, 2014, entitled FASTENER CARTRIDGE COMPRISING NON-UNIFORM FASTENERS, U.S. Patent Application Publication No. 2015/0297232, which has been herein incorporated by reference.

Returning to FIG. 107, the staple cartridge 4410 includes an outer rim 4414 that extends above the deck surface 4412. During surgery, the clinician can adjust the location of the anvil relative to the cartridge of a circular stapler. In at least one such embodiment, the staple cartridge 4410 further comprises deck features 4416 and 4418 that extend from the deck surface 4412. As can be seen in FIG. 107, a series of inner deck features 4416 are provided between the inner row 4420 of staple cavities 4422 and a centrally-disposed knife opening 4413 through which the knife or cutting member will pass during the firing process. The deck features 4416 may be shaped and located relative to the inner staple cavities and opening 4413 as shown in FIGS. 107, 109 and 110. For example, each inner deck feature 4416 may have a flat wall portion 4415 that is coextensive with the wall of the knife opening 4413 and a conical or sloping body portion 4417 that is adjacent to the row of inner staple cavities 4422. See FIGS. 109 and 110. In the embodiment depicted in FIG. 107, the deck features 4416 are oriented in the gap between two adjacent inner staple cavities 4422 and are staggered between pairs of staple cavities 4422 as shown. The cavity extension arrangements or deck features in this system may serve to lower pressure that is commonly encountered in flat deck cartridges. This disclosed arrangement may also help to mitigate tissue movement and slippage. Since slippage of the tissue is generally undesirable, the outside diameter holding features may be bigger and more numerous. The internal diameter features may serve to increase tissue tension/shear as the blade passes next to the inside internal diameter which may make the system cut better. However, the deck features 4416 may have different shapes and configurations and may be located in different locations on the deck surface 4412.

As can also be seen in FIGS. 107, 109 and 110, every other outer staple cavity 4442 includes an outer deck feature 4418 that is associated with each end thereof. Outer deck features 4418 extend above the deck surface 4412 and guide the outer staples 4450 toward the anvil when the staples 4450 are being ejected from the staple cartridge 4410. In such embodiments, the outer staples 4450 may not extend above the outer deck features 4418 until they are moved toward the anvil by the firing member. Referring primarily to FIG. 107, in at least one embodiment, the outer deck features 4418 do not extend around the entirety of the corresponding outer staple cavity 4442. A first outer deck feature 4418 is positioned adjacent a first end of a corresponding outer cavity 4442 and a second outer deck feature 4418 is positioned adjacent a second end of the outer cavity 4442. As can be seen in FIG. 107, the outer deck features 4418 are associated with every other one of the outer staple cavities 4442. Such arrangement may serve to lower overall pressure and minimize tissue stretch and movement. In other embodiments, first and second outer deck features 4418 may be associated with every one of the outer staple cavities 4442, however. In yet other embodiments, an outer deck feature may extend around the entire perimeter of a corresponding outer cavity. As can be seen in FIG. 109, the inner deck features 4416 are shorter than the outer deck features 4418. Stated another way, each inner deck feature protrudes above the deck surface 4412 a distance that is less than the distance that each outer deck feature 4418 protrudes above the deck surface 4412. Each outer deck feature may protrude above the deck surface 4412 the same distance that the outer rim 4414 protrudes above the deck surface 4412. In addition, as can also be seen in FIG. 109, each outer deck feature 4418 has a generally conical or tapered outer profile which may help to prevent tissue from snagging on the deck features during insertion of the stapler head through a patient's colon and rectum.

Figure 118:
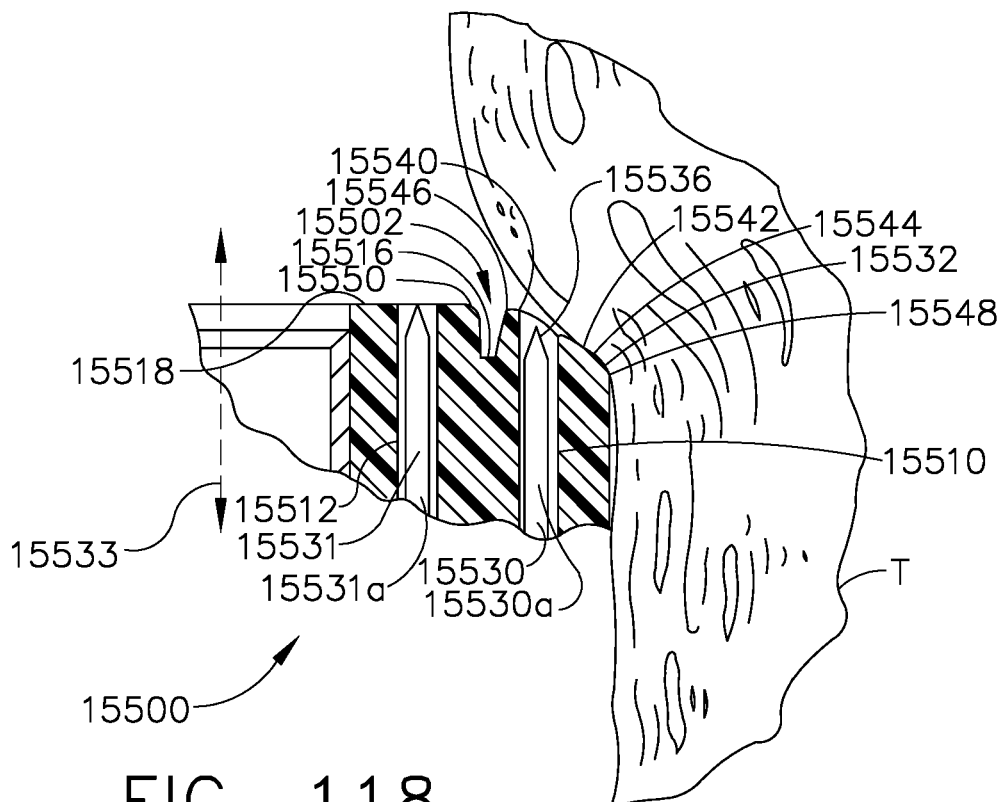

The above-mentioned deck feature arrangements may provide one or more advantages. For example, the upstanding outer rim may help to prevent tissue from sliding across the cartridge deck. This upstanding rim could also comprise a repeating pattern of highs and lows rather than being one continuous lip formation. The inside upstanding features may also help to retain the tissue adjacent to the blade and lead to improved cutting. The inside deck features could be between every cavity or in alternative arrangements, the deck feature(s) may comprise one continuous upstanding lip. It may be desirable to balance the number of deck features to minimize the number of high force/compression zones while attaining a desired amount of tissue immobilization. The cavity concentric features may serve the additional purpose of minimization of tissue flow in the areas where the staple legs project from. Such arrangements also facilitate desirable staple formation as the staple legs eject and transition to the receiving anvil pocket which may consist of corresponding forming pockets. Such localized pocket features increase the low compression zones while facilitating leg support from the cartridge as the staple exits the cartridge. This arrangement thereby minimizes the distance that the staple must "jump" before it meets the anvil pocket. Tissue flow tends to increase going from the center of the cartridge radially outward. Referring to FIG. 118, the improved standing outside row extensions have a tendency to stage tissue as they are inserted up through the colon because it is a tube.

FIGS. 109 and 110 illustrate use of the surgical staple cartridge 4410 in connection with an anvil 4480. The anvil 4480 comprises an anvil head portion 4482 that operably supports a staple forming insert or portion 4484 and a knife washer 4490. The knife washer 4490 is supported in confronting relationship to the knife 4492 that is supported in the stapler head. In the illustrated embodiment, the staple forming insert 4484 is fabricated from, for example, steel, stainless steel, etc. and contains an inner row of inner staple forming pockets 4486 and an outer row of outer staple forming pockets 4488. Each inner staple forming pocket 4486 corresponds to one of the inner staple cavities 4422 and each outer staple forming pocket 4488 corresponds to one of the outer staple cavities 4442. In the illustrated arrangement, when the anvil 4480 is moved to its firing position relative to the cartridge deck surface 4412, the inner staple forming pockets 4486 are closer to the cartridge deck surface 4412 than are the outer staple forming pockets 4488. Stated another way, the first gap $g_1$ or first staple forming distance between a first staple forming portion 4485 and the cartridge deck surface 4412 is less than the second gap $g_2$ or second staple forming distance between a second staple forming portion 4487 and the cartridge deck surface 4412.

As can be further seen in FIGS. 109 and 110, the inner staples 4430 are each supported within their corresponding inner staple cavity 4422 on a corresponding inner driver portion 4502 of a pusher assembly 4500 and each of the outer staples 4450 are supported within their corresponding outer staple cavity 4442 on a corresponding outer driver portion 4504. Advancement of the pusher assembly 4500 toward the anvil 4480 will cause the inner and outer staples 4430, 4450 to be driven into forming contact with their respective corresponding staple forming pockets 4486, 4488 as shown in FIG. 110. In addition, the knife 4492 is advanced distally through the tissue that is clamped between the anvil 4480 and the deck surface 4412 and through a frangible bottom 4491 of the knife washer 4490. Such arrangement serves to provide the outer staples 4450 with a formed height $FH_O$ that is larger than the formed height $FH_I$ of the inner staples 4430. Stated another way, the outer row 4440 of outer staples 4450 are formed into a larger "B" formation resulting in a greater capture volume and/or taller staple forming height to alleviate high tissue compression near the outer row of staples 4440. A larger B formation may also improve blood flow toward the inner rows. In various instances, the outer row 4440 of outer staples 4450 comprise a greater resistance to unfolding by utilizing a larger staple crown, staple leg widths, and/or staple leg thicknesses.

The quantity of staples used in each row of staples can vary. In one embodiment, for example, there are more outer staples 4450 than there are inner staples 4430. Another embodiment employs more inner staples 4430 than outer staples 4450. In various instances, the wire diameter of the outer staples 4450 is larger than the wire diameter of the inner staples 4430. The inner and outer staples 4430, 4450 may have the same unformed heights UFH. The crown widths $CW_O$ in the outer row 4440 of outer staples 4450 are larger than the crown widths $CW_I$ of the inner row 4420 of inner staples 4430. The gullwing configuration of the outer staples 4450 employs bends that are located at different distances from their respective crown. Use of the stepped anvil configuration with a flat (unstepped) cartridge deck surface 4412 with uniform driver or pusher travel yield staples with different formed heights.

Figure 111:
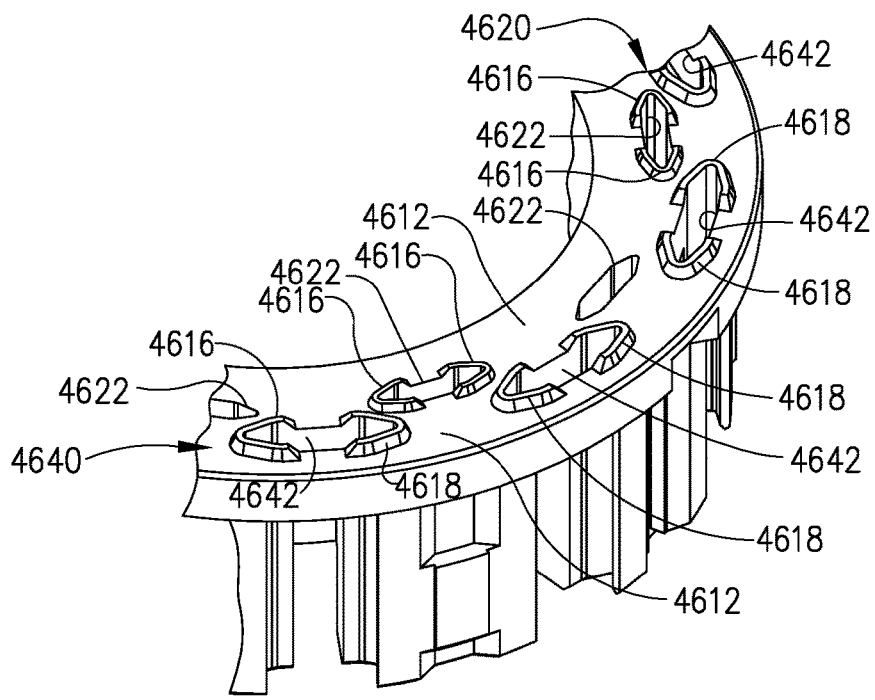
FIG. 111 is a perspective view of a portion of a surgical staple cartridge for use with a circular surgical stapling instrument in accordance with at least one embodiment.

FIG. 111 illustrates another staple cartridge embodiment 4610. As can be seen in FIG. 111, the staple cartridge 4610 includes a cartridge deck 4612 that includes an inner annular row 4620 of spaced inner staple cavities 4622 and an outer annular row 4640 of outer spaced staple cavities 4642. The inner staple cavities 4622 are staggered relative to the outer spaced staple cavities 4642 as can be seen in FIG. 111. Supported within each inner staple cavity 4622 is an inner surgical staple 4630 and supported within each outer staple cavity 4642 is an outer surgical staple 4650. In addition, an outer rim 4614 extends above the deck surface 4612. In various embodiments, further to the above, the staples 4630, 4650 do not protrude above the deck surface 4612 until they are moved toward the anvil by the firing member. Such embodiments may frequently utilize small staples relative to the depth of their respective staple cavity in which they are stored. In other embodiments, the legs of the staples protrude above the deck surface 4612 when the staples are in their unfired positions. In at least one such embodiment, the staple cartridge 4610 further comprises deck features 4616 and 4618 that extend from the deck surface 4612.

As can also be seen in FIG. 111, every other inner staple cavity 4622 includes an inner deck feature 4616 that is associated with each end thereof. Inner deck features 4616 extend above the deck surface 4612 and guide the corresponding inner staples 4630 toward the anvil when the corresponding inner staples 4630 are being ejected from the staple cartridge 4610. In such embodiments, the inner staples 4630 may not extend above the inner deck features 4616 until they are moved toward the anvil by the firing member. In the illustrated example, the inner deck features 4616 do not extend around the entirety of the corresponding inner staple cavity 4622. A first inner deck feature 4616 is positioned adjacent a first end of a corresponding inner cavity 4622 and a second inner deck feature 4616 is positioned adjacent a second end of the inner cavity 4622. In other embodiments, the inner deck features 4416 may be associated with every one of the inner staple cavities 4622, however. In yet other embodiments, an inner deck feature may extend around the entire perimeter of a corresponding inner staple cavity. By employing deck features that have different heights in concentric patterns wherein they are associated with every other cavity may provide more lower pressure tissue gap areas, while balancing them with the desire to guide as many and as much of the staple leg for as long as possible. Stated another way, such arrangement may minimize the amount of tissue flow reducing the overall amount of pressure applied to the target tissue.

Figure 112:
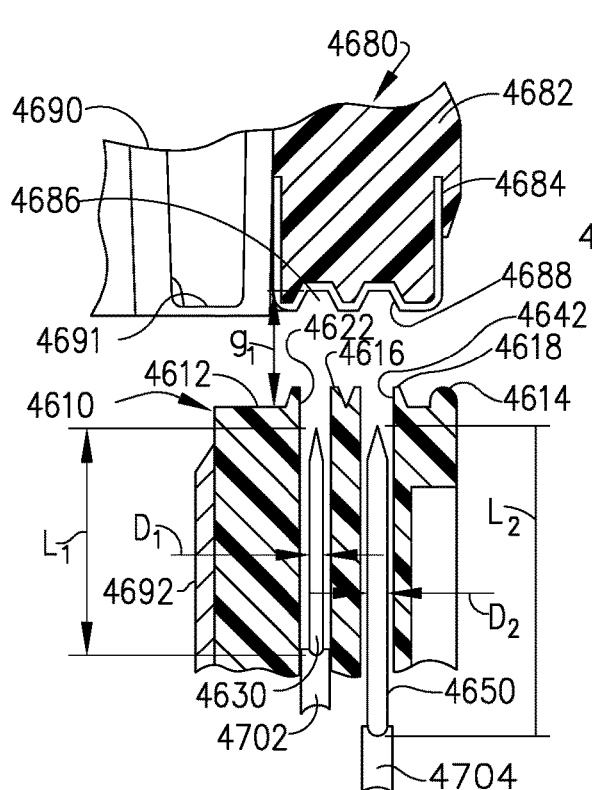
FIG. 112 is a cross-sectional view of a portion of an anvil in relation to a portion of the surgical staple cartridge of FIG. 111 prior to actuation of the staple forming process.
Figure 113:
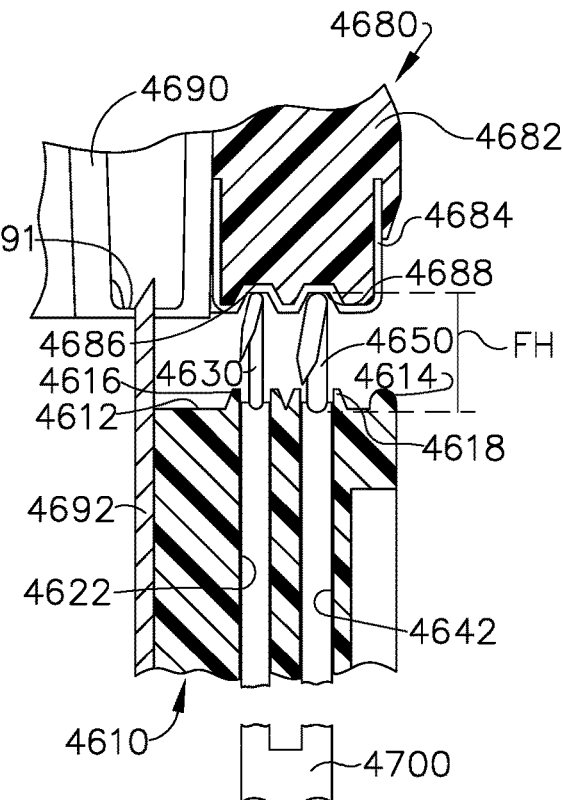
FIG. 113 is another cross-sectional view of the anvil and staple cartridge of FIG. 112 after the staples have been formed.

Still referring to FIG. 111, each outer staple cavity 4642 includes an outer deck feature 4618 that is associated with each end thereof. Outer deck features 4618 extend above the deck surface 4612 and guide the outer staples 4650 toward the anvil when the staples 4650 are being ejected from the staple cartridge 4610. In such embodiments, the outer staples 4650 may not extend above the outer deck features 4618 until they are moved toward the anvil by the firing member. As can be seen in FIG. 111, in the illustrated example, the outer deck features 4618 do not extend around the entirety of the corresponding outer staple cavity 4642. A first outer deck feature 4618 is positioned adjacent a first end of a corresponding outer cavity 4642 and a second outer deck feature 4618 is positioned adjacent a second end of the outer cavity 4642. As can be seen in FIG. 111, outer deck features 4618 are associated with every one of the outer staple cavities 4642. In other embodiments, first and second outer deck features 4618 may be associated with every other one of the outer staple cavities 4642, however. In yet other embodiments, an outer deck feature may extend around the entire perimeter of a corresponding outer cavity. As can be seen in FIGS. 112 and 113, the inner deck features 4616 and the outer deck features 4618 extend above the deck surface 4612 the same distance. Stated another way, they have the same heights. In addition, as can also be seen in FIGS. 112 and 113, each inner deck feature 4416 and each outer deck feature 4618 has a generally conical or tapered outer profile which may help to prevent tissue from snagging on the deck features during insertion of the stapler head through a patient's colon and rectum.

FIGS. 112 and 113 illustrate use of the surgical staple cartridge 4610 in connection with an anvil 4680. The anvil 4680 comprises an anvil head portion 4682 that operably supports a staple forming insert or portion 4684 and a knife washer 4690. The knife washer 4690 is supported in confronting relationship to a knife 4692 that is supported in the stapler head. In the illustrated embodiment, the staple forming insert 4684 is fabricated from, for example, steel, stainless steel, etc. and contains an inner row of inner staple forming pockets 4686 and an outer row of outer staple forming pockets 4688.

Each inner staple forming pocket 4686 corresponds to one of the inner staple cavities 4622 and each outer staple forming pocket 4688 corresponds to one of the outer staple cavities 4642. In the illustrated arrangement, the inner staple forming pockets 4686 are located the same distance $g_1$ from the deck surface 4612 as are the outer staple forming pockets 4688.

As can be further seen in FIGS. 112 and 113, an inner staple 4630 is supported within a corresponding inner staple cavity 4622 on a corresponding inner driver portion 4702 of a pusher assembly 4700. An outer staple 4650 is supported within a corresponding outer staple cavity 4642 on a corresponding outer driver portion 4704. Advancement of the pusher assembly 4700 toward the anvil 4680 will cause the inner and outer staples 4630, 4650 to be driven into forming contact with their respective corresponding staple forming pockets 4686, 4688 as shown in FIG. 113. In addition, the knife 4692 is advanced distally through the tissue that is clamped between the anvil 4680 and the deck surface 4612 and through a frangible bottom 4691 of the knife washer 4690. In the example illustrated in FIGS. 112 and 113, each inner staple 4630 is formed from a first staple wire that has a first wire diameter $D_1$ and has a first unformed height $L_1$. For example, the first wire diameter $D_1$ may be approximately 0.0079"-0.015" (increments are usually 0.0089", 0.0094", and 0.00145") and the first unformed height $L_1$ may be approximately 0.198"-0.250". Each outer staple 4650 is formed from a second staple wire that has a second wire diameter $D_2$ and has a second unformed height $L_2$. In the embodiment depicted in FIGS. 112 and 113, $D_1 < D_2$ and $L_1 < L_2$. However, as can be seen in FIG. 113, the inner and outer staples 4630, 4650 are formed with the same formed heights FH's. The thicker wire staples on the outside tend to provide high tear and burst strengths as compared to the inside row of smaller diameter staples which tend to hold better hemostatically. Stated another way, the tighter inside rows of staples may hold better hemostatically while the outer rows of less compressed staples may facilitate better healing and blood flow. In addition, the staples with longer legs, even when formed at the same heights as staples with shorter legs, may ensure more B-bending which may make the longer legged staples stronger and more likely to be properly formed enough to hold in high load conditions. The quantity of staples used in each row of staples can vary. In one embodiment, for example, the inner row 4620 has the same number of inner staples 4630 as does the outer row 4640 of outer staples 4650. In various arrangements, the crown widths of the staples 4650 is larger than the crown widths of the inner staples 4630. In other embodiments, the staples 4630, 4650 may have identical crown widths. In other arrangements, the staples 4630, 4650 may be of the gullwing design described above. For example, at least one leg of the staple may include an end portion that is bent inwardly or both legs may include end portions that are bent inwardly toward each other. Such staples may be employed in the inner annular row or the outer annular row or in both of the inner and outer annular rows.

Figure 114:
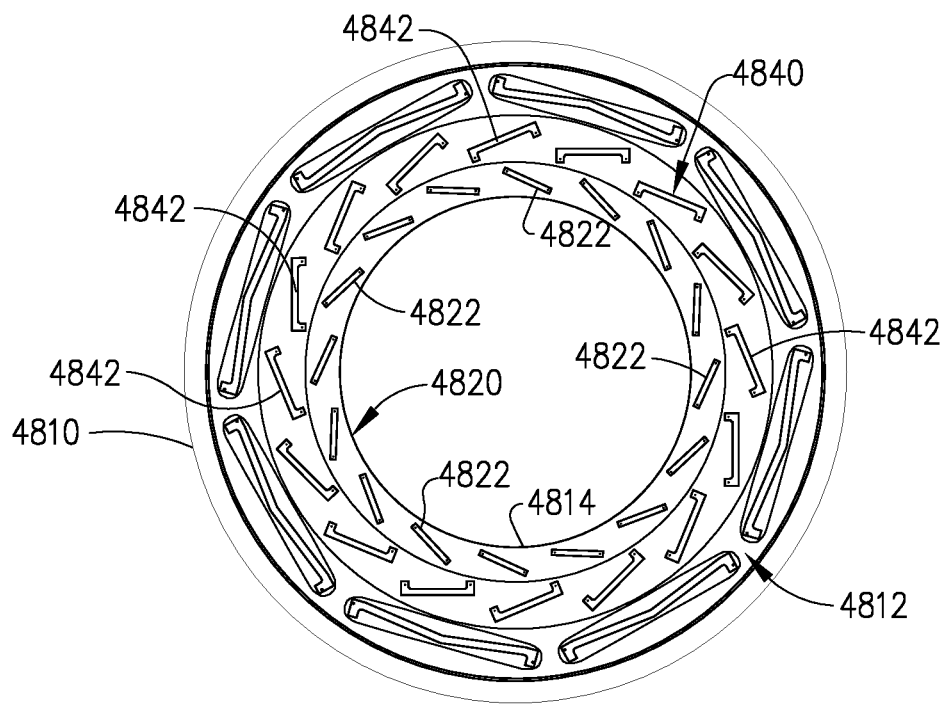
FIG. 114 is a top view of a staple cartridge in accordance with at least one embodiment.
Figure 117:
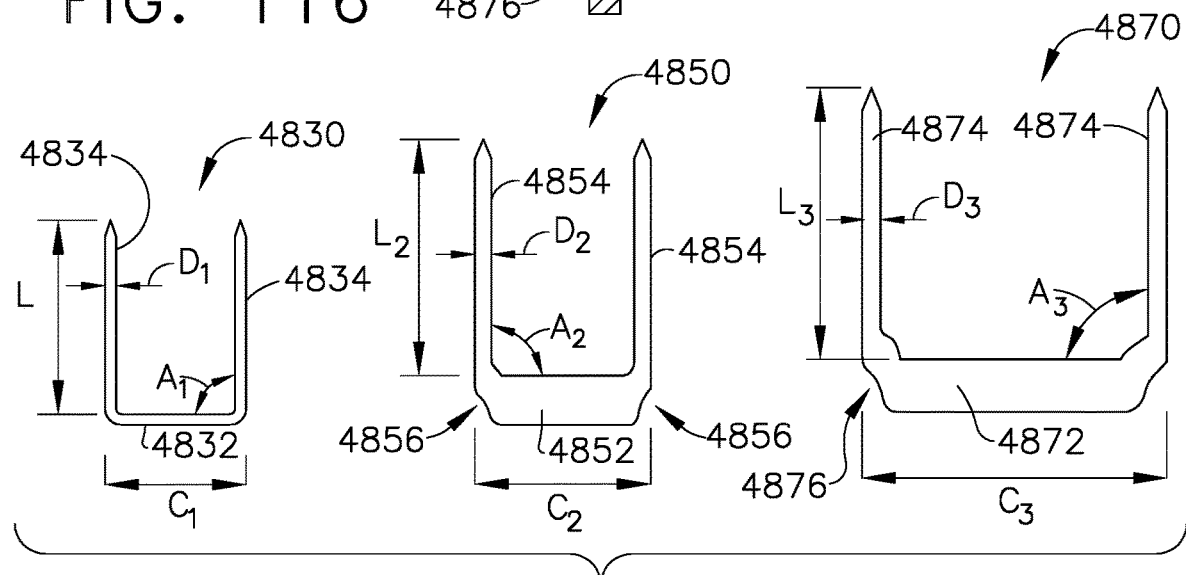

FIG. 114 illustrates another circular staple cartridge embodiment 4810 that includes a cartridge deck 4812 that includes three annular rows 4820, 4840, 4860 of spaced staple cavities. The inner or first row 4820 contains a first plurality of inner or first staple cavities 4822 that are each arranged at a first angle. Each inner staple cavity 4822 operably supports a corresponding inner or first staple 4830 therein. The inner cavities 4822 orient the first staples 4830 at the same uniform angle relative to the tangential direction. In the illustrated example, each inner staple 4830 is formed from a first staple wire that has a first staple diameter $D_1$. In one example, the first staple wire diameter $D_1$ may be approximately 0.0079"-0.015" (increments are usually 0.0089", 0.0094", and 0.00145"). Referring to FIG. 117, each inner staple 4830 includes a first crown 4832 and two first legs 4834. The first crown has a first crown width $C_1$ and each first leg 4834 has a first unformed leg length $L_1$. In one example, the first crown width $C_1$ may be approximately 0.100"-0.300" and the first unformed leg length $L_1$ may be approximately 0.198"-0.250". The first legs 4834 may be each arranged at an angle $A_1$ relative to the first staple crown 4832. The angle $A_1$ may be approximately 90° or it may be slightly greater than 90° such that the first legs 4834 are slightly splayed outward to assist in retaining the first staple 4830 in its corresponding first staple cavity 4822.

Figure 115:
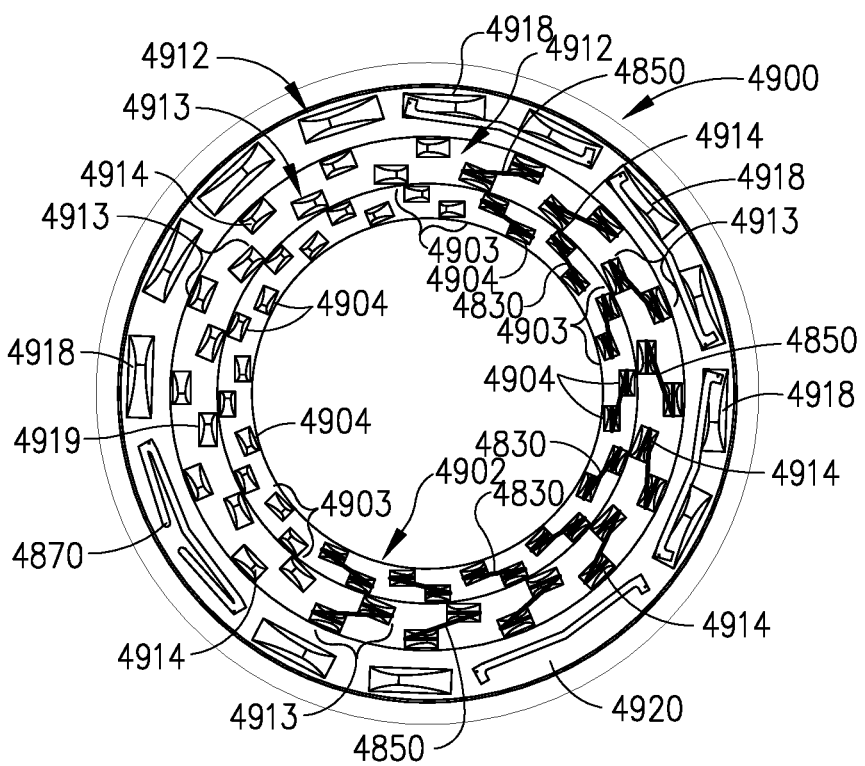
FIG. 115 is a bottom view of an anvil in accordance with at least one embodiment.
Figure 116:
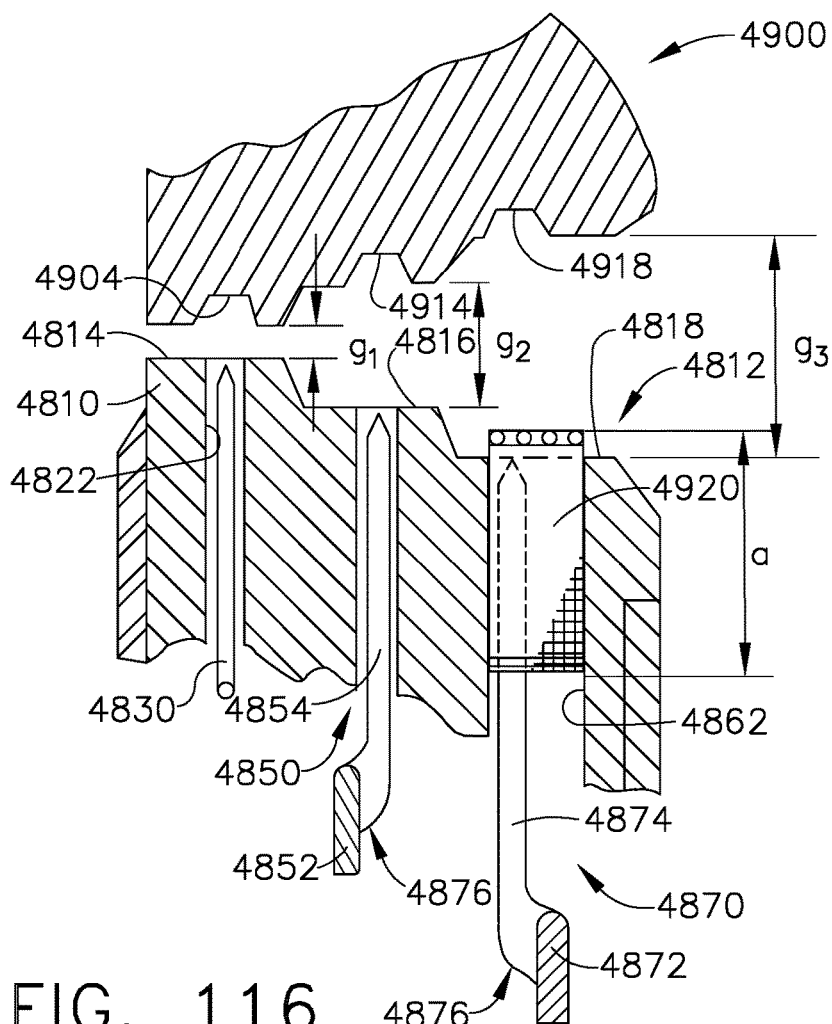

Turning to FIGS. 115 and 116, the staple cartridge 4810 is intended to be used in connection with an anvil 4900 that includes two inner or first rows 4902 of staggered or angled first pairs 4903 of first staple forming pockets 4904. Each first pair 4903 of first staple forming pockets 4904 correspond to one first staple 4830. One first staple forming pocket 4904 corresponds to one first staple leg 4834 and the other first staple forming pocket 4904 of the pair 4903 corresponds to the other first staple leg 4834. Such arrangement serves to establish a formed staple configuration wherein the first staple legs 4834 of a first staple 4830 are formed out of plane with the first crown 4832 of that particular first staple 4830 such that one first leg 4834 is formed on one side of the first crown 4832 and the other first leg 4834 is formed on the other side of the first crown 4832. This "three-dimensional" formed staple configuration is shown with respect to some of the first staple forming pockets 4904 in FIG. 115.

As can be most particularly seen in FIG. 116, the cartridge deck 4812 is of "stepped" construction. The cartridge deck 4812 includes an inner or first cartridge deck portion 4814 that corresponds to the inner or first annular row 4820 of inner or first staple cavities 4822. As can be further seen in FIG. 116, when the anvil 4900 is moved to the closed or clamping position, the portion of the anvil 4900 containing the first staple forming pockets 4904 is spaced from the deck portion 4814 a first gap distance $g_1$.

Referring again to FIGS. 114, 116 and 117, the middle or second row 4840 contains a second plurality of middle or second staple cavities 4842 that are each arranged at a second angle. Each middle staple cavity 4842 operably supports a corresponding middle or second staple 4850 therein. The middle cavities 4842 orient the middle or second staples 4850 at the same uniform second angle relative to the tangential direction. However, the second angle differs from the first angle. Stated another way, when the first and second staples are supported in their respective first and second cavities, the axis of the first crown of each first staple 4830, when extended, would ultimately intersect the extended axis of the second crown of an adjacent second staple 4850. As can be seen in FIGS. 116 and 117, each second or middle staple 4850 comprises a second staple crown or base 4852 and two second legs 4854. The staple base 4852 may have a somewhat rectangular cross-sectional shape and be formed from a flat sheet of material. The second staple legs 4854 may have a round cross-sectional profile, for example. The second or middle staples may comprise various staple configurations disclosed in, for example, U.S. patent application Ser. No. 14/836,110, filed Aug. 26, 2015, entitled SURGICAL STAPLING CONFIGURATIONS FOR CURVED AND CIRCULAR STAPLING INSTRUMENTS, which has been herein incorporated by reference in its entirety. Having round staple legs that extend from a staple base portion having the rectangular cross-sectional profile can provide a staple base portion and staple legs with no preferential bending planes. The second staple 4850 comprises bend portions 4856 where the staple legs 4854 extend from the staple base portion 4852. The bend portions 4856 may comprise a substantially square cross-sectional profile. The square profile and the rectangular profile of the bend portions 4856 and the staple base portion 4852, respectively, provide a stiff connection and backbone to the round staple legs 4854. The round staple legs 4854 eliminate preferential bending planes that staple legs with a square, rectangular, or any shape with vertices or a non-uniform shape, cross-sections could have. Each of the second staple legs 4854 has a second diameter $D_2$. In at least one embodiment, $D_2 > D_1$. The second base or crown 4852 has a second crown width $C_2$. In one arrangement, $C_2 > C_1$. The second legs 4854 may be each arranged at an angle $A_2$ relative to the second base or crown 4852. The angle $A_2$ may be approximately 90° or it may be slightly greater than 90° such that the second legs 4854 are slightly splayed outward to assist in retaining the second staple 4850 in its corresponding second staple cavity 4842.

Turning to FIGS. 115 and 116, the anvil 4900 further comprises two middle or second rows 4912 of staggered or angled second pairs 4913 of second staple forming pockets 4914. Each second pair 4913 of second staple forming pockets 4914 correspond to one second staple 4850. One second staple forming pocket 4914 corresponds to one second staple leg 4854 and the other second staple forming pocket 4914 of the pair 4913 corresponds to the other second staple leg 4854. Such arrangement serves to establish a formed staple configuration wherein the second legs 4854 are formed out of plane with the second base 4852 of the particular second staple 4850. This "three-dimensional" formed staple configuration is shown with respect to some of the second staple forming pockets 4914 in FIG. 115.

As can be most particularly seen in FIG. 116, the cartridge deck 4812 further comprises a second cartridge deck portion 4816 that corresponds to the middle or second annular row 4840 of middle or second staple cavities 4842. As can be further seen in FIG. 116, when the anvil 4900 is moved to the closed or clamping position, the portion of the anvil 4900 containing the second staple forming pockets 4914 is spaced from the deck portion 4816 a second gap distance $g_2$. In the illustrated example, $g_2 > g_1$.

Referring again to FIGS. 114, 116 and 117, the outside or third row 4860 contains a third plurality of outside or third staple cavities 4862 that are sized relative to the second staple cavities 4842 such that each outer or third staple cavity 4862 spans a distance between two adjacent second cavities 4842. Each outer staple cavity 4862 operably supports a corresponding outer or third staple 4870 therein. The outer cavities 4862 orient the outer or third staples 4870 tangent to the circumferential direction. As can be seen in FIGS. 116 and 117, each third or outer staple 4870 comprises a third staple crown or base 4872 and two third legs 4874. The staple base 4872 may have a somewhat rectangular cross-sectional shape and be formed from a flat sheet of material. The third staple legs 4874 may have a round cross-sectional profile, for example. The third or outer staples 4870 may comprise various staple configurations disclosed in, for example, U.S. patent application Ser. No. 14/836,110, filed Aug. 26, 2015, entitled SURGICAL STAPLING CONFIGURATIONS FOR CURVED AND CIRCULAR STAPLING INSTRUMENTS, which has been herein incorporated by reference in its entirety. Having round staple legs that extend from a staple base portion having the rectangular cross-sectional profile can provide a staple base portion and staple legs with no preferential bending planes. The third staple 4870 comprises bend portions 4876 where the staple legs 4874 extend from the staple base portion 4872. The bend portions 4876 may comprise a substantially square cross-sectional profile. The square profile and the rectangular profile of the bend portions 4876 and the staple base portion 4872, respectively, provide a stiff connection and backbone to the round staple legs 4874. The round staple legs 4874 eliminate preferential bending planes that staple legs with a square, rectangular, or any shape with vertices or a non-uniform shape, cross-sections could have. In at least one embodiment, $D_3 > D_2$. The third base or crown 4872 has a third crown width $C_3$ and each third leg 4874 has a third unformed leg length $L_3$. In one arrangement, $C_3 > C_2$ and $L_3 > L_2$. The third legs 4874 may be each arranged at an angle $A_3$ relative to the third base or crown 4872. The angle $A_3$ may be approximately 90° or it may be slightly greater than 90° such that the third legs 4874 are slightly splayed outward to assist in retaining the third staple 4870 in its corresponding third staple cavity 4862.

Turning to FIGS. 115 and 116, the anvil 4900 further comprises an outer row 4916 of outer or third staple forming pockets 4918. Each third staple forming pocket 4918 corresponds to one third staple 4870. As can be most particularly seen in FIG. 116, the cartridge deck 4812 further comprises a third cartridge deck portion 4818 that corresponds to the outer or third row 4860 of outer or third staple cavities 4862. As can be further seen in FIG. 116, when the anvil 4900 is moved to the closed or clamping position, the portion of the anvil 4900 containing the third staple forming pockets 4918 is spaced from the deck portion 4818 a third gap distance $g_3$. In the illustrated example, $g_3 > g_2$. As can be further seen in FIG. 116, in at least one embodiment, a tissue thickness compensator 4920 is employed in connection with each outer or third staple 4870. The tissue thickness compensator may comprise a woven material that is embedded with oxidized regenerated cellulose (ORC) to promote hemostasis. The tissue thickness compensator 4920 may comprise any of the various tissue thickness compensator arrangements disclosed in U.S. patent application Ser. No. 14/187,389, filed Feb. 24, 2014, entitled IMPLANTABLE LAYER ASSEMBLIES, U.S. Patent Application Publication No. 2015/0238187, the entire disclosure of which is hereby incorporated by reference herein. As can be seen in FIG. 116, the tissue thickness compensator 4920 has a thickness designated as "a". In one embodiment, the tissue thickness compensator has a thickness of approximately 0.015"-0.045". However, other thicknesses may be employed.

Thus, in at east one embodiment as depicted in FIGS. 114-117, the staple cartridge 4810 may employ a different number of staples in each of the three rows of staples. In one arrangement, the inner row of staples comprises conventional staples with the smallest wire diameter and the shortest unformed leg length. Each first staple has the shortest crown width and each first staple is oriented at a uniform angle relative to the tangential direction. The middle staples have a configuration that differs from the first staple configuration. Each leg of the middle staples comprises a moderate wire diameter and unformed leg length. Each middle staple has a slightly larger crown width than the crown widths of the inner staples and each middle staple is oriented at a uniform angle relative to the tangential direction, but at a different angle relative to the inner row of inner staples. Each outer staple has a configuration that is similar to the configuration of the middle staples. Each of the third legs of each outer staple comprises the largest wire diameter as compared to the wire diameters of the legs of the inner and middle staples. The crown width of each outer staple is significantly larger than the crown widths of the inner and middle staples. Each outer staple is oriented tangentially to the circumferential direction of the cartridge. The outer row of staples employs woven tissue thickness compensators (spacer fabric) that is embedded with ORC to promote hemostasis. The stepped anvil and the stepped cartridge deck yield different formed staple heights with the staples having the shortest formed heights being in the inner row and the staples having the longest formed heights being in the outer row. The anvil pockets corresponding to the inner and middle rows of staples are "tilted" to create three dimensional staples in the inner and middle rows. "Bathtub-type" anvil pockets correspond to the outer row of staples. In at least one embodiment, the staples may be sequentially fired. For example, the staples in the inner and middle rows may be fired first and the staples in the outer row fired thereafter. The annular knife cuts the clamped tissue during the firing process.

As described in various embodiments of the present disclosure, a circular stapling instrument includes an anvil and a staple cartridge. One or both of the anvil and the staple cartridge is movable relative to the other between an open configuration and a closed configuration to capture tissue therebetween. The staple cartridge houses staples inside, or at least partially inside, circular rows of staple cavities. The staples are deployed in circular rows from their respective staple cavities into the captured tissue and are formed against corresponding circular rows of forming pockets in the anvil. A firing drive is configured to eject the staples from the staple cartridge during a firing stroke of the firing drive.

An anvil of a circular stapling instrument generally comprises a tissue compression surface and an annular array of staple forming pockets defined in the tissue compression surface. The anvil further comprises an attachment mount and a stem extending from the attachment mount. The stem is configured to be releasably attached to a closure drive of the circular stapling instrument so that the anvil can be moved toward and away from a staple cartridge of the circular stapling instrument.

The staple cartridge and the anvil can travel separately within a patient and are combined at the surgical field. In various instances, the staple cartridge, for example, travels through a narrow tubular body of the patient such as, for example, a colon. A staple cartridge may include several tissue-contacting features such as, for example, stepped decks and pocket extenders. To avoid unintentional injury to the patient as the staple cartridge travels toward a target tissue, the present disclosure, among other things, presents various modifications to several tissue-contacting features.

Referring to FIG. 118, a partial cross-sectional view depicts a staple cartridge 15500 of a circular surgical instrument pressing against tissue (T) as the staple cartridge 15500 travels within a patient's body. Multiple structural features of the staple cartridge 15500 are modified to create an especially contoured outer frame 15502 to protect the tissue.

The staple cartridge 15500 includes a plurality of annular rows of staple cavities. In at least one example, an outer row 15504 of staple cavities 15510 at least partially surrounds an inner row 15506 of staple cavities 15512, as illustrated in FIG. 118. The staple cavities 15510 and 15512 are configured to house staples 15530 and 15531, respectively.

The terms inner and outer delineate a relationship with reference to a central axis 15533. For example, an inner tissue-contacting surface 15518 is closer to the central axis 15533 than outer tissue-contacting surface 15516.

Figure 119:
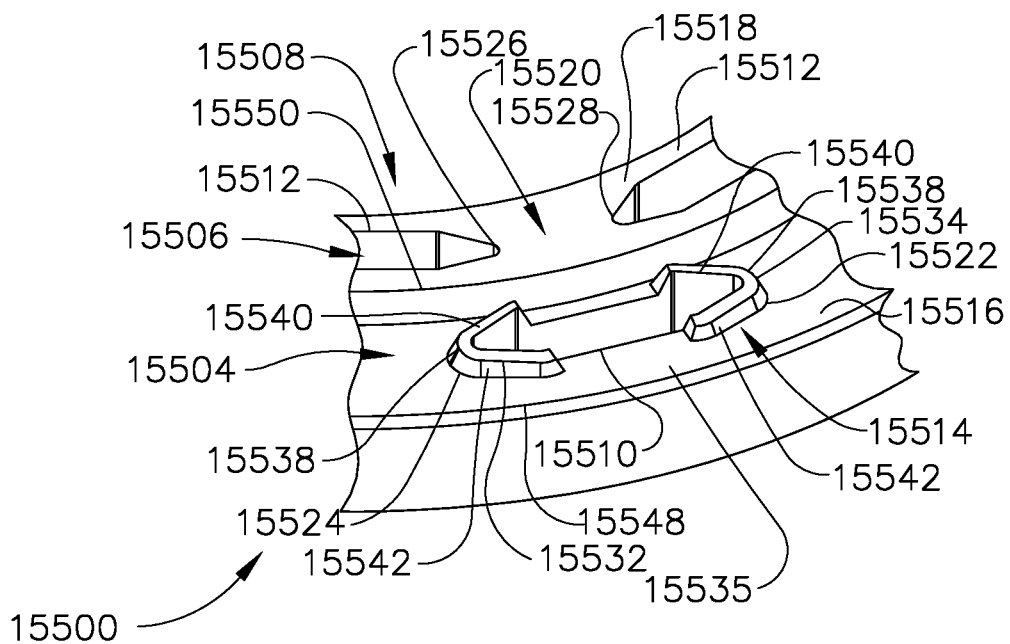

As illustrated in FIG. 119, the staple cartridge 15500 comprises a stepped cartridge deck 15508. The outer row 15504 is defined in an outer tissue-contacting surface 15516 of the stepped cartridge deck 15508 while the inner row 15506 is defined in an inner tissue-contacting surface 15518 of the stepped cartridge deck 15508. The outer tissue-contacting surface 15516 is stepped down from the inner tissue-contacting surface 15518 which creates a gradient that reduces friction as the staple cartridge 15500 is pressed against the tissue.

In certain instances, the outer tissue-contacting surface 15516 is parallel, or at least substantially parallel, to the inner tissue-contacting surface 15518. In other instances, the outer tissue-contacting surface 15516 is slanted such that a first plane defined by the outer tissue-contacting surface 15516 is transverse to a second plane defined by the inner tissue-contacting surface 15518. An angle is defined between the first plane and the second plane. The angle can be an acute angle. In at least one instance, the angle can be any angle selected from a range of greater than about 0° and less than or equal to about 30°, for example. In at least one instance, the angle can be any angle selected from a range of greater than about 5° and less than or equal to about 25°, for example. In at least one instance, the angle can be any angle selected from a range of greater than about 10° and less than or equal to about 20°, for example. A slanted outer tissue-contacting surface 15516 can reduce friction against, or snagging of, tissue as the staple cartridge 15500 is moved relative to the tissue. In at least one instance, a slanted outer tissue-contacting surface 15516 is also stepped down from the inner tissue-contacting surface 15518.

In at least one instance, an inner portion of the outer tissue-contacting surface 15516 is planar, or at least substantially planar while an outer edge 15548 of the outer tissue-contacting surface 15516 is pitched, radiused, and/or beveled to reduce friction against, or snagging of, tissue as the staple cartridge 15500 is moved relative to the tissue. The staple cavities 15510 reside in the planar inner portion of the outer tissue-contacting surface 15516, for example. An outer edge 15550 of the inner tissue-contacting surface 15518 can also be pitched, beveled and/or radiused to reduce friction against, or snagging of, tissue as the staple cartridge 15500 is moved relative to the tissue.

To accommodate staples with the same, or at least substantially the same, unformed heights in the staple cavities 15510 of the outer row 15504 and the staple cavities 15512 of the inner row 15504, the staple cavities 15510 of the outer row 15504 comprise pocket extenders 15514. The pocket extenders 15514 are configured to control and guide the staples 15530 as they are ejected from their respective staple cavities 15510. In certain instances, the pocket extenders 15514 can be configured to accommodate staples with a greater unformed height s that the staples of the inner tissue-contacting surface 15518, for example.

As illustrated in FIG. 119, a staple cavity 15510 in the outer row 15504 is laterally aligned, or at least substantially aligned, with a gap 15520 between two adjacent staple cavities 15512 in the inner row 15506. The staple cavity 15510 includes a first end 15522 and a second end 15524. The second end 15524 overlaps with a first end 15526 of one of the two consecutive staple cavities 15512 such that a staple leg 15530*a* positioned at the second end 15524 is radially aligned, or at least substantially aligned, with a staple leg 15531*a* positioned at the first end 15526, as illustrated in FIG. 118. Likewise, the first end 15522 of the staple cavity 15510 overlaps with a second end 15528 of the other one of the two consecutive staple cavities 15512.

A pocket extender 15514 comprises a first jacket 15532 protruding from the outer tissue-contacting surface 15516 to conceal a tip 15536 of the staple leg 15530*a* that extends beyond the outer tissue-contacting surface 15516. The first jacket 15532 comprises an end 15538 protruding from the first end 15522, an inner side wall 15540 and an outer side wall 15542 extending away from the end 15538 to form the first jacket 15532. In at least one instance, the first jacket 15532 defines, or at least substantially defines, a "C" shaped wall extending on a portion of a perimeter 15535 of the staple cavity 15510 that comprises the first end 15522.

To reduce friction against the tissue, the inner side wall 15540 protrudes from the outer tissue-contacting surface 15516 to a greater height than the outer side wall 15542. Said another way, the outer side wall 15542 is lower in height than the inner side wall 15540. This arrangement creates a gradient for a smooth transition from the inner side wall 15540 to the outer side wall 15542 to the outer tissue-contacting surface 15516. In at least one example, the inner side wall 15540 and the inner tissue-contacting surface 15518 comprise the same, or at least substantially the same, height with reference to the outer tissue-contacting surface 15516. Alternatively, the inner side wall 15540 and the inner tissue-contacting surface 15518 comprise different heights with reference to the outer tissue-contacting surface 15516. In certain instances, the inner side wall 15540 is lower in height relative to the inner tissue-contacting surface 15518 with reference to the outer tissue-contacting surface 15516. This arrangement creates a gradient for a smooth transition from the inner tissue-contacting surface 15518 to the inner side wall 15540 to the outer side wall 15542 to the outer tissue-contacting surface 15516.

The inner tissue-contacting surface 15518, the inner side wall 15540, the outer side wall 15542, and/or the outer tissue-contacting surface 15516 define discrete portions of the contoured outer frame 15502; nonetheless, as illustrated in FIG. 118, such portions are kept sufficiently close to one another so that tissue cannot be trapped therebetween as the staple cartridge 15500 presses against the tissue. Furthermore, one or more of the portions may include slanted, contoured, curved, radiused, and/or beveled outer surfaces to reduce friction against the tissue. As illustrated in FIG. 118, an upper surface 15544 of the outer side wall 15542 and an upper surface 15546 of the inner side wall 15540 are slanted, contoured, curved, radiused, and/or beveled to define the contoured outer frame 15502.

In at least one instance, the upper surface 15544 and the upper surface 15546 define a slanted plane that is transverse to a first plane defined by the outer tissue-contacting surface 15516 and a second plane defined by the inner tissue-contacting surface 15518. In at least one instance, a first angle is defined between the slanted plane and the first plane. A second angle can also be defined between the slanted plane and the second plane. The first and second angles can be the same, or at least substantially the same in value. Alternatively, the first angle can be different from the second angle in value. In at least one instance, the first angle and/or the second angle are acute angles. In at least one instance, the first angle is any angle selected from a range of greater than about 0° and less than or equal to about 30°, for example. In at least one instance, the first angle is any angle selected from a range of greater than about 5° and less than or equal to about 25°, for example. In at least one instance, the first angle is any angle selected from a range of greater than about 10° and less than or equal to about 20°, for example. In at least one instance, the second angle is any angle selected from a range of greater than about 0° and less than or equal to about 30°, for example. In at least one instance, the second angle is any angle selected from a range of greater than about 5° and less than or equal to about 25°, for example. In at least one instance, the second angle is any angle selected from a range of greater than about 10° and less than or equal to about 20°, for example.

Further to the above, the pocket extender 15514 includes a second jacket 15534 that is similar in many respects to the first jacket 15532. Like the first jacket 15532, the second jacket 15534 protrudes from the outer tissue-contacting surface 15516 to conceal a tip of a staple leg that extends beyond the outer tissue-contacting surface 15516. The second jacket 15534 comprises an end 15538 protruding from the second end 15524, an inner side wall 15540 and an outer side wall 15542 extending from the end 15538 to form the second jacket 15534.

Although one pocket extender 15514 is illustrated in FIG. 119, it is understood that one or more other pocket extenders 15514 may protrude from the outer tissue-contacting surface 15516, for example. In at least one instance, the first jacket 15532 and the second jacket 15534 are connected via side walls to define a pocket extender that completely surrounds a staple cavity, for example.

Figure 82A:
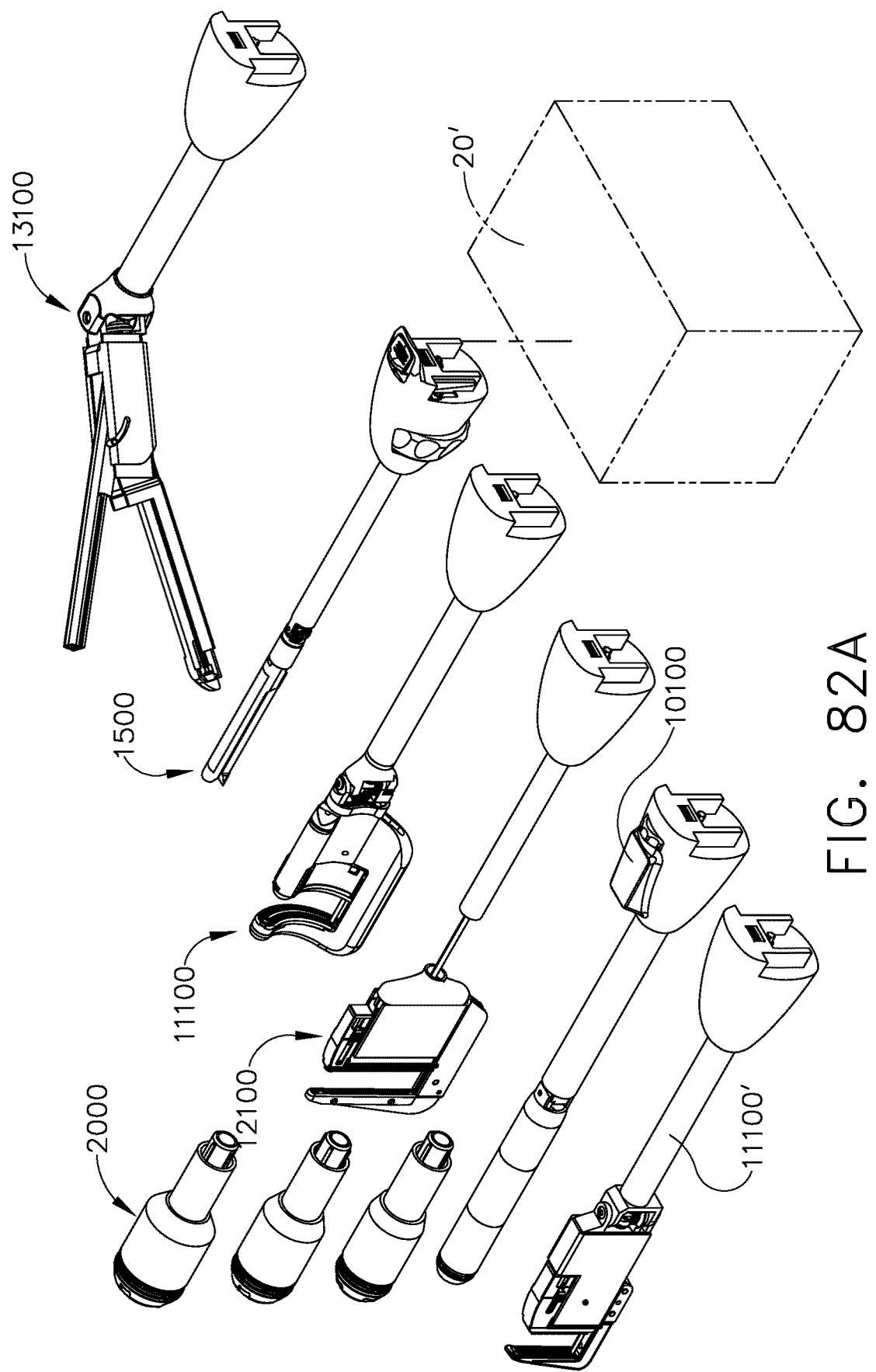
FIG. 82A is a schematic of a robotic surgical instrument system comprising a plurality of attachable end effectors in accordance with at least one embodiment.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. FIG. 82A schematically depicts a robotic surgical instrument system 20'; however, U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

European Patent Application No. EP 795298, entitled LINEAR STAPLER WITH IMPROVED FIRING STROKE, which was filed on Mar. 12, 1997;

U.S. Pat. No. 5,605,272, entitled TRIGGER MECHANISM FOR SURGICAL INSTRUMENTS, which issued on Feb. 25, 1997;

U.S. Pat. No. 5,697,543, entitled LINEAR STAPLER WITH IMPROVED FIRING STROKE, which issued on Dec. 16, 1997;

U.S. Patent Application Publication No. 2005/0246881, entitled METHOD FOR MAKING A SURGICAL STAPLER, which published on Nov. 10, 2005;

U.S. Patent Application Publication No. 2007/0208359, entitled METHOD FOR STAPLING TISSUE, which published on Sep. 6, 2007;

U.S. Pat. No. 4,527,724, entitled DISPOSABLE LINEAR SURGICAL STAPLING INSTRUMENT, which issued on Jul. 9, 1985;

U.S. Pat. No. 5,137,198, entitled FAST CLOSURE DEVICE FOR LINEAR SURGICAL STAPLING INSTRUMENT, which issued on Aug. 11, 1992;

U.S. Pat. No. 5,405,073, entitled FLEXIBLE SUPPORT SHAFT ASSEMBLY, which issued on Apr. 11, 1995;

U.S. Pat. No. 8,360,297, entitled SURGICAL CUTTING AND STAPLING INSTRUMENT WITH SELF ADJUSTING ANVIL, which issued on Jan. 29, 2013;

U.S. patent application Ser. No. 14/813,242, entitled SURGICAL INSTRUMENT COMPRISING SYSTEMS FOR ASSURING THE PROPER SEQUENTIAL OPERATION OF THE SURGICAL INSTRUMENT, which was filed on Jul. 30, 2015;

U.S. patent application Ser. No. 14/813,259, entitled SURGICAL INSTRUMENT COMPRISING SEPARATE TISSUE SECURING AND TISSUE CUTTING SYS1EMS, which was filed on Jul. 30, 2015;

U.S. patent application Ser. No. 14/813,266, entitled SURGICAL INSTRUMENT COMPRISING SYSTEMS FOR PERMITTING THE OPTIONAL TRANSECTION OF TISSUE, which was filed on Jul. 30, 2015;

U.S. patent application Ser. No. 14/813,274, entitled SURGICAL INSTRUMENT COMPRISING A SYS1EM FOR BYPASSING AN OPERATIONAL STEP OF THE SURGICAL INSTRUMENT; which was filed on Jul. 30, 2015;

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYS1EM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Patent Application Publication No. 2014/0263551;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An end effector for use with a surgical stapler, wherein said end effector comprises:
   a cartridge body comprising a longitudinal axis;
   a plurality of staple cavities defined in said cartridge body, comprising:
      a first annular row of staple cavities extending around said longitudinal axis; and
      a second annular row of staple cavities extending around said longitudinal axis;
   staples removably stored in said staple cavities; and
   a ramp rotatable about said longitudinal axis along a spiral firing path to eject said staples from said staple cavities, wherein said cartridge body comprises a spiral slot configured to guide said ramp, and wherein said spiral slot extends around said longitudinal axis while constantly approaching said longitudinal axis.

2. The end effector of claim 1, wherein said ramp is configured to eject said staples distally from said staple cavities.

3. An end effector for use with a surgical stapler, wherein said end effector comprises:
   a cartridge body comprising a longitudinal axis;
   a plurality of staple cavities defined in said cartridge body, comprising:
      a first annular row of staple cavities extending around said longitudinal axis; and
      a second annular row of staple cavities extending around said longitudinal axis;
   staples removably stored in said staple cavities; and
   a ramp rotatable about said longitudinal axis along a spiral firing path to eject said staples from said staple cavities, wherein said cartridge body comprises a spiral slot configured to guide said ramp, and wherein said spiral slot extends around said longitudinal axis while constantly receding from said longitudinal axis.

4. The end effector of claim 3, wherein said ramp is configured to eject said staples distally from said staple cavities.

5. An end effector for use with a surgical stapler, wherein said end effector comprises:
   a cartridge body comprising a longitudinal axis;
   a plurality of staple cavities defined in said cartridge body, comprising:
      a first annular row of staple cavities extending around said longitudinal axis; and
      a second annular row of staple cavities extending around said longitudinal axis;
   staples removably stored in said staple cavities; and
   a ramp rotatable about said longitudinal axis along a spiral firing path to eject said staples from said staple cavities, wherein said cartridge body comprises a curved slot configured to receive said ramp, and wherein said curved slot extends around said longitudinal axis while approaching said longitudinal axis.

6. The end effector of claim 5, wherein said ramp is configured to eject said staples from said staple cavities in a direction parallel to said longitudinal axis.

7. An end effector for use with a surgical stapler, wherein said end effector comprises:
   a cartridge body comprising a longitudinal axis;
   a plurality of staple cavities defined in said cartridge body, comprising:
      a first annular row of staple cavities extending around said longitudinal axis; and
      a second annular row of staple cavities extending around said longitudinal axis;
   staples removably stored in said staple cavities; and
   a ramp rotatable about said longitudinal axis along a spiral firing path to eject said staples from said staple cavities, wherein said cartridge body comprises a curved slot configured to receive said ramp, and wherein said curved slot extends around said longitudinal axis while constantly receding from said longitudinal axis.

8. The end effector of claim 7, wherein said ramp is configured to eject said staples from said staple cavities in a direction parallel to said longitudinal axis.

9. An end effector for use with a surgical stapler, wherein said end effector comprises:
   a cartridge body comprising a longitudinal axis;
   a plurality of staple cavities defined in said cartridge body, comprising:
      a first annular row of staple cavities extending around said longitudinal axis; and
      a second annular row of staple cavities extending around said longitudinal axis;
   staples removably stored in said staple cavities; and a ramp rotatable about said longitudinal axis along a spiral firing path to eject said staples from said staple cavities, wherein said staples comprise:
a plurality of first staples, wherein each said first staple is positioned in said first annular row of staple cavities, and wherein each said first staple is defined by a first unformed height; and
a plurality of second staples, wherein each said second staple is positioned in said second annular row of staple cavities, and wherein each said second staple is defined by a second unformed height which is different than said first unformed height.

10. The end effector of claim 9, further comprising staple drivers, wherein said ramp is configured to sequentially engage said staple drivers to sequentially eject said staples from said staple cavities.

11. The end effector of claim 10, wherein said ramp sequentially ejects said staples stored in said first annular row of staple cavities before sequentially ejecting said staples stored in said second annular row of staple cavities.

12. The end effector of claim 9, further comprising an anvil configured to deform said staples, wherein said anvil is configured to deform said first staples to a first formed height and said second staples to a second formed height, and wherein said first formed height is different than said second formed height.

13. The end effector of claim 9, wherein said ramp is configured to eject said staples distally from said staple cavities.

14. An end effector of a surgical stapler, wherein said end effector comprises:
a cartridge body comprising a longitudinal axis;
a plurality of staple cavities defined in said cartridge body;
staples removably stored in said staple cavities; and
a firing member rotatable about said longitudinal axis to sequentially eject said staples from said staple cavities, wherein said cartridge body comprises a spiral slot configured to guide said firing member, and wherein said spiral slot extends around said longitudinal axis while constantly approaching said longitudinal axis.

15. The end effector of claim 14, wherein said firing member is configured to eject said staples distally from said staple cavities.

16. An end effector of a surgical stapler, wherein said end effector comprises:
a cartridge body comprising a longitudinal axis;
a plurality of staple cavities defined in said cartridge body;
staples removably stored in said staple cavities; and
a firing member rotatable about said longitudinal axis to sequentially eject said staples from said staple cavities, wherein said cartridge body comprises a spiral slot configured to guide said firing member, and wherein said spiral slot extends around said longitudinal axis while constantly receding from said longitudinal axis.

17. The end effector of claim 16, wherein said firing member is configured to eject said staples distally from said staple cavities.

18. An end effector of a surgical stapler, wherein said end effector comprises:
a cartridge body comprising a longitudinal axis;
a plurality of staple cavities defined in said cartridge body;
staples removably stored in said staple cavities; and
a firing member rotatable about said longitudinal axis to sequentially eject said staples from said staple cavities, wherein said cartridge body comprises a curved slot configured to receive said firing member, and wherein said curved slot extends around said longitudinal axis while approaching said longitudinal axis.

19. The end effector of claim 18, wherein said firing member is configured to eject said staples from said staple cavities in a direction parallel to said longitudinal axis.

20. An end effector of a surgical stapler, wherein said end effector comprises:
a cartridge body comprising a longitudinal axis;
a plurality of staple cavities defined in said cartridge body;
staples removably stored in said staple cavities; and
a firing member rotatable about said longitudinal axis to sequentially eject said staples from said staple cavities, wherein said cartridge body comprises a curved slot configured to receive said firing member, and wherein said curved slot extends around said longitudinal axis while constantly receding from said longitudinal axis.

21. The end effector of claim 20, wherein said firing member is configured to eject said staples from said staple cavities in a direction parallel to said longitudinal axis.

22. An end effector of a surgical stapler, wherein said end effector comprises:
a cartridge body comprising a longitudinal axis;
a plurality of staple cavities defined in said cartridge body;
staples removably stored in said staple cavities; and
a firing member rotatable about said longitudinal axis to sequentially eject said staples from said staple cavities, wherein said plurality of staple cavities comprises:
a first annular row of staple cavities extending around said longitudinal axis; and
a second annular row of staple cavities extending around said longitudinal axis, wherein said firing member sequentially ejects said staples stored in said first annular row of staple cavities before sequentially ejecting said staples stored in said second annular row of staple cavities, wherein said staples comprise:
a plurality of first staples, wherein each said first staple is positioned in said first annular row of staple cavities, and wherein each said first staple is defined by a first unformed height; and
a plurality of second staples, wherein each said second staple is positioned in said second annular row of staple cavities, and wherein each said second staple is defined by a second unformed height which is different than said first unformed height.

23. The end effector of claim 22, further comprising staple drivers, wherein said firing member is configured to sequentially engage said staple drivers to sequentially eject said staples from said staple cavities.

24. The end effector of claim 22, further comprising an anvil configured to deform said staples, wherein said anvil is configured to deform said first staples to a first formed height and said second staples to a second formed height, and wherein said first formed height is different than said second formed height.

25. The end effector of claim 22, wherein said firing member is configured to eject said staples distally from said staple cavities.

26. An end effector for use with a surgical stapler configured to apply annular rows of staples, said end effector comprising:
a cartridge body;
a plurality of staple cavities defined in said cartridge body, comprising:

a first annular row of staple cavities;

a second annular row of staple cavities;

a first group of staples removably stored in said first annular row of staple cavities;

a second group of staples removably stored in said second annular row of staple cavities;

a plurality of staple drivers, wherein each said staple driver is configured to eject a said staple from a said staple cavity;

a drive slot defined along an arcuate path, wherein said arcuate path includes a first portion which extends under said first annular row of staple cavities and a subsequent portion which extends under said second annular row of staple cavities; and a ramp slideable within said drive slot, wherein said ramp is configured to engage said staple drivers and eject said staples from said staple cavities.

27. The end effector of claim 26, wherein said ramp is configured to eject said staples distally from said staple cavities.

* * * * *